United States Patent
Choi et al.

(10) Patent No.: US 10,957,865 B2
(45) Date of Patent: Mar. 23, 2021

(54) ORGANIC LIGHT EMITTING COMPOUND AND ORGANIC LIGHT EMITTING DIODE INCLUDING THE SAME

(71) Applicant: SFC CO., LTD., Cheongju-si (KR)

(72) Inventors: Yeongtae Choi, Yongin-si (KR); Se-jin Lee, Daejeon (KR); Seok-bae Park, Geumsan-gun (KR); Taejung Yu, Yongin-si (KR); Byung-sun Yang, Namwon-si (KR); Dajung Lee, Bucheon-si (KR)

(73) Assignee: SFC CO., LTD., Cheongju-si (KR)

( * ) Notice: Subject to any disclaimer, the term of this patent is extended or adjusted under 35 U.S.C. 154(b) by 145 days.

(21) Appl. No.: 15/660,388

(22) Filed: Jul. 26, 2017

(65) Prior Publication Data

US 2018/0040834 A1 Feb. 8, 2018

(30) Foreign Application Priority Data

Jul. 27, 2016 (KR) ........................ 10-2016-0095499
Oct. 6, 2016 (KR) ........................ 10-2016-0128791
Jul. 5, 2017 (KR) ........................ 10-2017-0085283

(51) Int. Cl.

| | |
|---|---|
| *H01L 51/00* | (2006.01) |
| *C07D 405/04* | (2006.01) |
| *C07D 405/10* | (2006.01) |
| *C07D 491/048* | (2006.01) |
| *C07D 495/04* | (2006.01) |
| *C07D 409/14* | (2006.01) |
| *C09K 11/06* | (2006.01) |
| *C07D 405/14* | (2006.01) |
| *H01L 51/50* | (2006.01) |
| *H01L 51/52* | (2006.01) |

(52) U.S. Cl.
CPC ........ *H01L 51/0073* (2013.01); *C07D 405/04* (2013.01); *C07D 405/10* (2013.01); *C07D 405/14* (2013.01); *C07D 409/14* (2013.01); *C07D 491/048* (2013.01); *C07D 495/04* (2013.01); *C09K 11/06* (2013.01); *H01L 51/0052* (2013.01); *H01L 51/0067* (2013.01); *H01L 51/0072* (2013.01); *H01L 51/0074* (2013.01); *C09K 2211/1007* (2013.01); *C09K 2211/1011* (2013.01); *C09K 2211/1018* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| | | | |
|---|---|---|---|
| 2016/0308147 A1* | 10/2016 | Parham | ............... C07F 15/0033 |
| 2017/0005274 A1 | 1/2017 | Kudo et al. | |
| 2017/0077416 A1 | 3/2017 | Kim et al. | |

FOREIGN PATENT DOCUMENTS

| | | |
|---|---|---|
| KR | 10-2015-0045809 A | 4/2015 |
| KR | 10-2015-0128583 A | 11/2015 |
| KR | 10-2016-0050361 A | 5/2016 |
| WO | WO-2015/090504 A2 * | 6/2015 |
| WO | 2016/006791 A1 | 1/2016 |
| WO | 2016/024637 A1 | 2/2016 |

* cited by examiner

*Primary Examiner* — Jay Yang
(74) *Attorney, Agent, or Firm* — NSIP Law

(57) ABSTRACT

Disclosed is an organic light emitting compound represented by Formula I:

$$HAr_1\text{-}(L)_n\text{-}HAr_2 \qquad (I).$$

Also disclosed is an organic light emitting diode including the organic light emitting compound. Particularly, the organic light emitting diode employs the organic light emitting compound as a material for electron injection and transport. The organic light emitting diode can be driven at a low voltage and has improved life characteristics compared to conventional organic light emitting diodes. Due to these advantages, the organic light emitting diode is useful in a variety of industrial applications, including displays and lighting systems.

1 Claim, No Drawings

ORGANIC LIGHT EMITTING COMPOUND AND ORGANIC LIGHT EMITTING DIODE INCLUDING THE SAME

BACKGROUND OF THE INVENTION

1. Field of the Invention

The present invention relates to an organic light emitting compound. More specifically, the present invention relates to an organic light emitting compound that has a specific structure for an electron transport layer and can be used to achieve long lifetime, low voltage and high-efficiency luminescence, and an organic light emitting diode including the organic light emitting compound.

2. Description of the Related Art

Organic light emitting diodes (OLEDs) are self-luminous display devices and have the advantage of large viewing angle. Organic light emitting diodes can be reduced in weight, thickness, and size and have short response time compared to liquid crystal display devices. Due to these advantages, the application of organic light emitting diodes to full-color displays or lighting systems is expected.

Generally, organic electroluminescence refers to the phenomenon in which electrical energy is converted into light energy using an organic material. A typical organic light emitting diode based on organic electroluminescence has a structure including an anode, a cathode, and an organic layer therebetween.

The organic layer usually consists of one or more layers, for example, a hole injecting layer, a hole transport layer, a light emitting layer, an electron transport layer, and an electron injecting layer that are composed of different materials to increase the efficiency and stability of the organic light emitting diode.

When a voltage is applied between the two electrodes of the organic light emitting diode, holes from the anode and electrons from the cathode are injected into the organic layer. As a result of recombination of the holes and the electrons, excitons are formed which return back to the ground state to emit light. Such an organic light emitting diode is known to have excellent characteristics, such as self-luminescence, high luminance, high efficiency, low driving voltage, large viewing angle, high contrast, and fast response speed.

Materials for organic layers of organic light emitting diodes can be divided into light emitting materials and charge transport materials, for example, hole injecting materials, hole transport materials, electron transport materials, and electron injecting materials, by their functions. Organic layers of organic light emitting diodes may further include one or more layers, for example, an electron blocking layer or a hole blocking layer.

Many materials for electron transport layers are known that possess an outstanding ability to transport electrons and block holes, have high luminance efficiency and can be formed into highly stable thin films. For example, Korean Patent Publication No. 10-2012-0104204 (Sep. 20, 2012) describes an organic compound in which a pyridoindole derivative is bonded to a substituted anthracene ring structures. Further, Japanese Patent Publication No. 2010-168363 (Aug. 5, 2010) describes an anthracene derivative having a pyridylnaphthyl group that is excellent in terms of external quantum efficiency and driving voltage.

Despite numerous attempts to develop methods for fabricating organic light emitting diodes with efficient luminescent properties in the prior art, including the above patent publications, there is still a continued need to develop organic light emitting diodes with long lifetime, low voltage, and high efficiency.

SUMMARY OF THE INVENTION

Therefore, the present invention has been made in an effort to solve the above problems and is directed to providing an organic light emitting compound having a specific structure that can be introduced into an electron transport layer to fabricate an organic light emitting diode with long lifetime, low voltage, and high efficiency.

The present invention is also directed to providing an organic light emitting diode that employs the organic light emitting compound as a light emitting material to achieve low driving voltage, high efficiency, and long lifetime.

One aspect of the present invention provides an organic light emitting compound represented by Formula I:

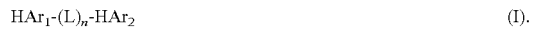

$$HAr_1\text{-}(L)_n\text{-}HAr_2 \qquad (I).$$

The structure and specific substituents of the compound of Formula I are described below.

A further aspect of the present invention provides an organic light emitting diode including the organic light emitting compound.

The organic light emitting diode of the present invention employs the organic light emitting compound, particularly, as a material for electron injection and transport. The organic light emitting diode of the present invention exhibits low driving voltage, long lifetime, and high efficiency compared to conventional organic light emitting diodes. Due to these advantages, the organic light emitting diode of the present invention is useful in a variety of industrial applications, including displays and lighting systems.

DETAILED DESCRIPTION OF THE INVENTION

The present invention will now be described in more detail.

The present invention is directed to an organic light emitting compound represented by Formula I:

$$HAr_1\text{-}(L)_n\text{-}HAr_2 \qquad (I)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_3$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_1$ is a substituted or unsubstituted $C_6$-$C_{30}$ aryl group or a substituted or unsubstituted $C_2$-$C_{30}$ heteroaryl group, and $HAr_2$ is selected from the following structures A to E:

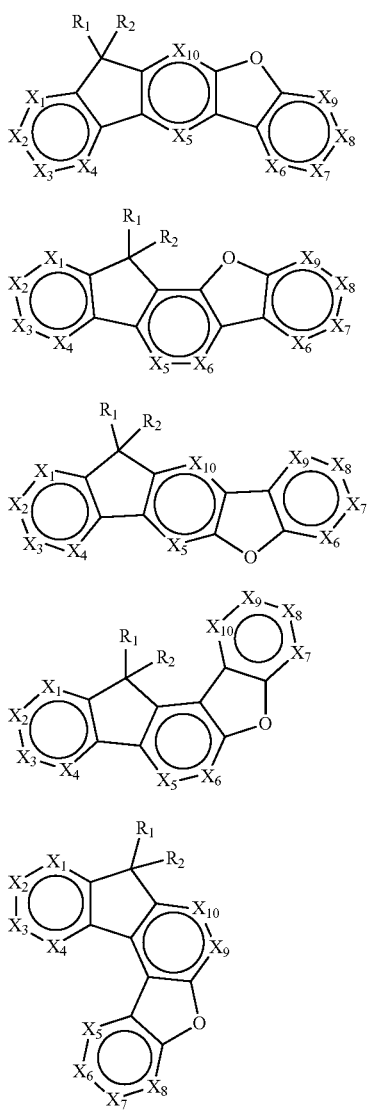

Structure A

Structure B

Structure C

Structure D

Structure E wherein $X_1$ is $CR_{11}$ or N, $X_2$ is $CR_{12}$ or N, $X_3$ is $CR_{13}$ or N, $X_4$ is $CR_{14}$ or N, $X_5$ is $CR_{15}$ or N, $X_6$ is $CR_{16}$ or N, $X_7$ is $CR_{17}$ or N, $X_8$ is $CR_{18}$ or N, $X_9$ is $CR_{19}$ or N, and $X_{10}$ is $CR_{20}$ or N, with the proviso that at least two of $X_1$ to $X_4$ are selected from $CR_{11}$ to $CR_{14}$, at least three of $X_5$ to $X_{10}$ are selected from $CR_{15}$ to $CR_{20}$, and one of $X_1$ to $X_{10}$ is a carbon atom linked to L, $R_1$, $R_2$, and $R_{11}$ to $R_{20}$ are identical to or different from each other and are each independently selected from a hydrogen atom, a deuterium atom, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_3$-$C_{30}$ cycloalkyl groups, substituted or unsubstituted $C_2$-$C_{30}$ heterocycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_6$-$C_{30}$ arylthioxy groups, substituted or unsubstituted $C_1$-$C_{30}$ alkylamine groups, substituted or unsubstituted $C_6$-$C_{30}$ arylamine groups, substituted or unsubstituted $C_6$-$C_{50}$ aryl groups, substituted or unsubstituted $C_2$-$C_{50}$ heteroaryl groups containing O, N or S as a heteroatom, substituted or unsubstituted $C_1$-$C_{24}$ alkylsilyl groups, substituted or unsubstituted $C_6$-$C_{24}$ arylsilyl groups, an amino group, a thiol group, a cyano group, a hydroxyl group, a nitro group, and halogen groups.

According to one embodiment, L may be a single bond or may be selected from the following structures 1 to 9:

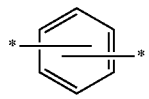

Structure 1

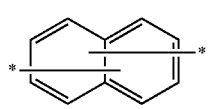

Structure 2

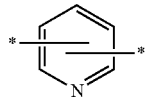

Structure 3

Structure 4

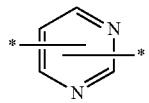

Structure 5

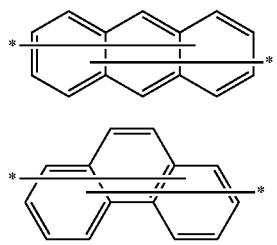

Structure 6

Structure 7

Structure 8

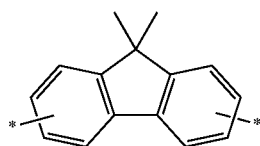

Structure 9

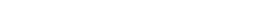

wherein hydrogen or deuterium atoms are bonded to the carbon atoms of the aromatic rings.

One of $R_{11}$ to $R_{20}$ is bonded to L and the remainders of $R_{11}$ to $R_{20}$ may be hydrogen or deuterium atoms. Only one of $X_1$ to $X_{10}$ may be a nitrogen atom or none of $X_1$ to $X_{10}$ may be nitrogen atoms.

The organic light emitting compound of the present invention can be employed as an electron injecting or transport material for an organic layer of an organic light emitting diode to improve the efficiency, life characteristics, and driving voltage characteristics of the diode.

The compound of Formula I is characterized by the presence of one of Structures A to E. A more detailed description will be given of Structures A to E. Each of Structures A to E has an indenodibenzofuran structure consisting of a 6-membered aromatic ring containing $X_1$ to $X_4$, a 5-membered ring containing a carbon atom linked to $R_1$ and $R_2$, a 6-membered aromatic carbocyclic ring containing $X_5$ and $X_{10}$, $X_5$ and $X_6$ or $X_9$ and $X_{10}$, a 5-membered ring containing an oxygen atom, and a 6-membered aromatic ring containing $X_6$ to $X_9$, $X_7$ to $X_{10}$ or $X_5$ to $X_8$, which are fused to each other, and optionally including at least one nitrogen atom in the ring structure. One of $X_1$ to $X_{10}$ in these fused rings is linked to L.

$HAr_1$ is preferably a substituted or unsubstituted $C_2$-$C_{30}$ heteroaryl group.

According to a preferred embodiment of the present invention, $HAr_1$ is selected from the following structures E1 to E33:

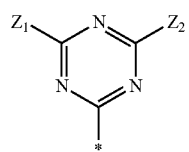
<E1>

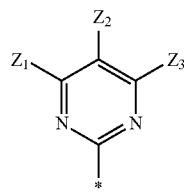
<E2>

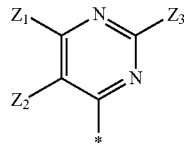
<E3>

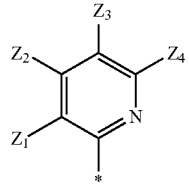
<E4>

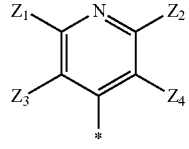
<E5>

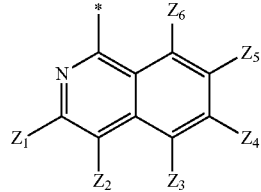
<E6>

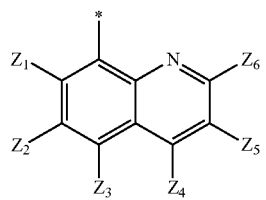
<E7>

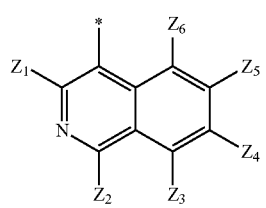
<E8>

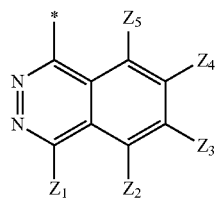
<E9>

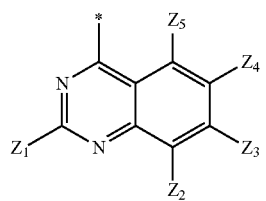
<E10>

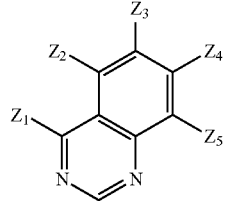
<E11>

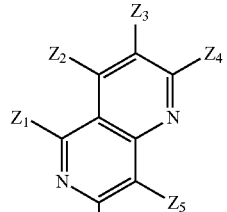
<E12>

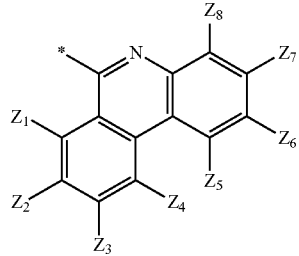
<E13>

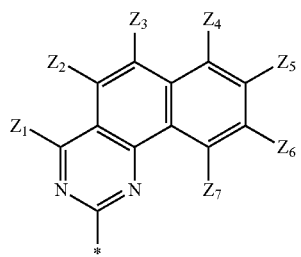
<E14>
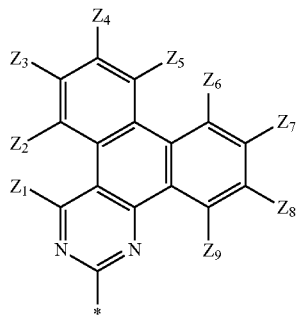
<E15>
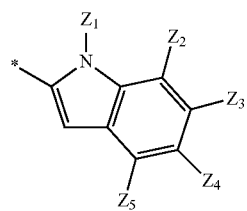
<E16>
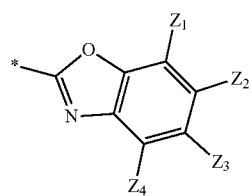
<E17>
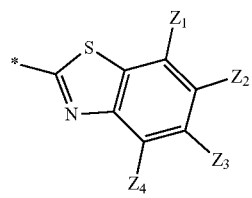
<E18>
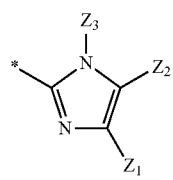
<E19>
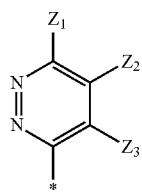
<E20>
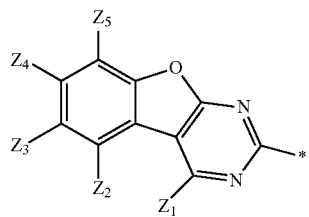
<E21>
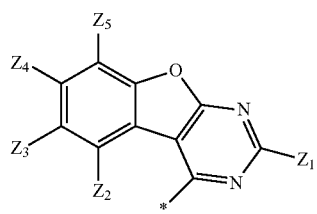
<E22>
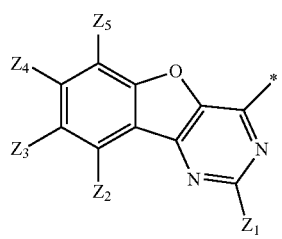
<E23>
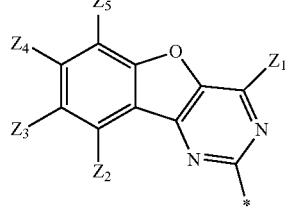
<E24>
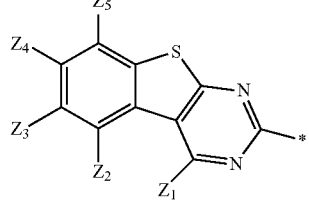
<E25>
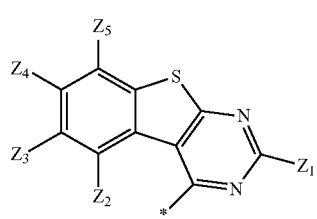
<E26>
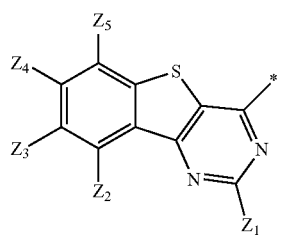
<E27>

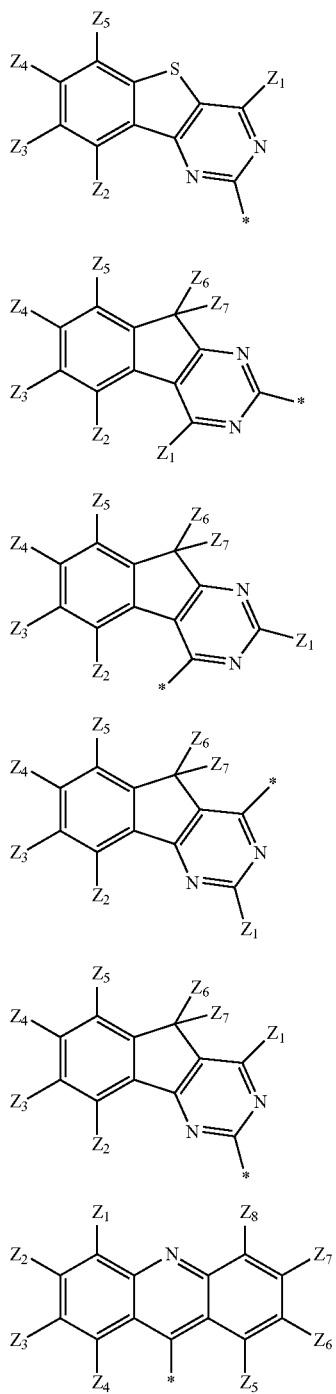

wherein $Z_1$ to $Z_8$ are identical to or different from each other and each independently have the same meanings as $R_1$, $R_2$, and $R_{11}$ to $R_{20}$, and each of $Z_1$ to $Z_8$ and substituents thereof may optionally form an aliphatic, aromatic, heteroaliphatic or heteroaromatic fused ring with the adjacent group.

The term "substituted" in the definition of "substituted or unsubstituted" used herein refers to substitution with at least one substituent selected from the group consisting of deuterium, a cyano group, halogen groups, a hydroxyl group, a nitro group, $C_1$-$C_{24}$ alkyl groups, $C_1$-$C_{24}$ halogenated alkyl groups, $C_2$-$C_{24}$ alkenyl groups, $C_2$-$C_{24}$ alkynyl groups, $C_1$-$C_{24}$ heteroalkyl groups, $C_6$-$C_{24}$ aryl groups, $C_7$-$C_{24}$ arylalkyl groups, $C_2$-$C_{24}$ heteroaryl groups, $C_2$-$C_{24}$ heteroarylalkyl groups, $C_1$-$C_{24}$ alkoxy groups, $C_1$-$C_{24}$ alkylamino groups, $C_1$-$C_{24}$ arylamino groups, $C_1$-$C_{24}$ heteroarylamino groups, $C_1$-$C_{24}$ alkylsilyl groups, $C_6$-$C_{24}$ arylsilyl groups, and $C_6$-$C_{24}$ aryloxy groups.

In the "substituted or unsubstituted $C_1$-$C_{30}$ alkyl groups", "substituted or unsubstituted $C_6$-$C_{30}$ aryl groups", etc., the number of carbon atoms in each alkyl or aryl group is considered as the number of carbon atoms constituting the unsubstituted alkyl or aryl moiety and the number of carbon atoms in the substituent(s) is excluded therefrom. For example, a phenyl group substituted with a butyl group at the para-position corresponds to a $C_6$ aryl group substituted with a $C_4$ butyl group.

Specific examples of the alkyl groups used in the present invention include methyl, ethyl, propyl, isobutyl, sec-butyl, tert-butyl, pentyl, iso-amyl, hexyl, heptyl, octyl, stearyl, trichloromethyl, and trifluoromethyl groups. At least one hydrogen atom of each alkyl group may be substituted with a deuterium atom, a halogen atom, a hydroxyl group, a nitro group, a cyano group, a trifluoromethyl group, a silyl group (herein referred to as an "alkylsilyl group"), a substituted or unsubstituted amino group (—$NH_2$, —NH(R) or —N(R') (R''), in which R, R', and R'' are each independently a $C_1$-$C_{24}$ alkyl group (the —NH(R) and —N(R')(R'') are referred to as "alkylamino groups"), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_2$-$C_{24}$ alkenyl group, a $C_2$-$C_{24}$ alkynyl group, a $C_1$-$C_{24}$ heteroalkyl group, a $C_5$-$C_{24}$ aryl group, a $C_6$-$C_{24}$ arylalkyl group, a $C_3$-$C_{24}$ heteroaryl group or a $C_3$-$C_{24}$ heteroarylalkyl group.

Specific examples of the alkoxy groups used in the present invention include methoxy, ethoxy, propoxy, isobutyloxy, sec-butyloxy, pentyloxy, iso-amyloxy, and hexyloxy groups. The alkoxy groups may be substituted with the same substituents as in the alkyl groups.

Specific examples of the halogen groups used in the present invention include fluoro (F), chloro (Cl), bromo (Br), and iodo (I) groups.

The aryloxy groups used in the present invention refer to —O-aryl radicals in which the aryl group is as defined above. Specific examples of the aryloxy groups include phenoxy, naphthoxy, anthracenyloxy, phenanthrenyloxy, fluorenyloxy, and indenyloxy. At least one hydrogen atom of each aryloxy group may be substituted.

Specific examples of the silyl groups used in the present invention include trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl.

The aryl groups used in the present invention are organic radicals derived from aromatic hydrocarbons by removal of a hydrogen atom. Such aryl groups include 5- to 7-membered, preferably 5- or 6-membered single or fused ring systems. When the aryl group is substituted, the substituent may be fused with an adjacent substituent to form a ring.

Specific examples of the aryl groups include aromatic groups, such as phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, crycenyl, naphthacenyl, and fluoranthenyl groups.

Each aryl group may also be substituted with at least one substituent. More specifically, at least one hydrogen atom of each aryl group may be substituted with a deuterium atom, a halogen atom, a hydroxyl group, a nitro group, a cyano group, a silyl group, an amino group (—NH$_2$, —NH(R), —N(R')(R") in which R, R' and R" are each independently a C$_1$-C$_{10}$ alkyl group (the —NH(R) and —N(R')(R") are referred to as "alkylamino groups")), an amidino group, a hydrazine group, a hydrazone group, a carboxyl group, a sulfonic acid group, a phosphoric acid group, a C$_1$-C$_{24}$ alkyl group, a C$_1$-C$_{24}$ halogenated alkyl group, a C$_1$-C$_{24}$ alkenyl group, a C$_1$-C$_{24}$ alkynyl group, a C$_1$-C$_{24}$ heteroalkyl group, a C$_6$-C$_{24}$ aryl group, a C$_6$-C$_{24}$ arylalkyl group, a C$_2$-C$_{24}$ heteroaryl group or a C$_2$-C$_2$a heteroarylalkyl group.

The heteroaryl groups used in the present invention refer to C$_2$-C$_{24}$ cyclic aromatic systems including one to three heteroatoms selected from N, O, P, Si, S, Ge, Se, and Te, with the remaining ring atoms being carbon. The rings may be fused together. One or more hydrogen atoms of each heteroaryl group may be substituted with the same substituents as in the aryl groups.

The heteroaromatic rings refer to aromatic hydrocarbon rings in which one or more aromatic carbon atoms are replaced with one or more heteroatoms selected from N, O, P, Si, S, Ge, Se, and Te.

The organic light emitting compound represented by Formula I may be selected from Compounds 1 to 564:

1

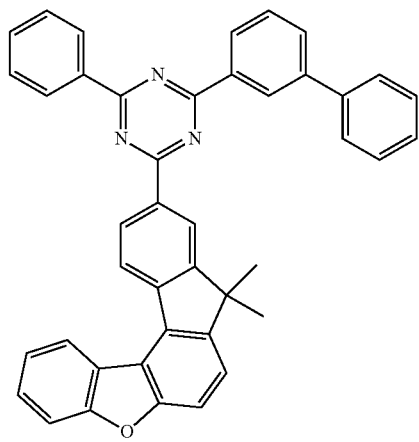

2

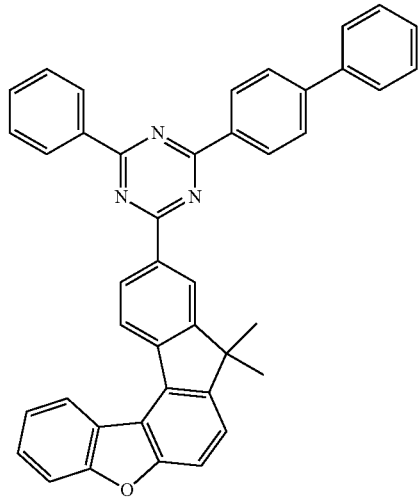

3


4

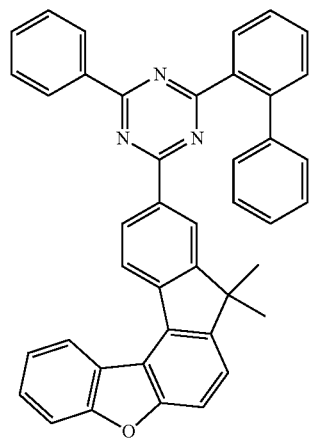

5

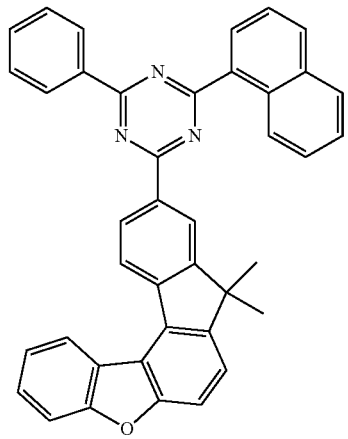

-continued
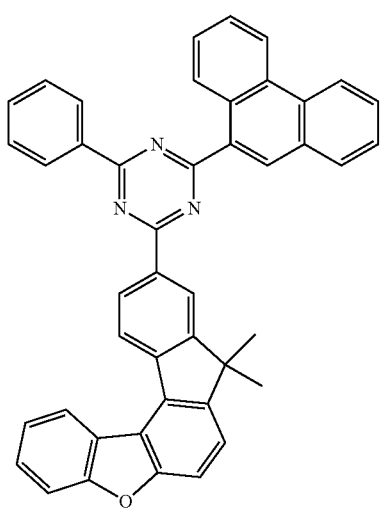
6
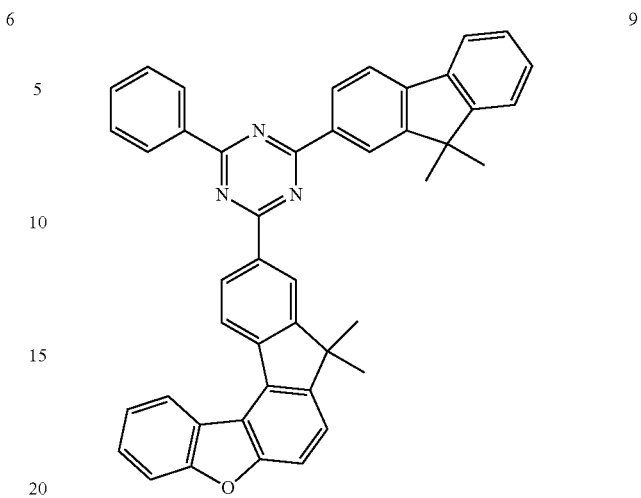
7
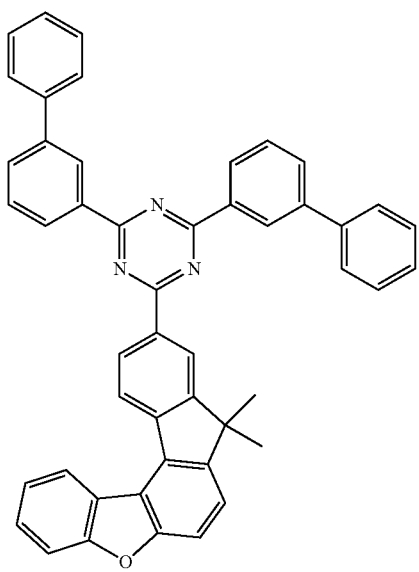
8
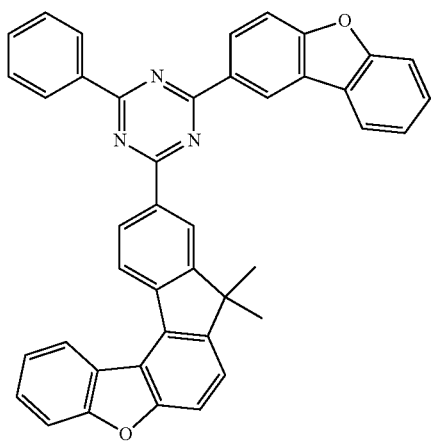
-continued
5
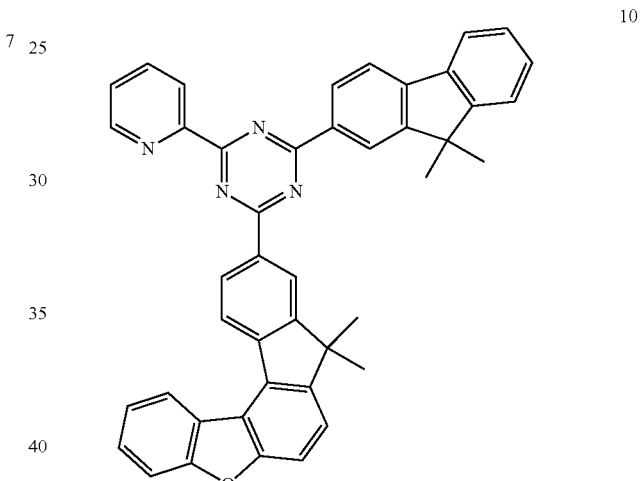
9
10
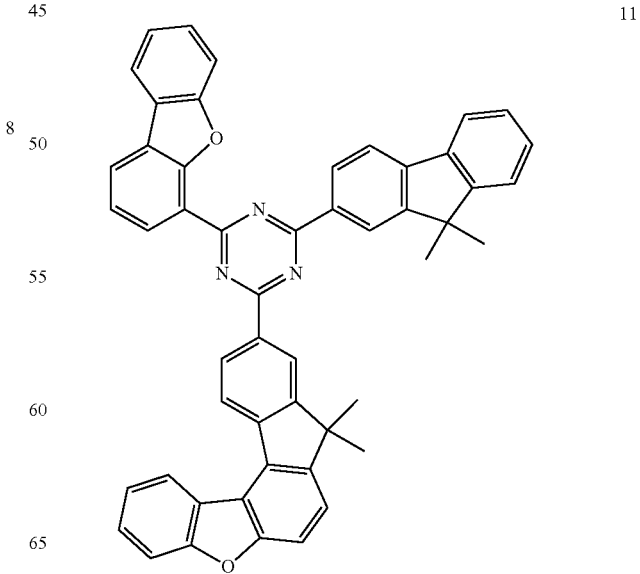
11

12
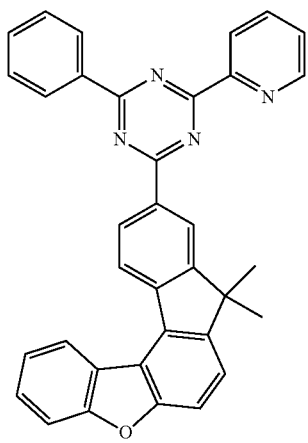
13
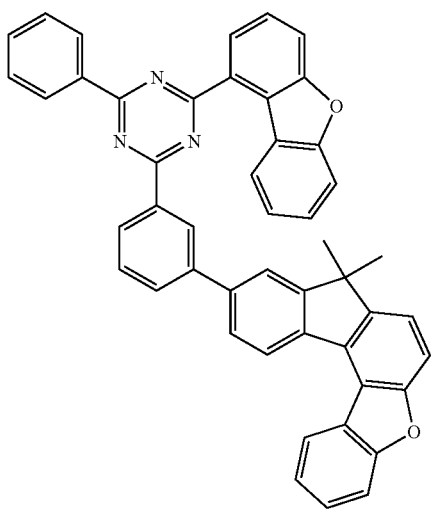
14
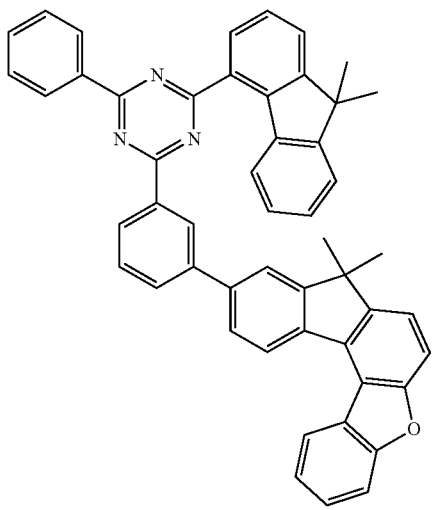
15
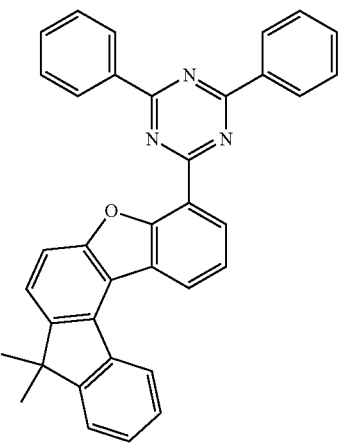
16
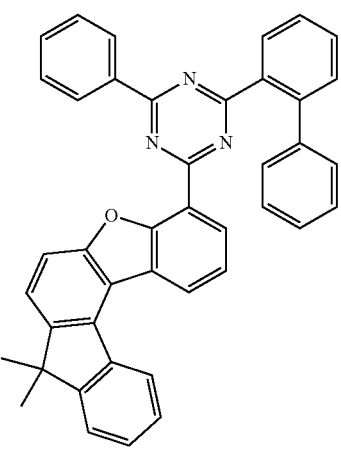
17
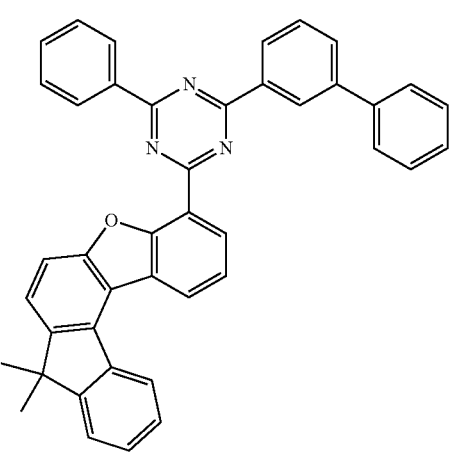

18
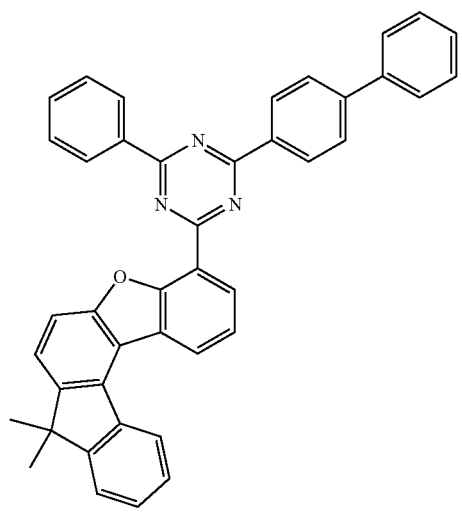
19
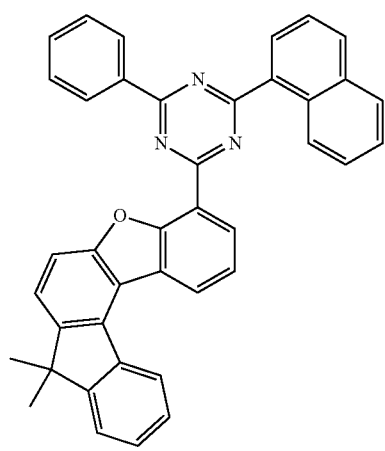
20
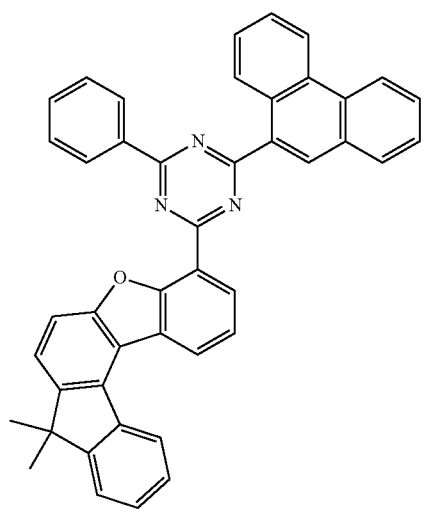
21
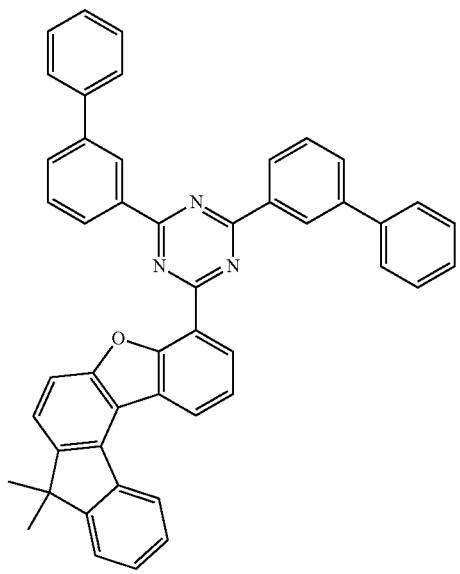
22
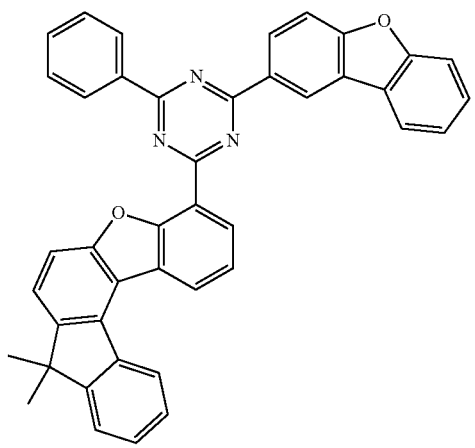
23
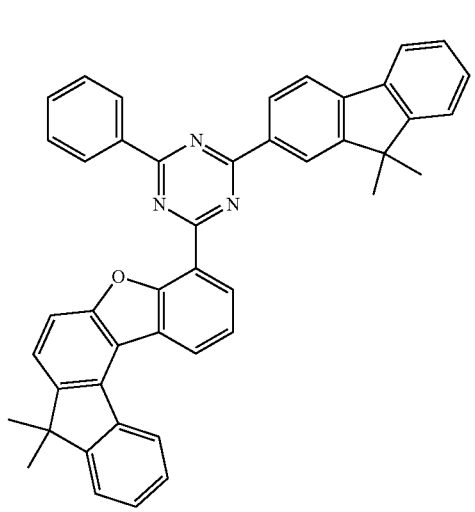

24
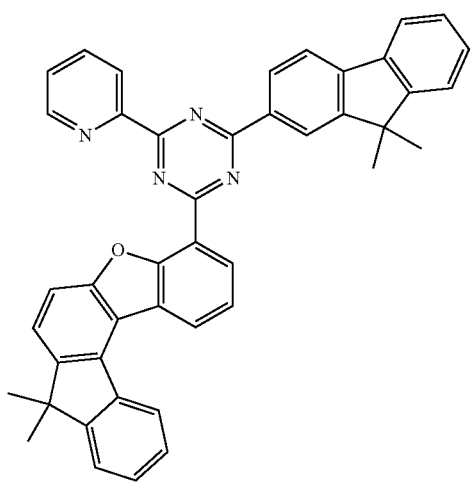
25
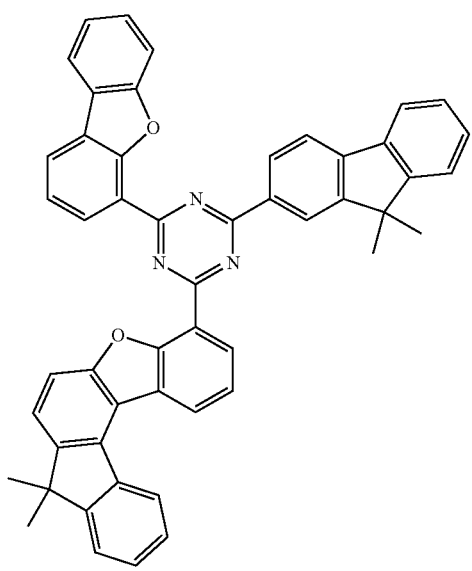
26
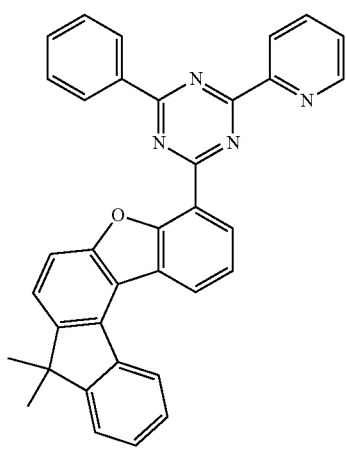
27
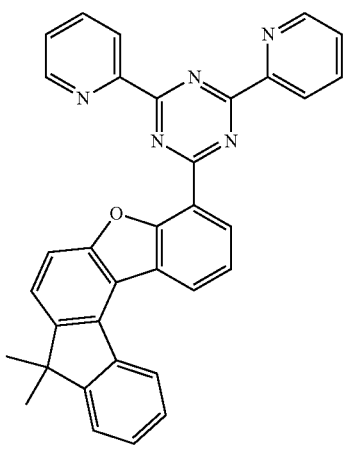
28
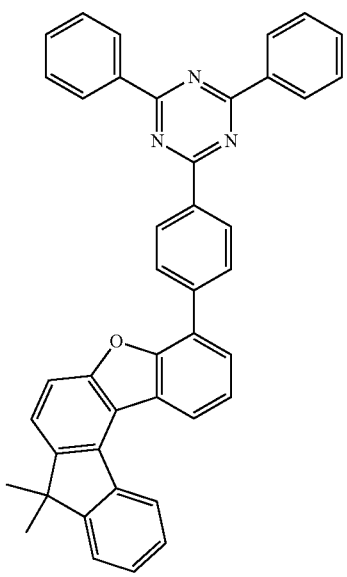
29
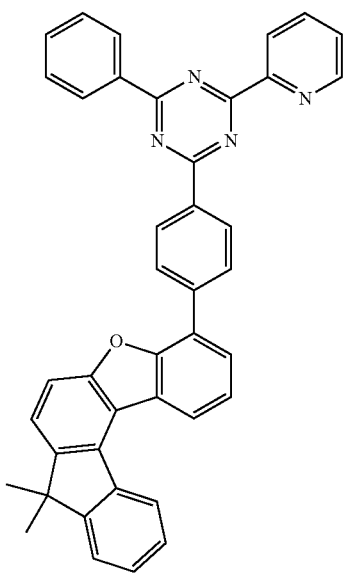

30
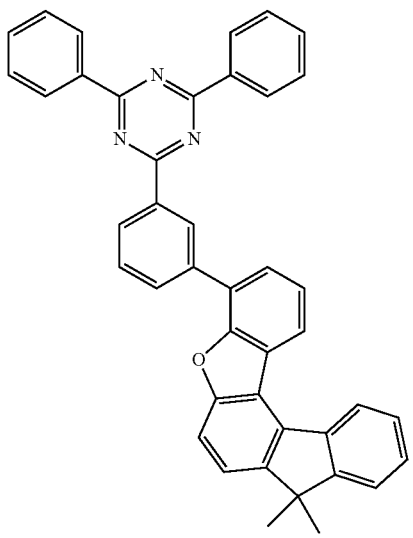
31
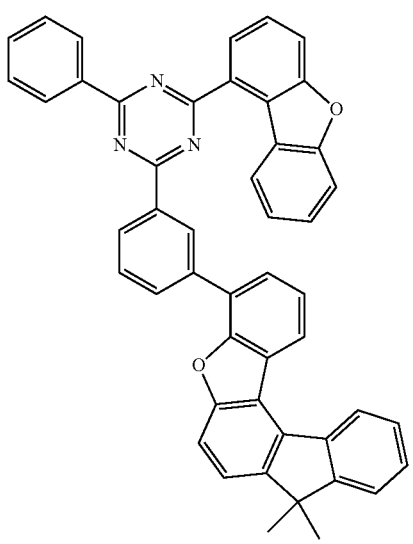
32
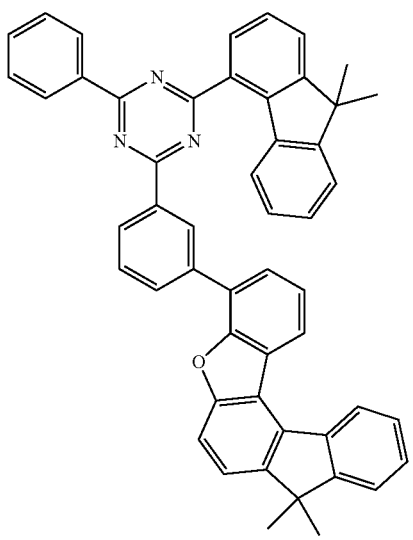
33
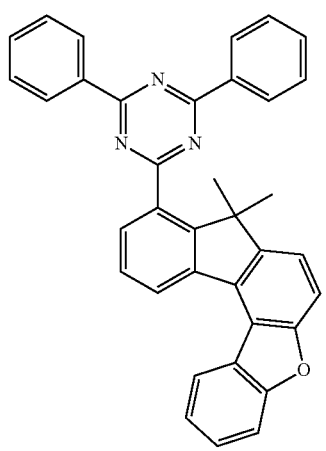
34
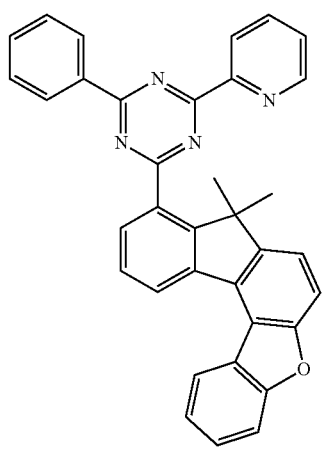
35
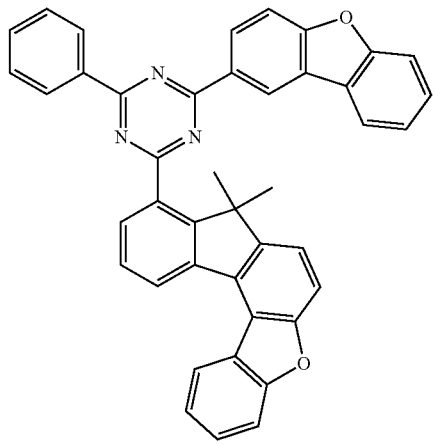

36
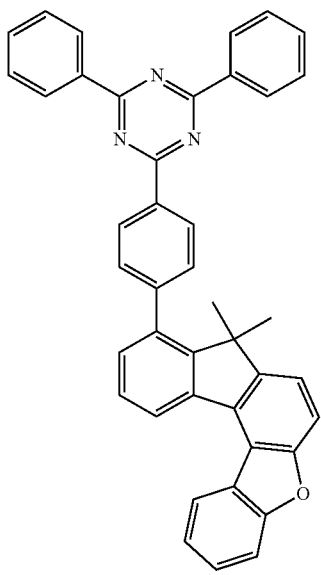
37
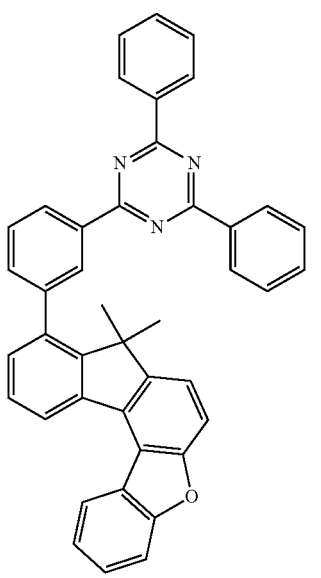
38
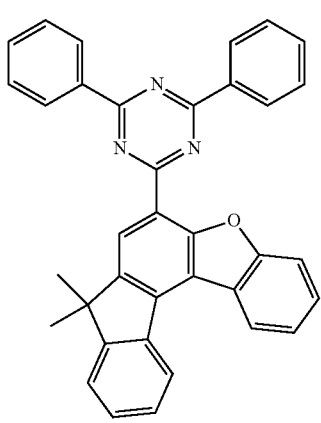
39
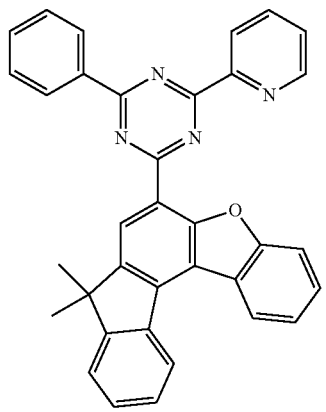
40
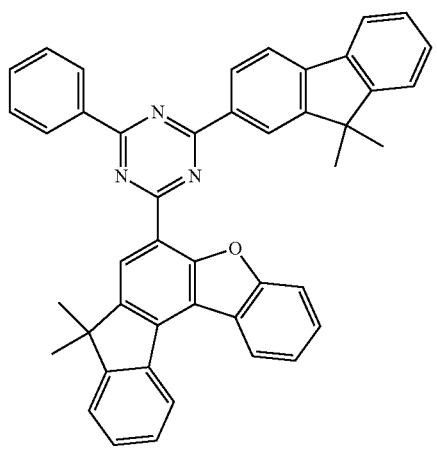
41
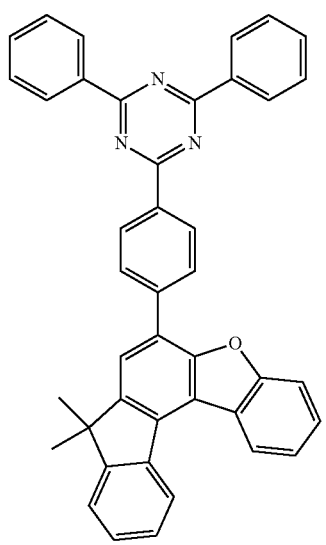

-continued
42
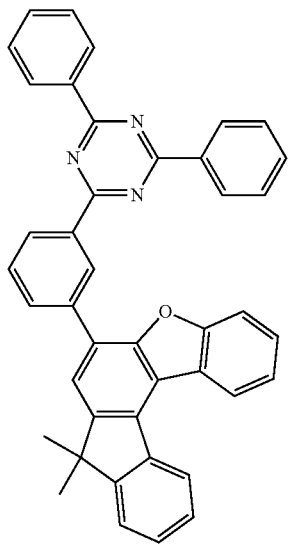
43
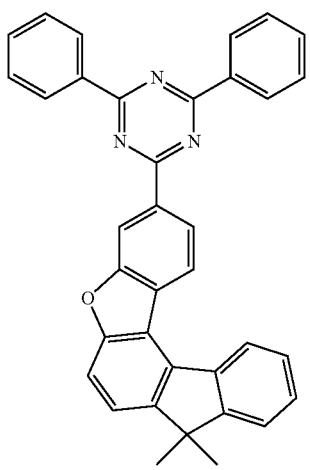
44
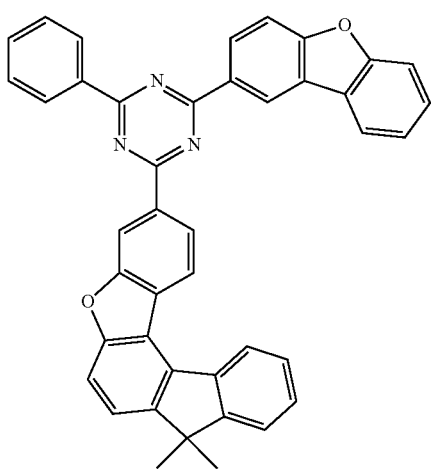
45
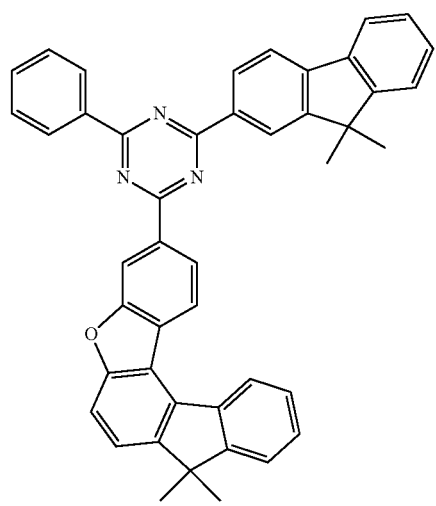
46
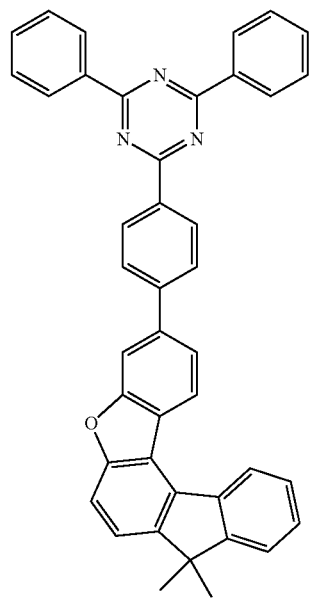
47
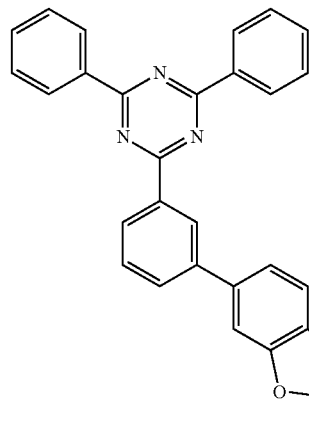

48
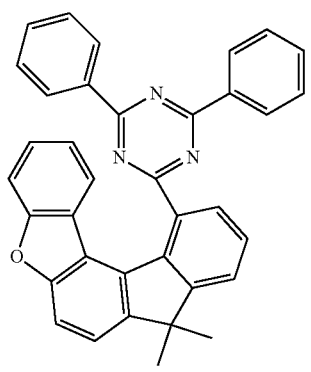
49
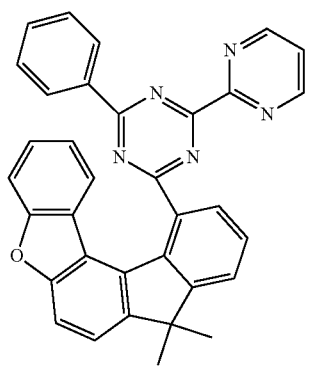
50
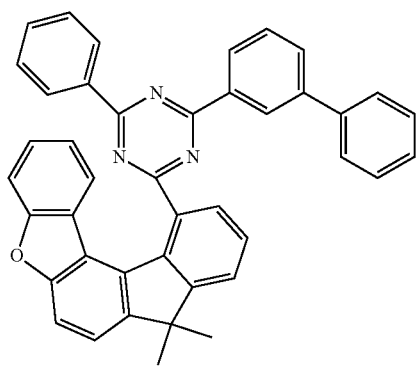
51
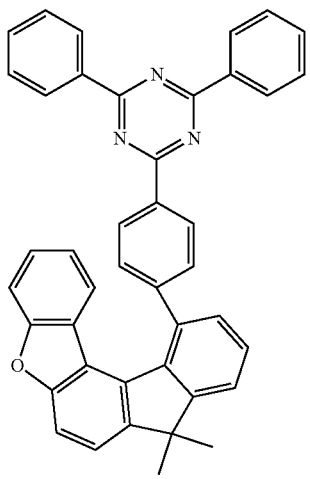
52
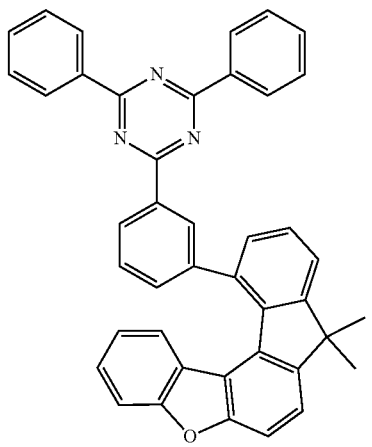
53
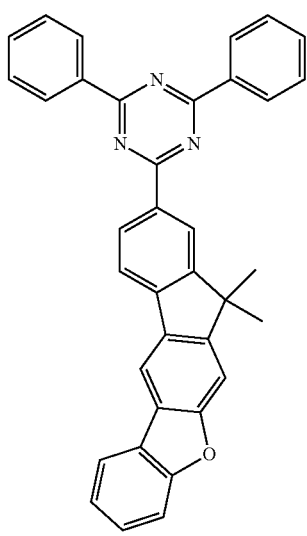
54
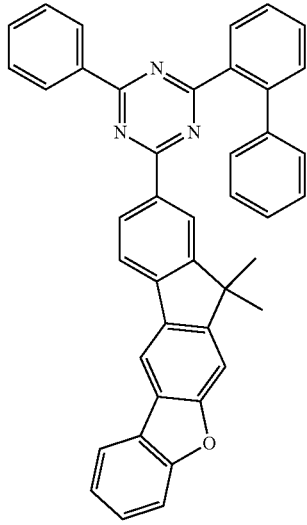

55
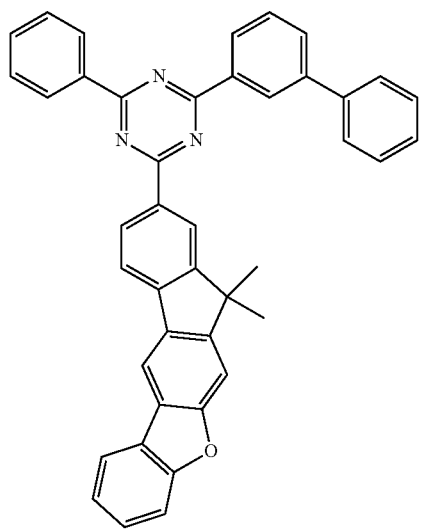
56
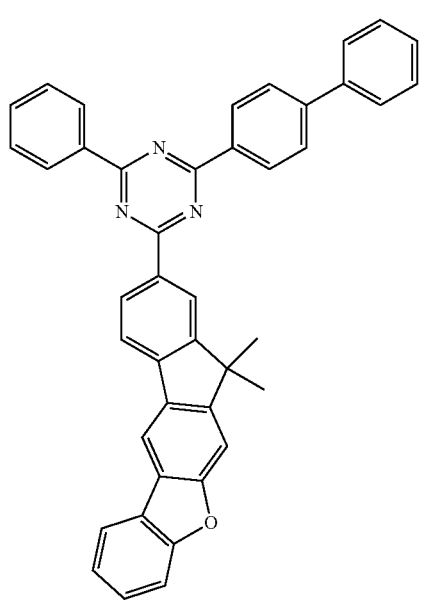
57
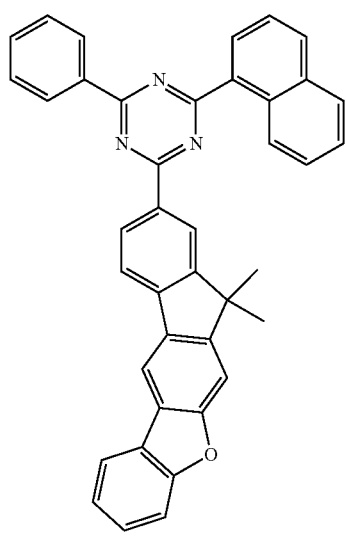
58
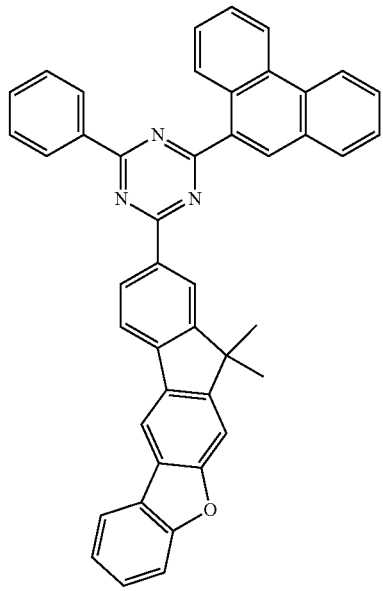
59
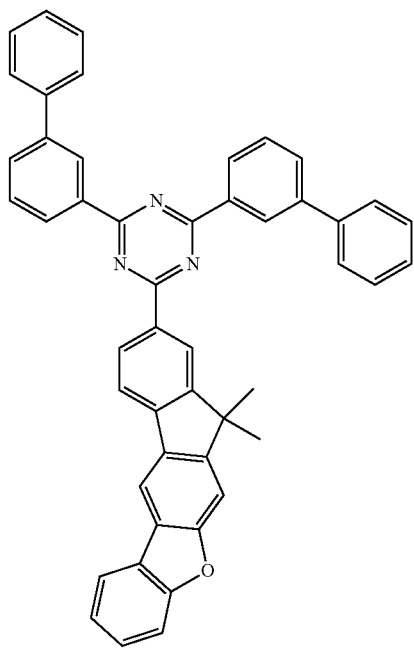

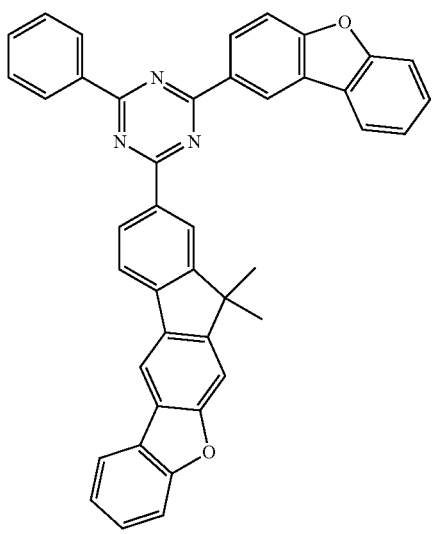
60
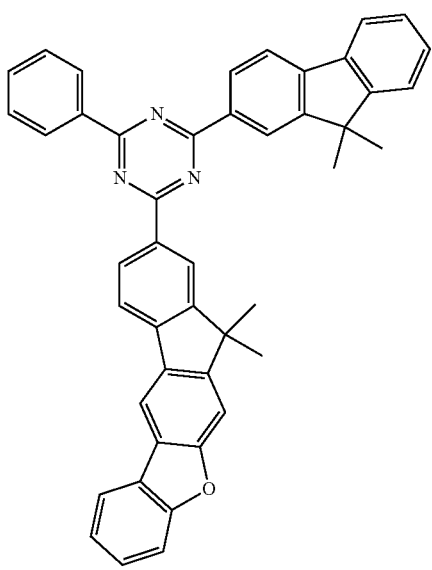
61
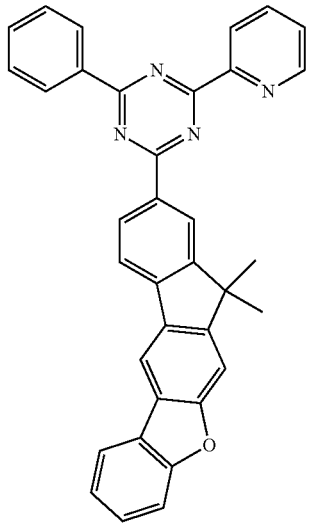
62
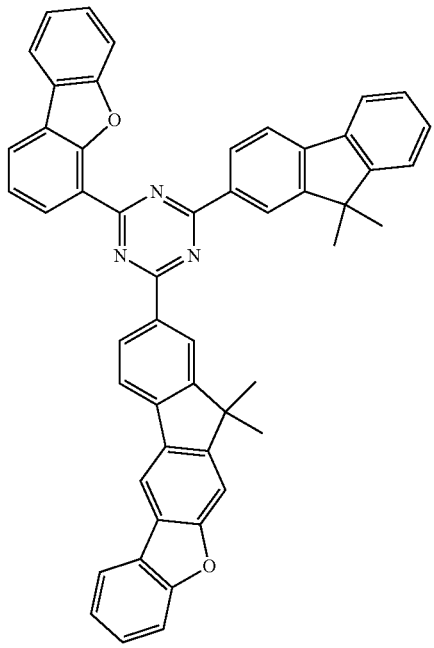
63
64

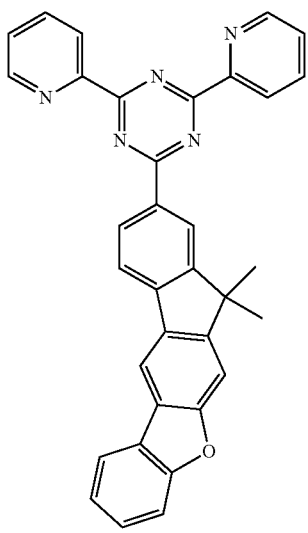
65
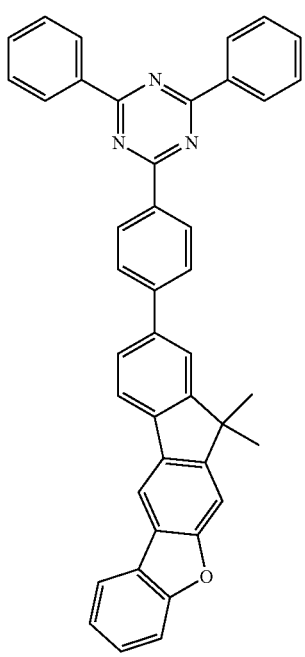
66
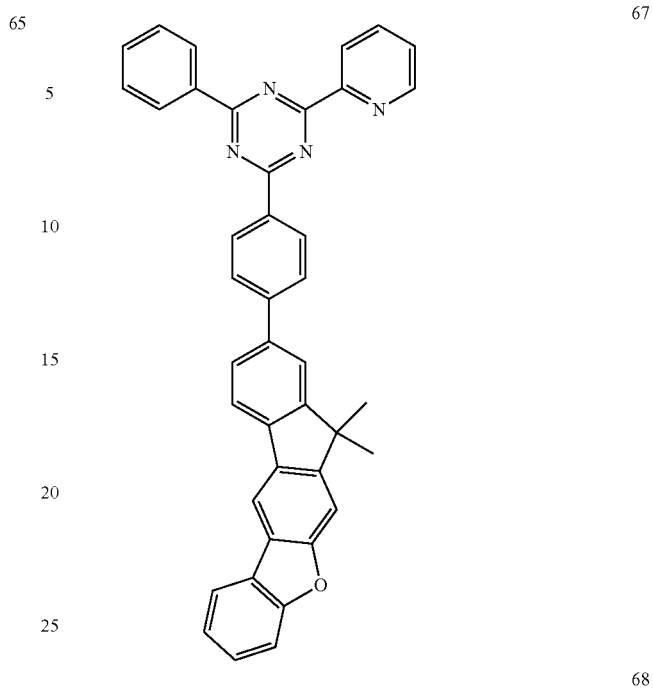
67
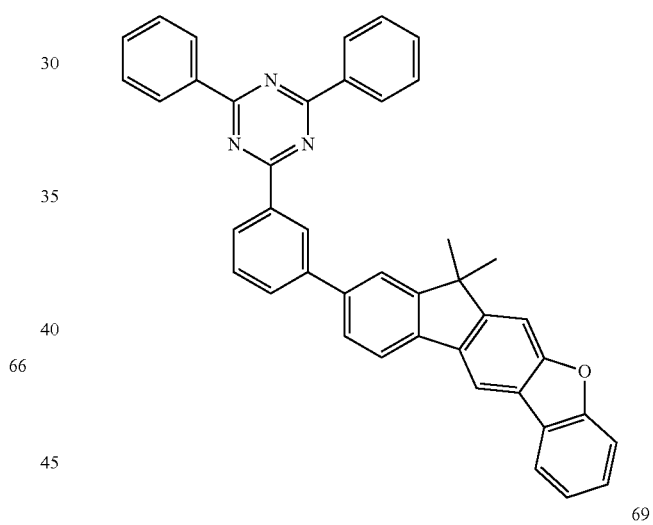
68
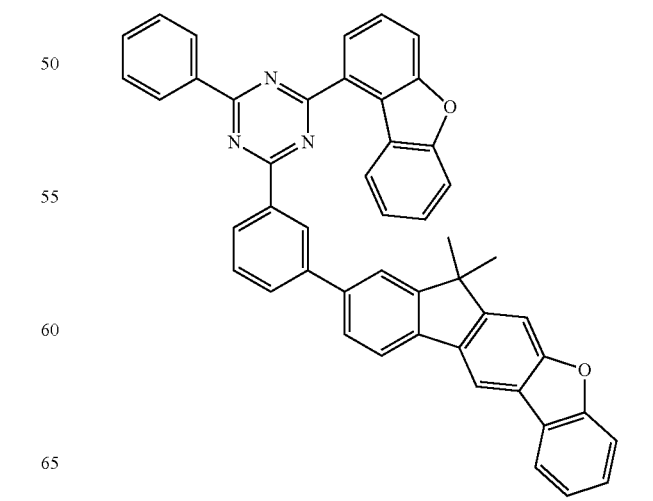
69

-continued
70
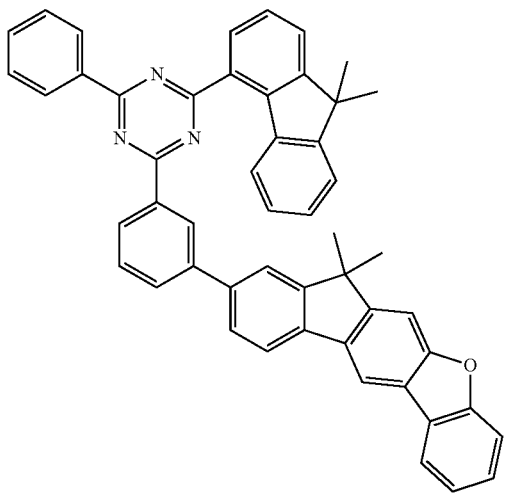
71
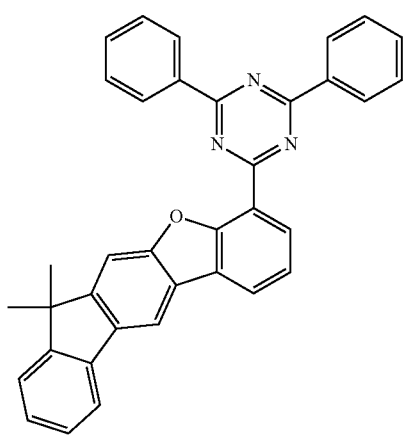
72
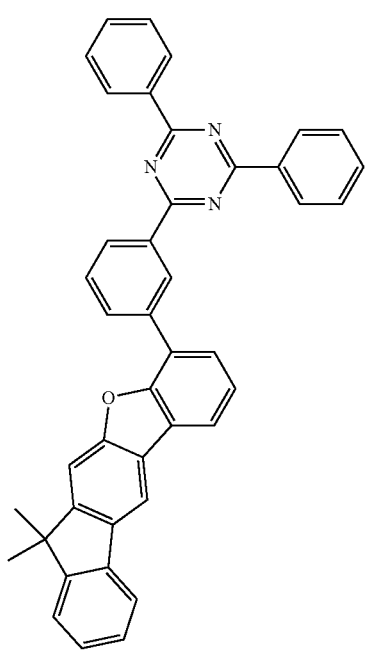
-continued
73
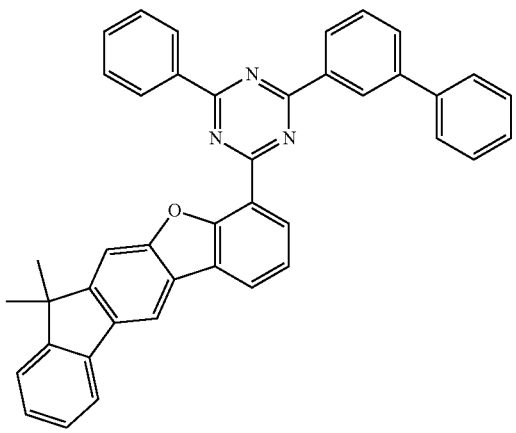
74
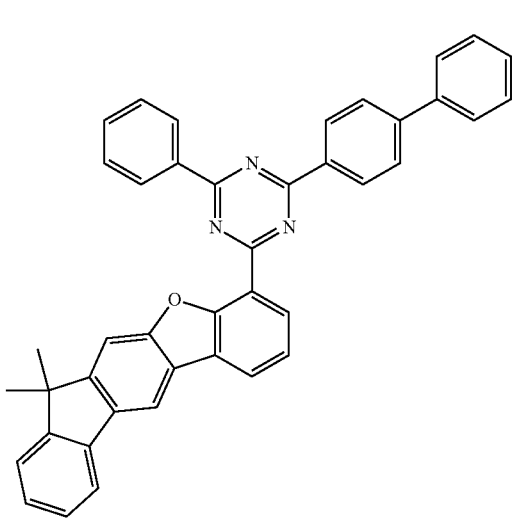
75
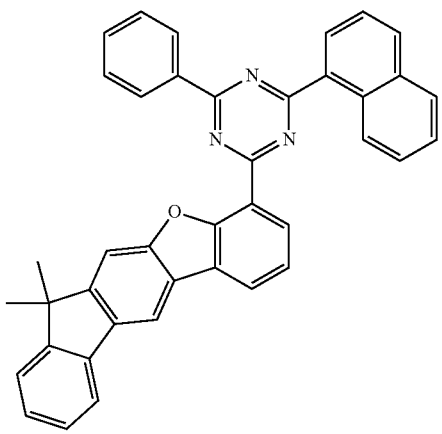

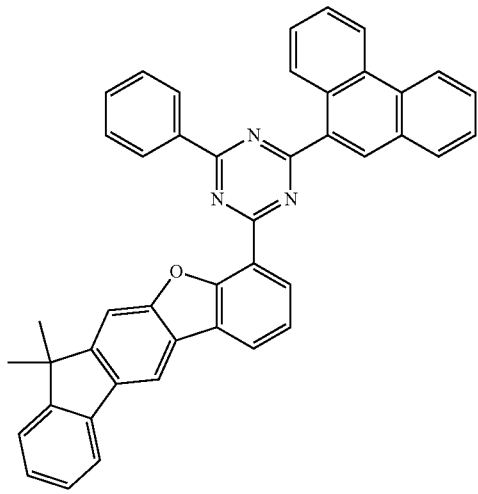
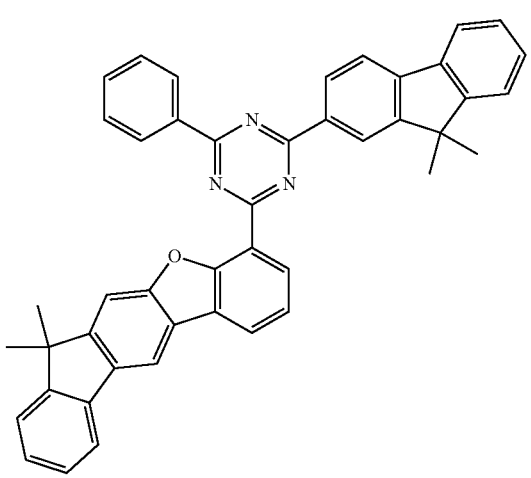
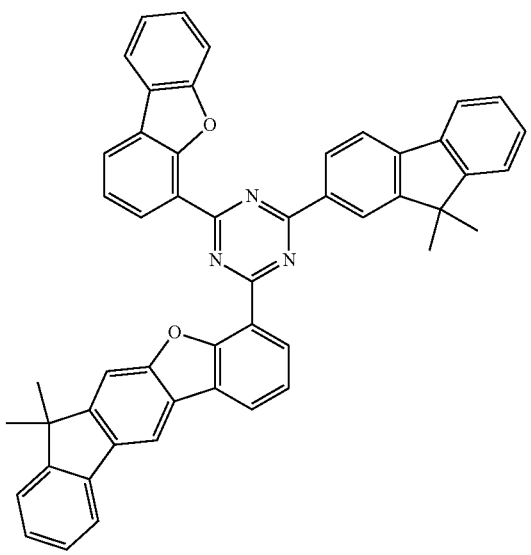

82
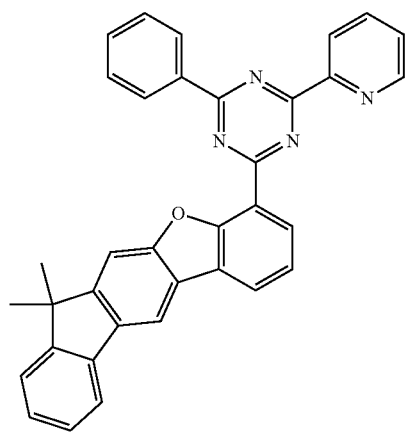
83
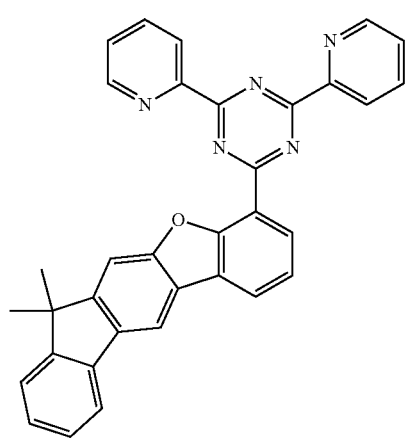
84
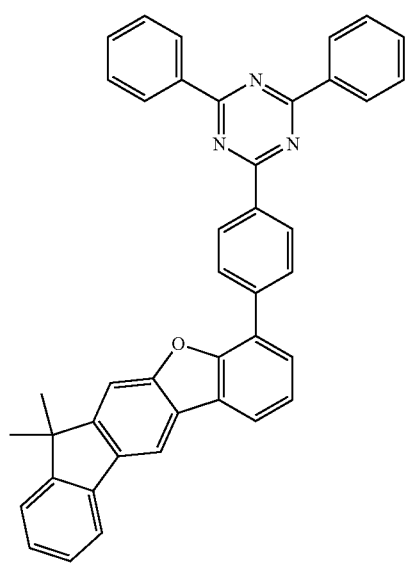
85
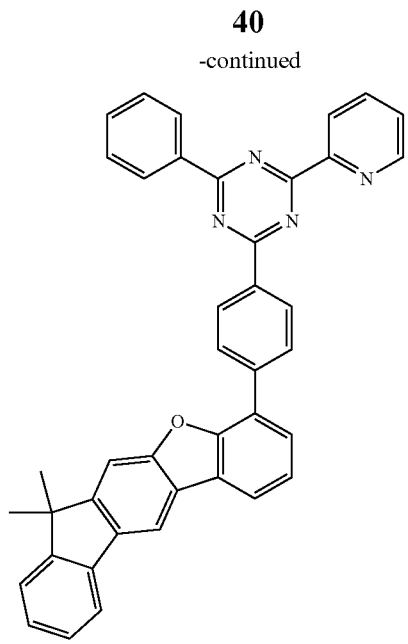
86
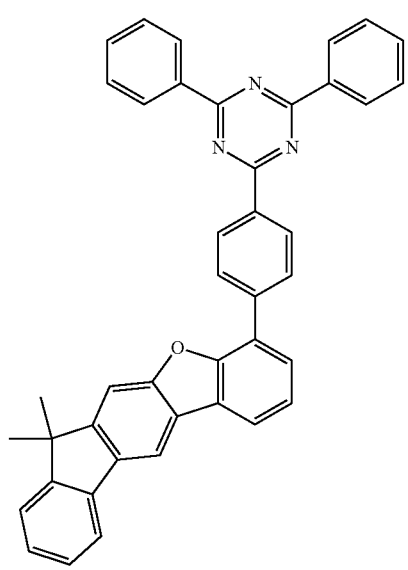
87
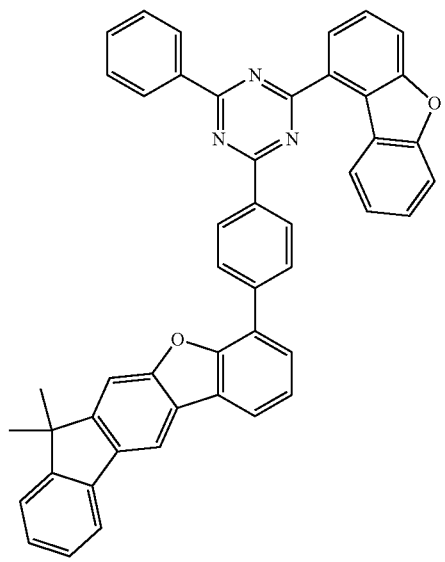

88
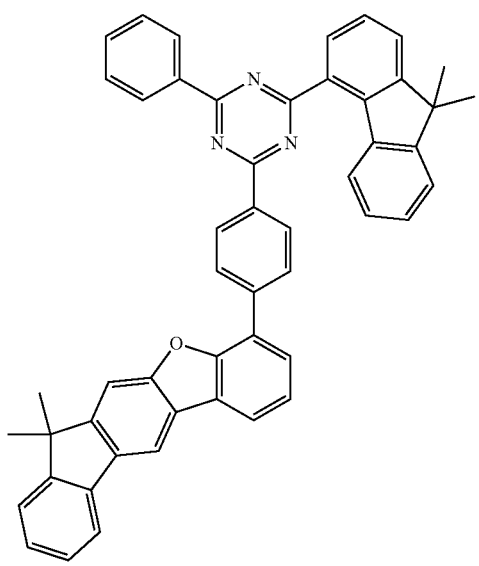
89
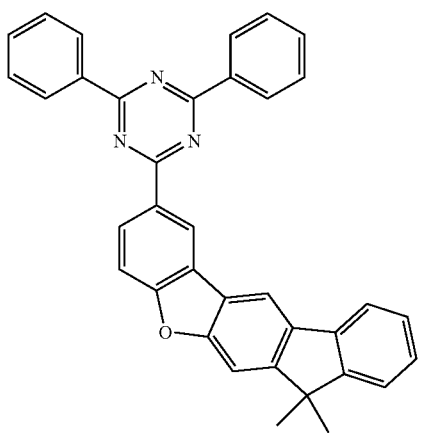
90
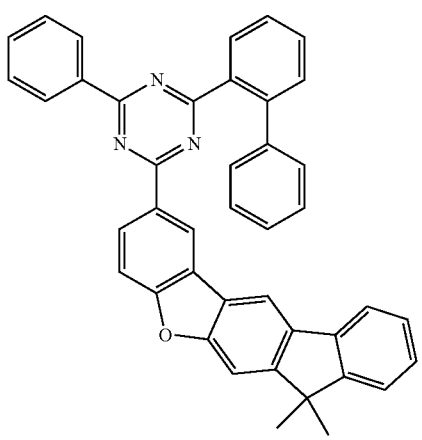
91
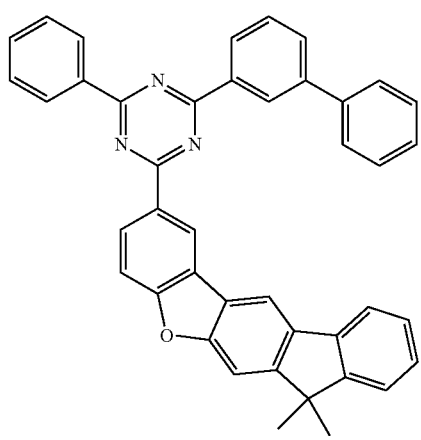
92
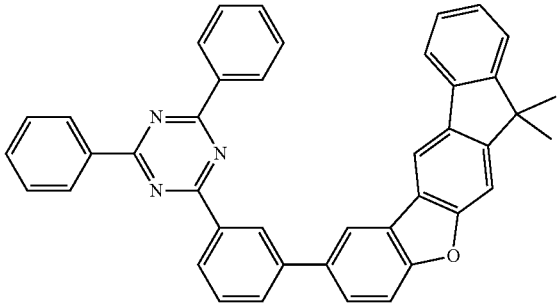
93
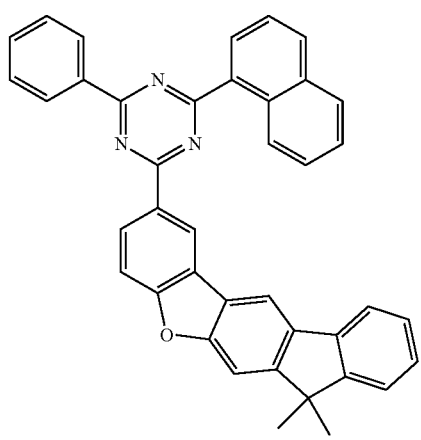

94
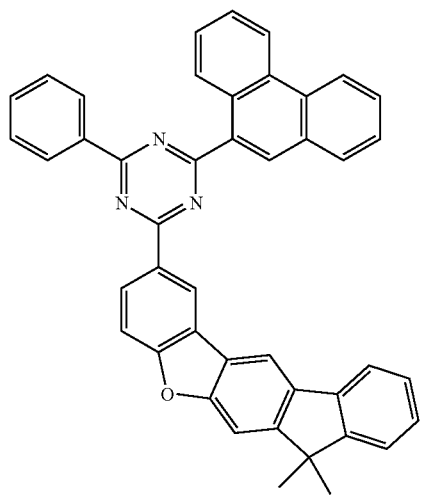
95
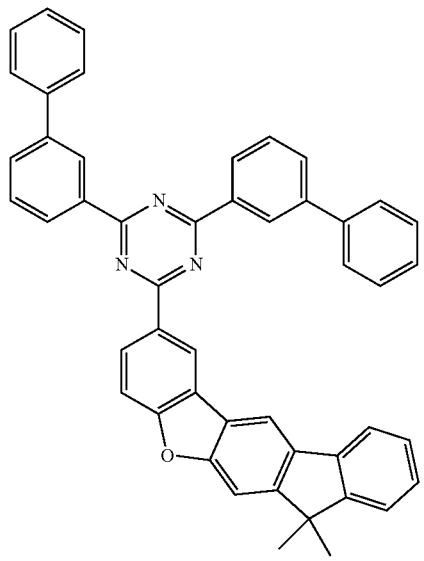
96
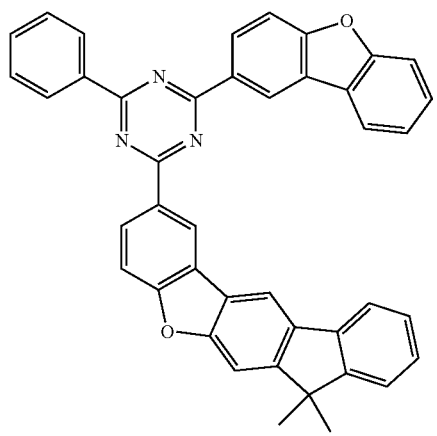
97
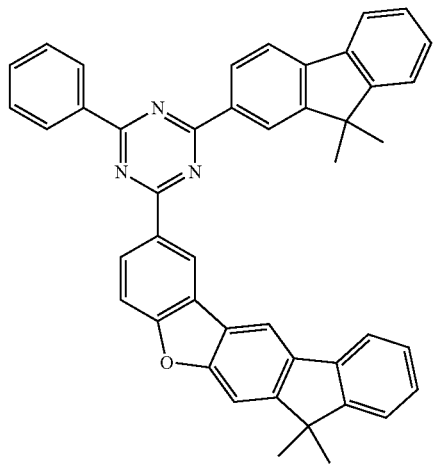
98
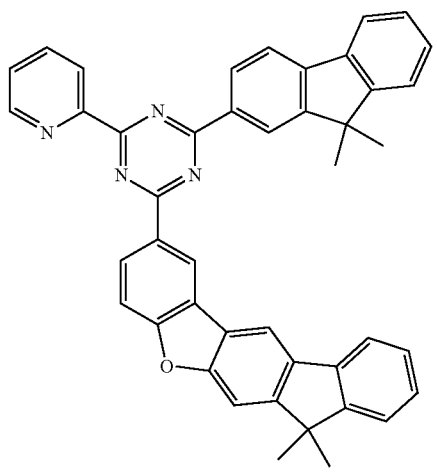
99
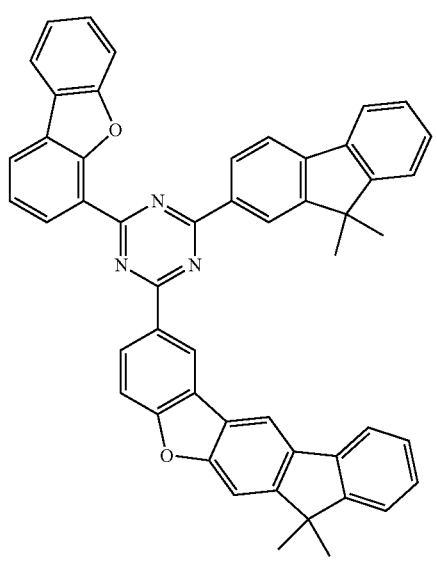

100
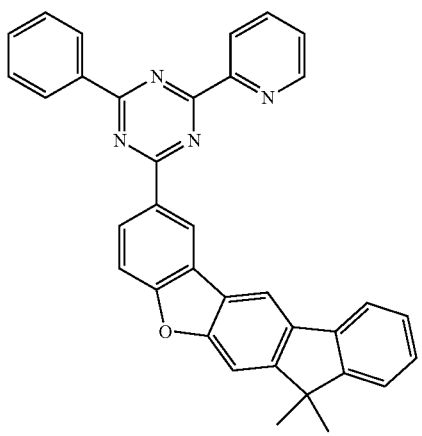
101
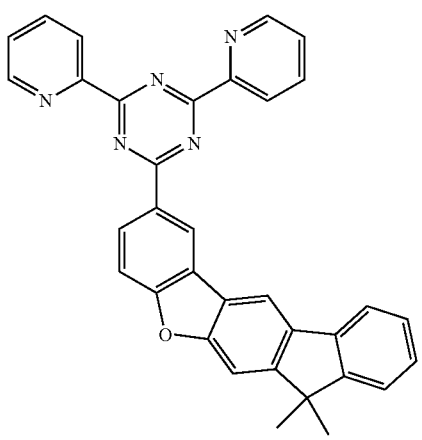
102
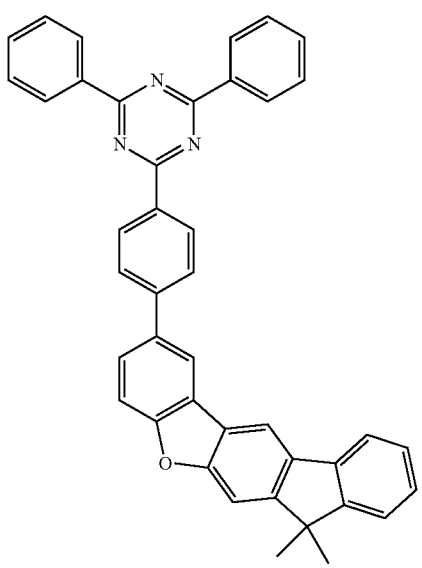
103
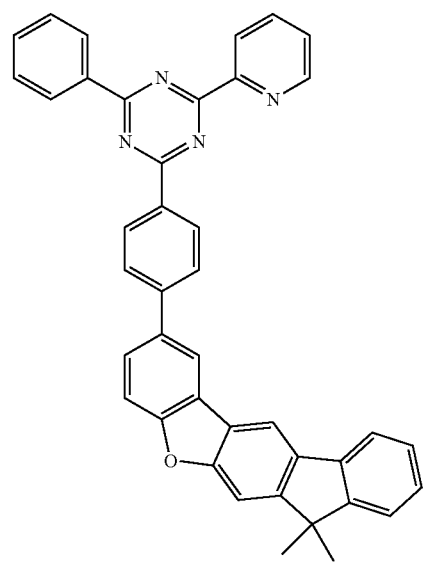
104
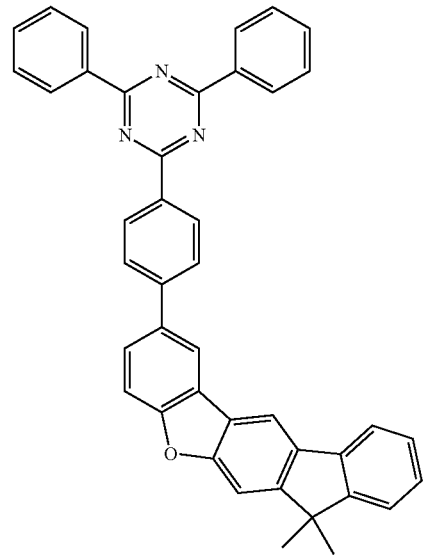

105
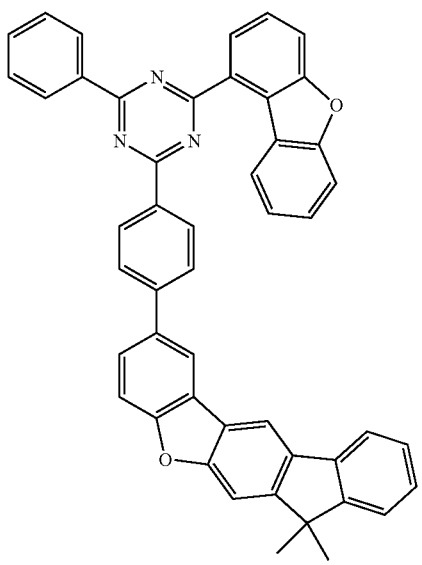
106
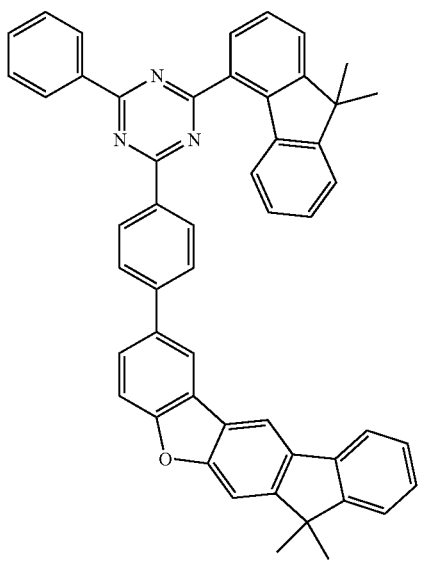
107
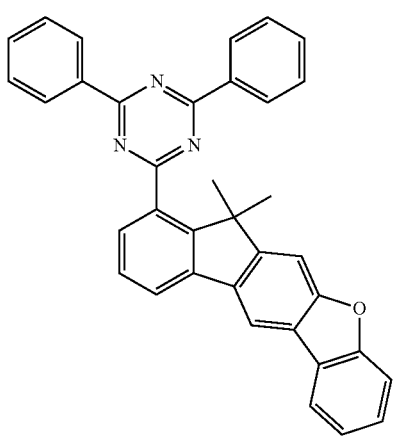
108
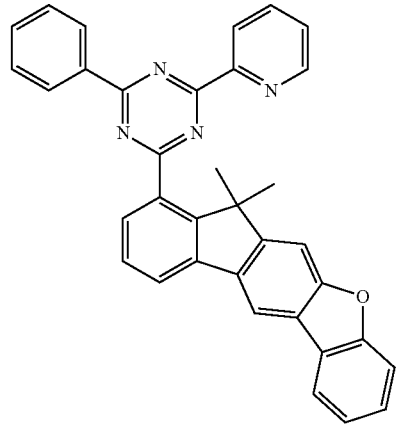
109
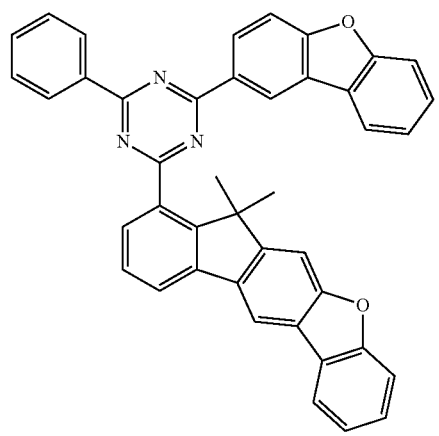
110
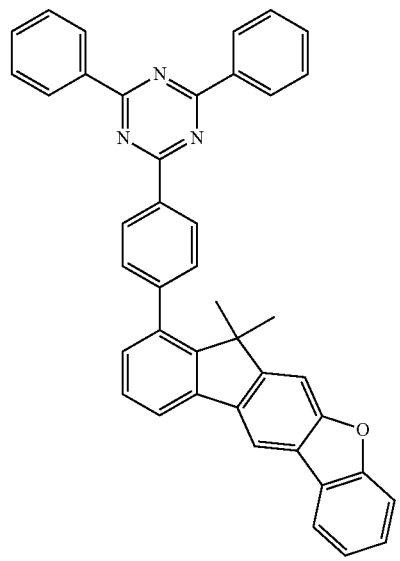

111
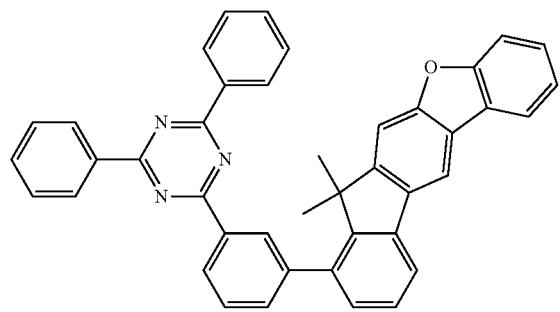
112
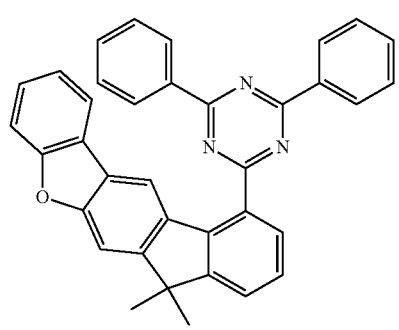
113
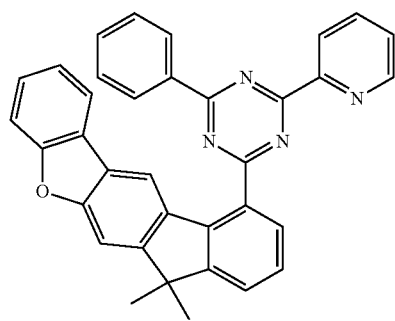
114
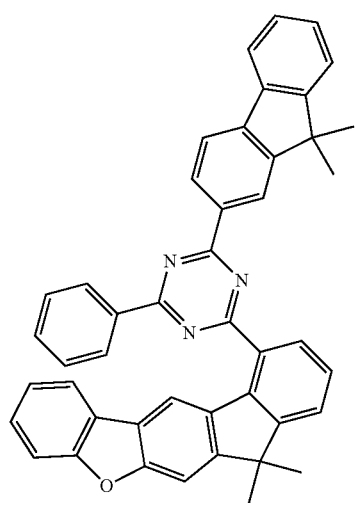
115
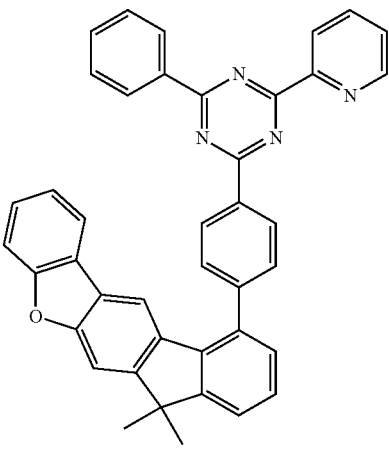
116
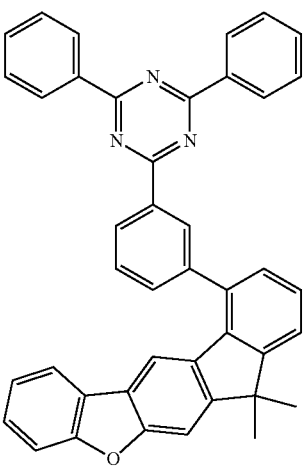
117
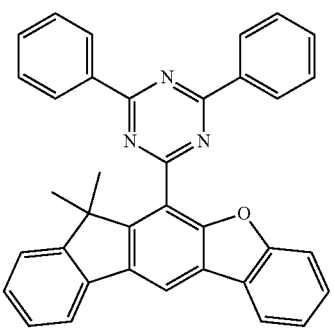
118
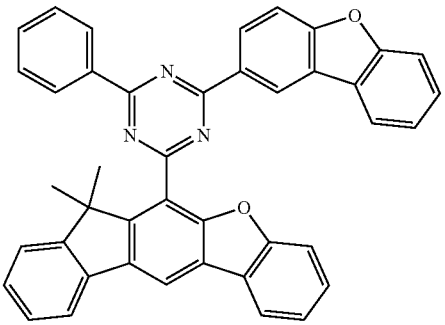

119 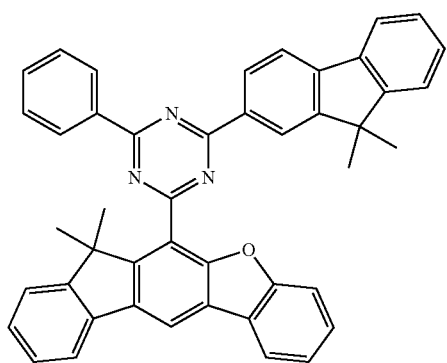
120 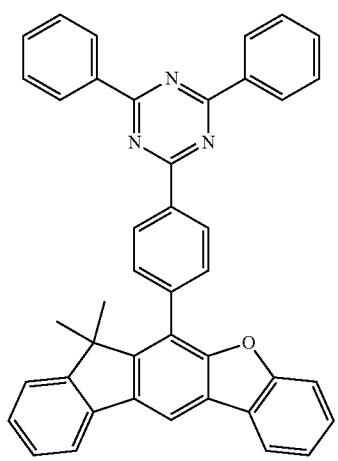
121 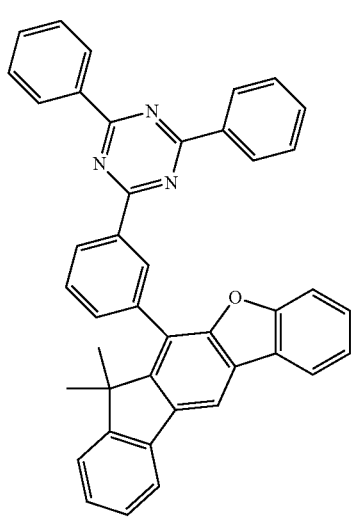
122 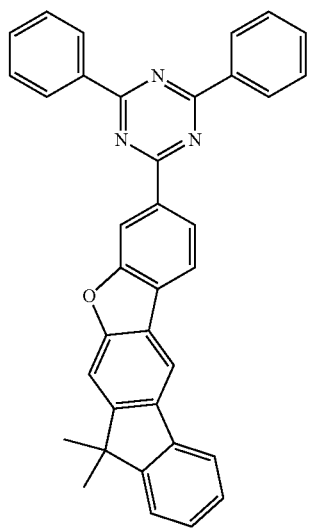
123 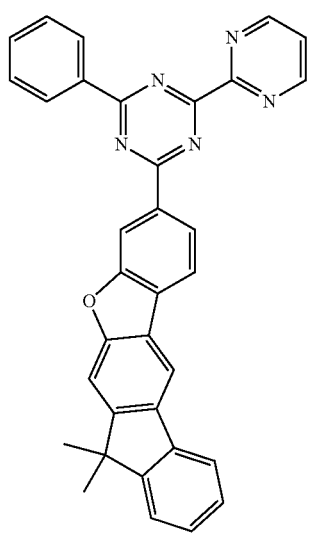
124 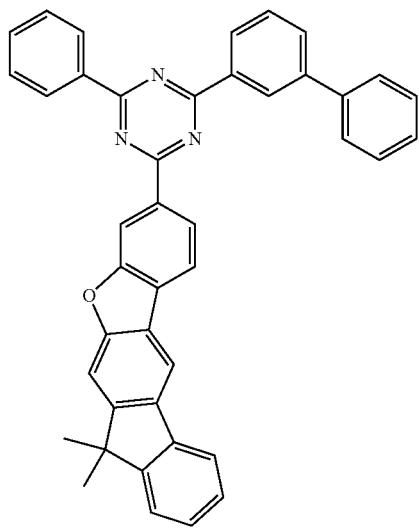

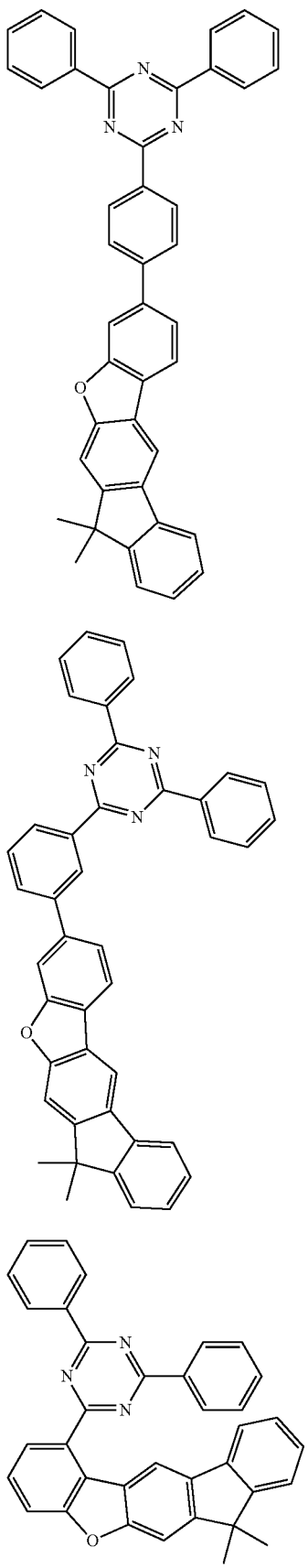
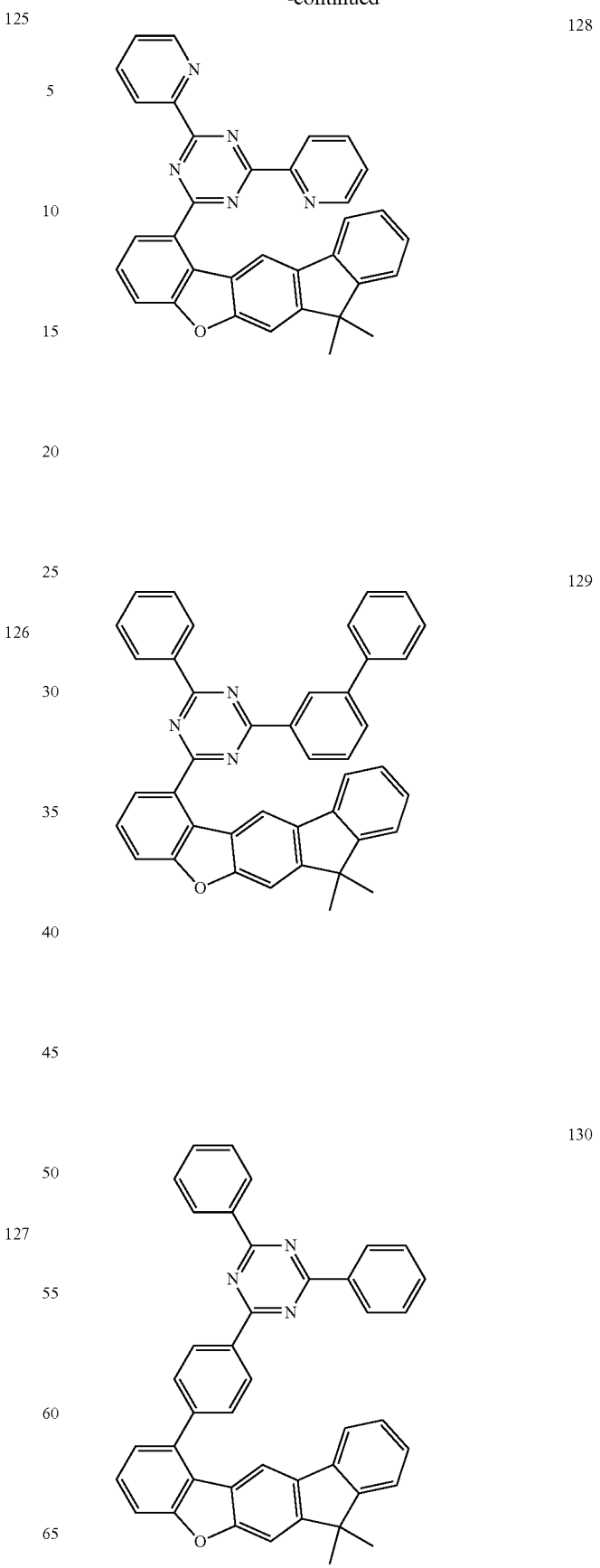

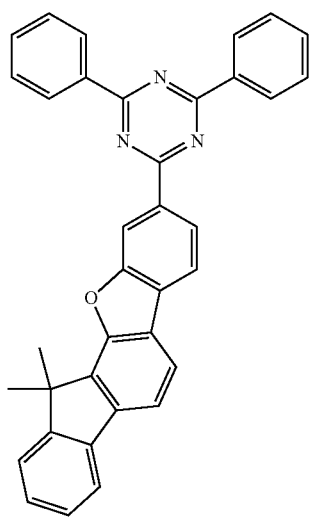
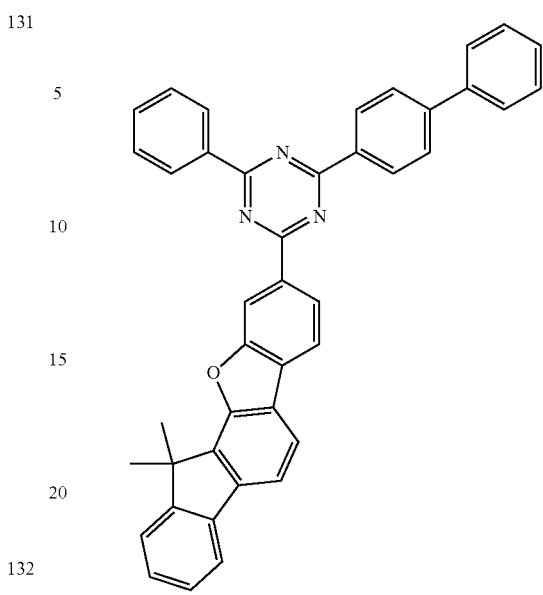
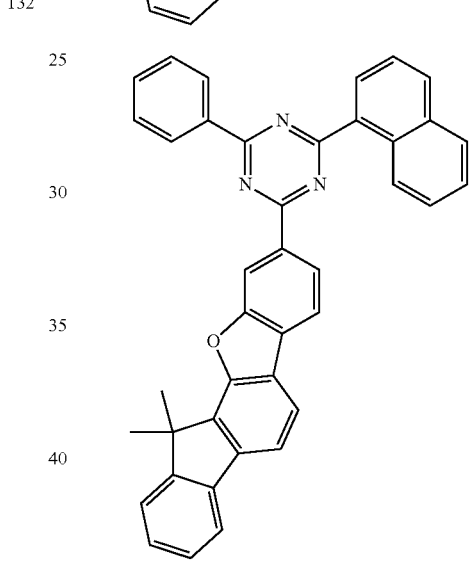

137
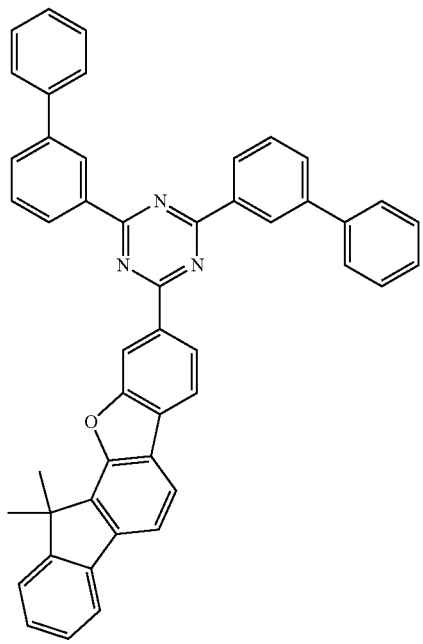
139
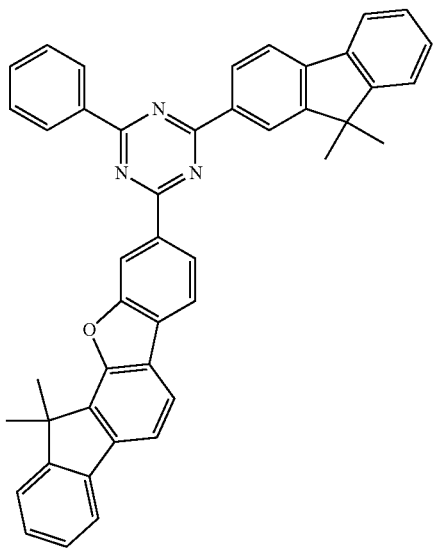
138
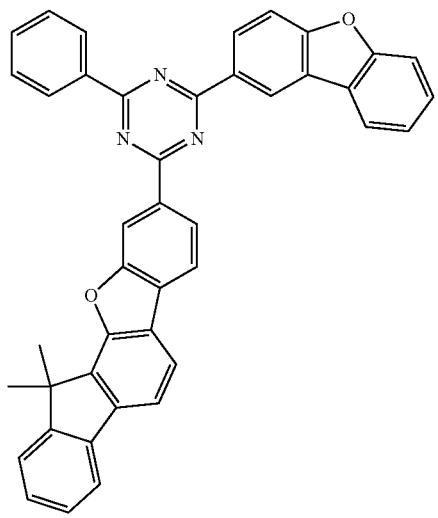
140
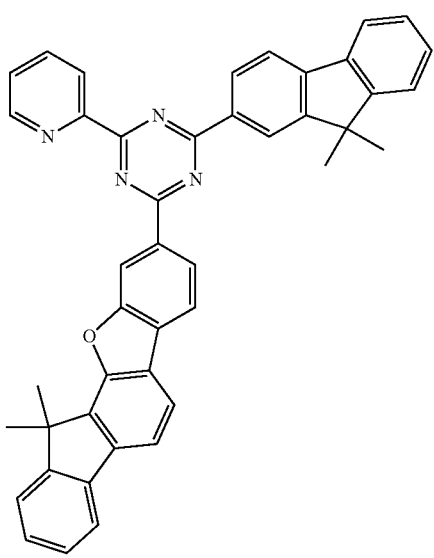

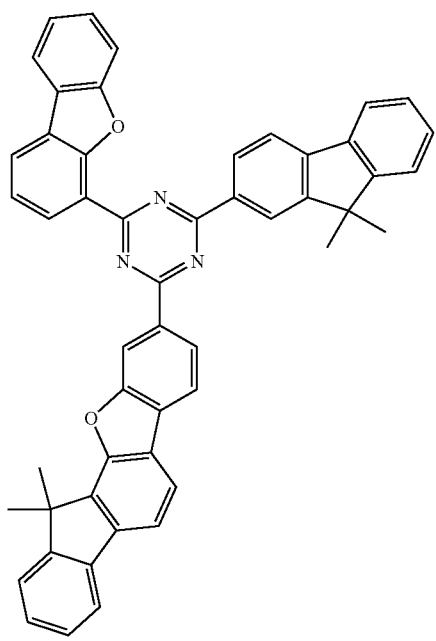
141
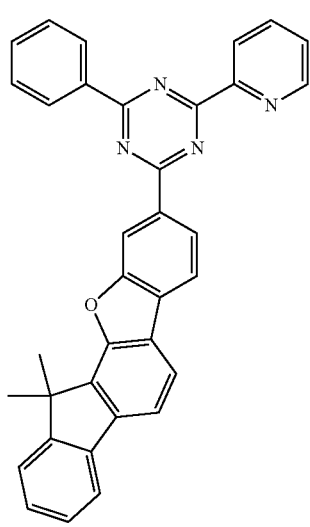
142
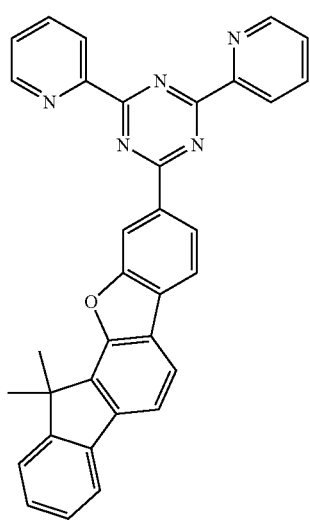
143
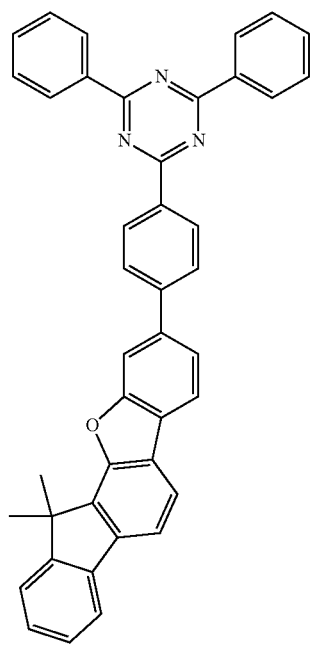
144
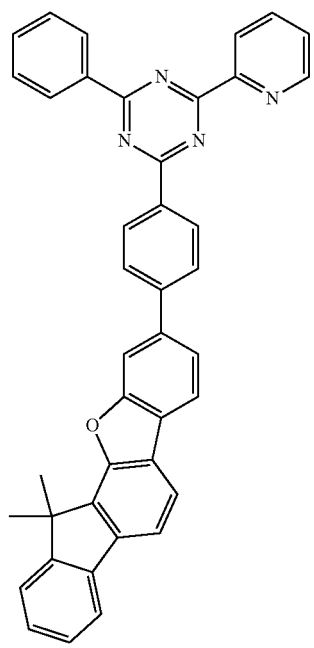
145

146
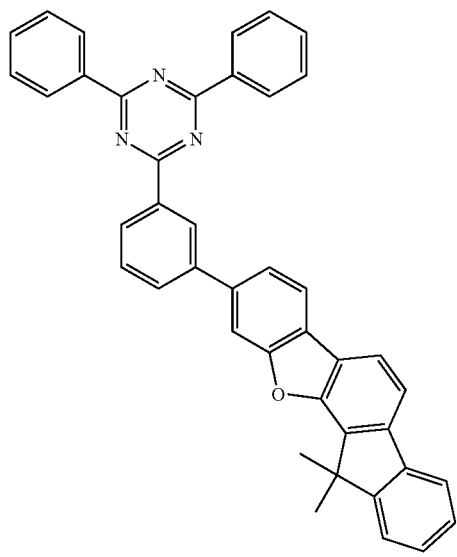
147
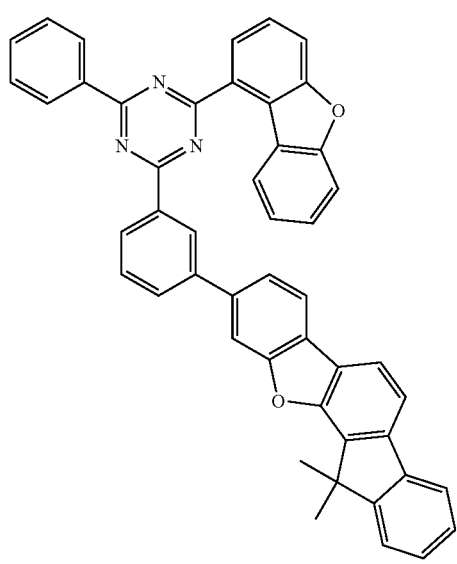
148
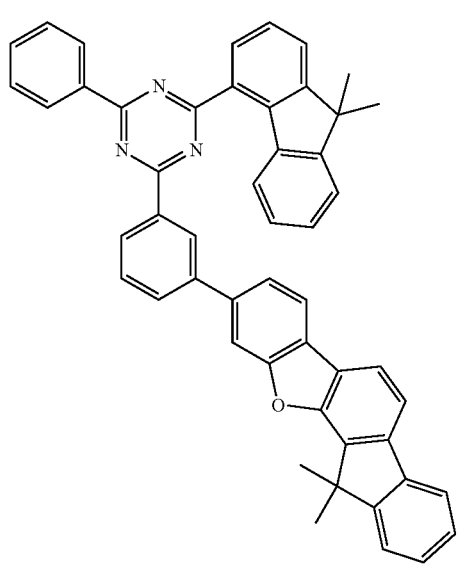
149
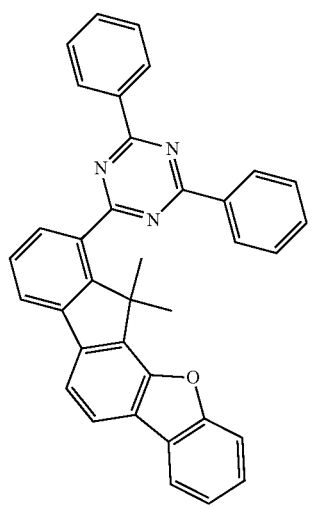
150
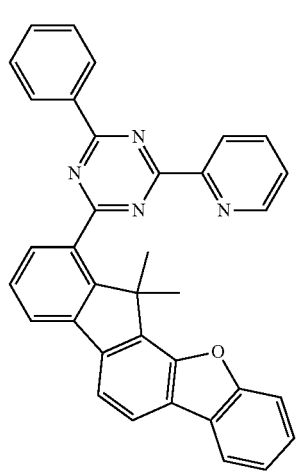
151
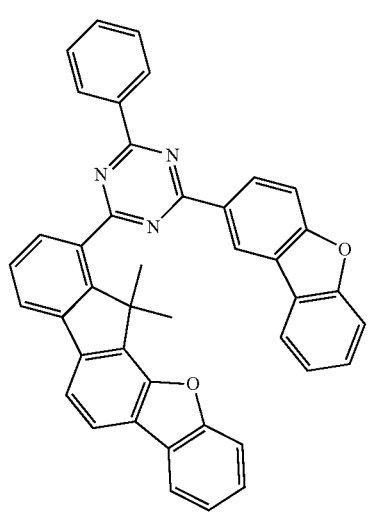

152
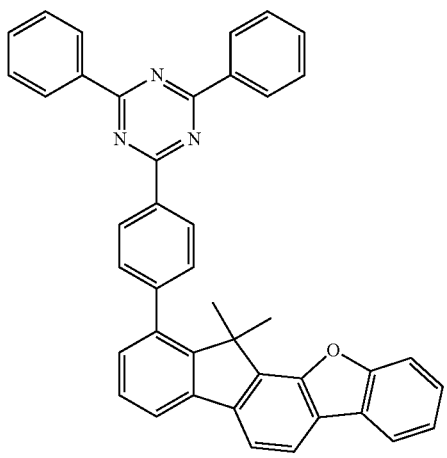
153
154
155
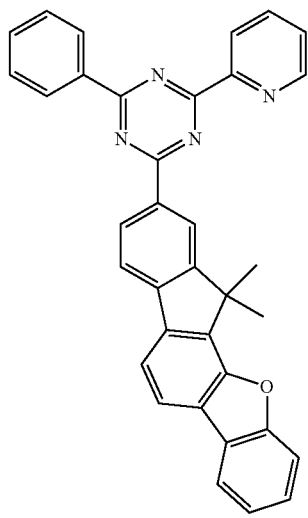
156
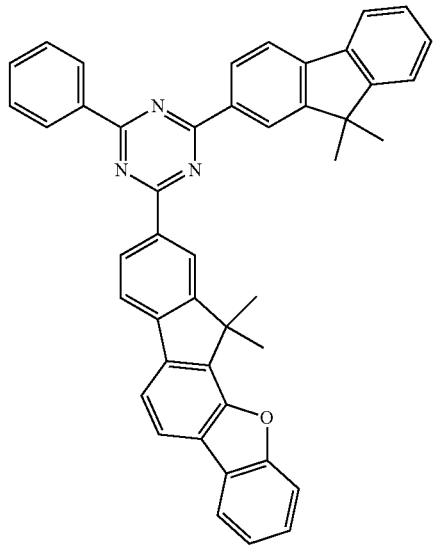

157
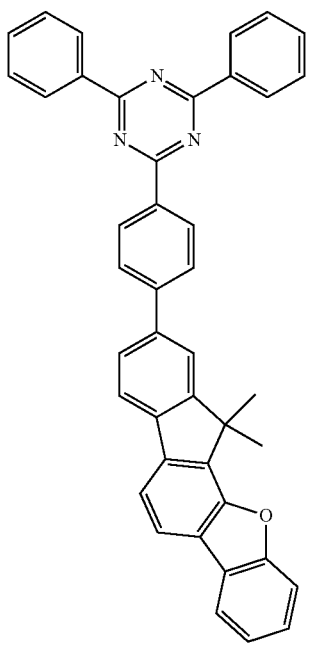
158
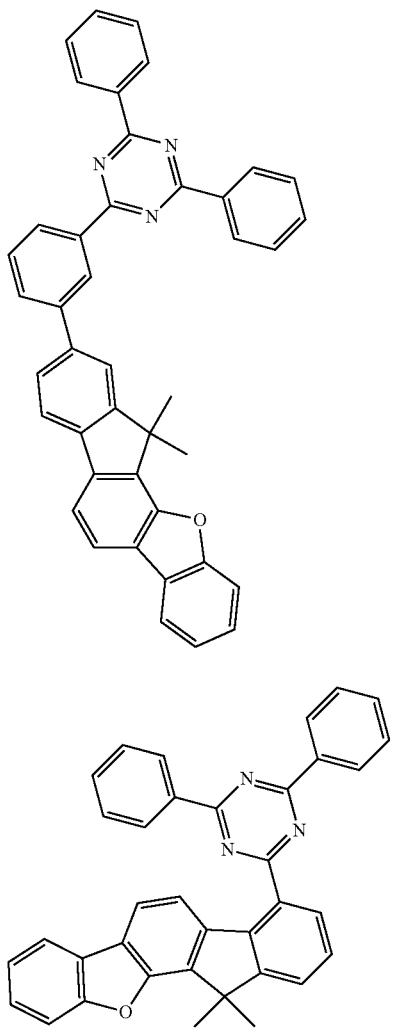
159
160
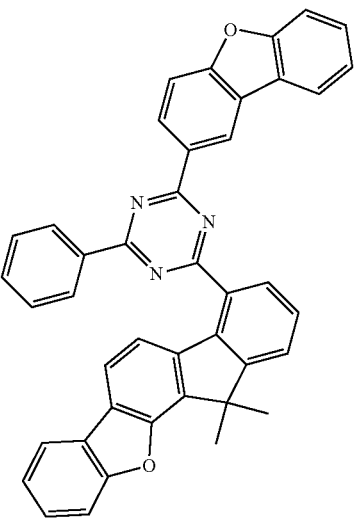
161
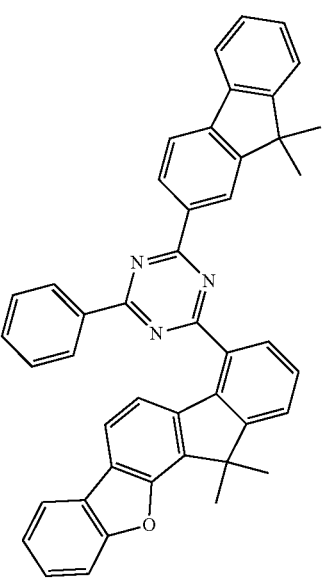
162
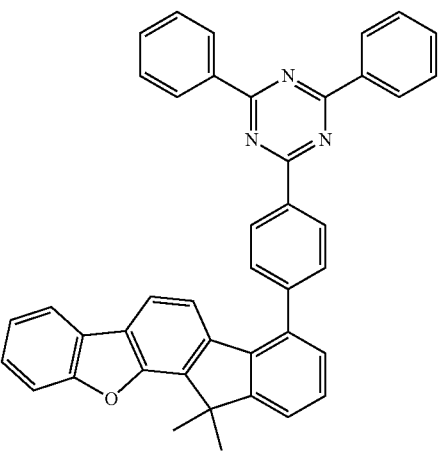

163
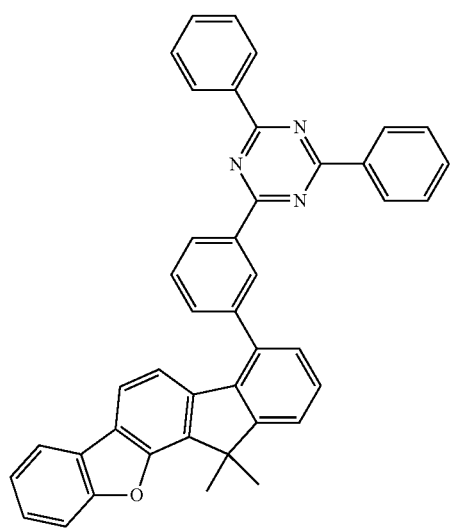
164
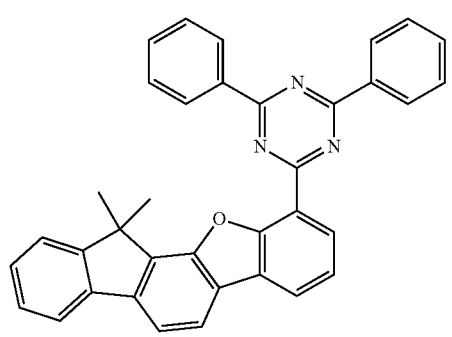
165
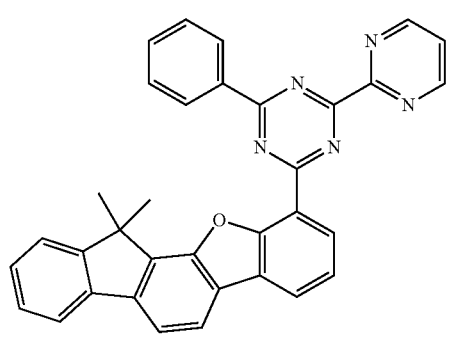
166
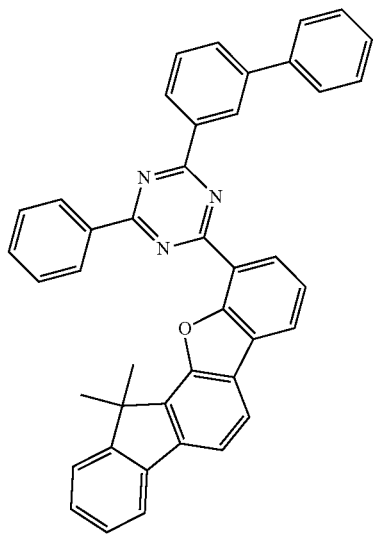
167
168

169
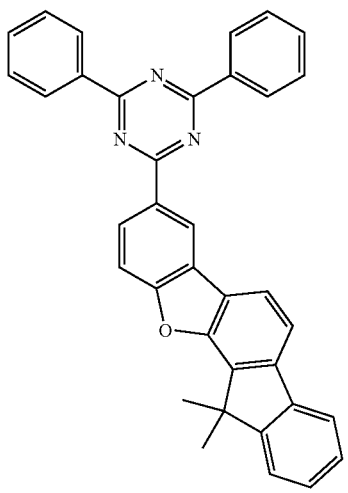
170
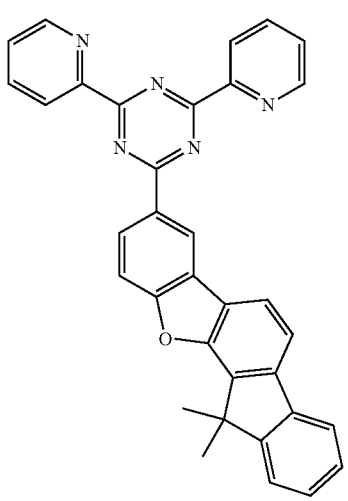
171
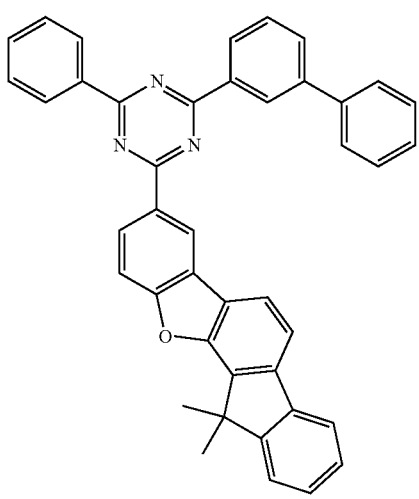
172
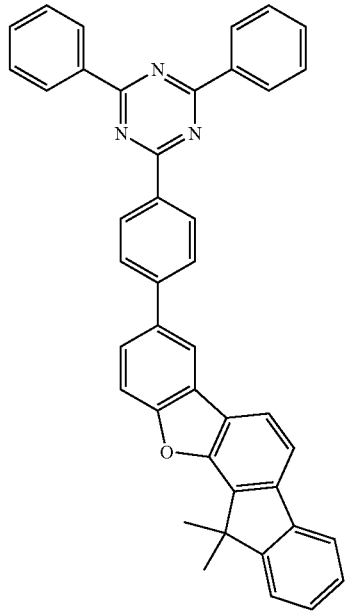
173
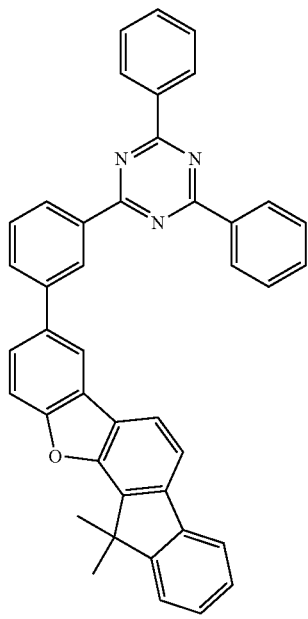
174
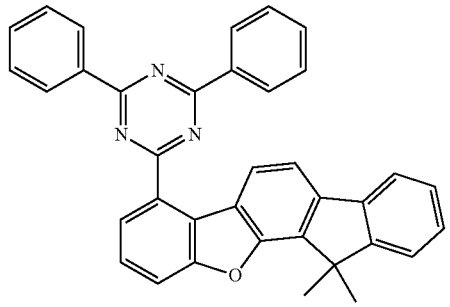

| 175 | 178 |
|---|---|
| 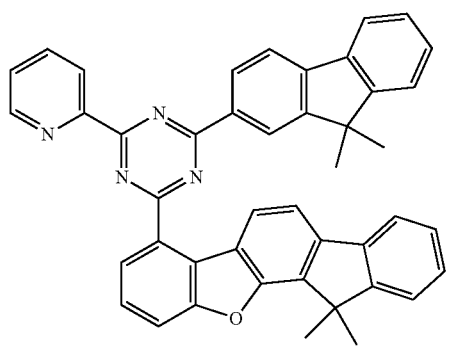 | 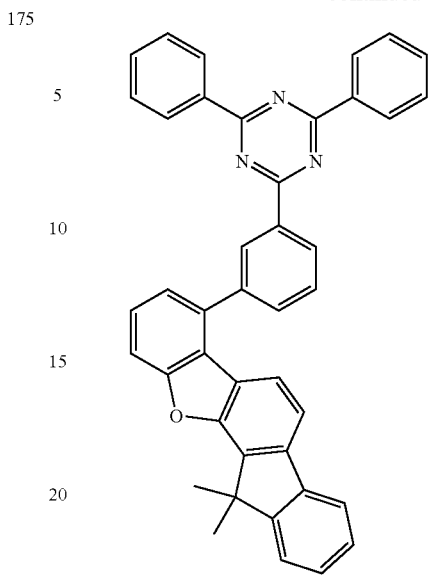 |
| 176 | 179 |
|---|---|
| 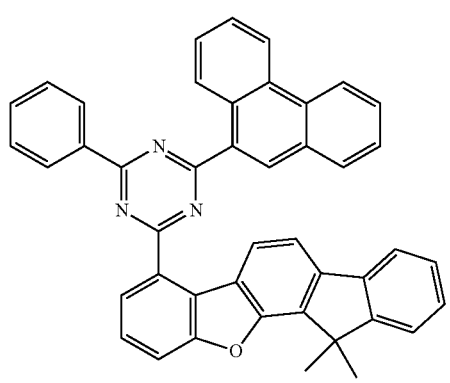 | 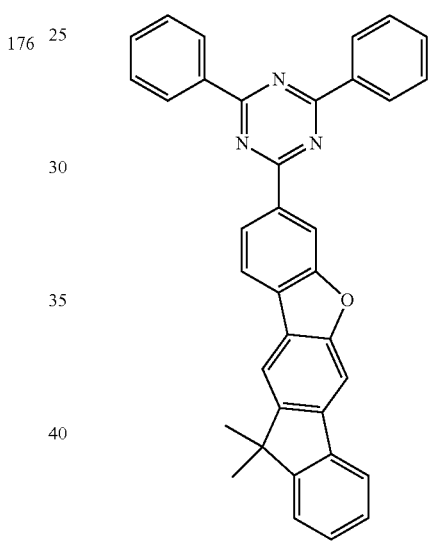 |
| 177 | 180 |
|---|---|
| 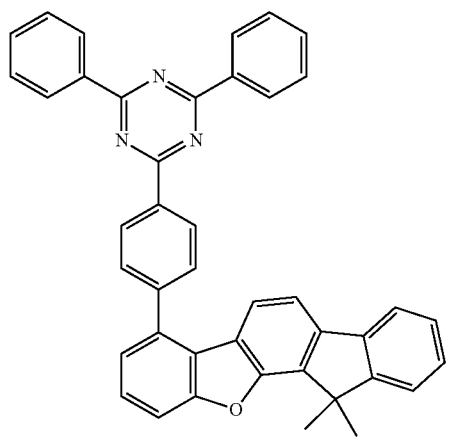 | 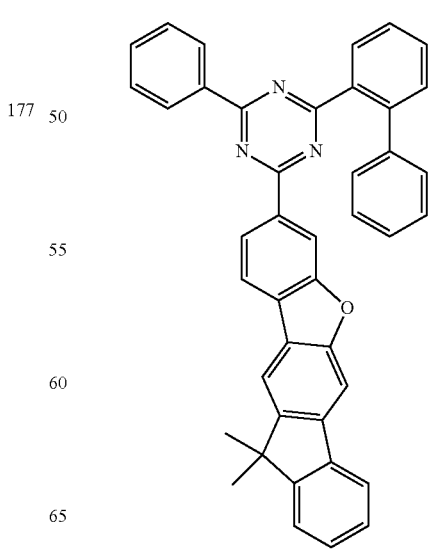 |

181
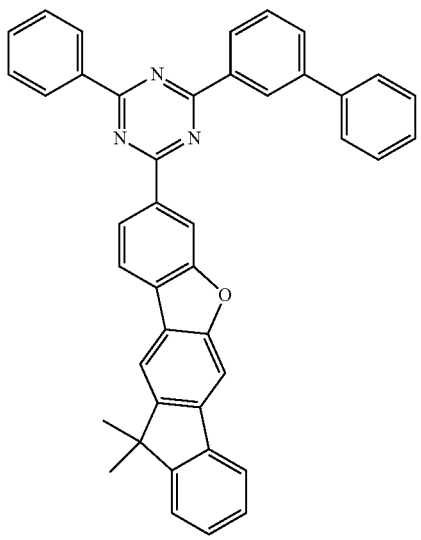
182
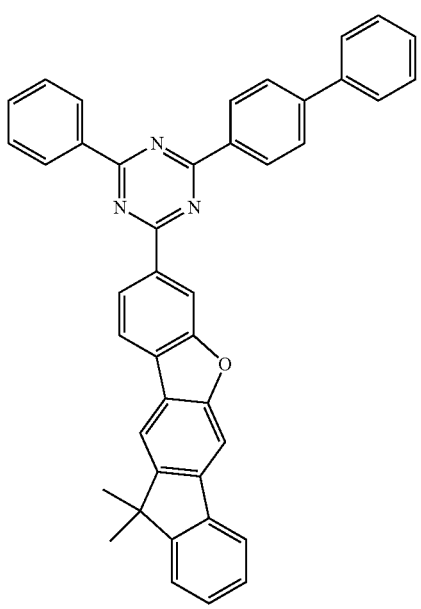
183
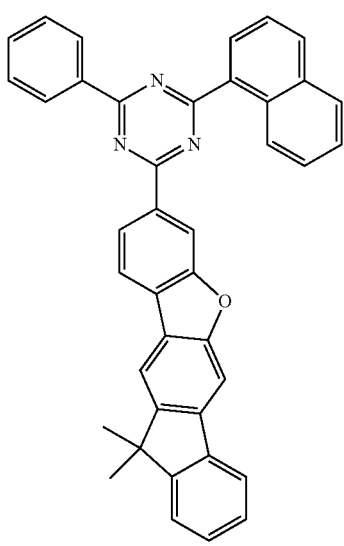
184
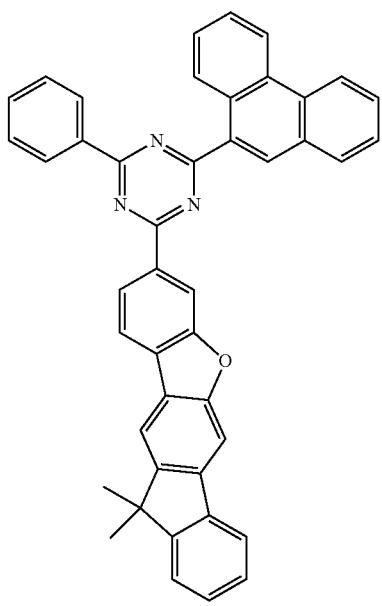
185
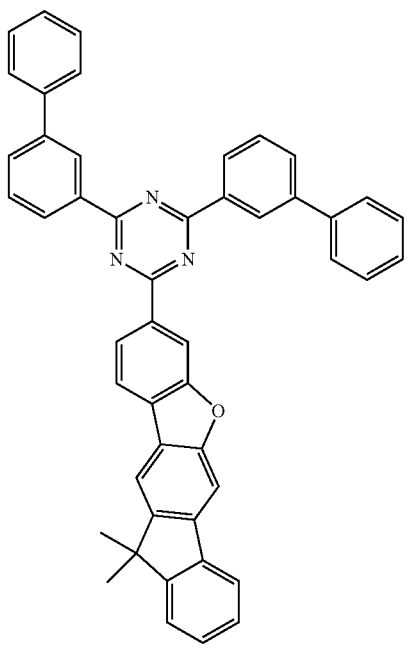

186
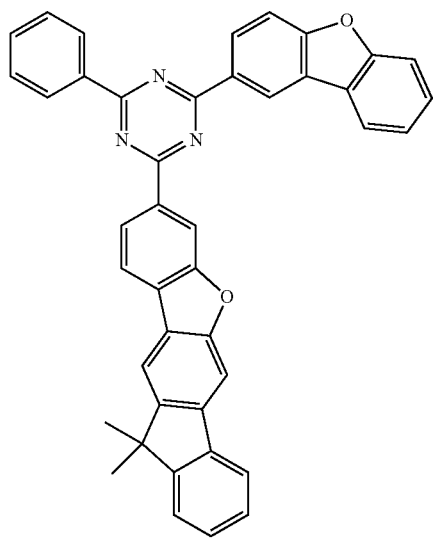
188
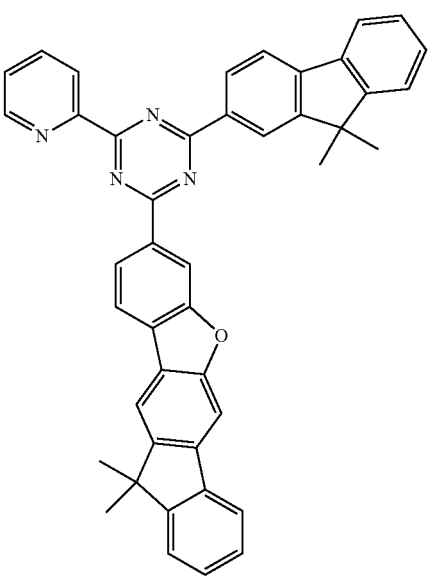
187
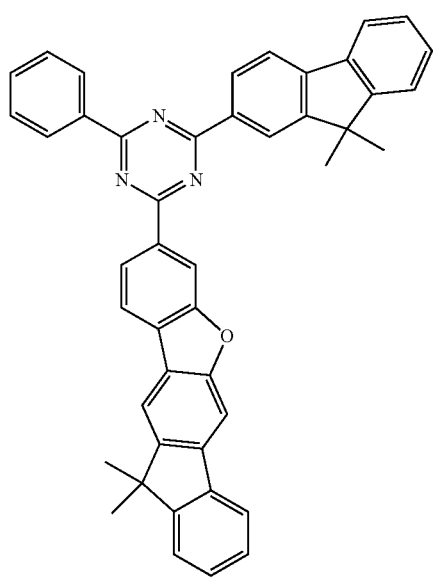
189
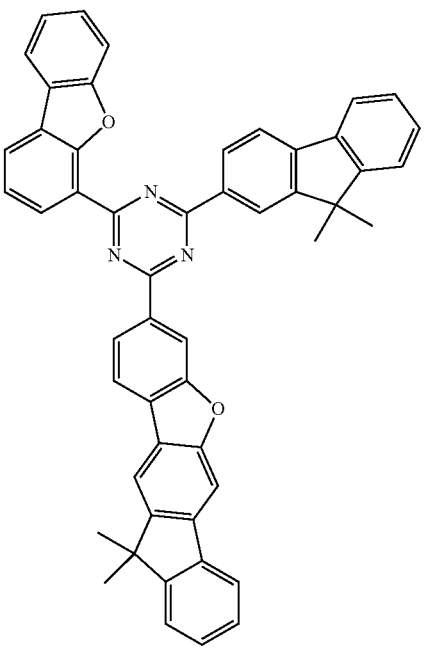

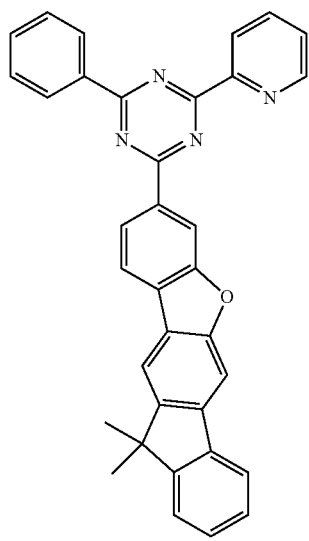
190

191
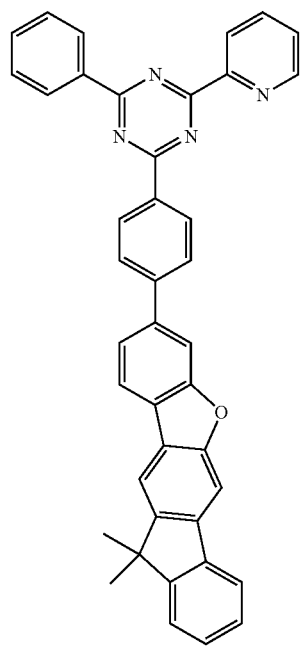
192
193

-continued
194
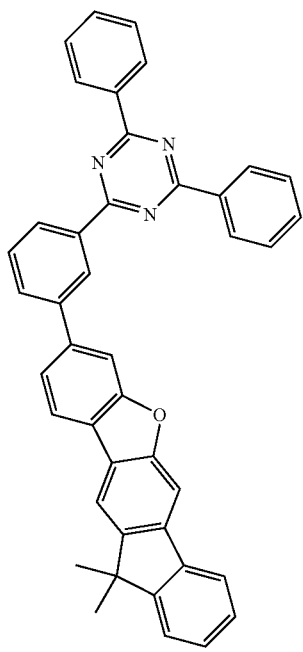
195
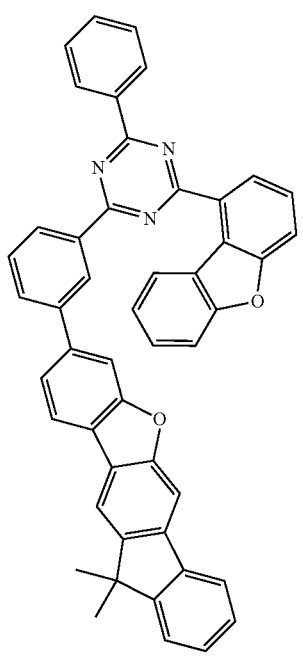
-continued
196
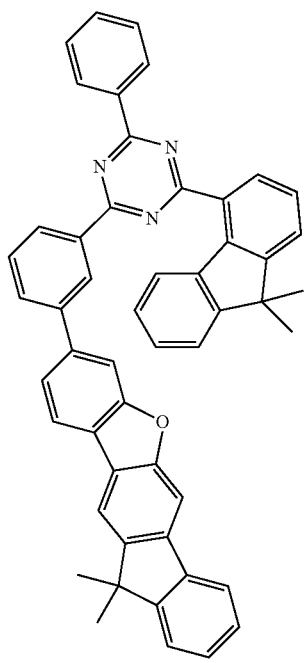
197
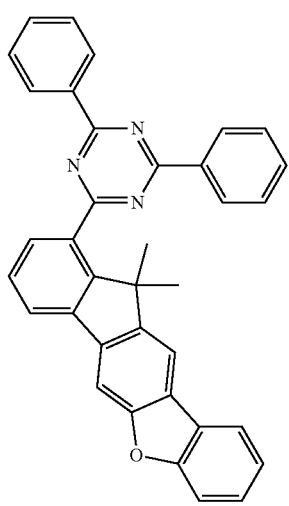

-continued
198
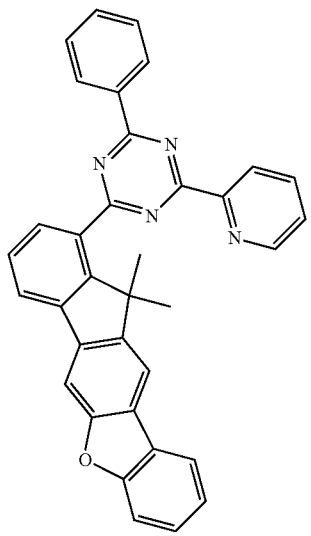
199
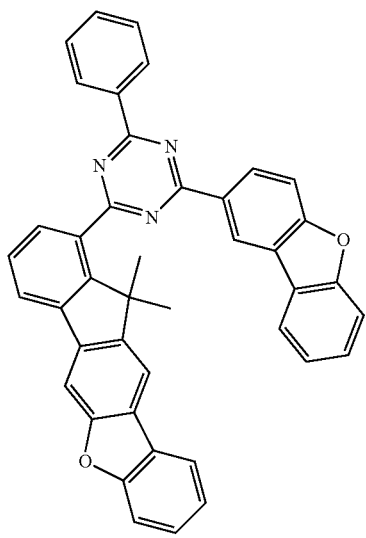
200
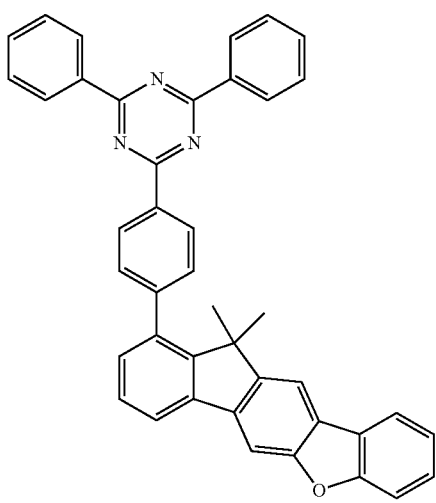
-continued
201
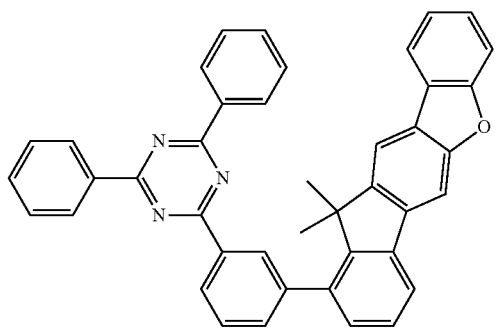
202
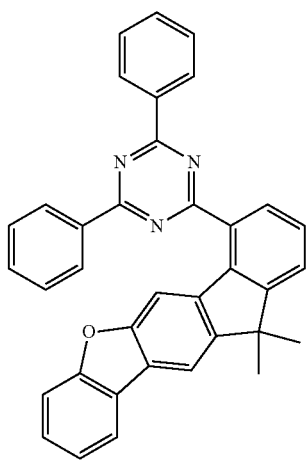
203
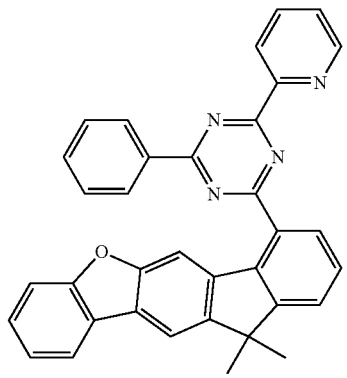

204
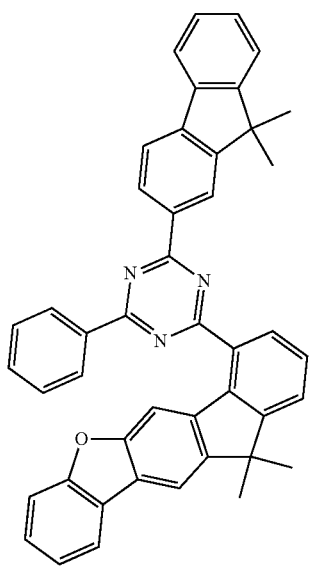
205
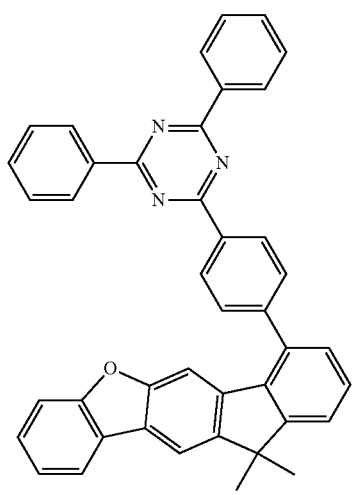
206
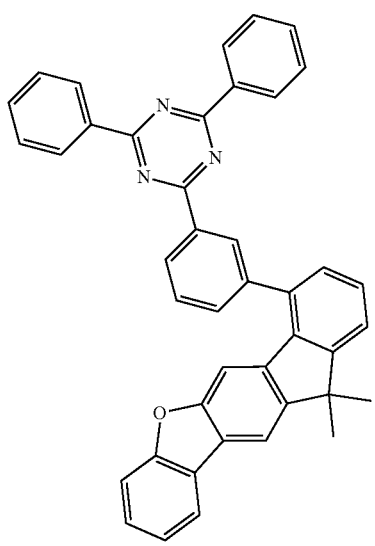
207
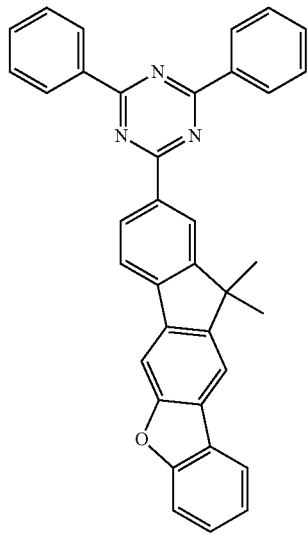
208
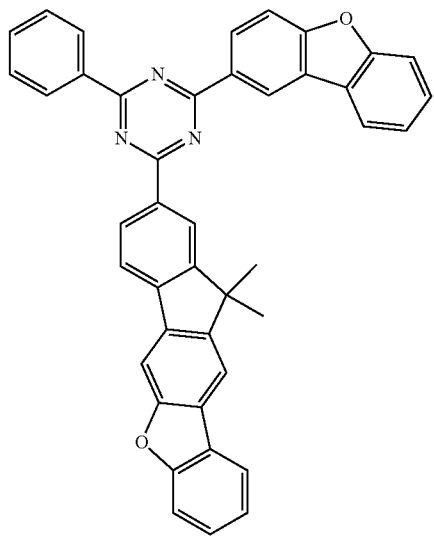
209
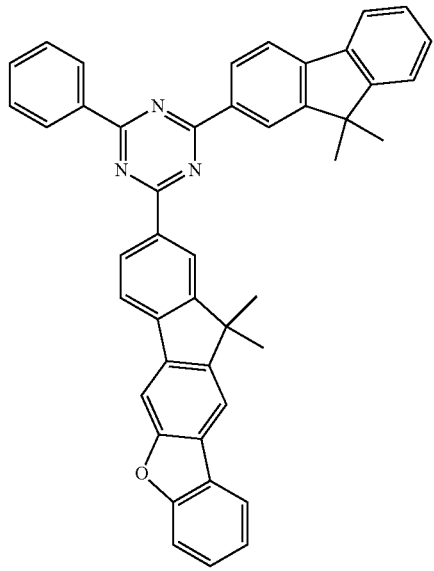

85
-continued
210
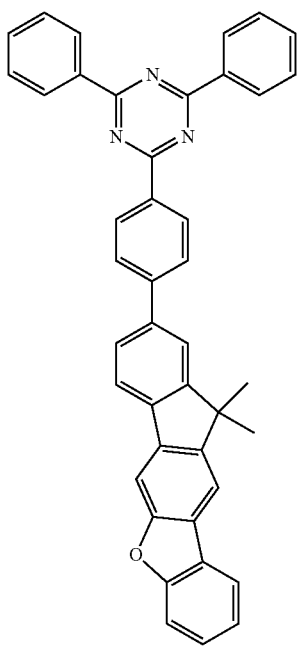
211
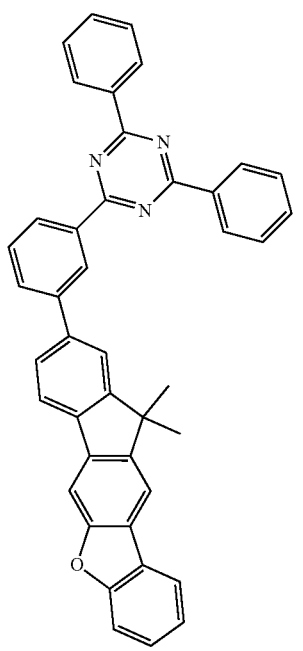
212
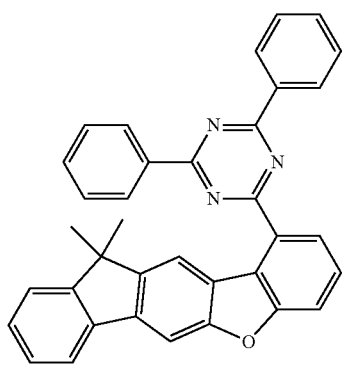
86
-continued
213
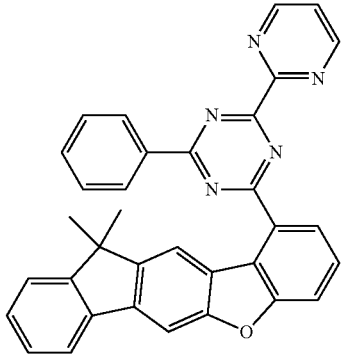
214
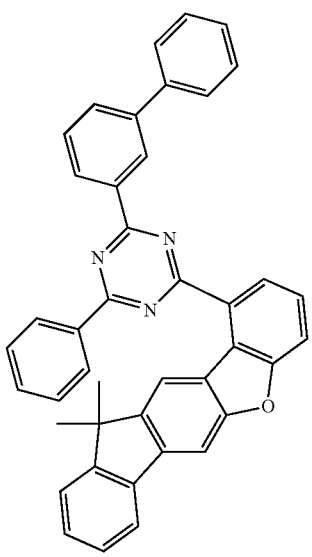
215
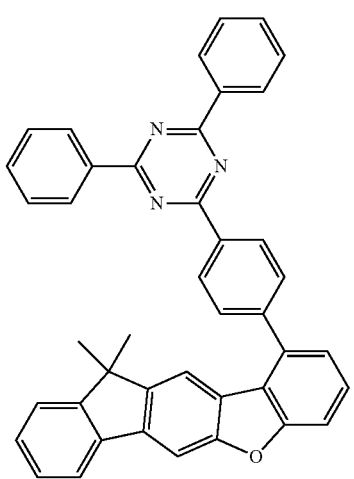

216
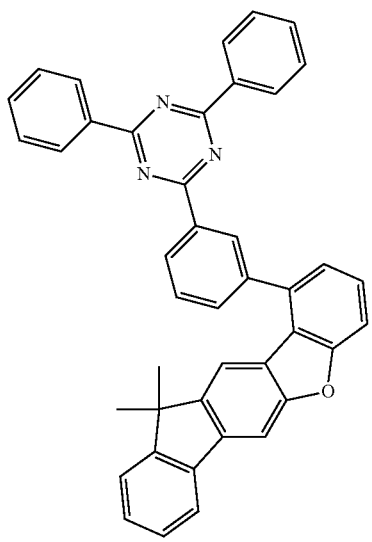
217
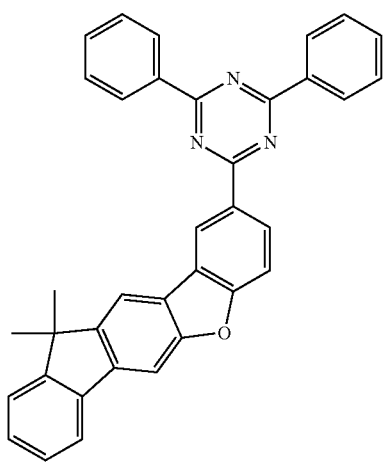
218
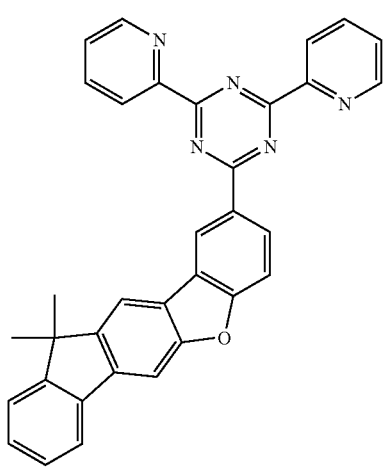
219
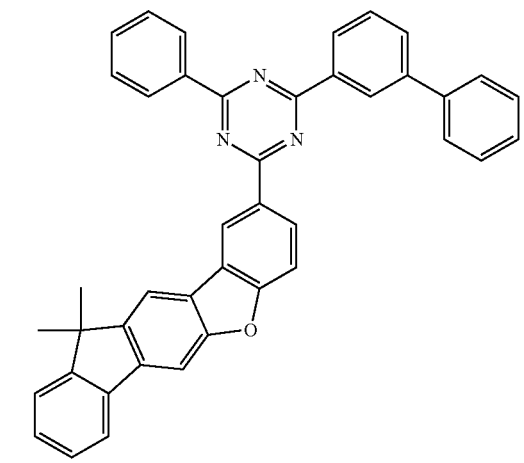
220
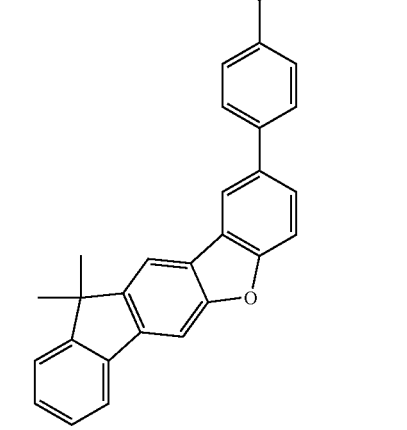
221
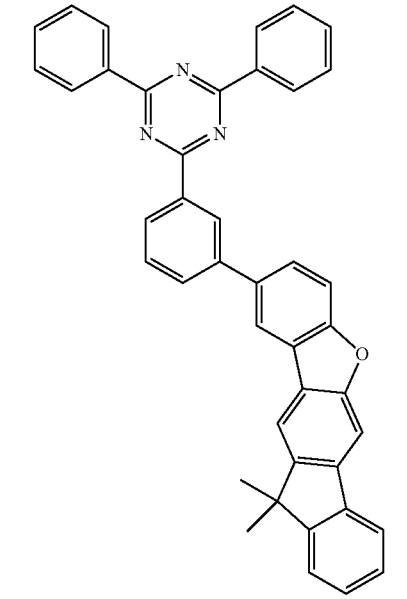

222
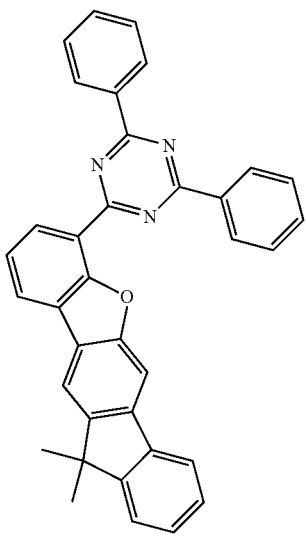
223
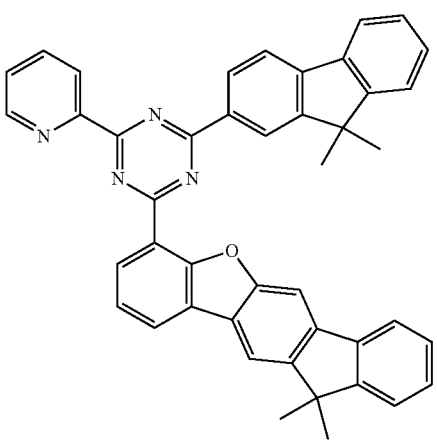
224
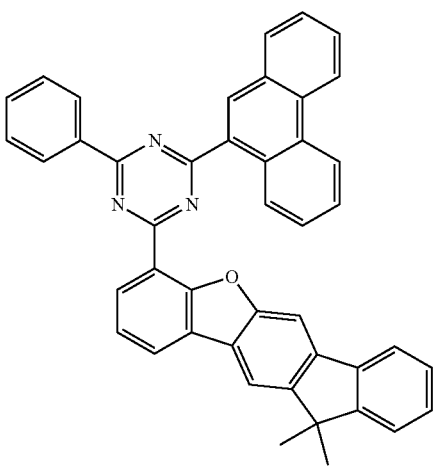
225
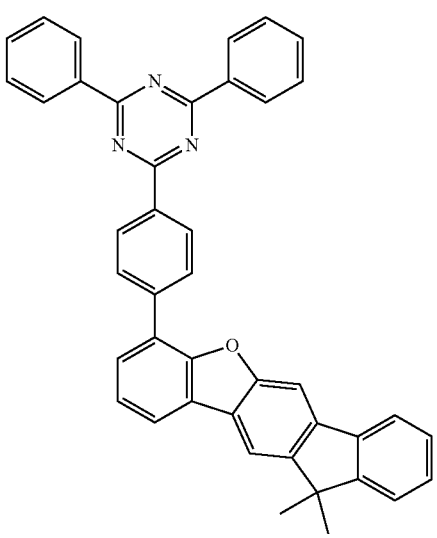
226
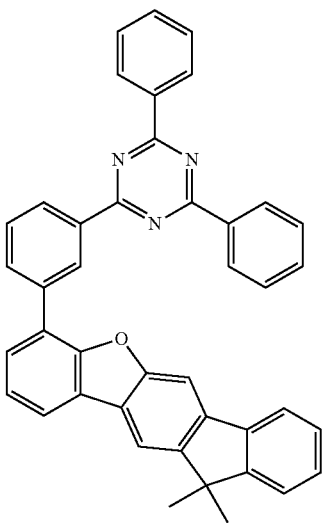
227
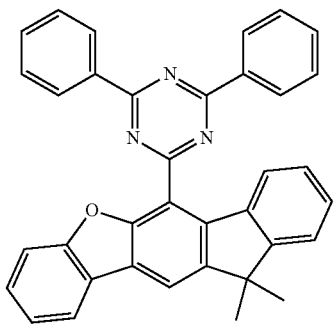

228
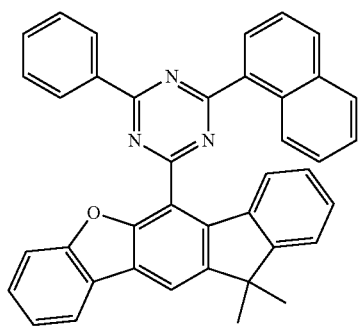
229
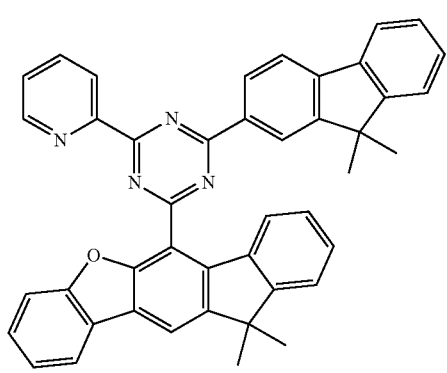
230
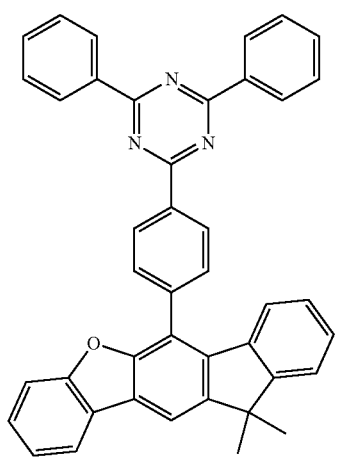
231
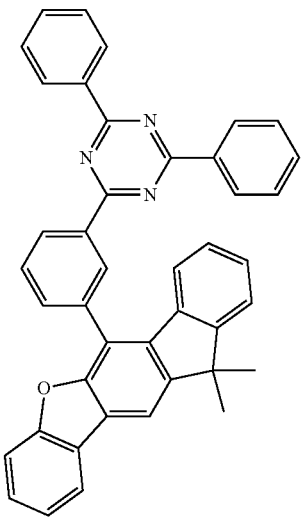
232
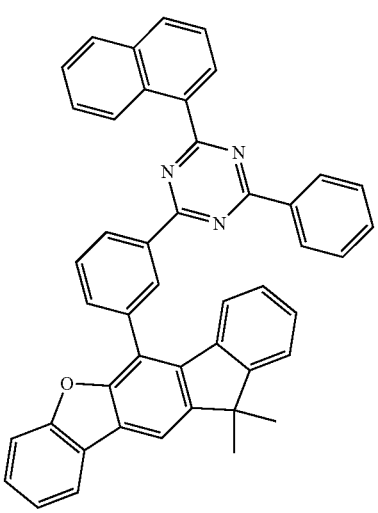
233
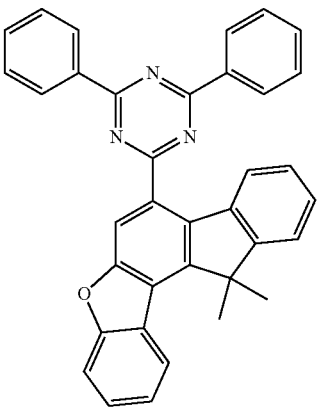

233
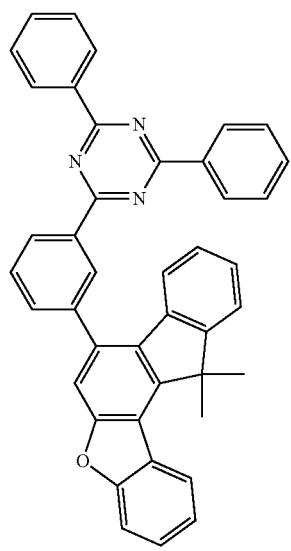
234
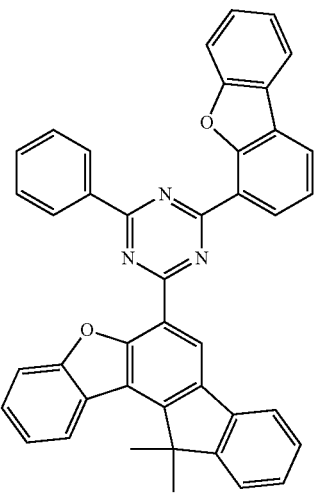
235
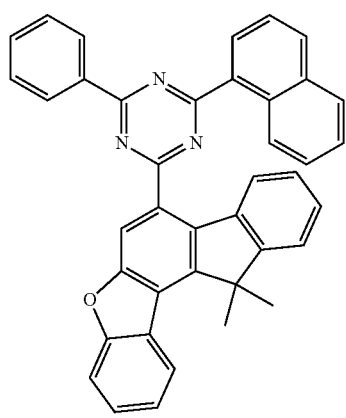
237
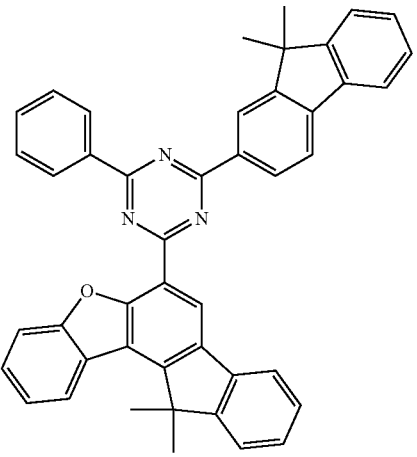
238
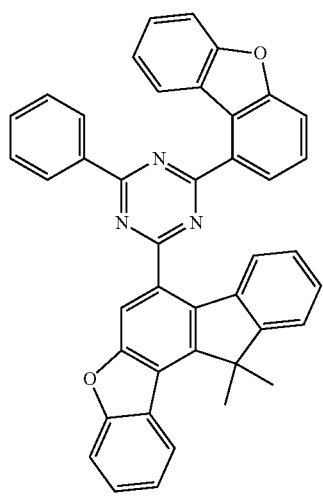
236
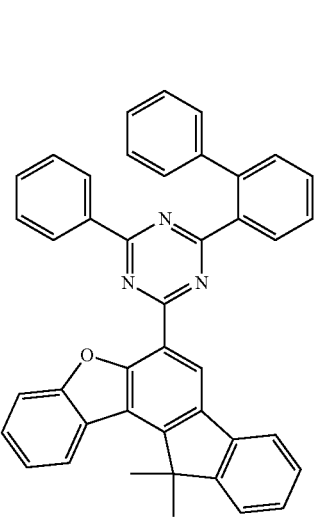
239

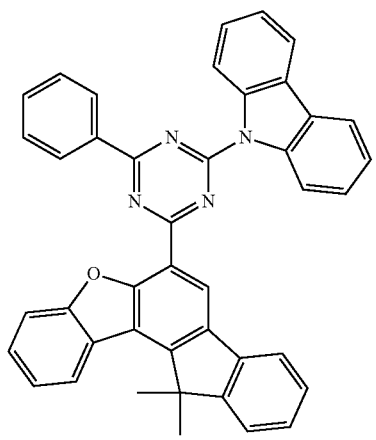
240
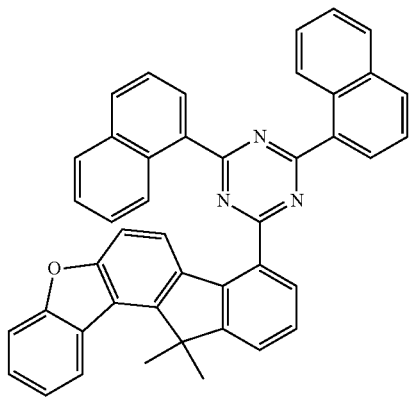
243
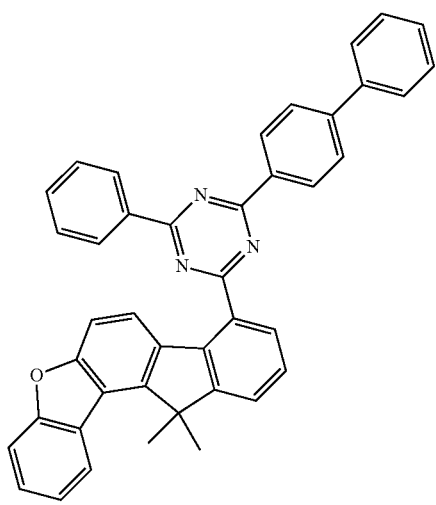
241
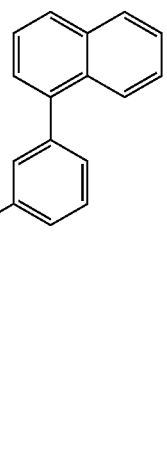
244
242
245

246
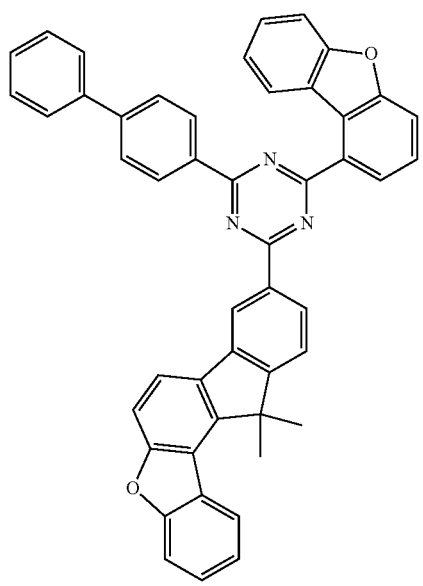
247
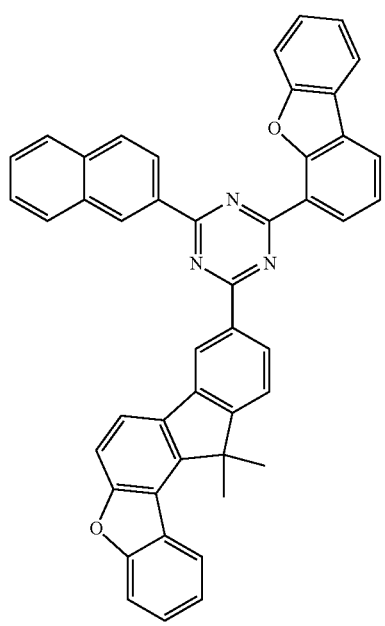
248
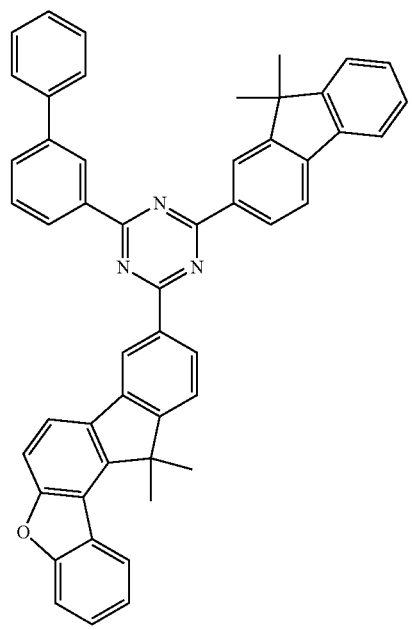
249
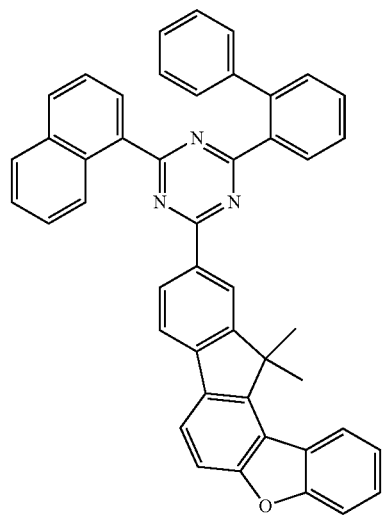

-continued
250
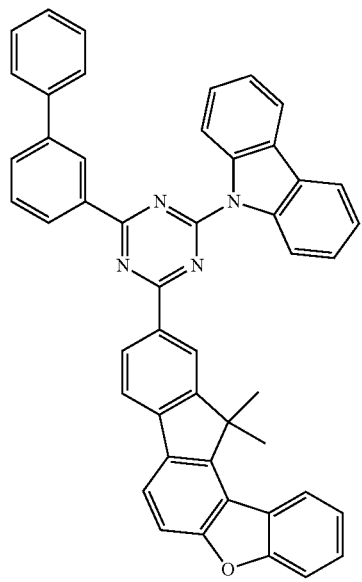
251
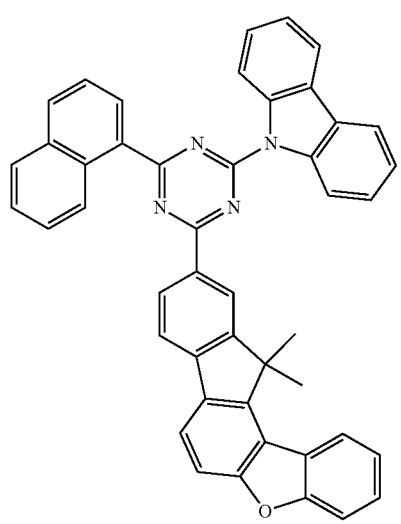
252
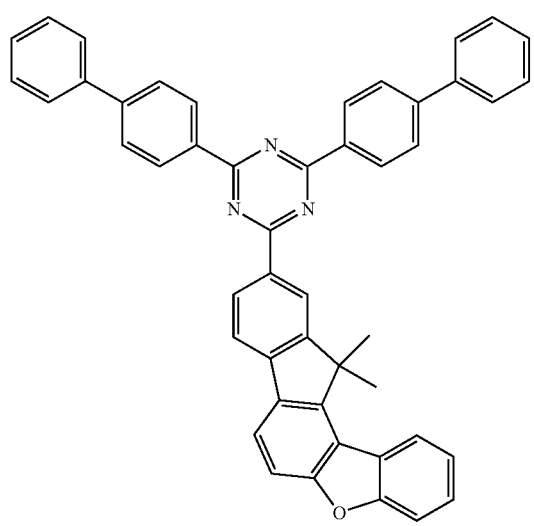
-continued
253
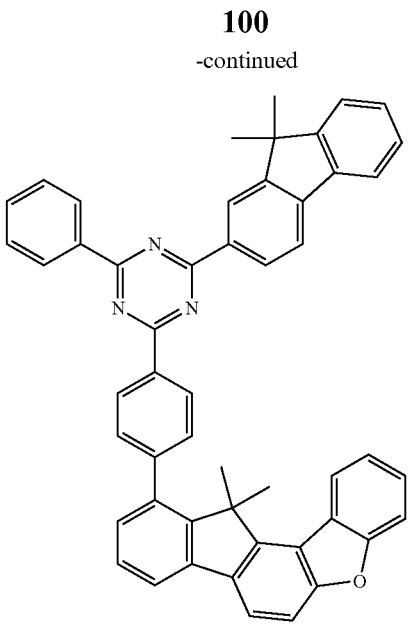
254
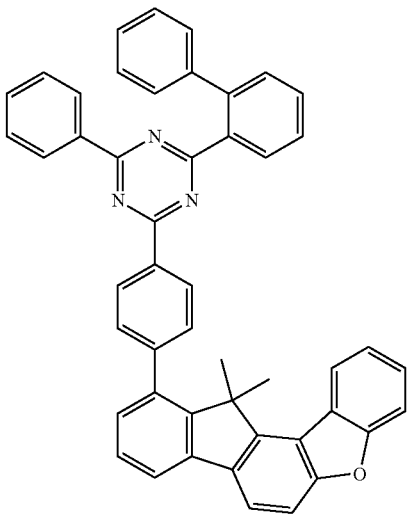
255
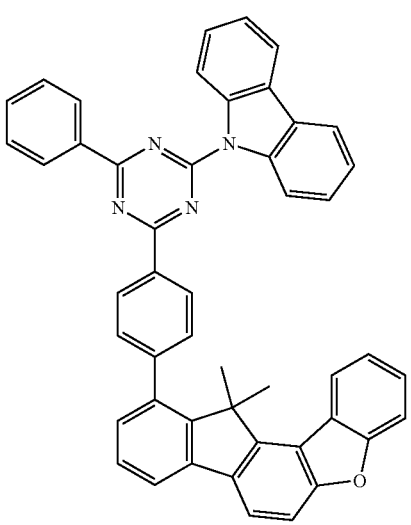

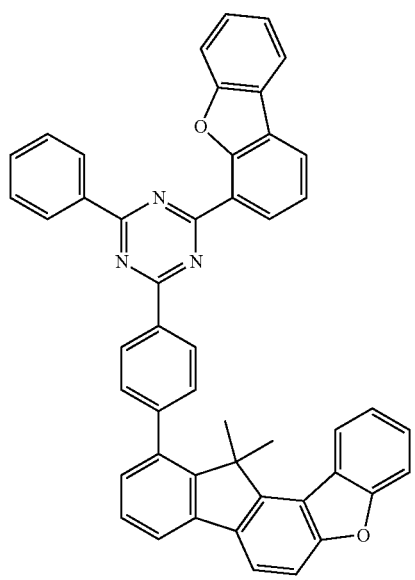
256
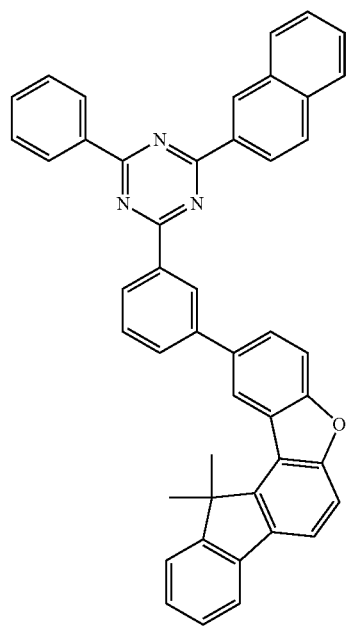
258
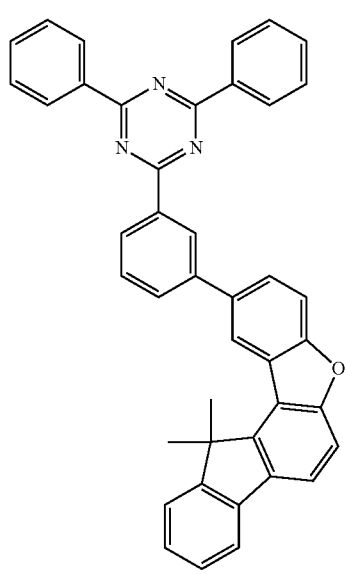
257
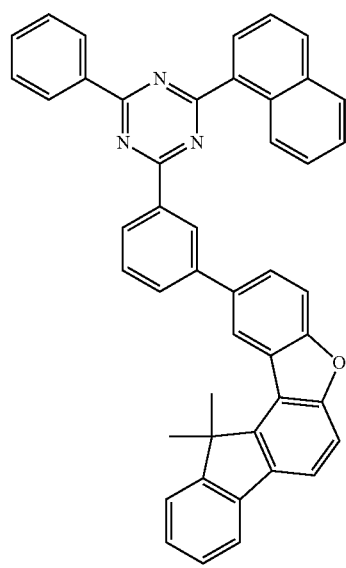
259

260
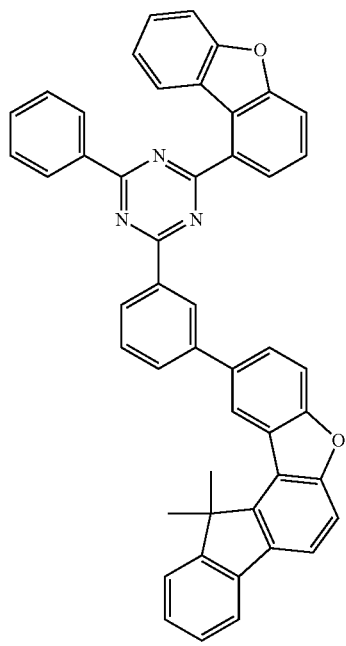
261
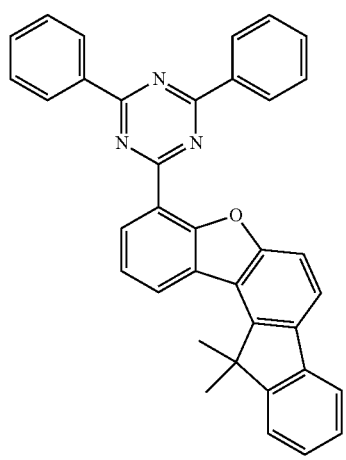
262
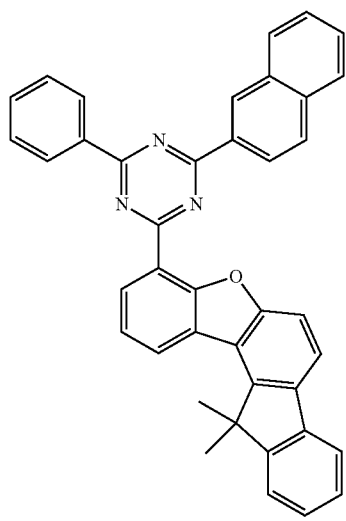
263
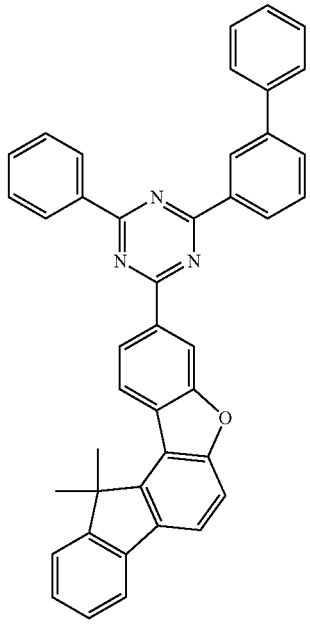
264
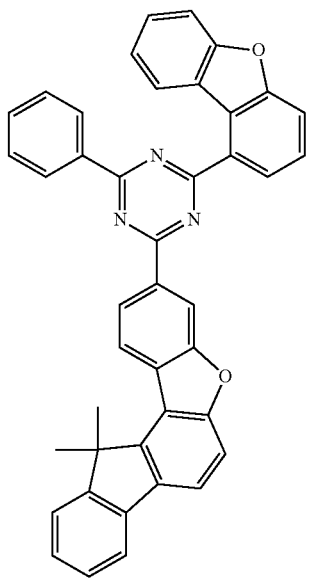

105 -continued
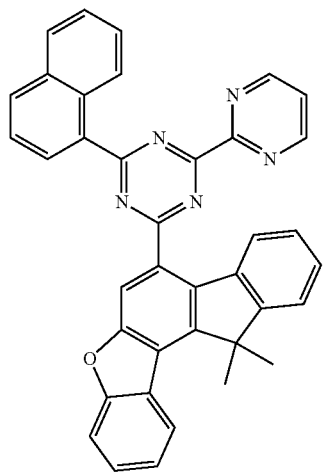
265
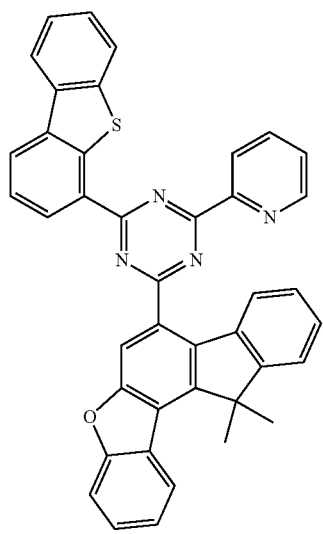
266
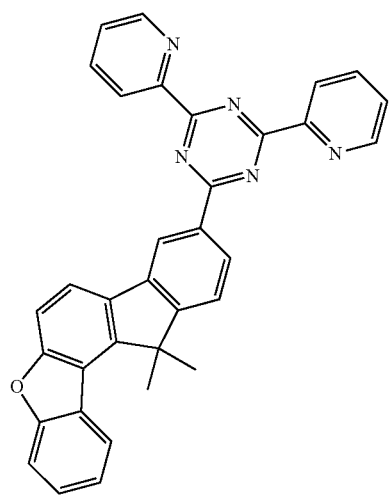
267
106 -continued
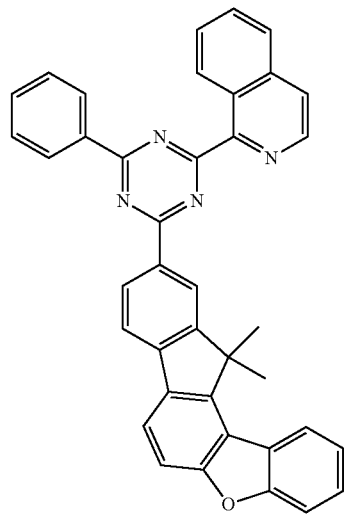
268
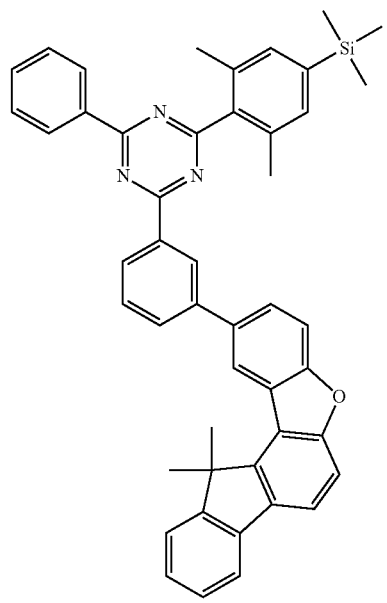
269

270
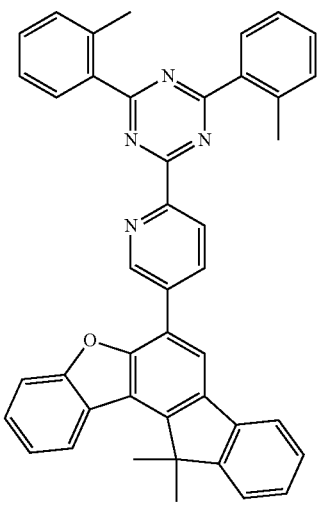
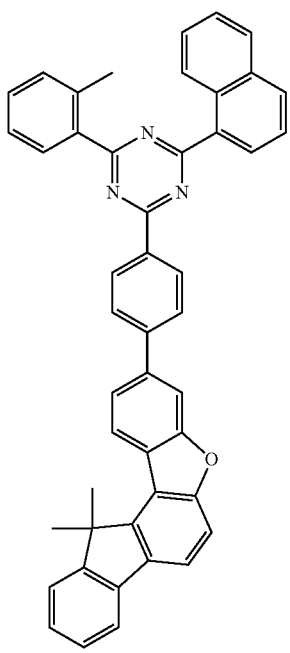
272
271
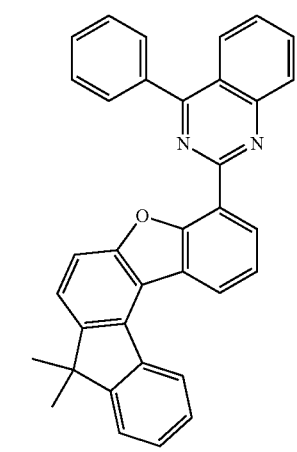
273
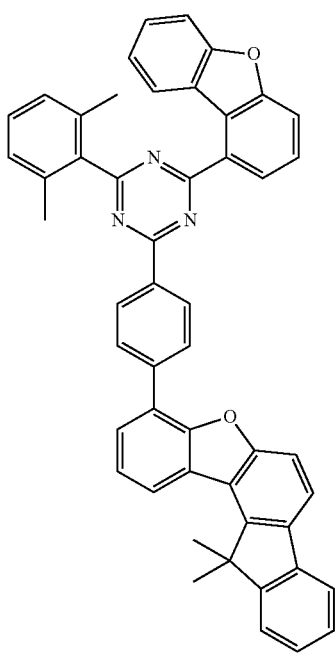
274
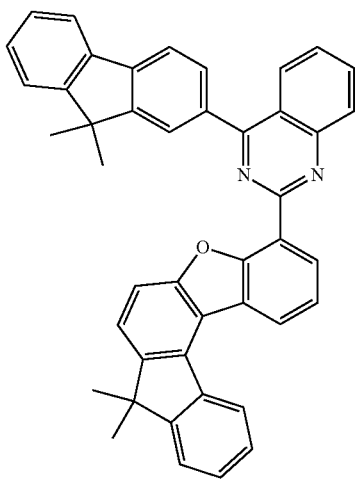

275
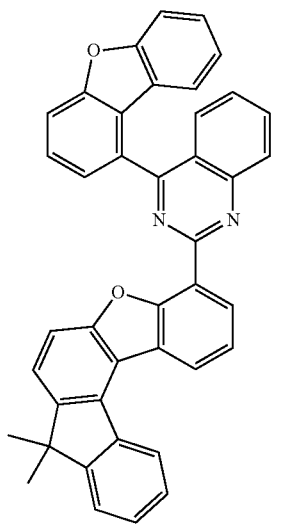
276
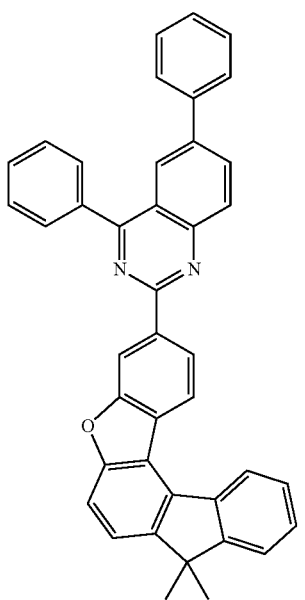
277
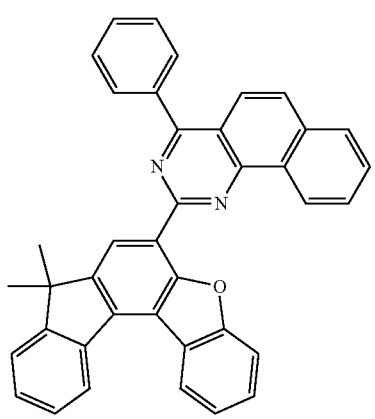
278
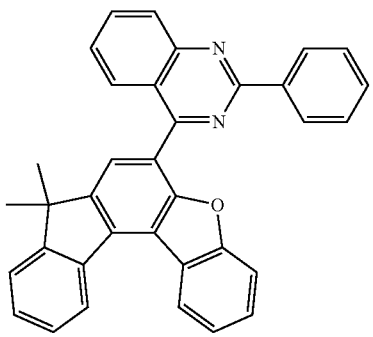
279
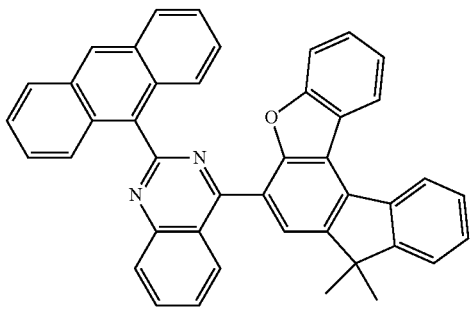
280
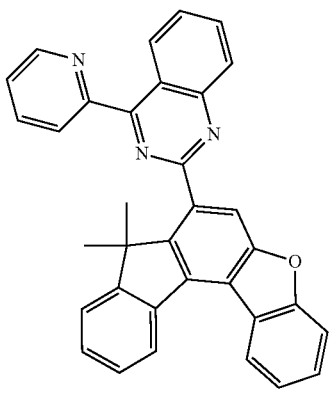
281
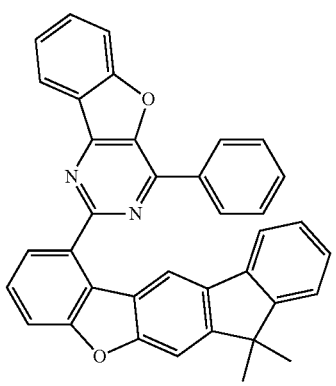

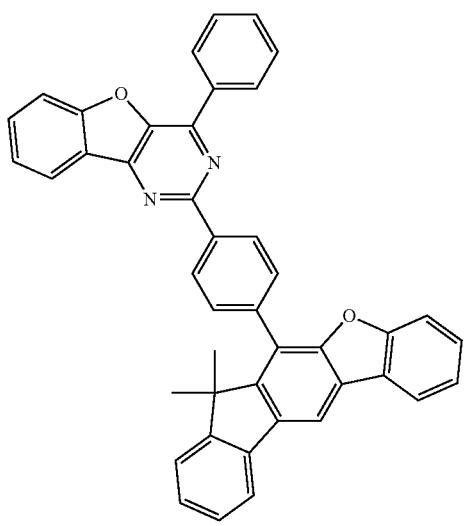
282
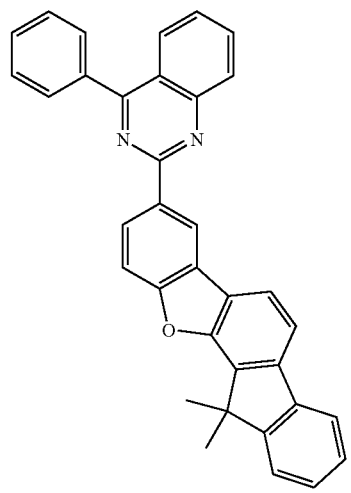
285
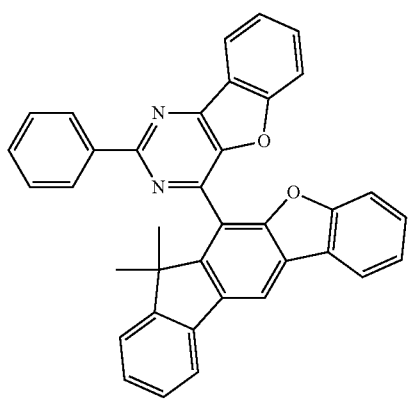
283
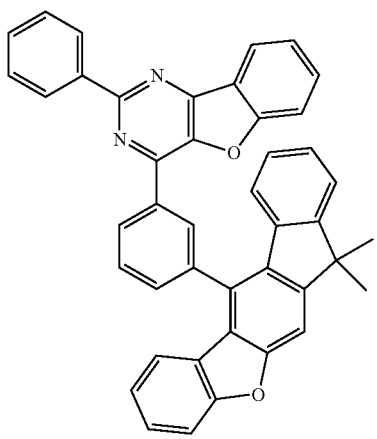
284
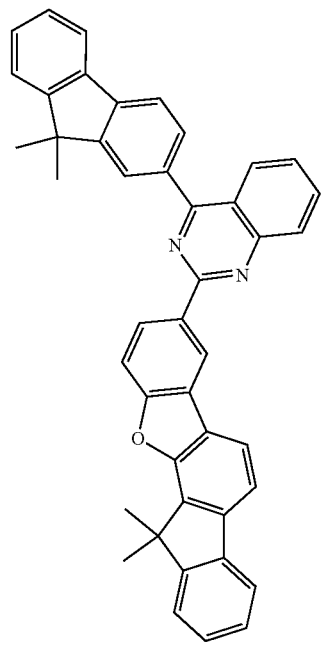
286

287
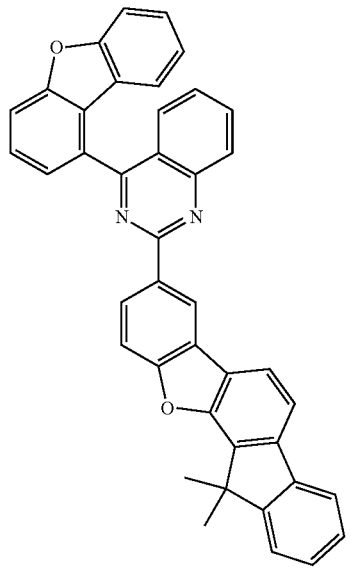
288
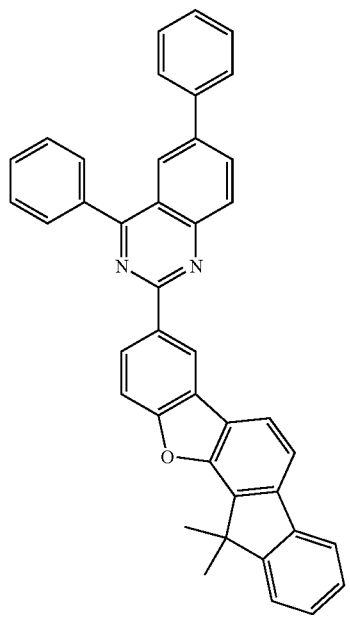
289
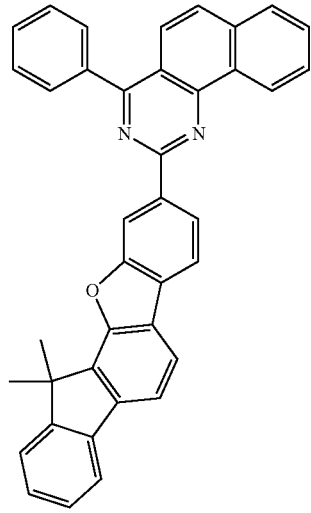
290
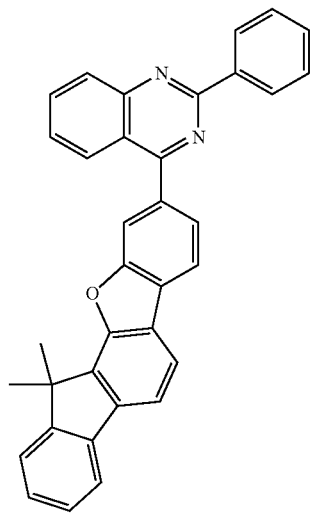
291

292
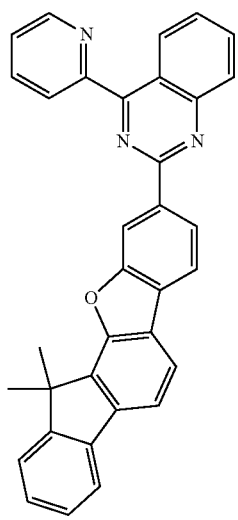
295
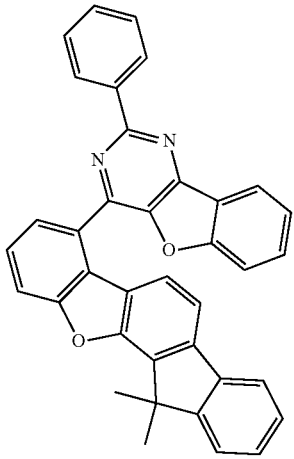
293
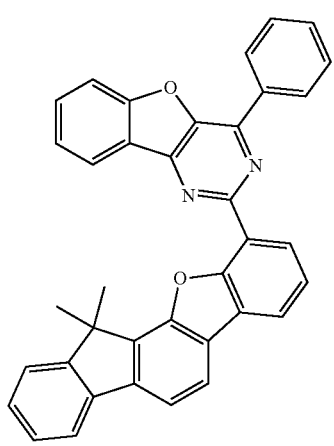
296
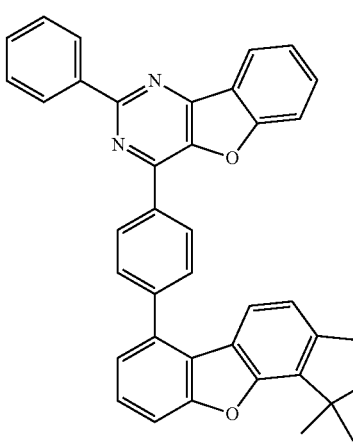
294
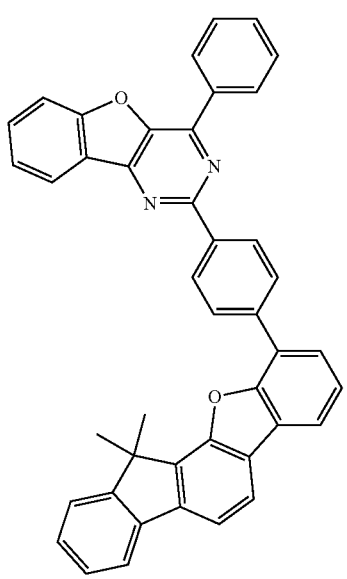
297
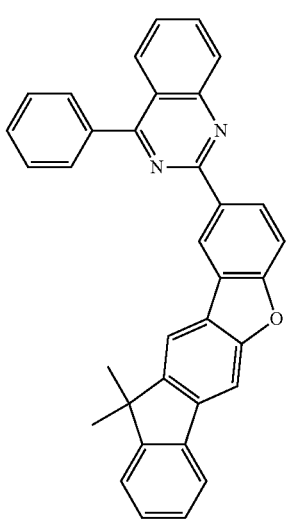

117
-continued
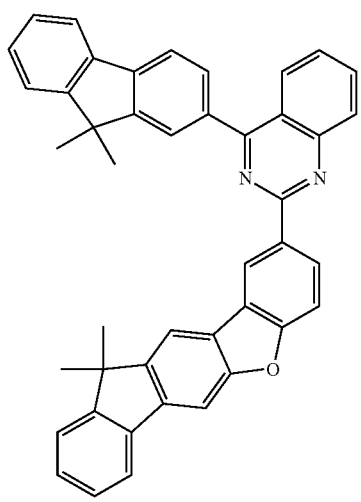
118
-continued
298
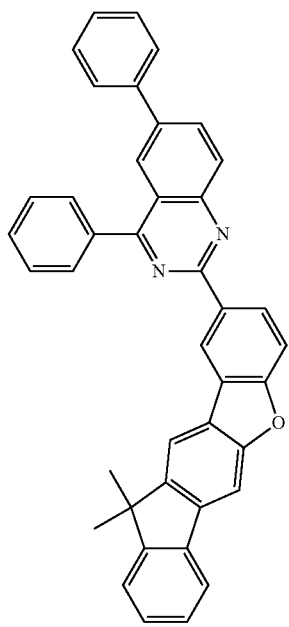
300
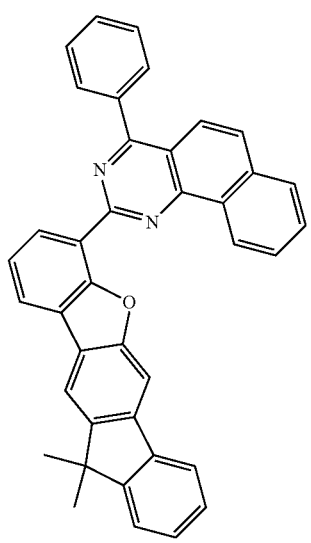
301
299
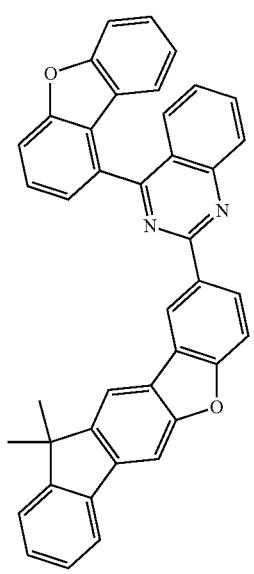
302
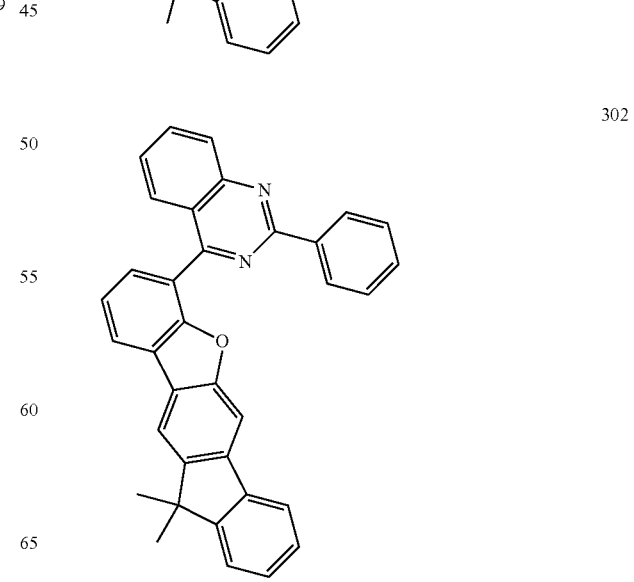

303
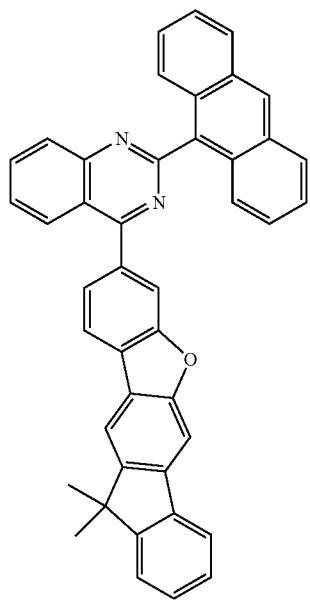
304
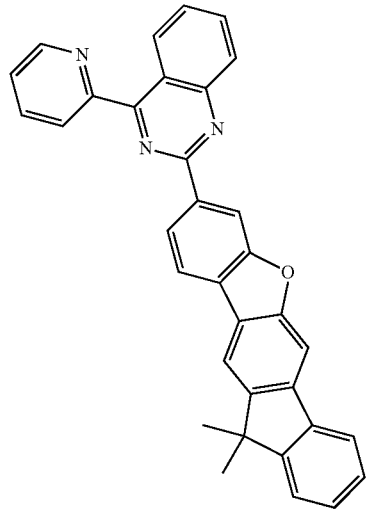
305
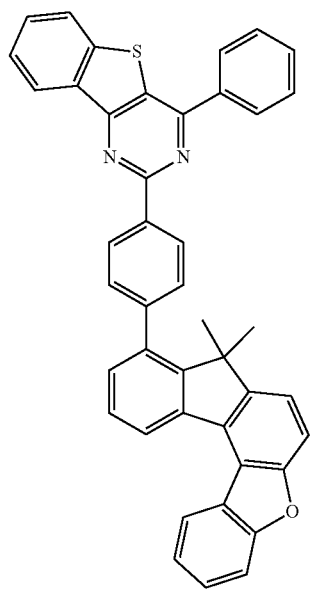
306
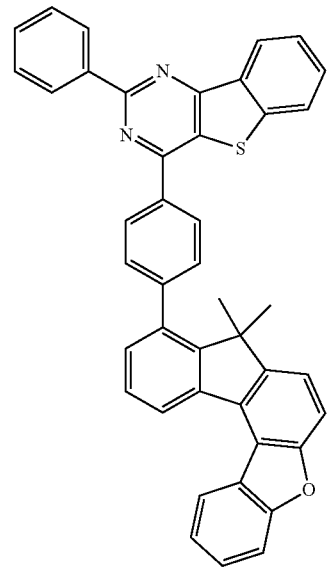
307

308 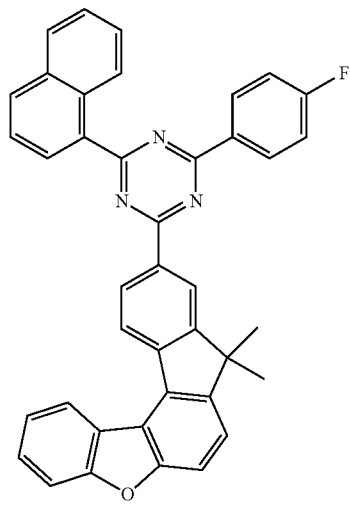
311 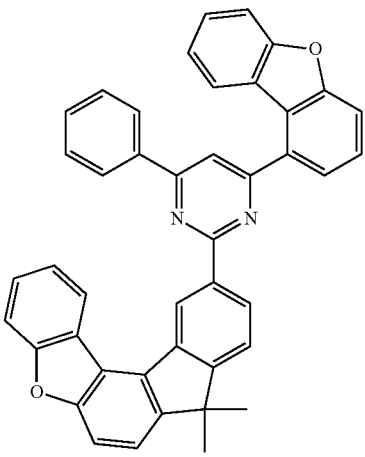
309 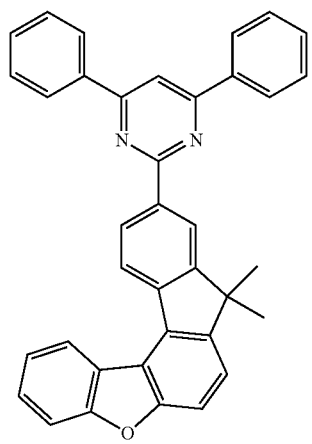
312 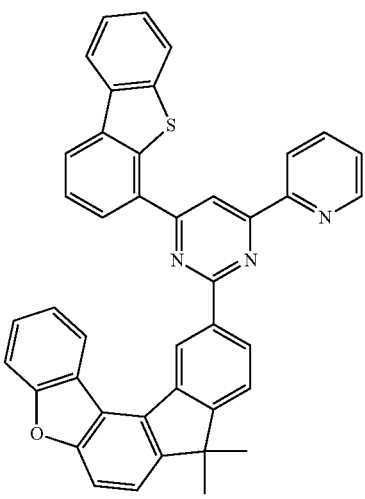
310 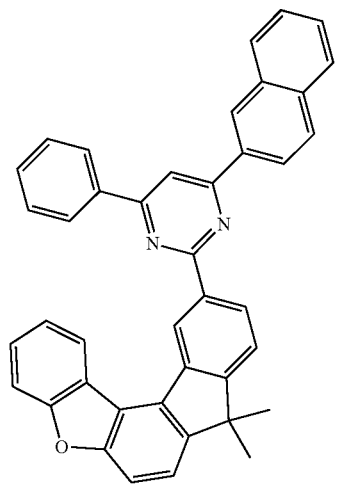
313 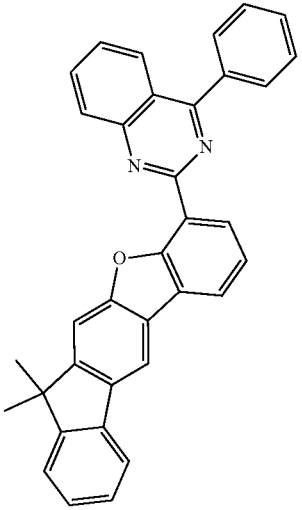

123
-continued
314
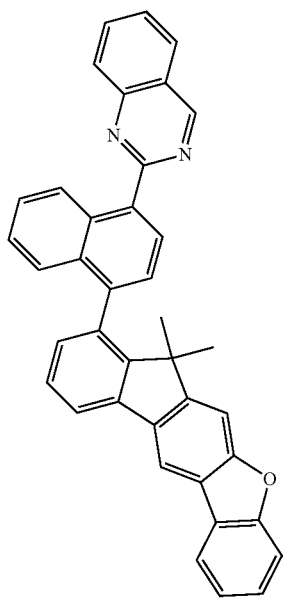
315
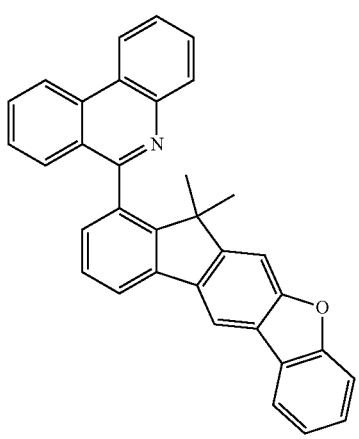
316
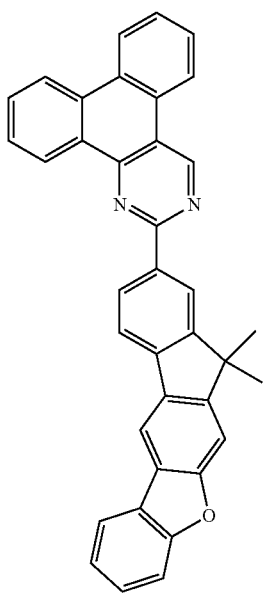
124
-continued
317
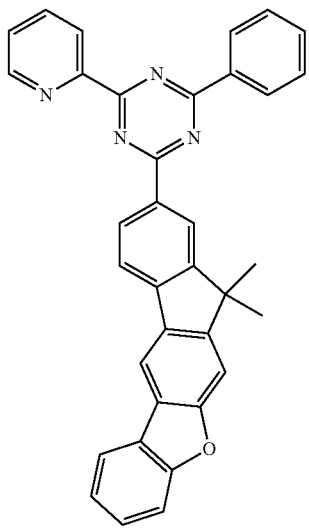
318
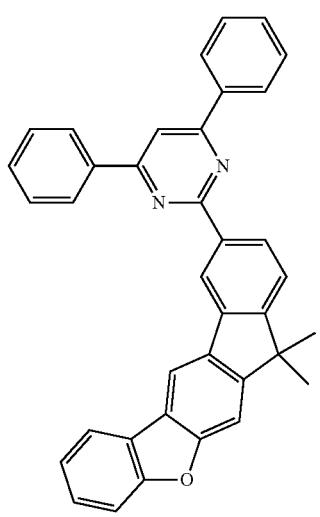
319
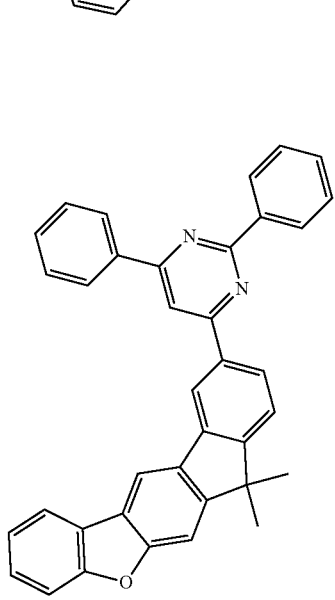

-continued
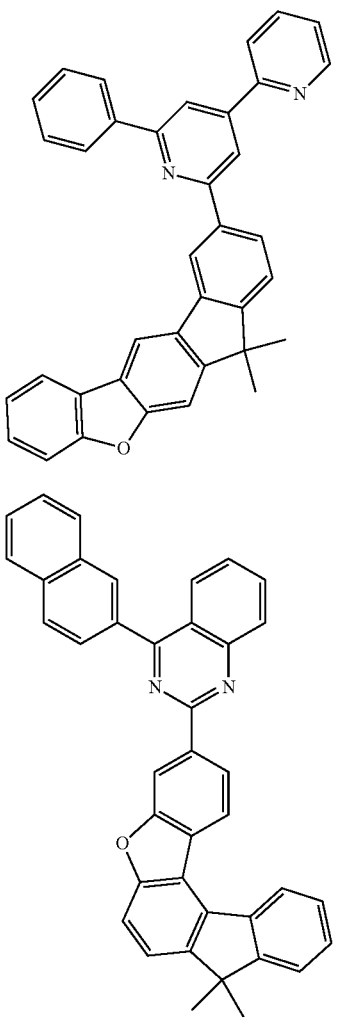
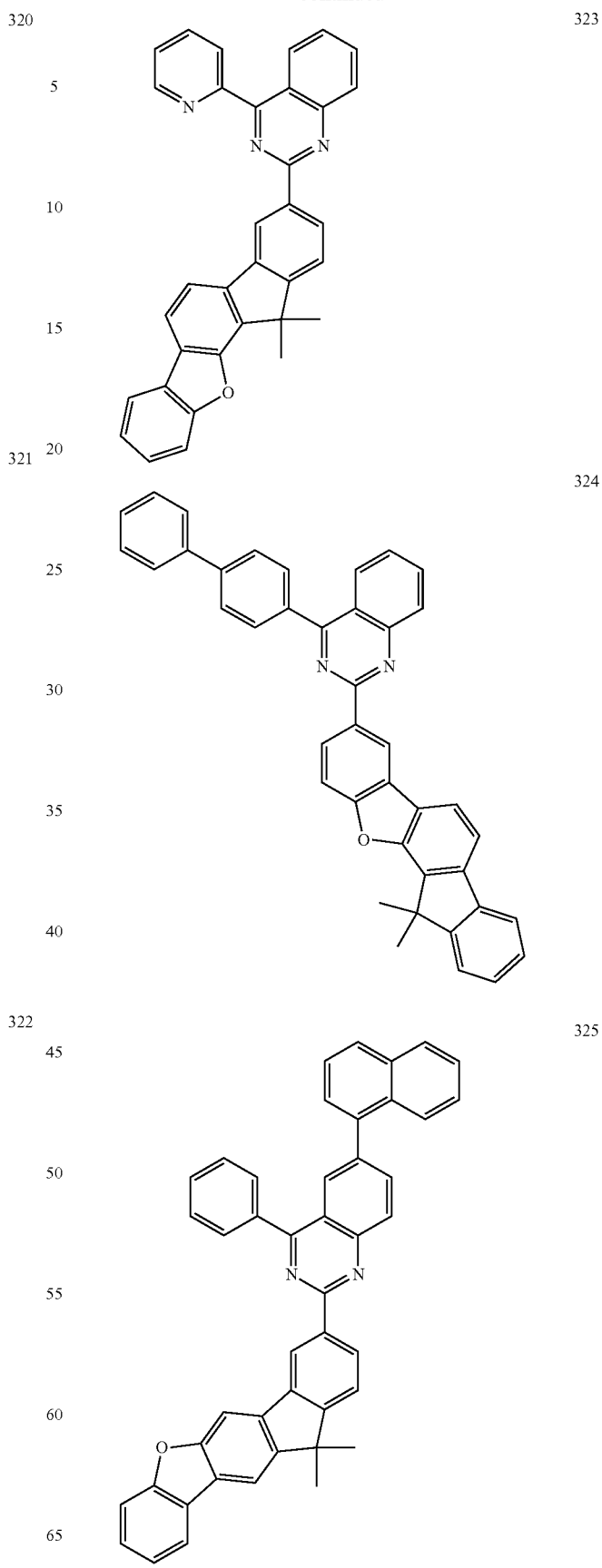

-continued
326
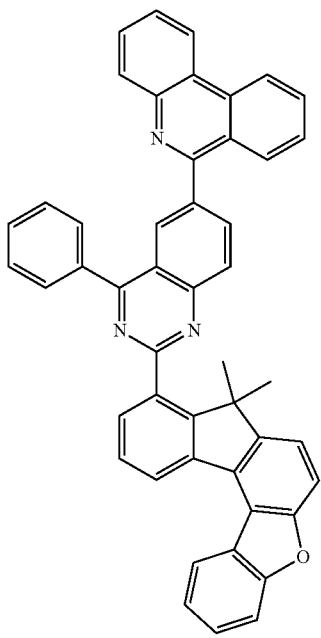
327
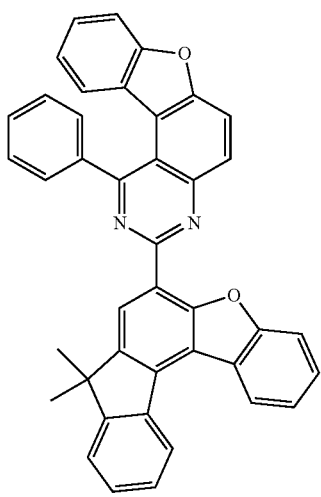
328
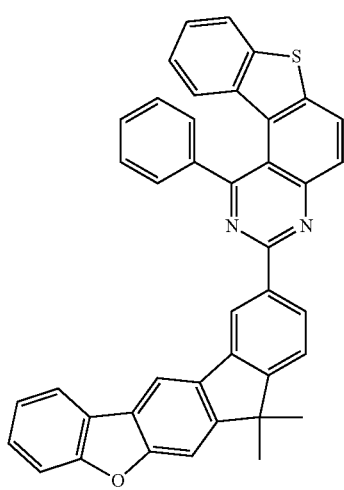
-continued
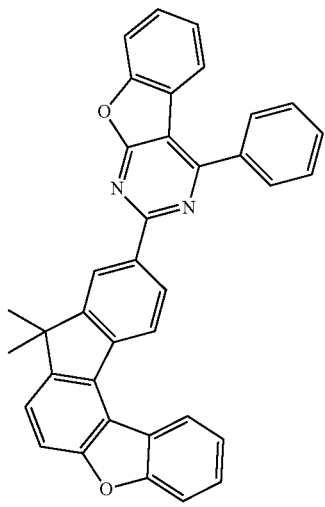
329
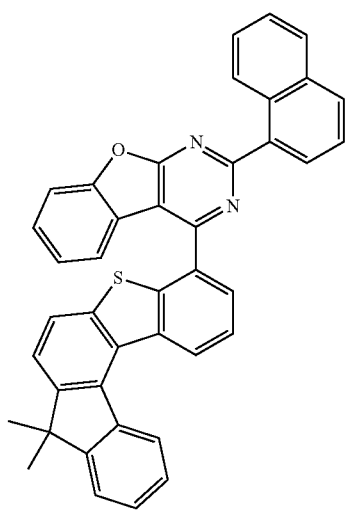
330
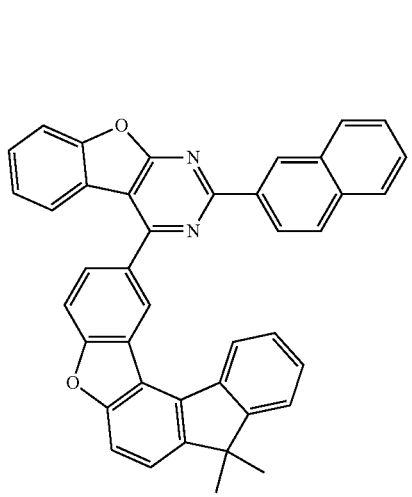
331

332
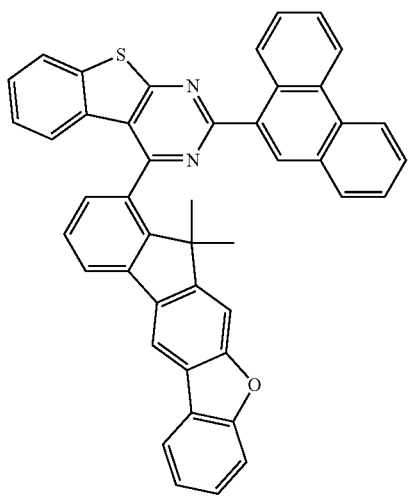
333
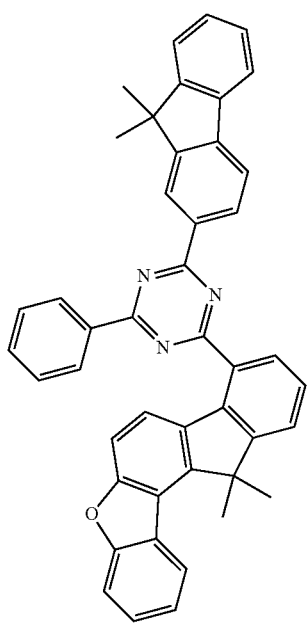
334
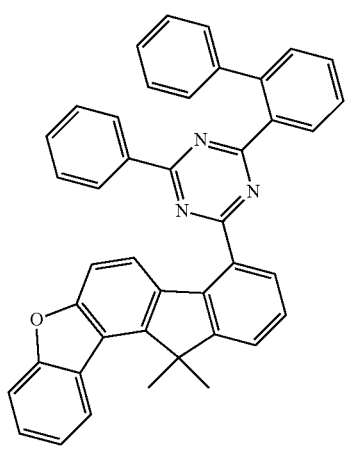
335
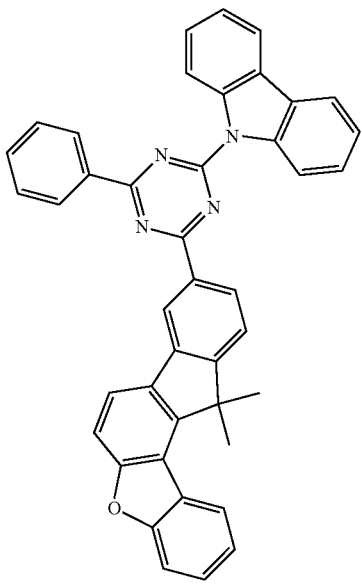
336
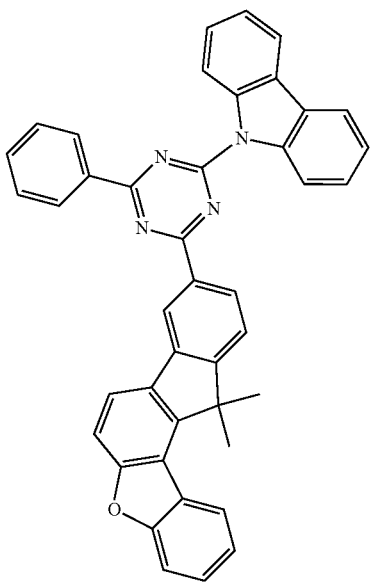

337
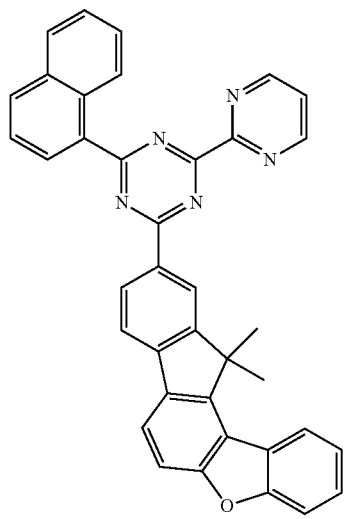
338
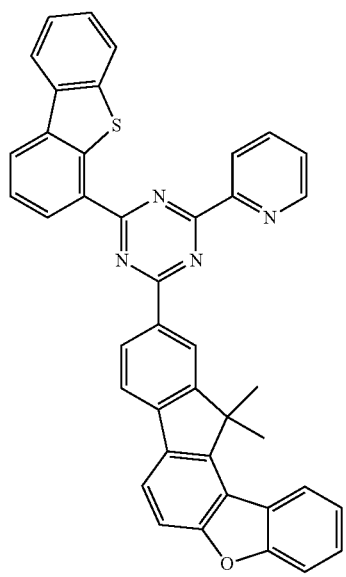
339
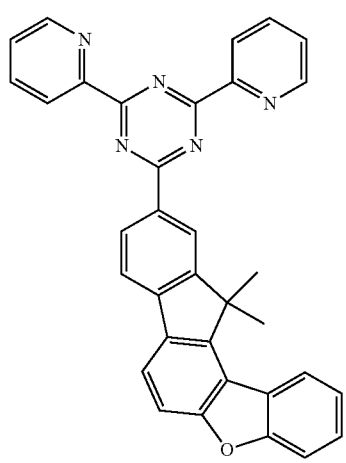
340
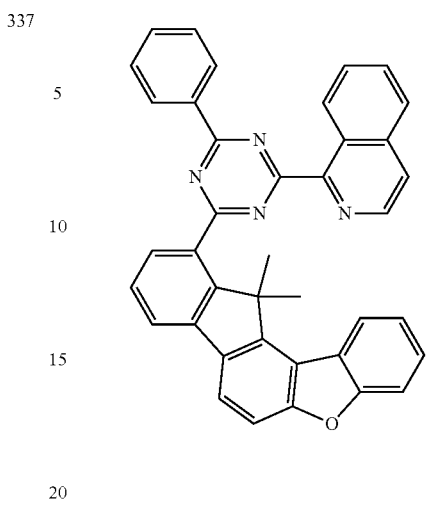
341
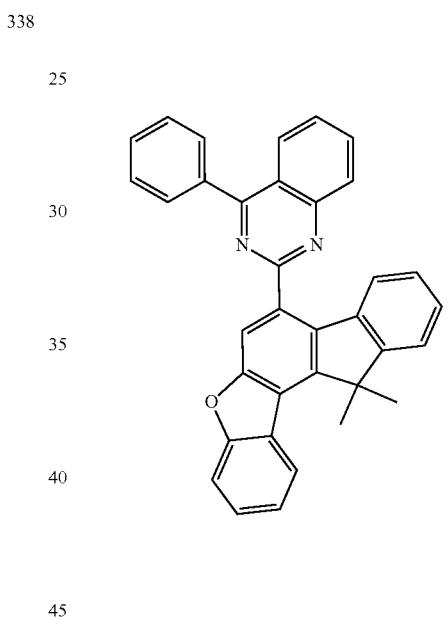
342
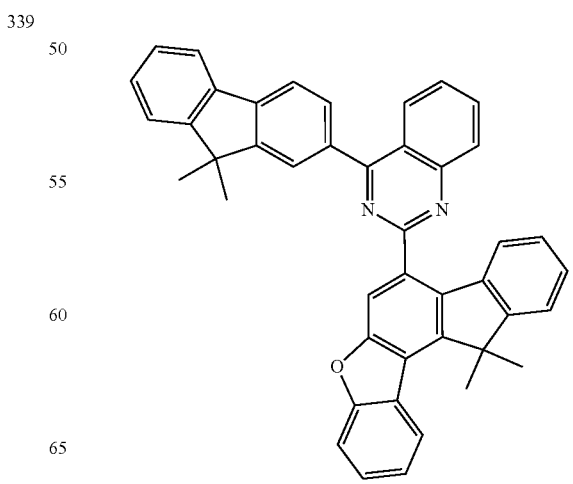

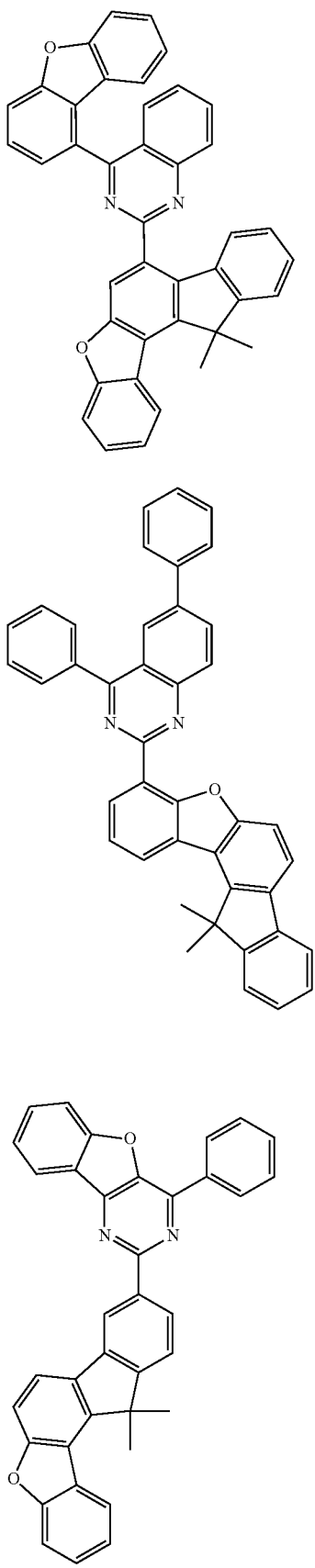
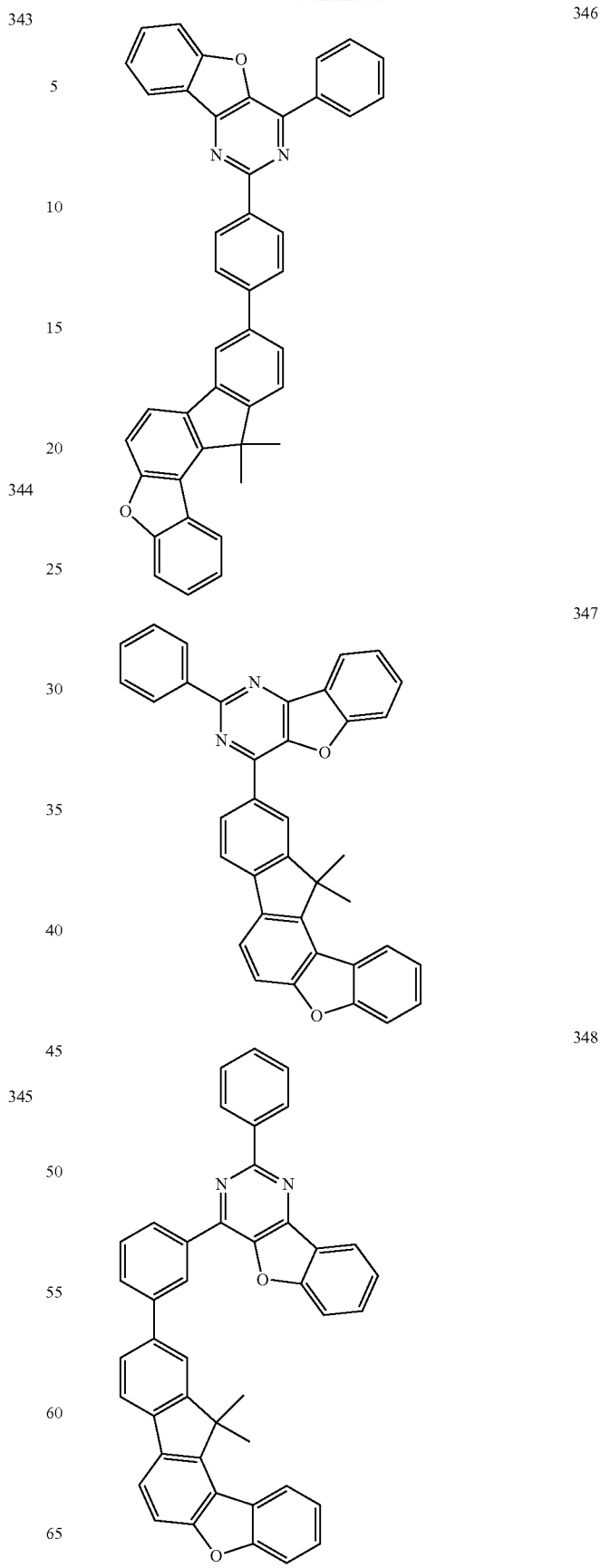

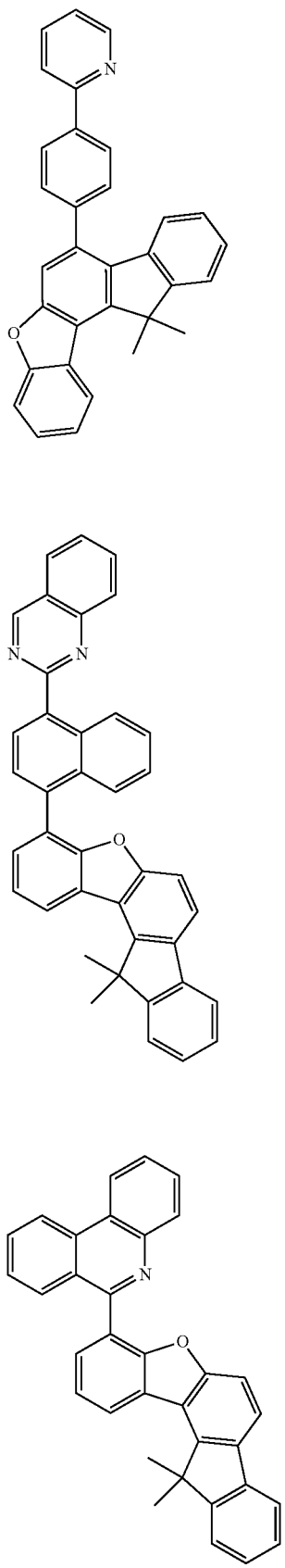
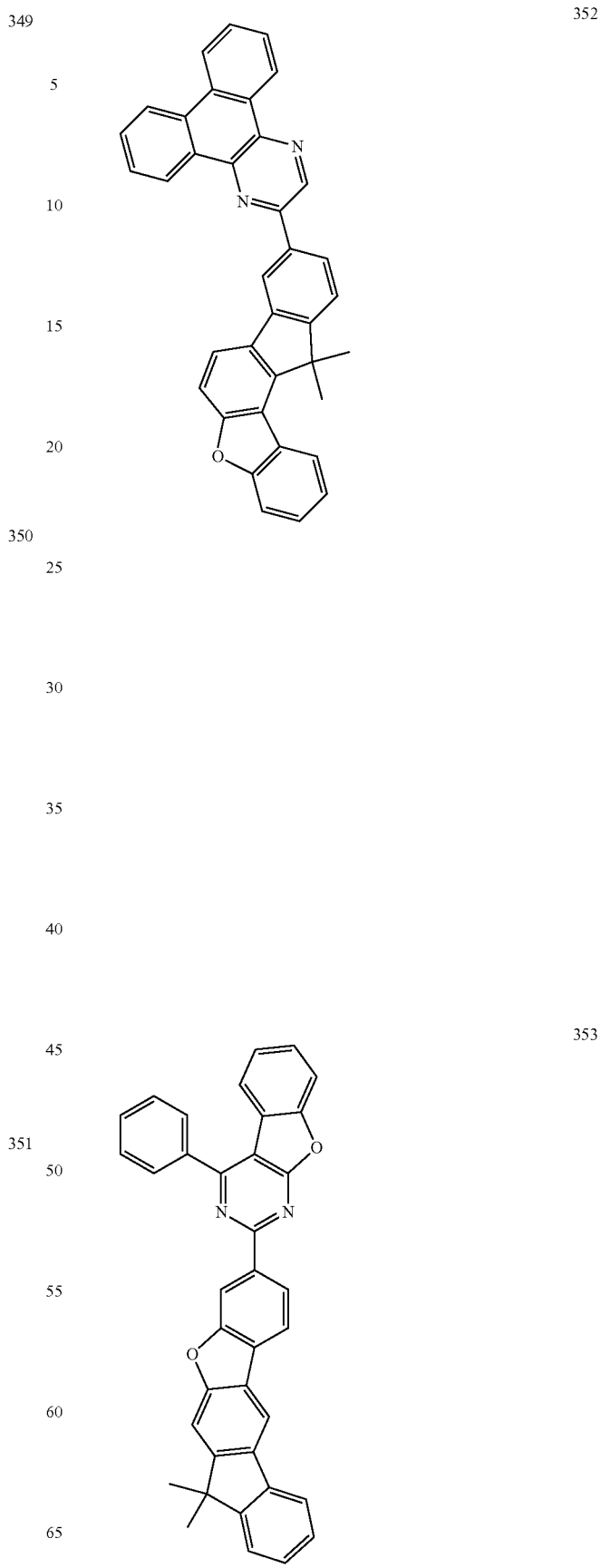

354
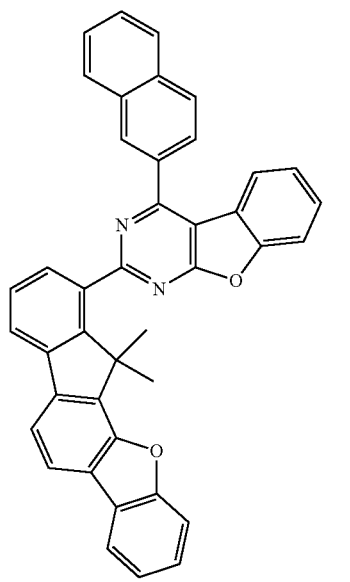
355
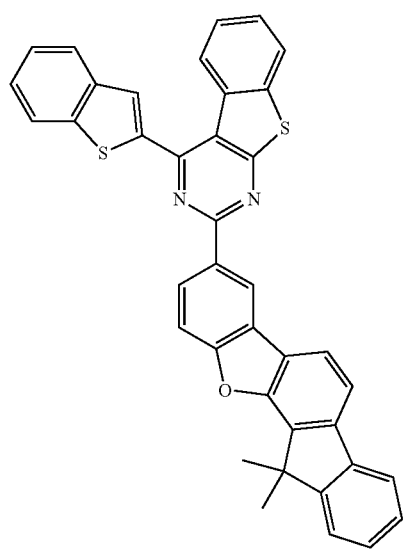
356
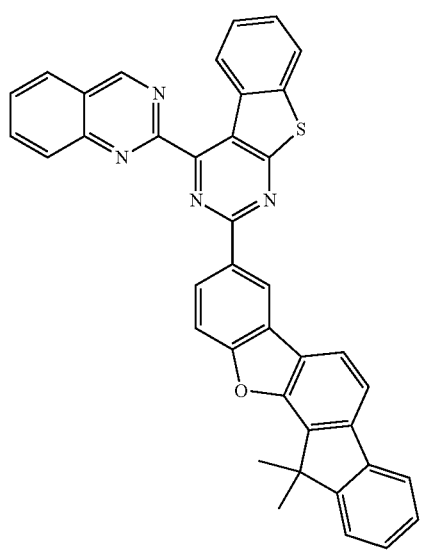
357
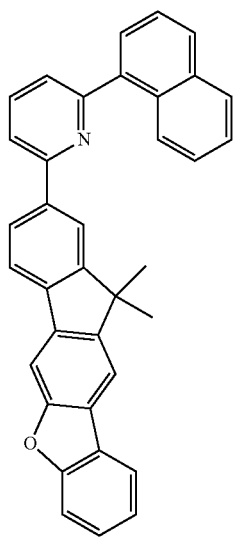
358
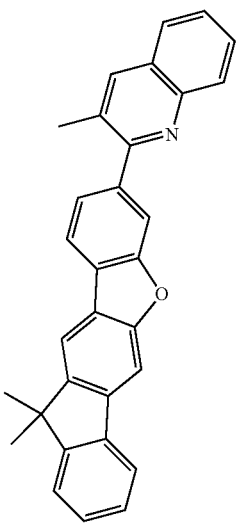
359
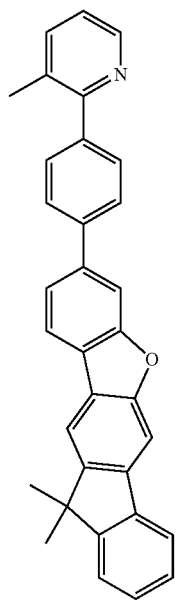

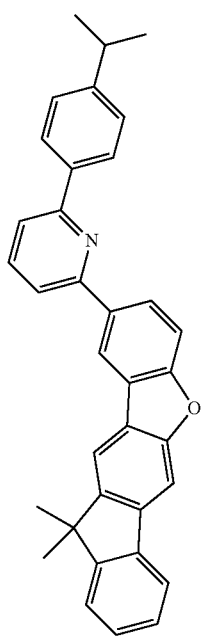
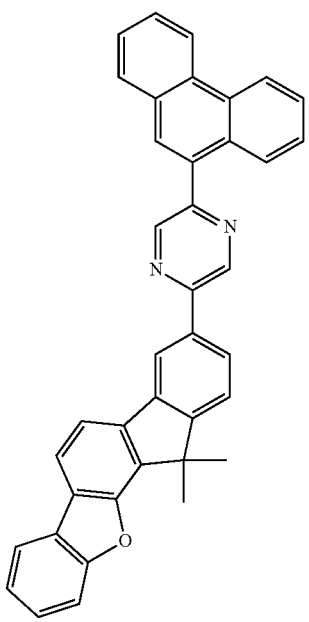
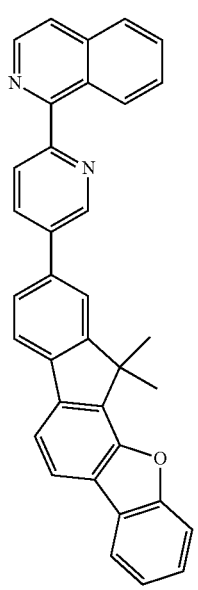
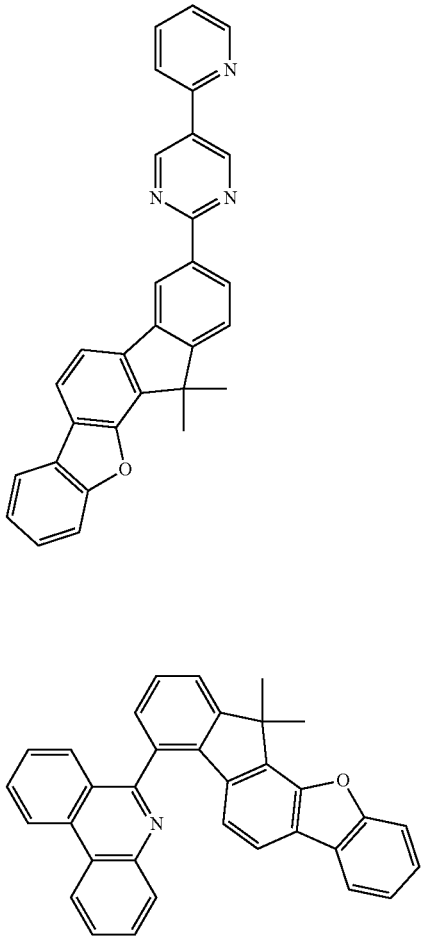

141
-continued
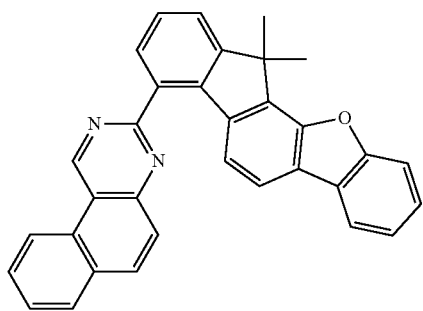
365
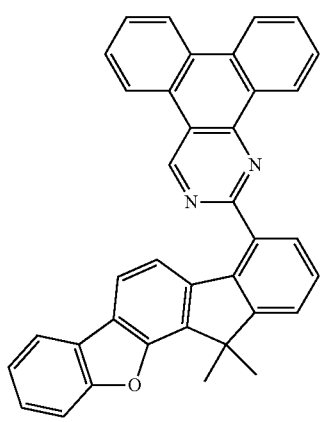
366
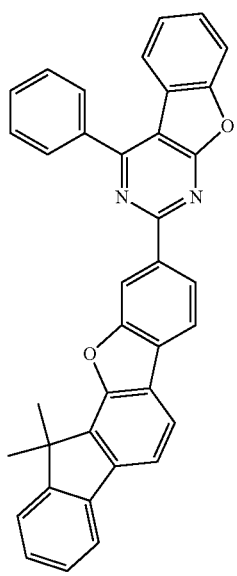
367
142
-continued
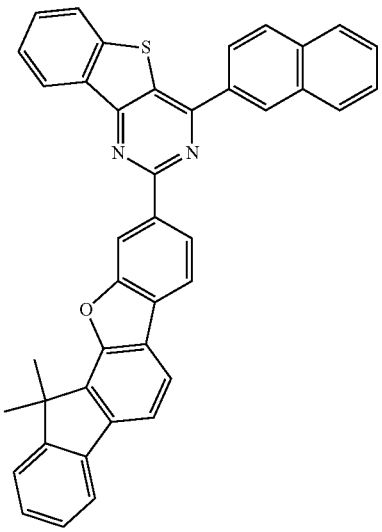
368
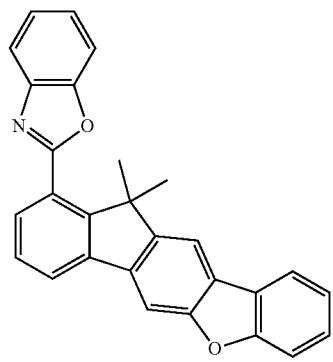
369
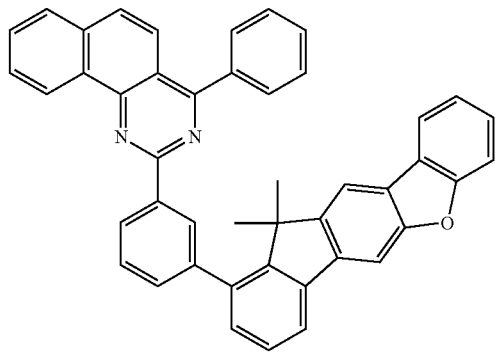
370

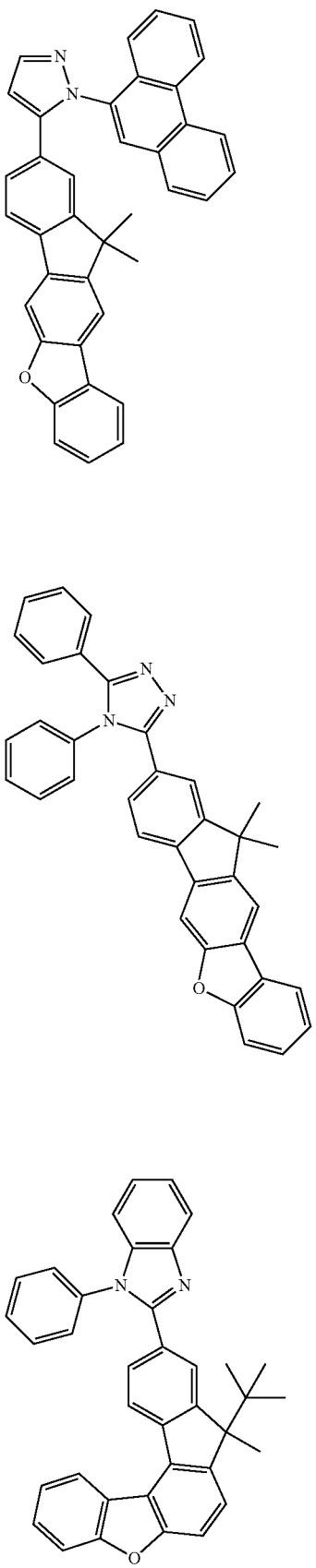
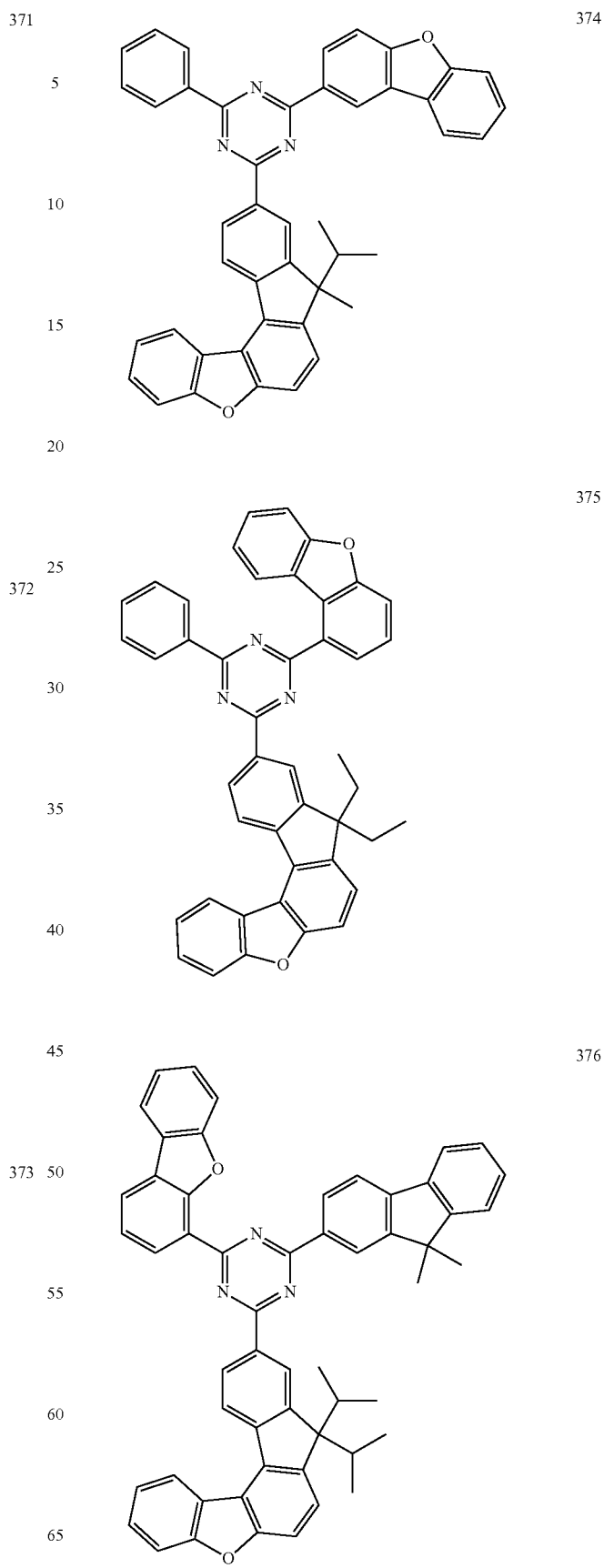

377
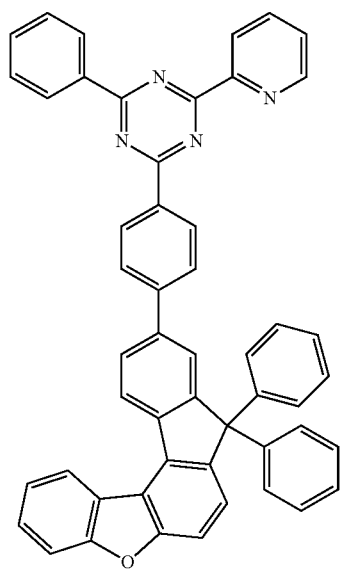
378
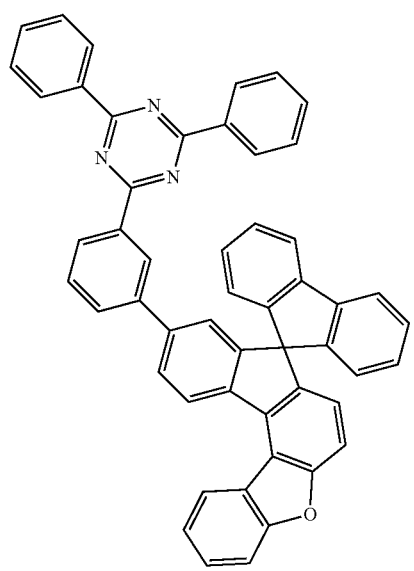
379
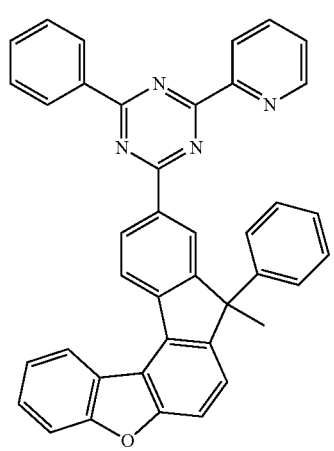
380
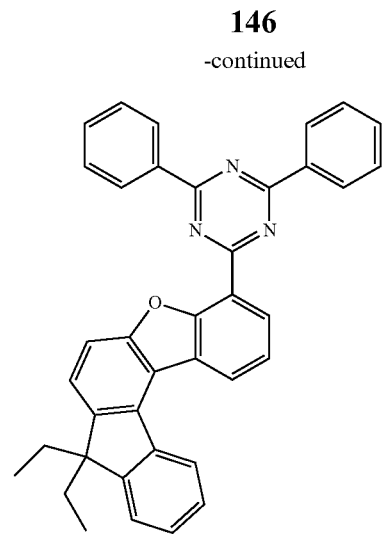
381
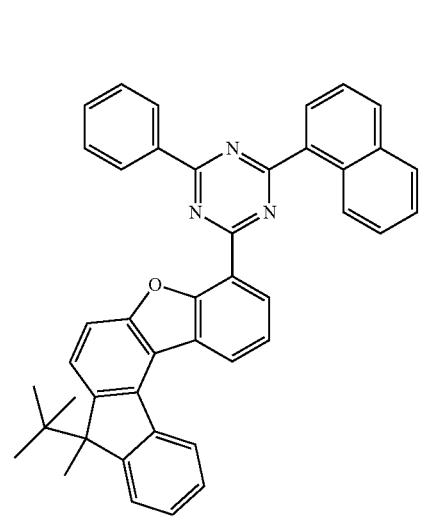
382
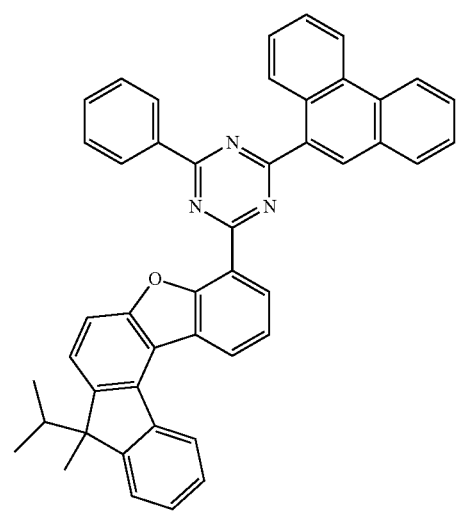

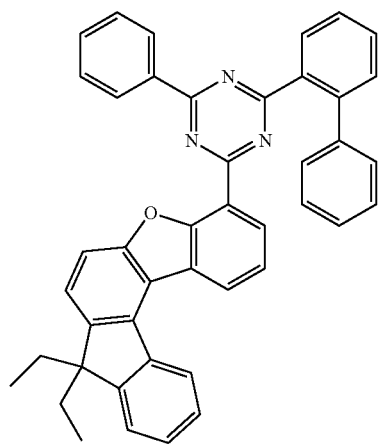
383
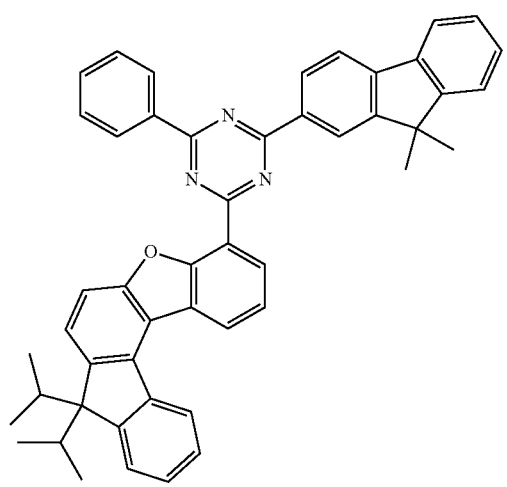
384
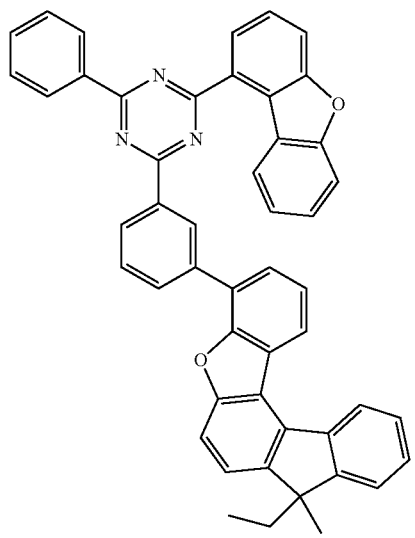
385
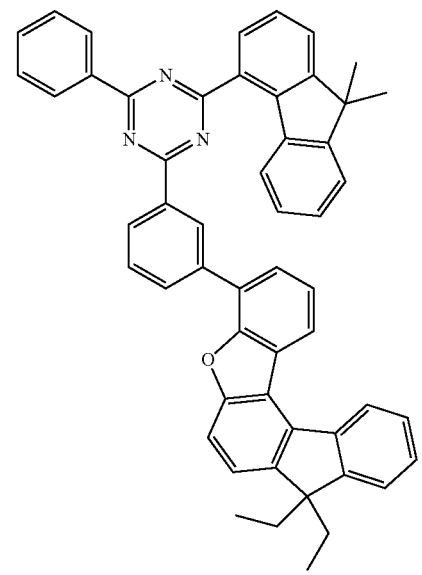
386
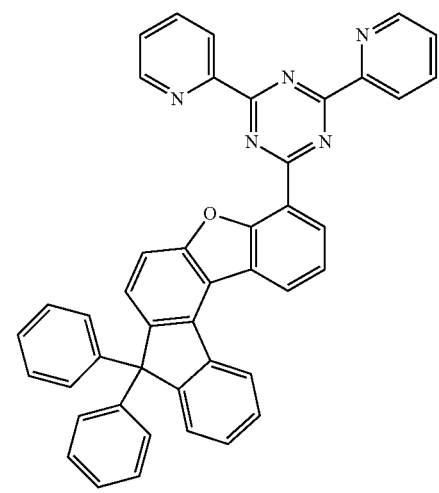
387
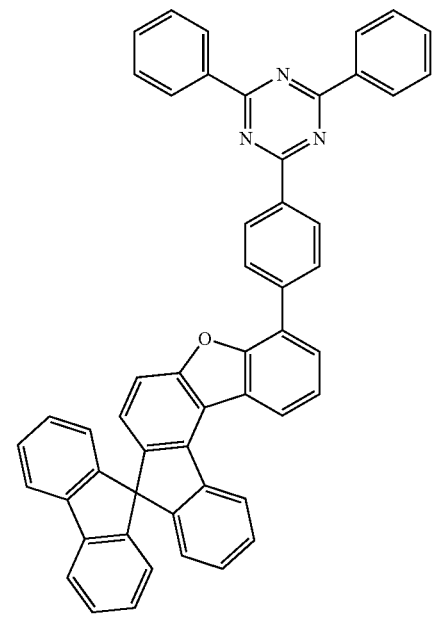
388

149
-continued
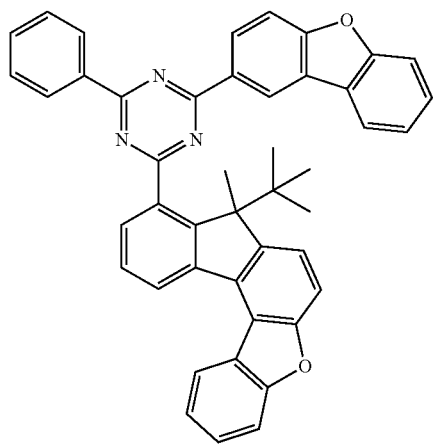
389
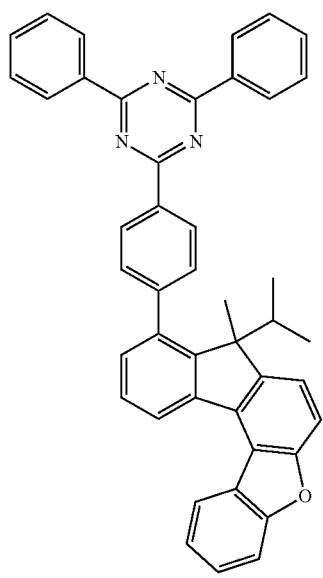
390
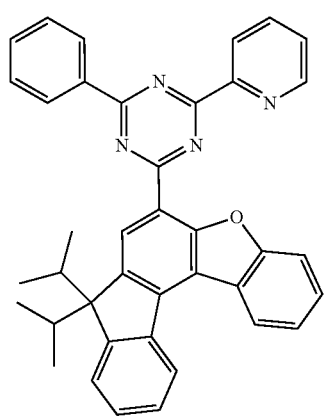
391
150
-continued
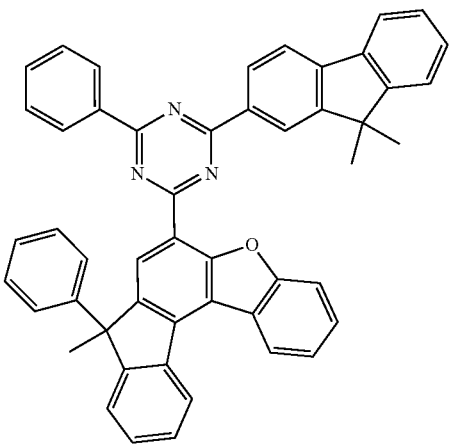
392
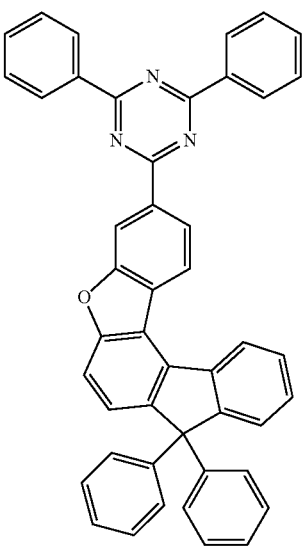
393
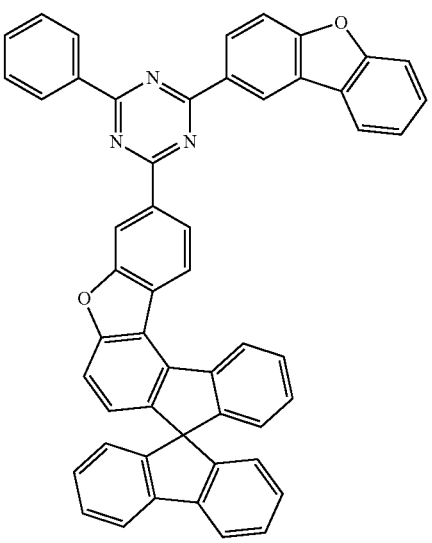
394

395
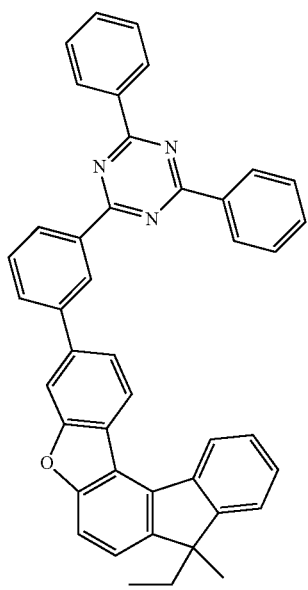
396
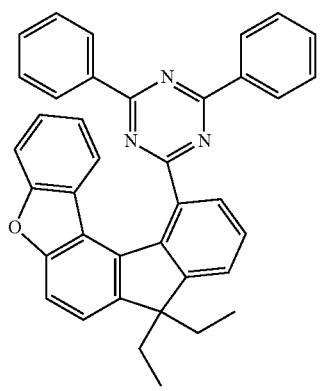
397
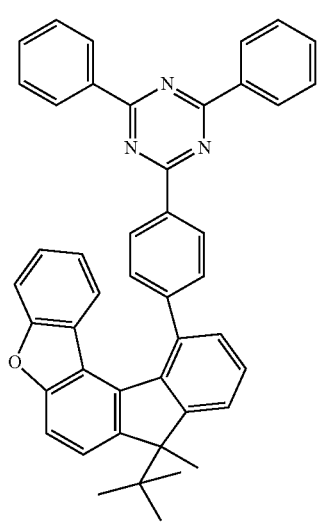
398
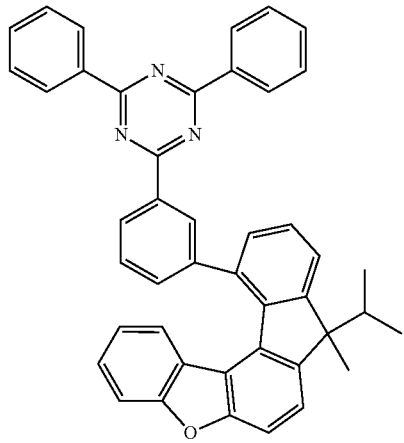
399
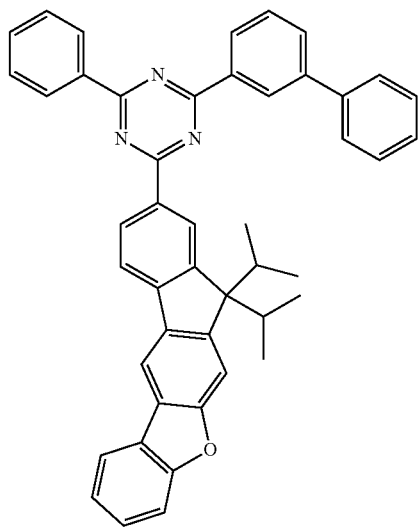
400
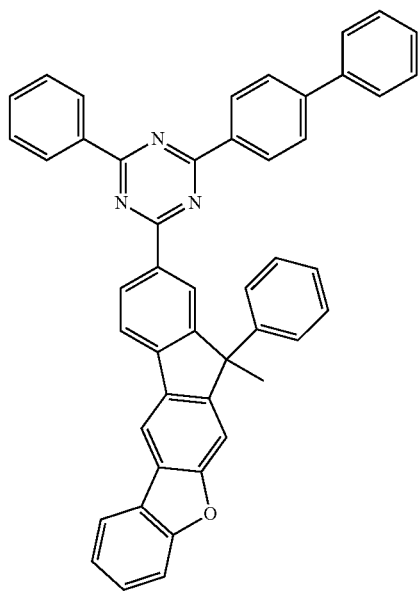

153
-continued
401
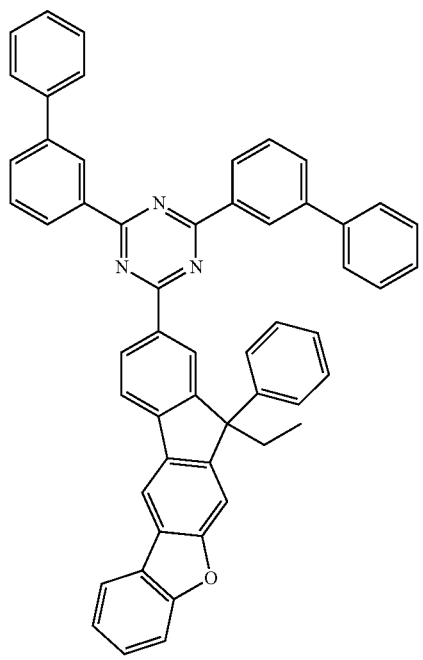
402
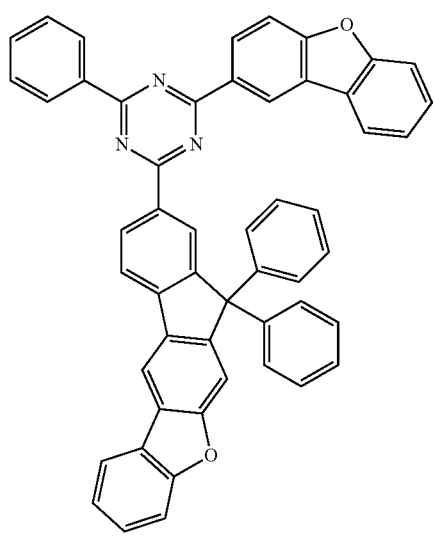
154
-continued
403
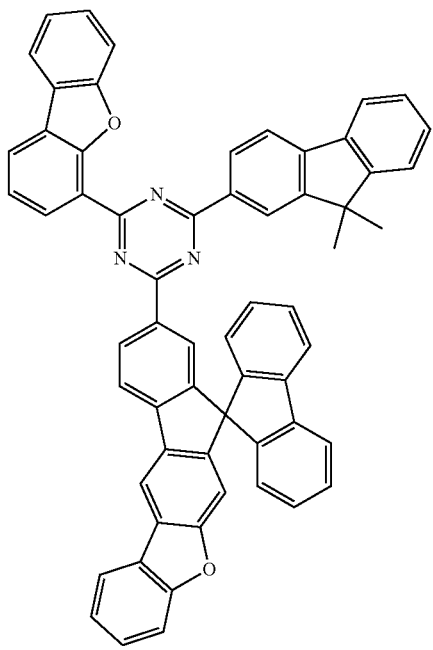
404
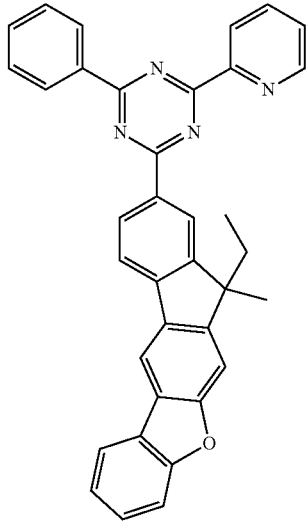

405
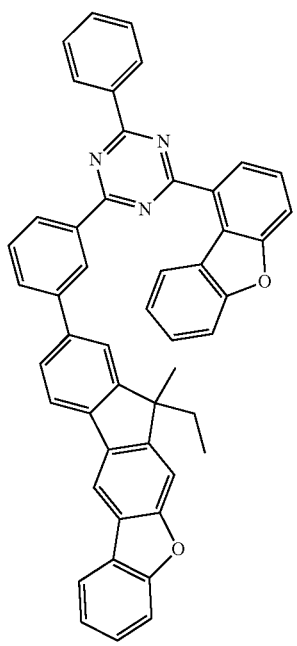
406
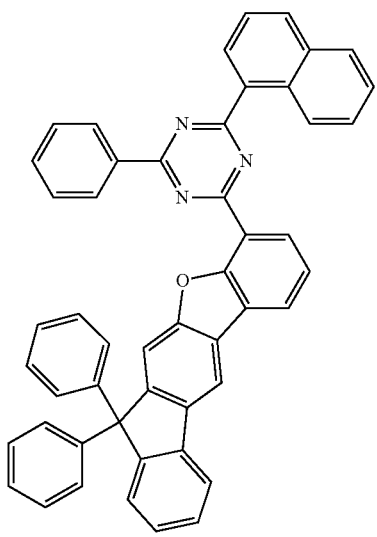
407
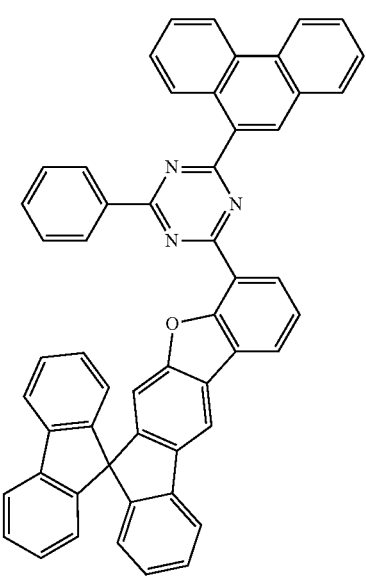
408
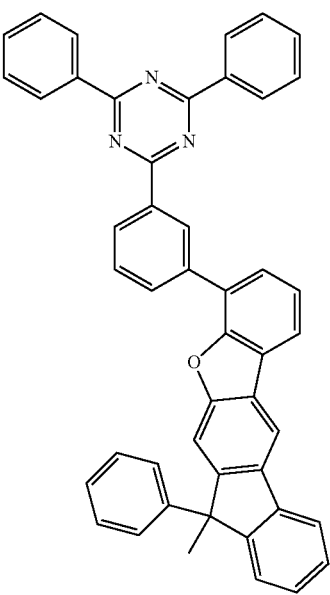

409
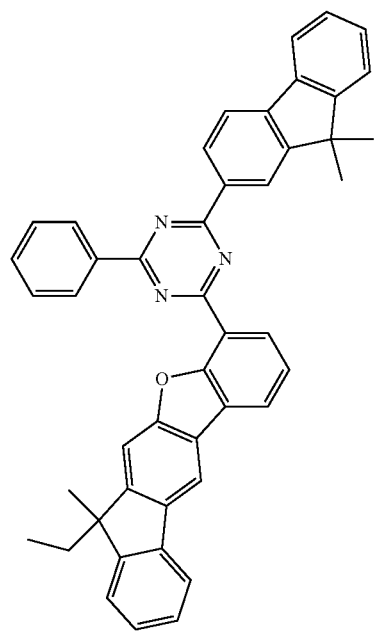
410
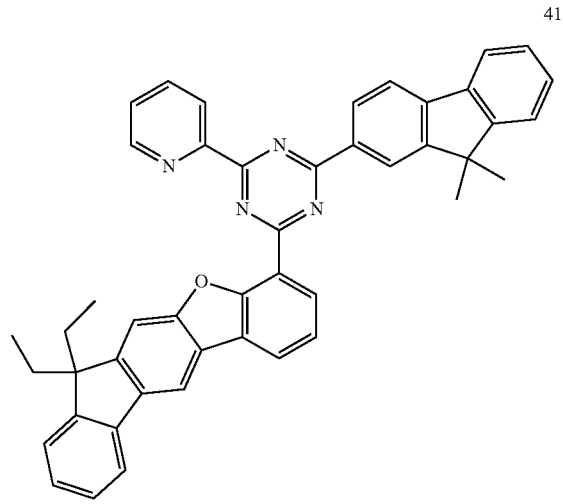
411
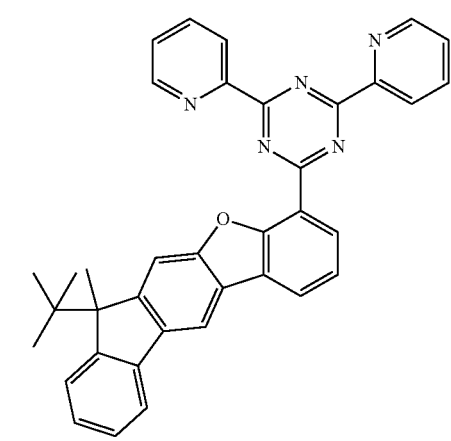
412
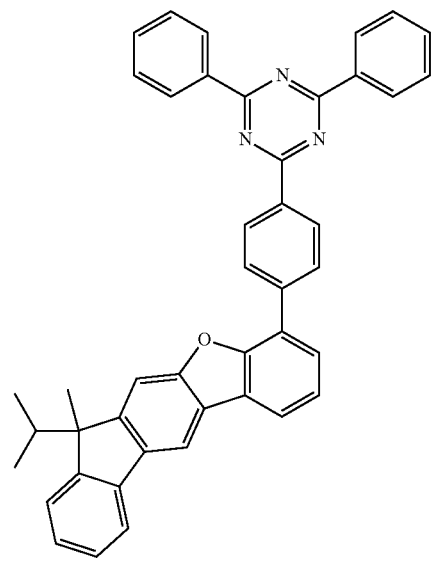
413
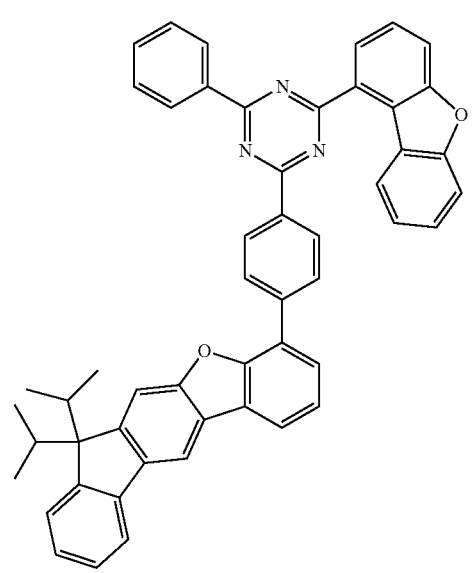
414
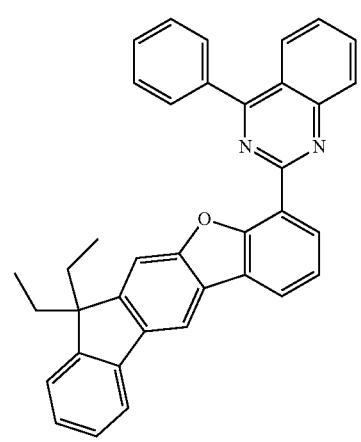

415
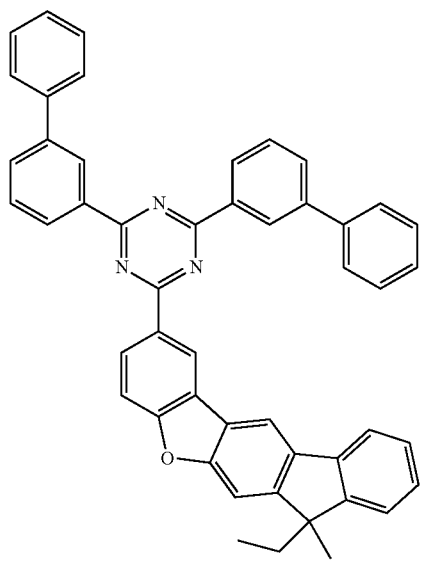
416
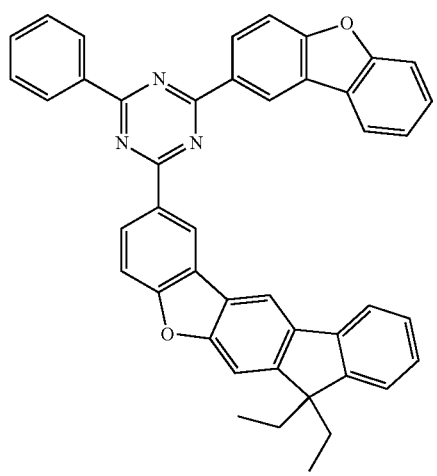
417
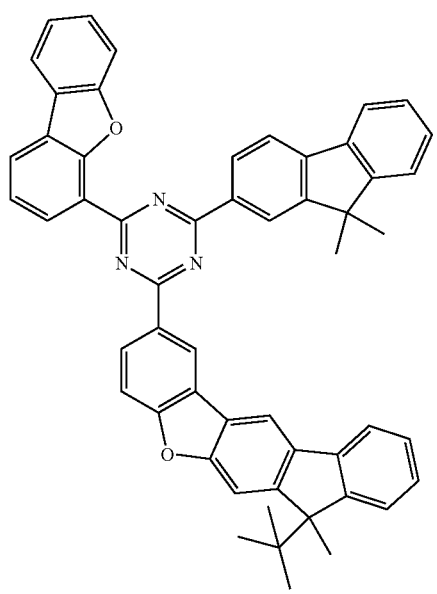
418
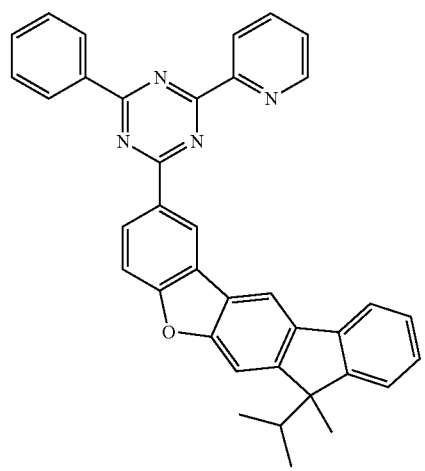
419
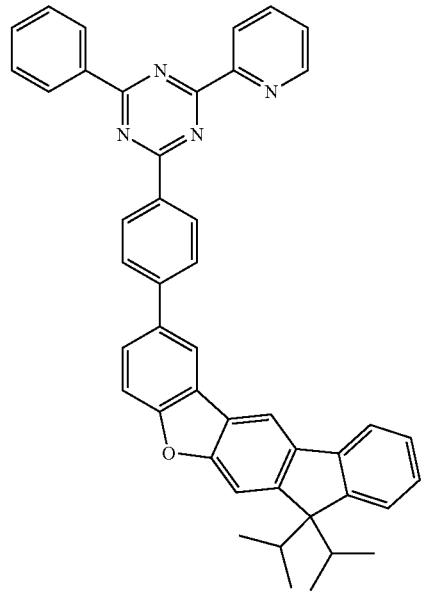

420
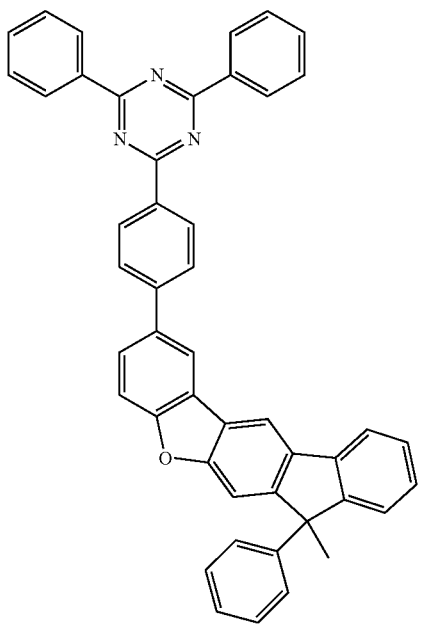
421
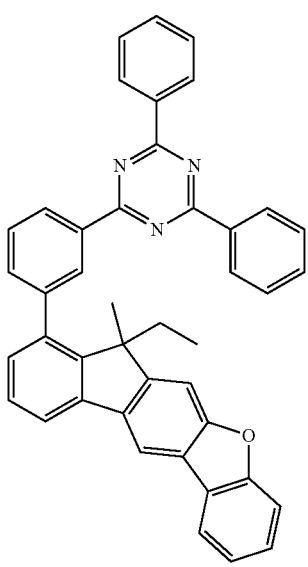
422
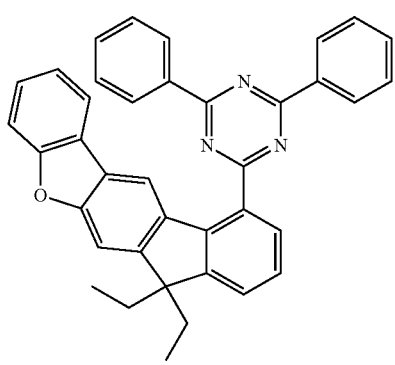
423
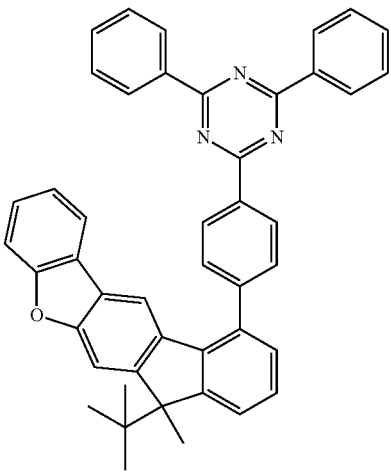
424
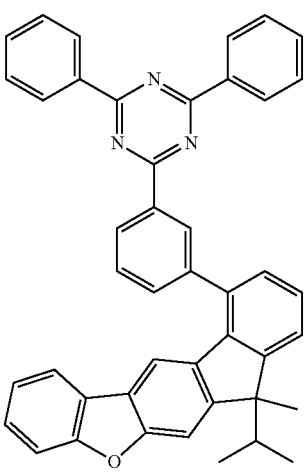
425
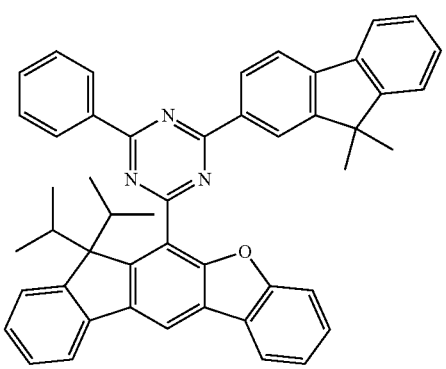

426
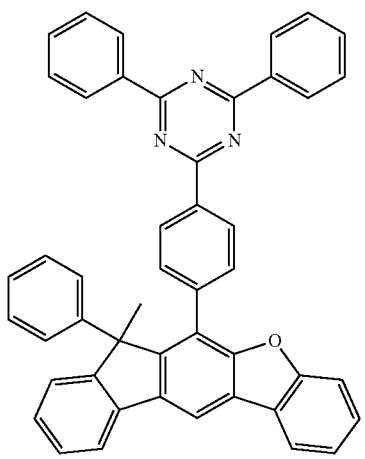
427
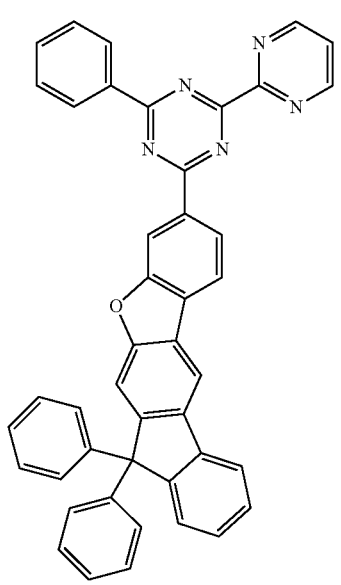
428
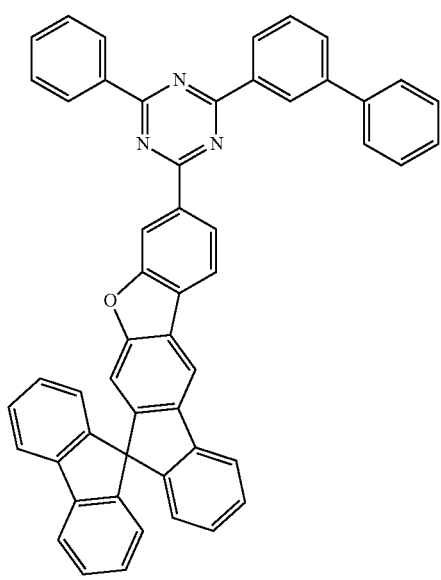
429
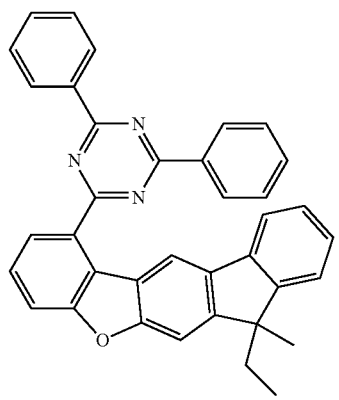
430
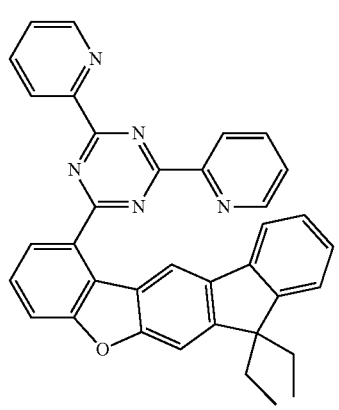
431
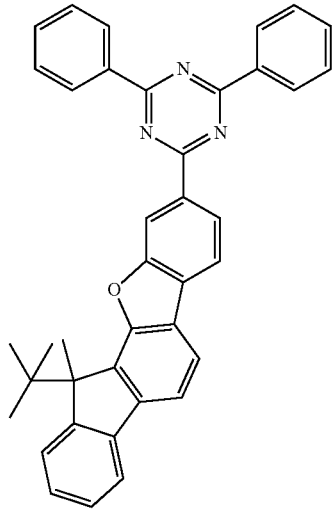

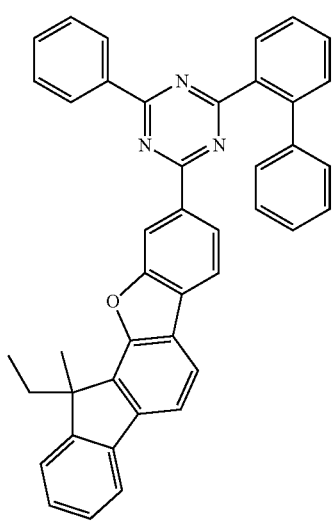
432
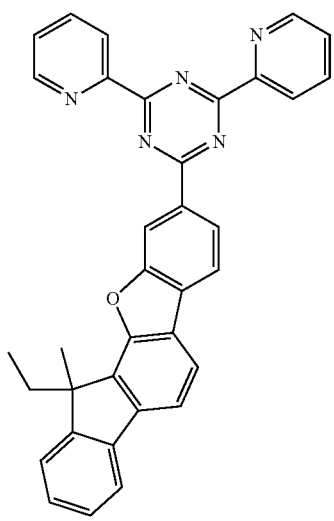
433
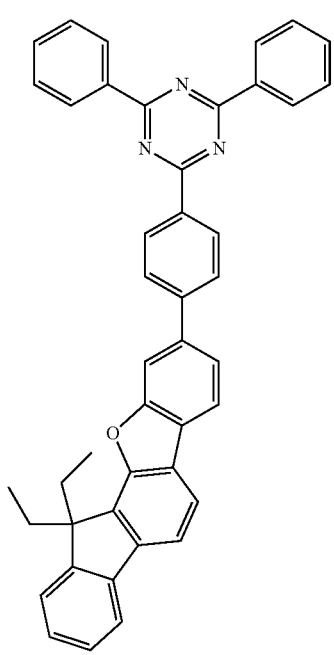
434
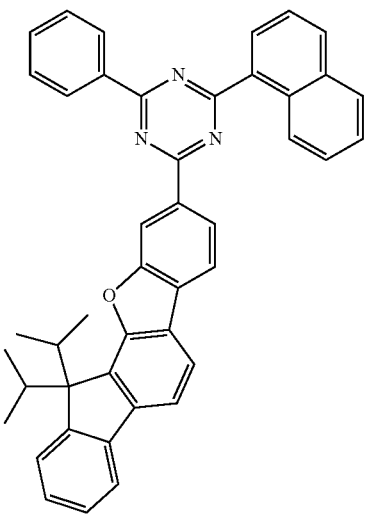
435
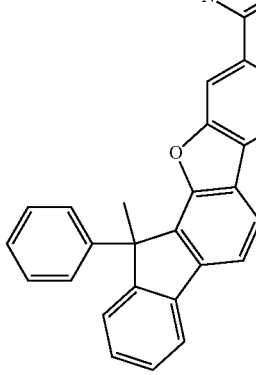
436
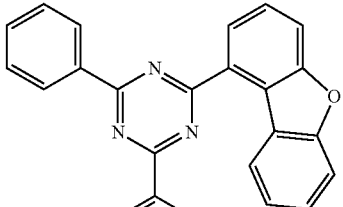
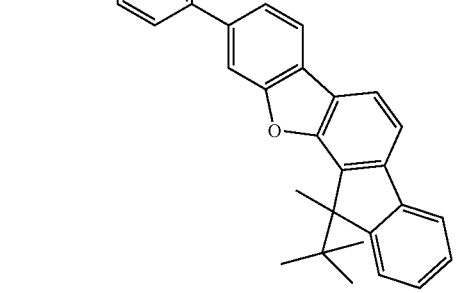

167
-continued
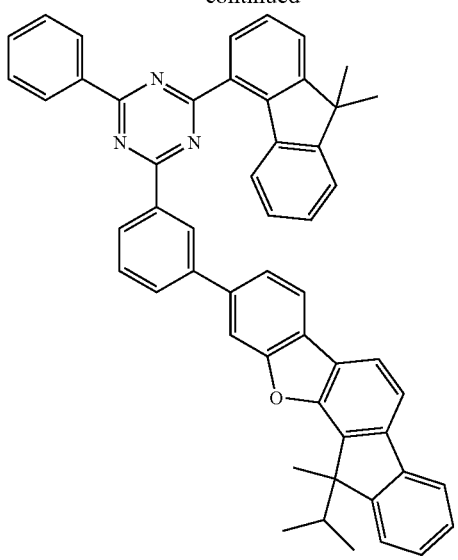
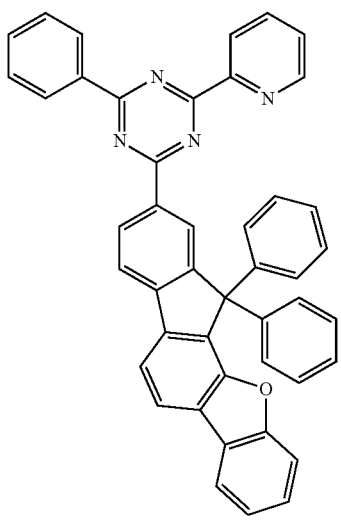
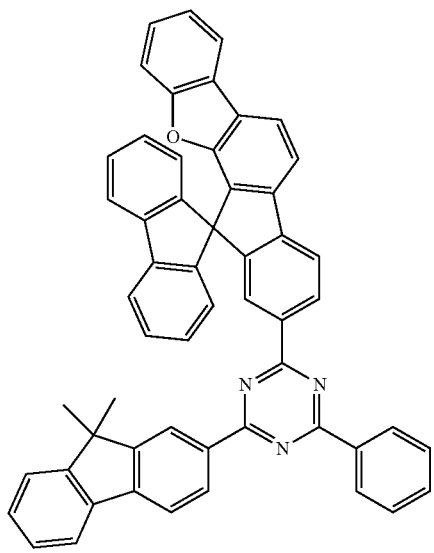
168
-continued
437
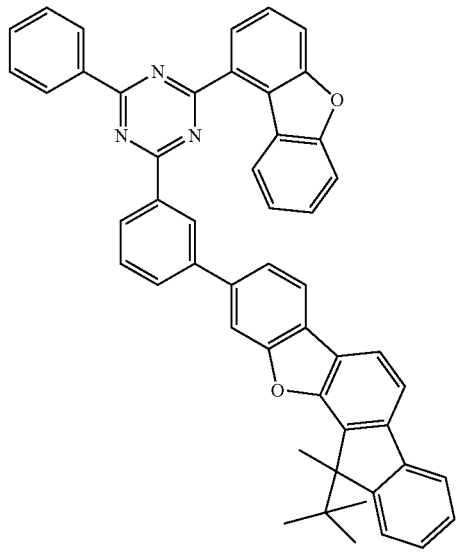
438
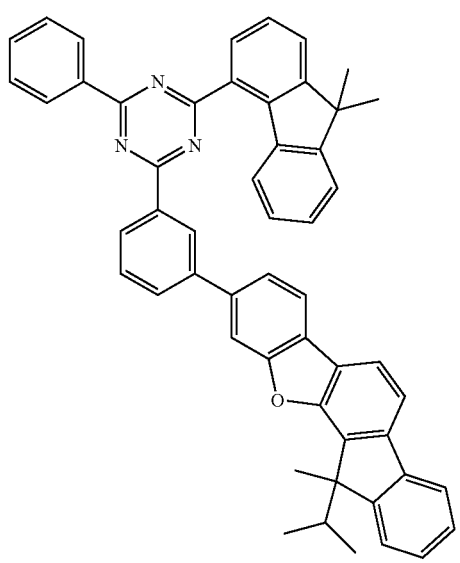
439
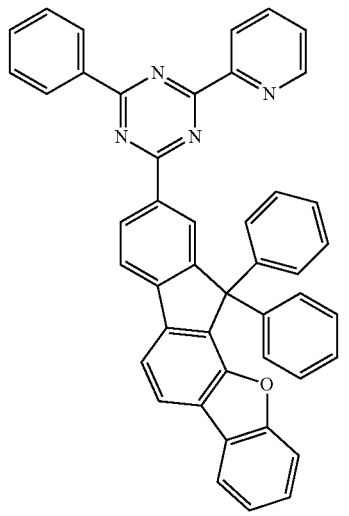

169
-continued
440
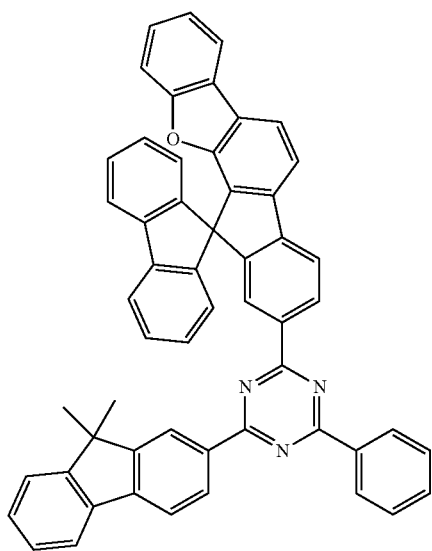
441
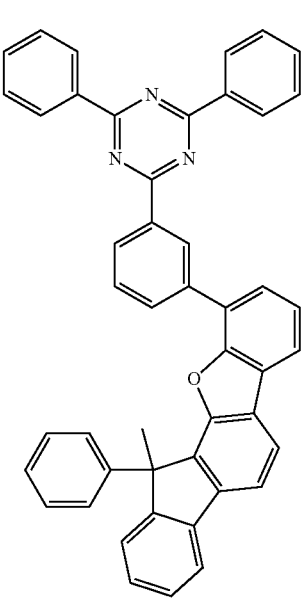
442
170
-continued
443
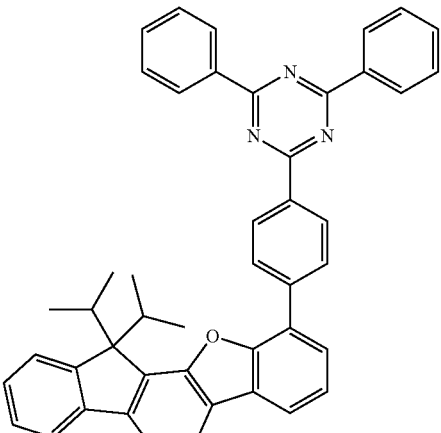
444
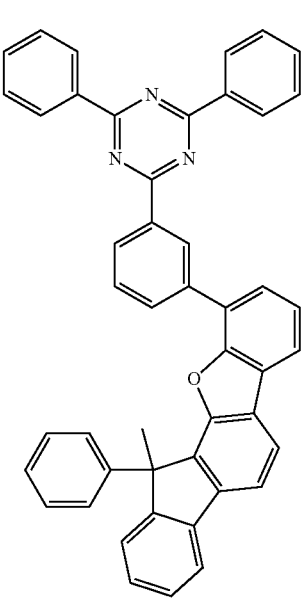
445
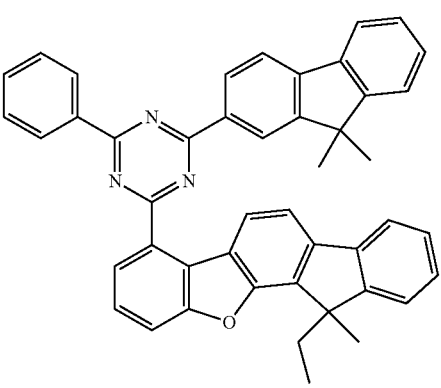

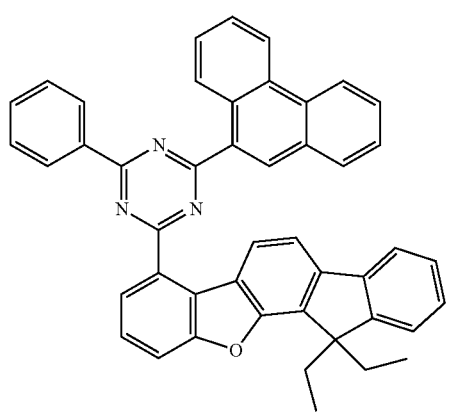
446
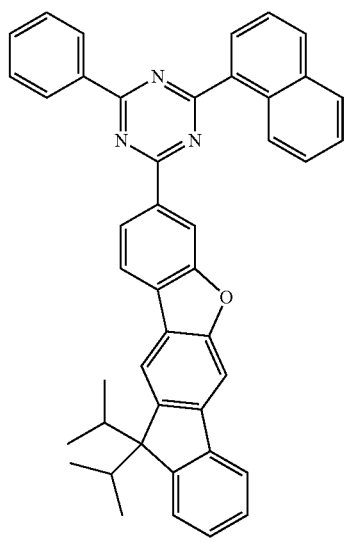
449
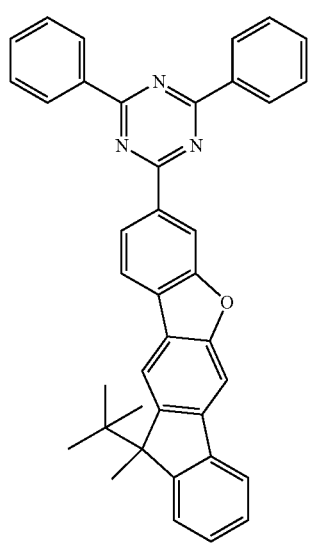
447
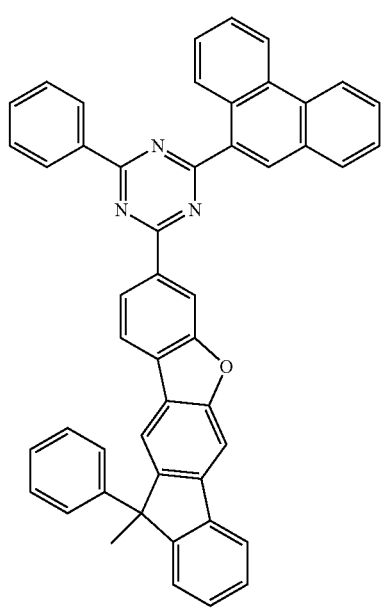
450
448

173
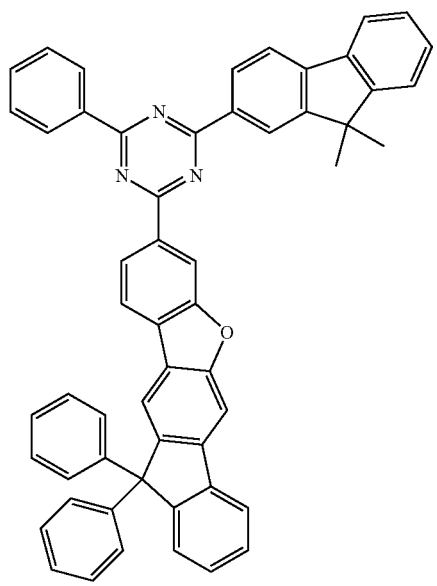
451
174
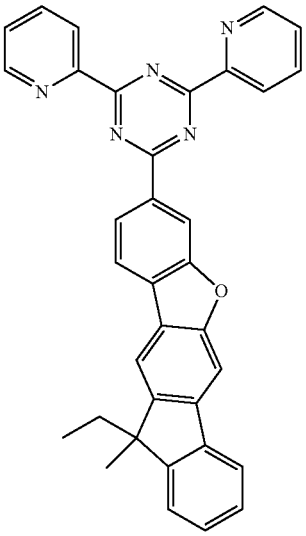
453
452
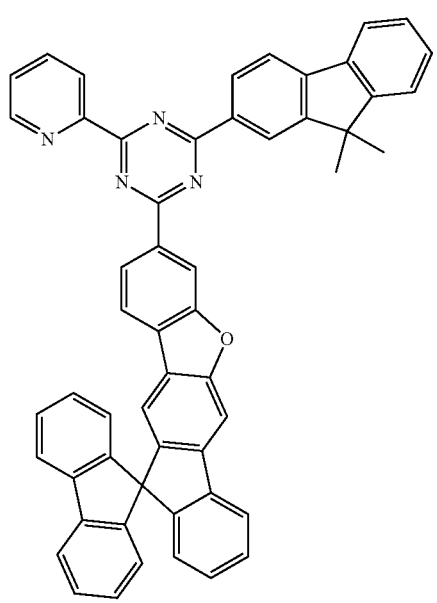
454
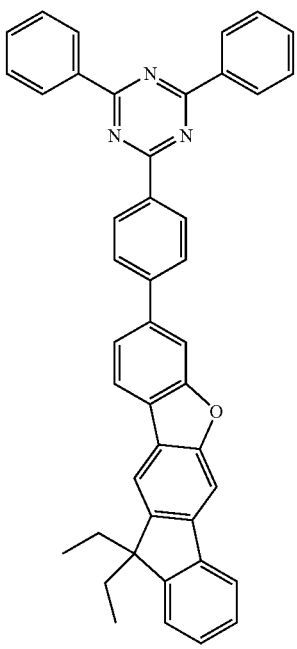

175
-continued
455
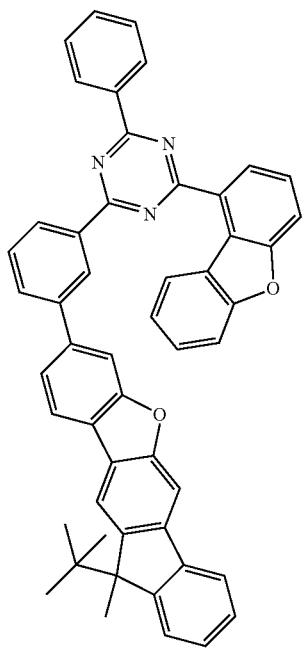
456
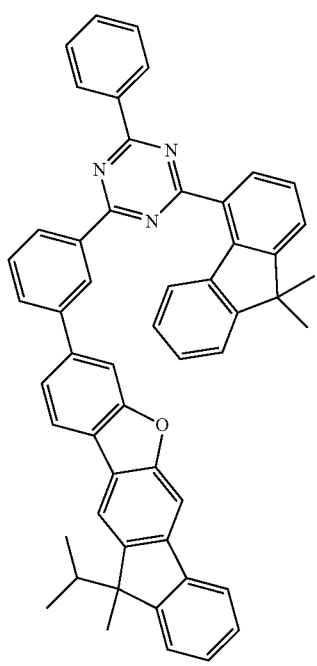
176
-continued
457
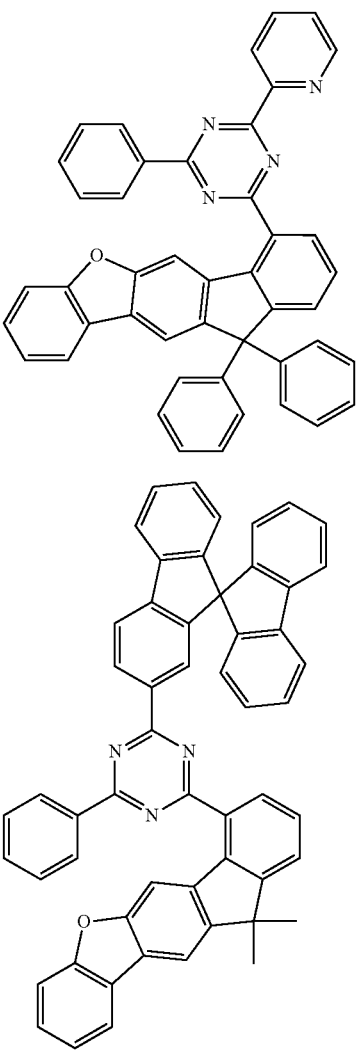
458
459
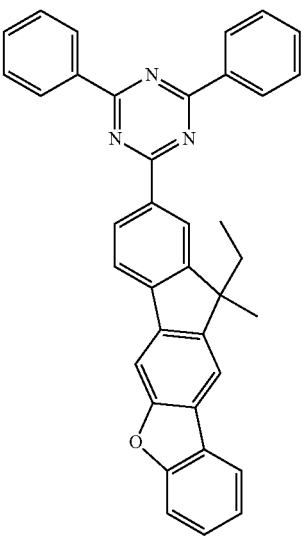

177
-continued
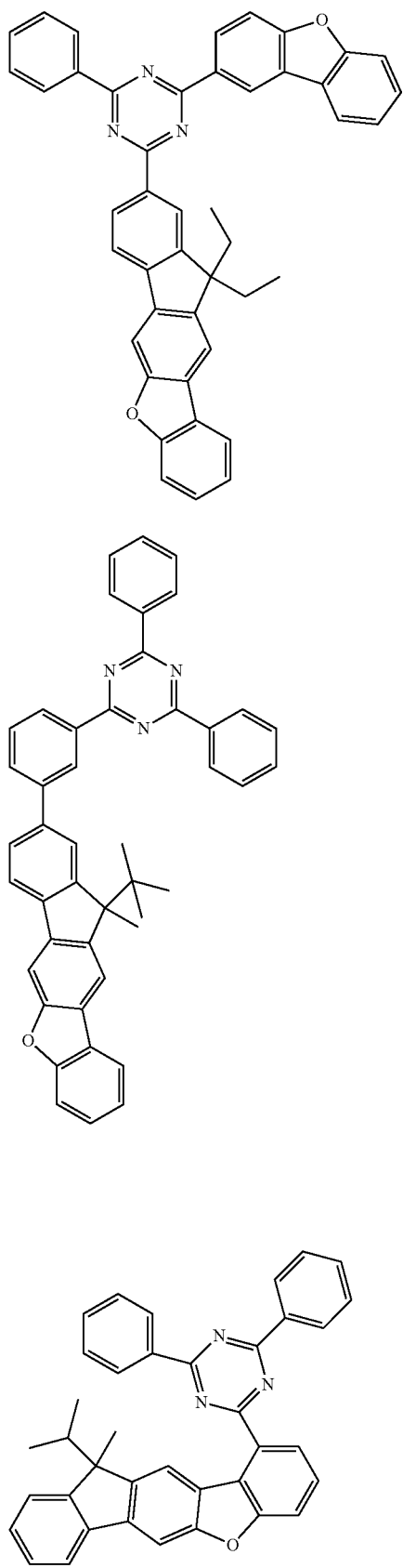
178
-continued
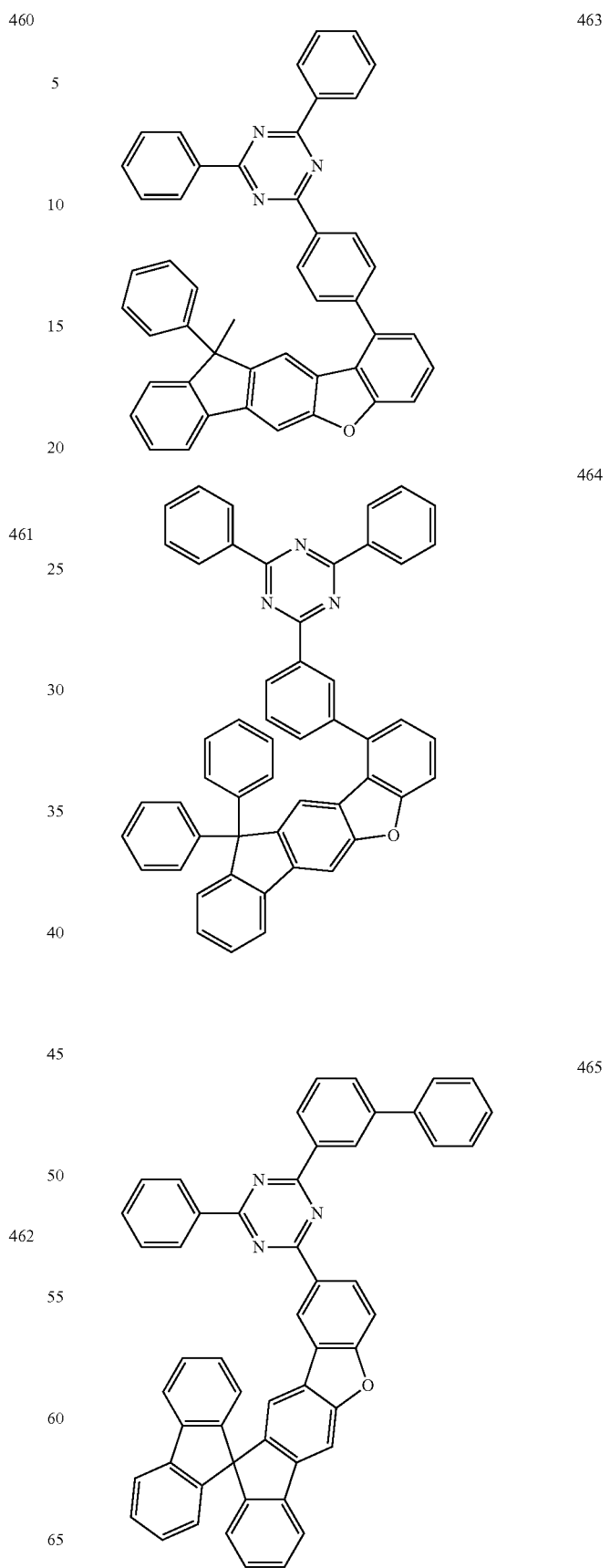

466
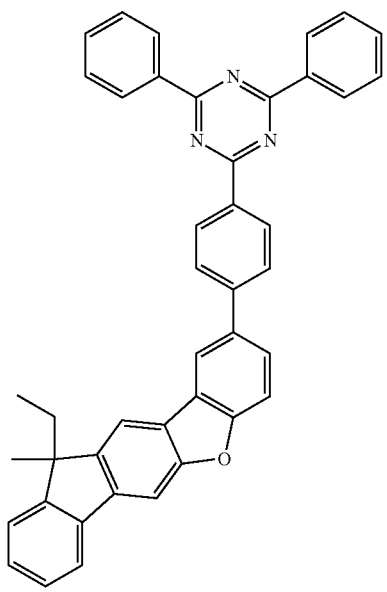
467
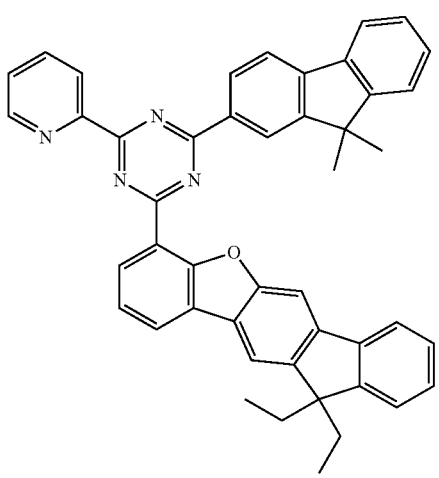
468
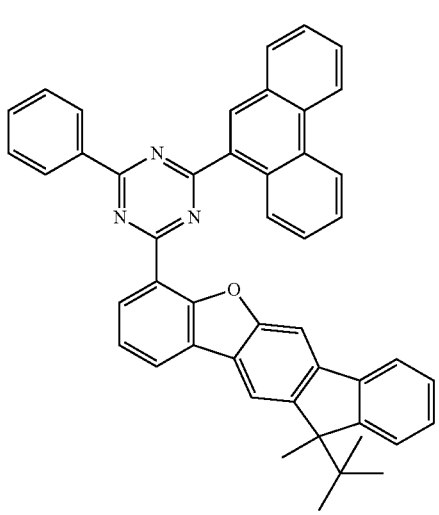
469
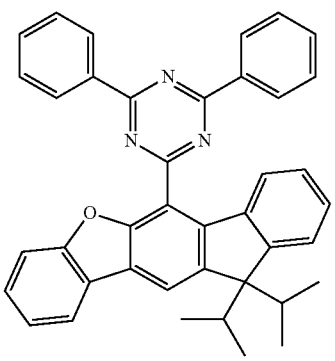
470
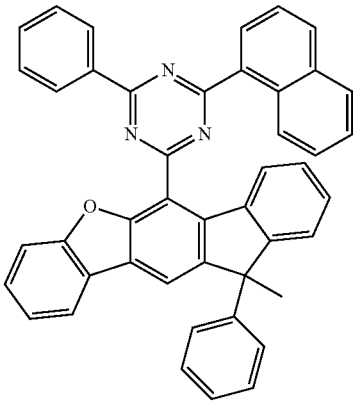
471
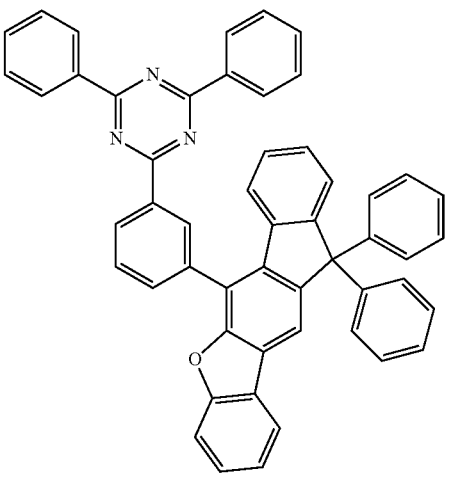

-continued
472
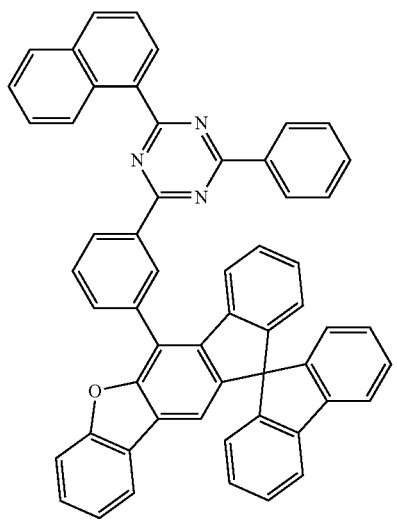
473
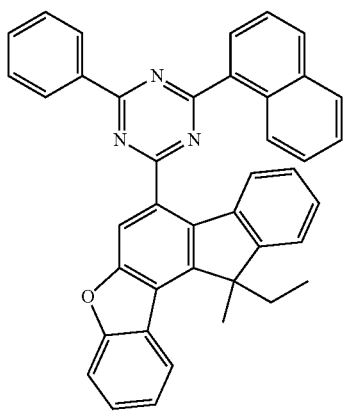
474
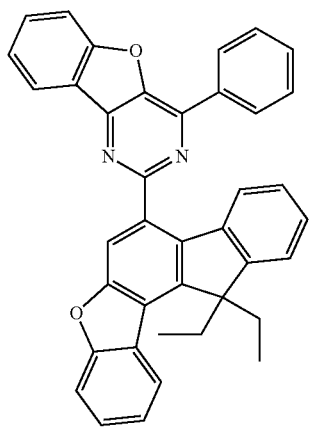
-continued
475
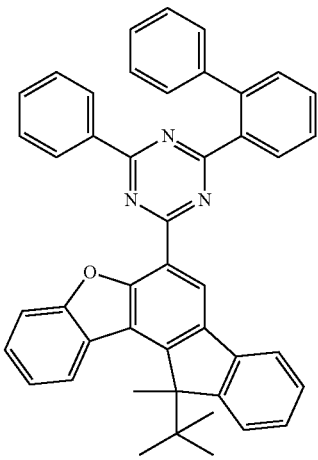
476
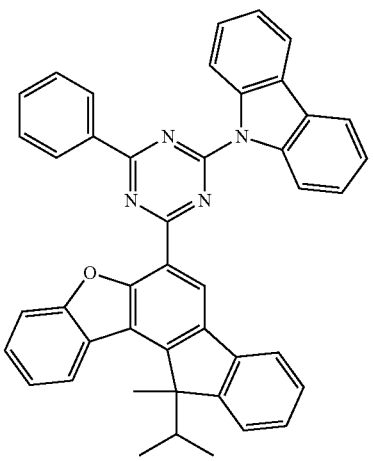
477
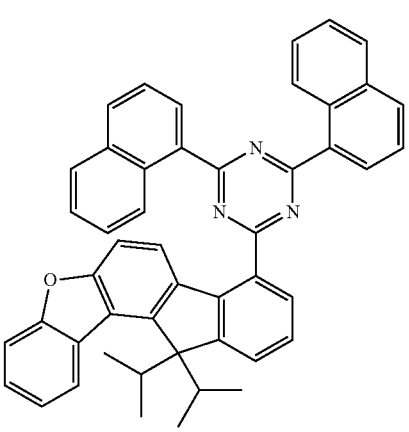

478
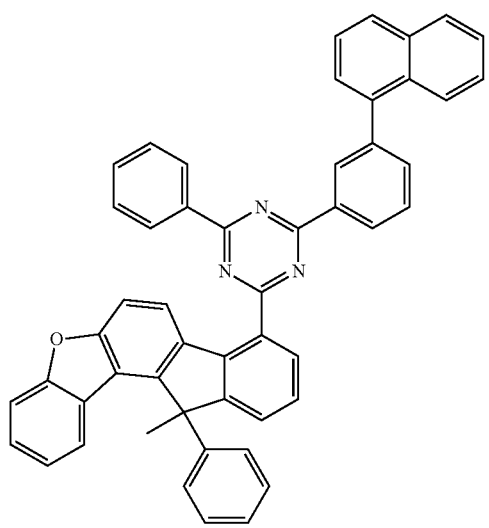
479
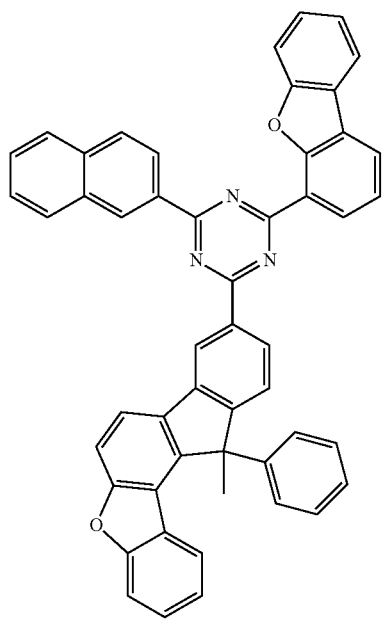
480
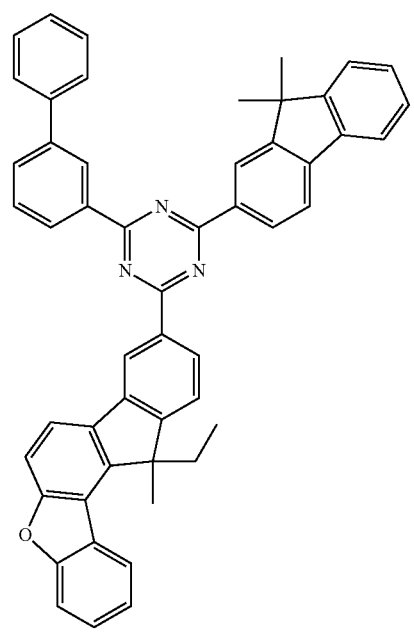
481
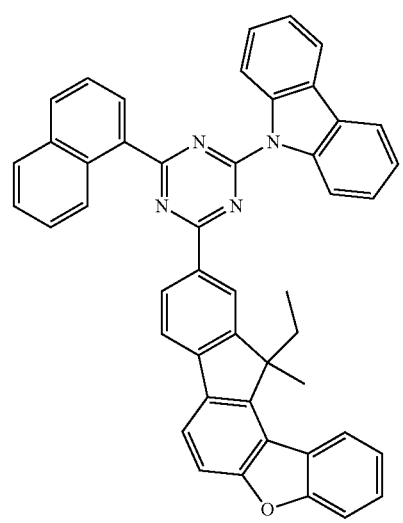

482
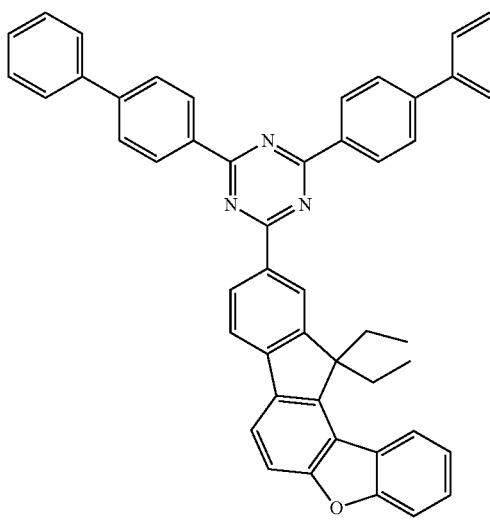
483
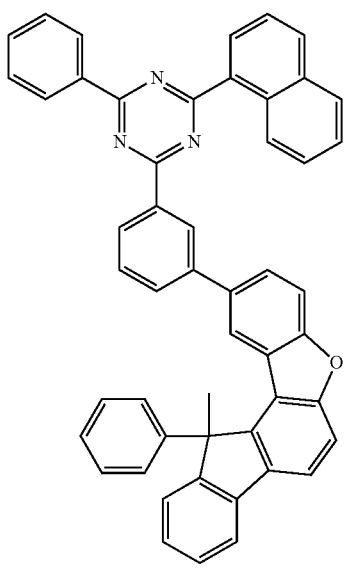
484
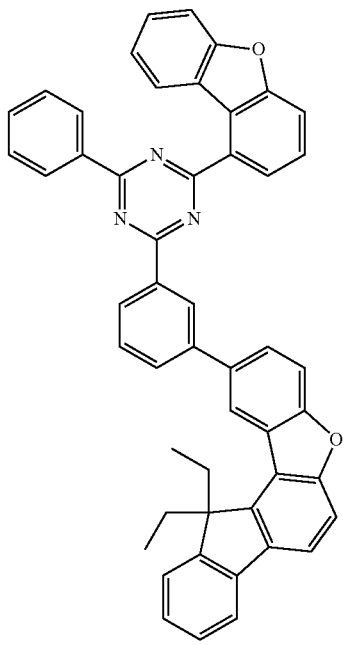
485
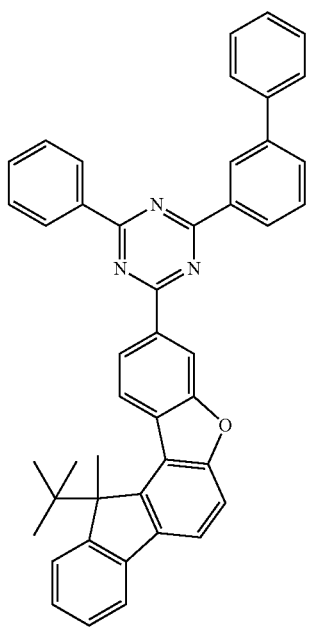

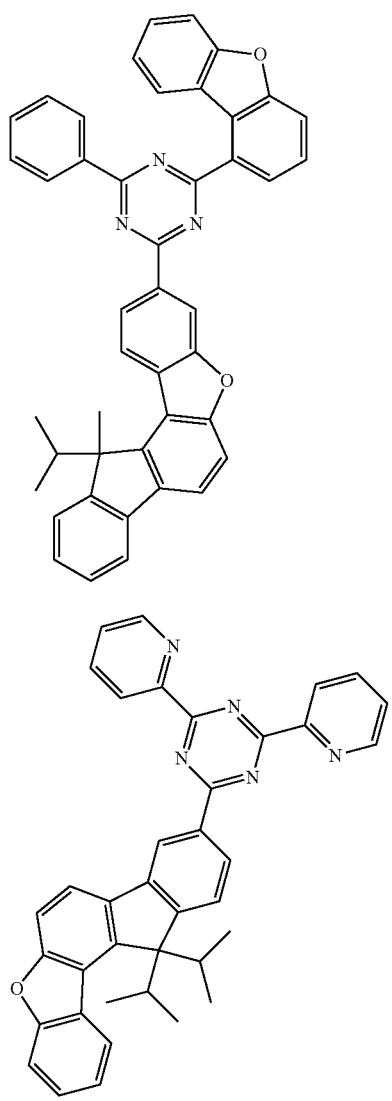
486
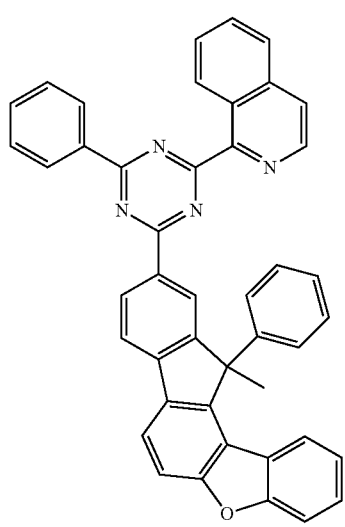
487
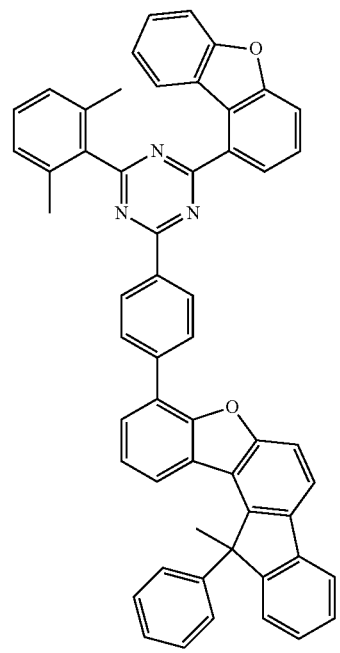
489
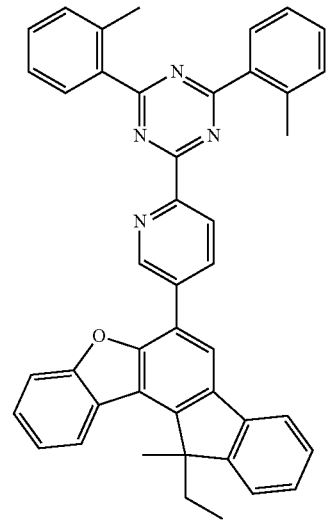
490

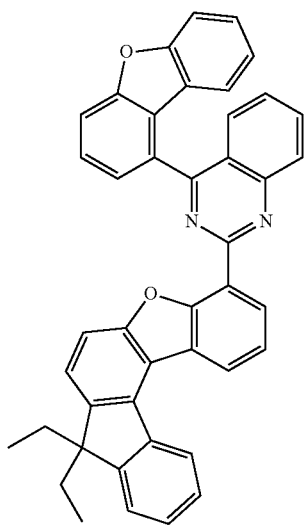
491
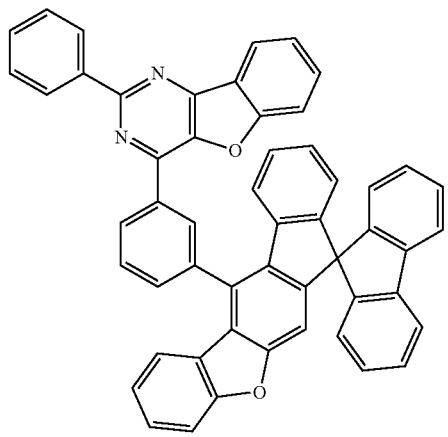
494
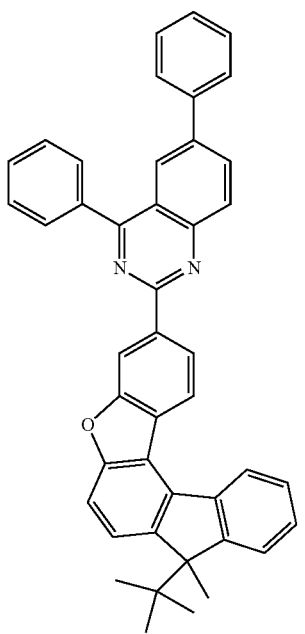
492
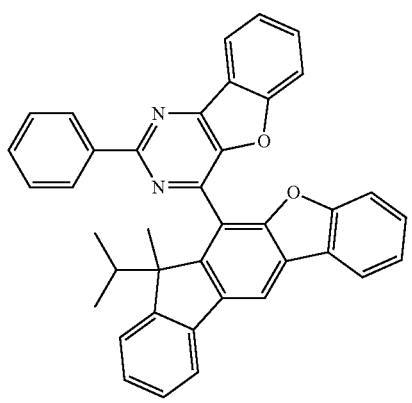
493
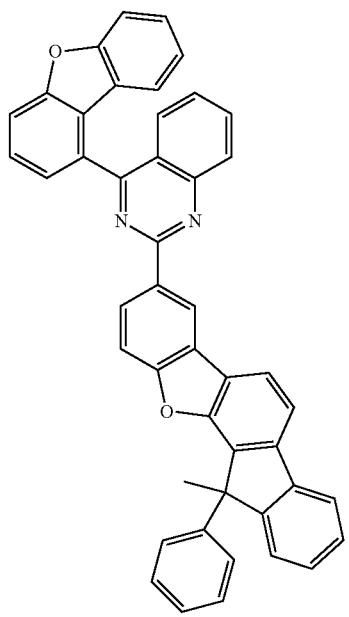
495

-continued
496
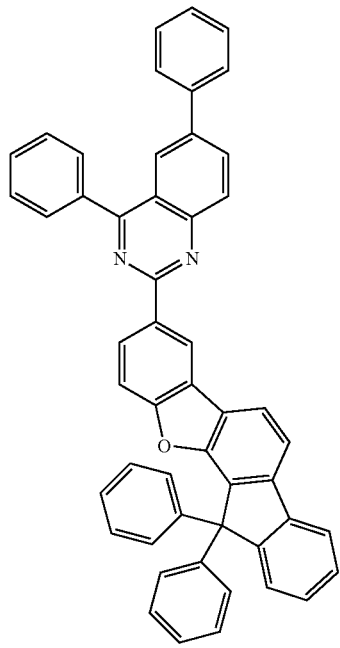
497
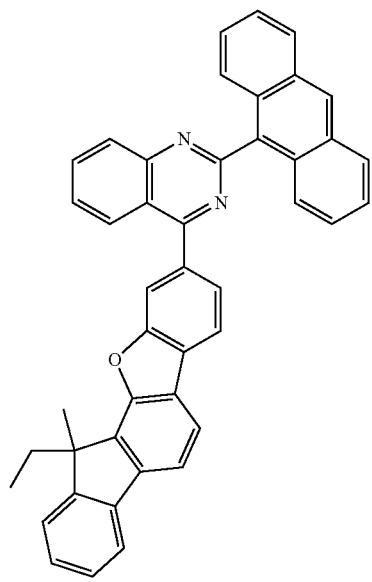
-continued
498
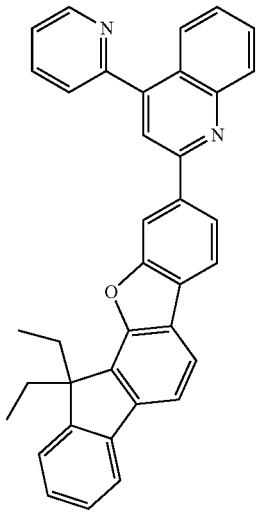
499
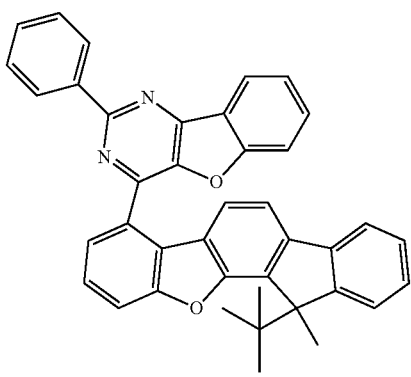
500
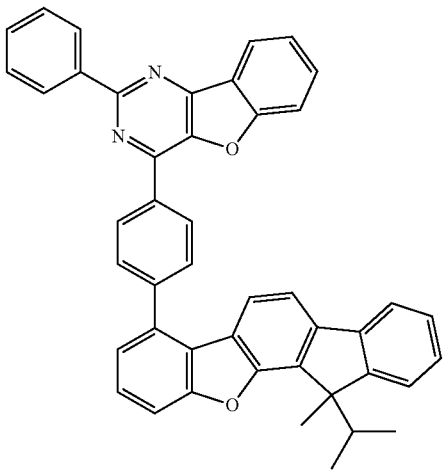

193
-continued
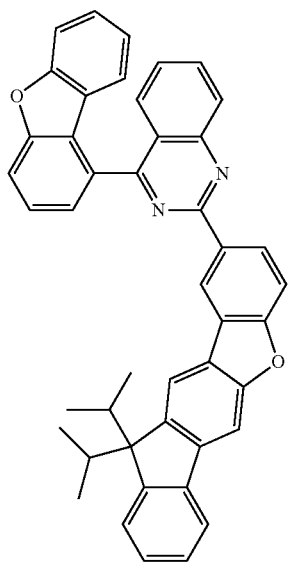
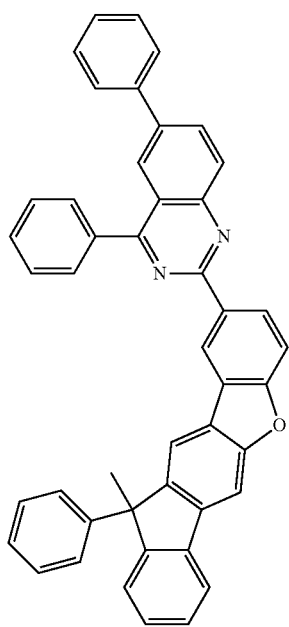
194
-continued
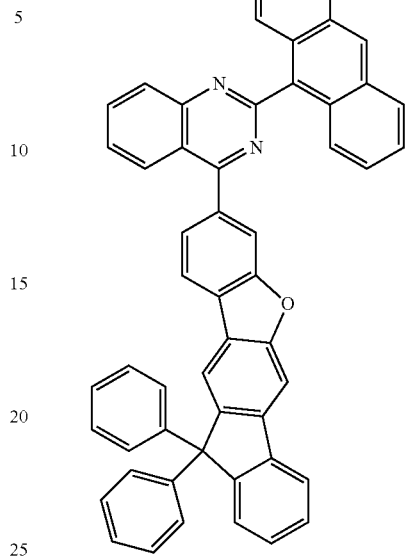
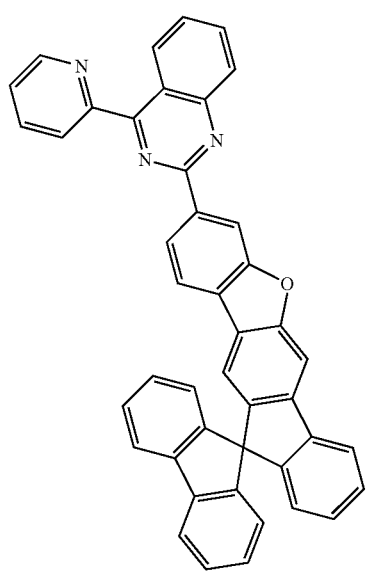

195
-continued
196
-continued
505
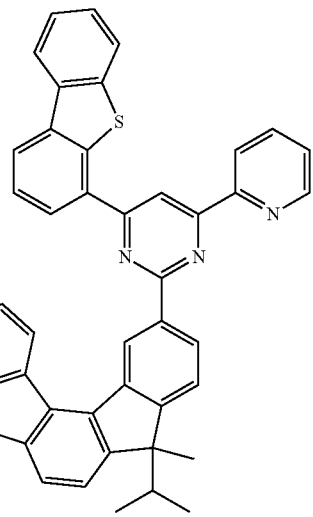
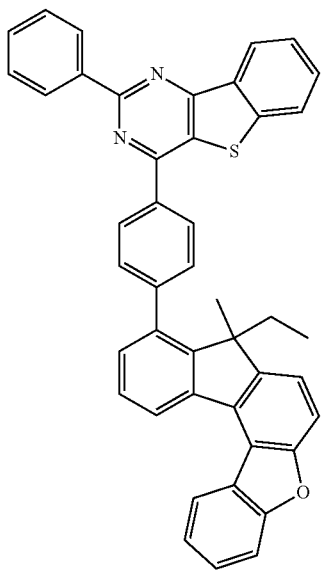
506
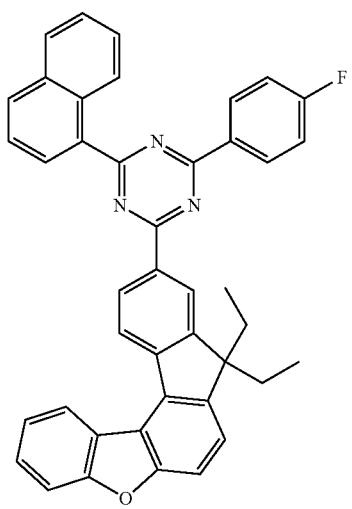
508
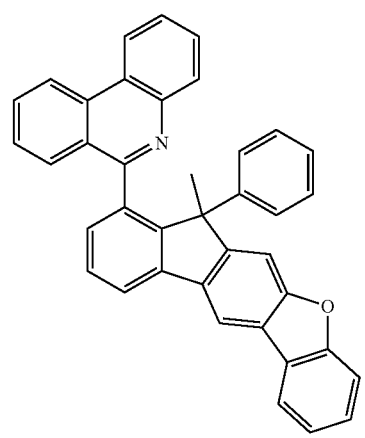
509
510
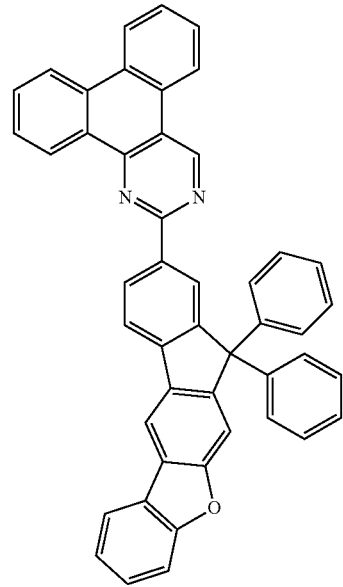
507
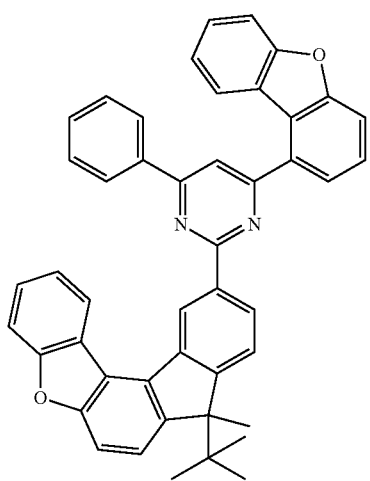

511 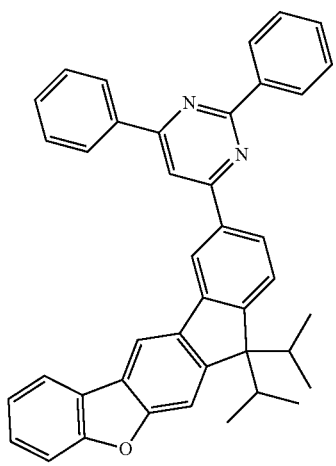
512 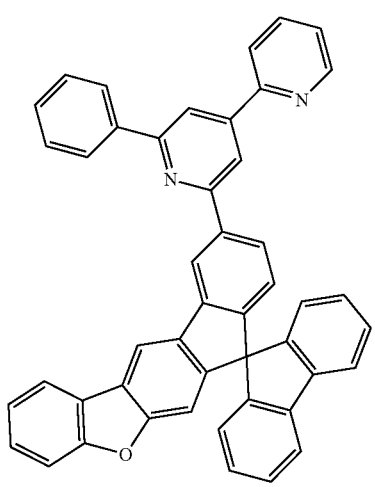
513 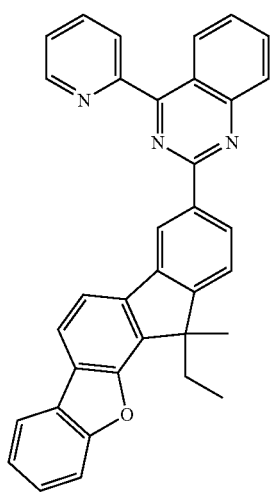
514 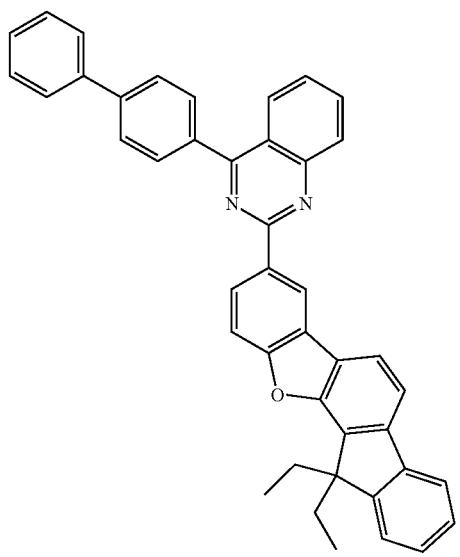
515 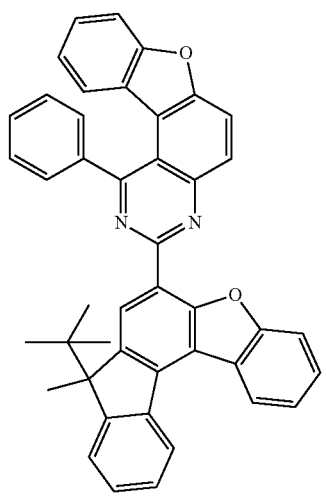
516 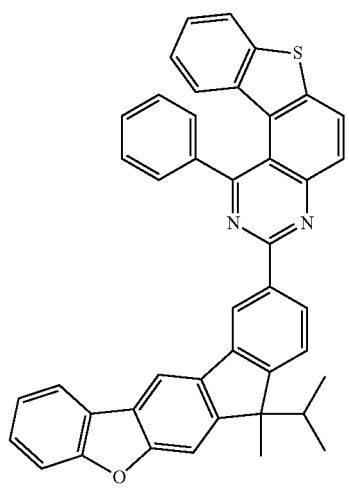

199
-continued
517
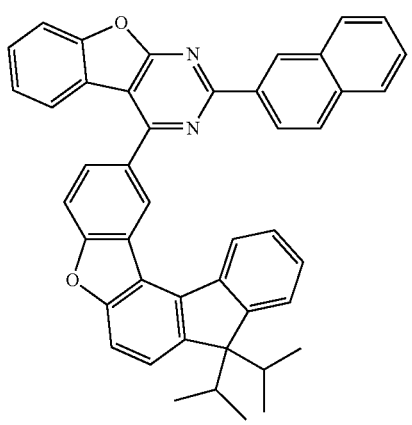
518
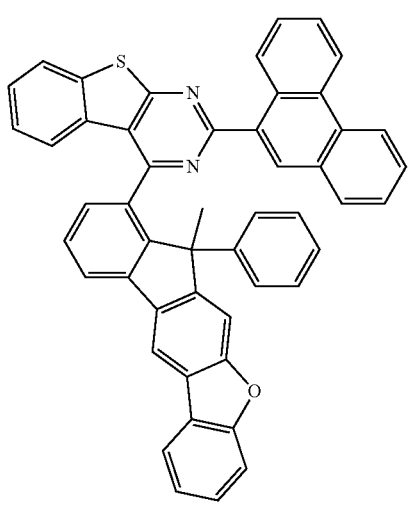
519
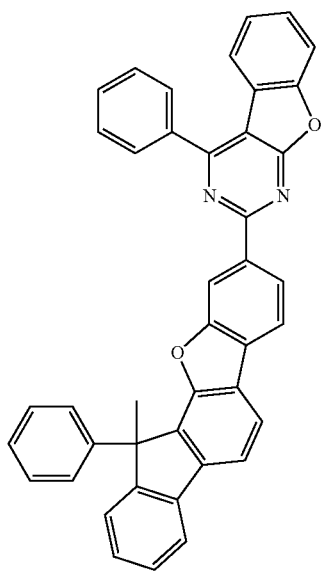
200
-continued
520
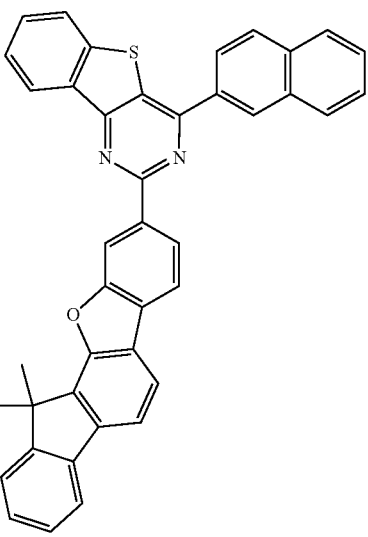
521
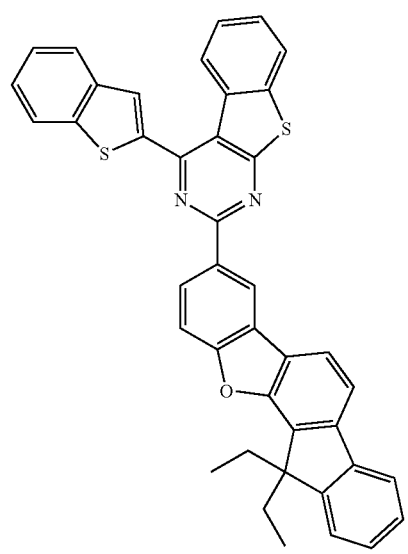
522
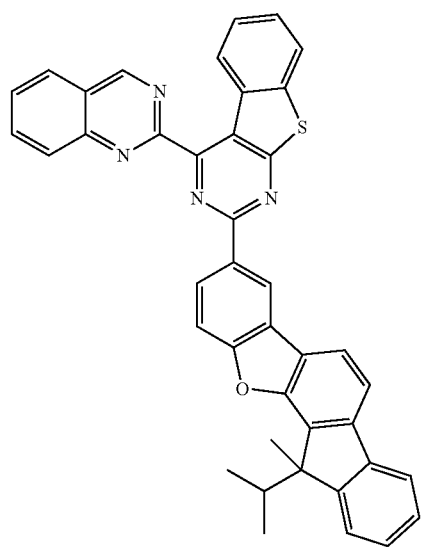

201
-continued
523
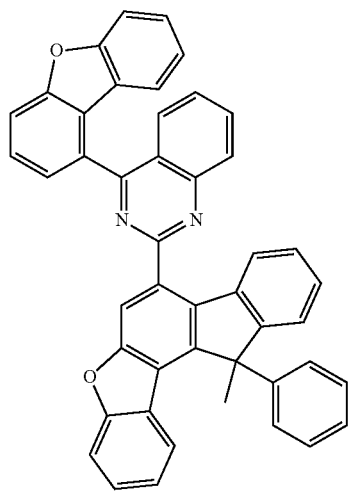
524
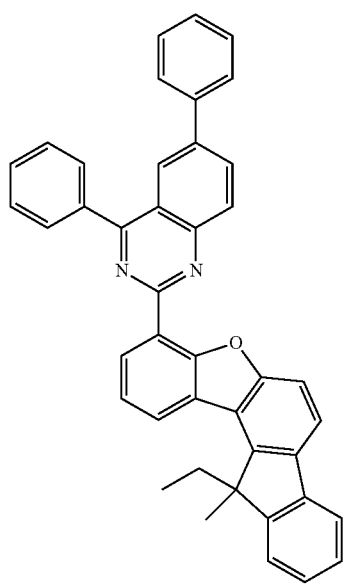
525
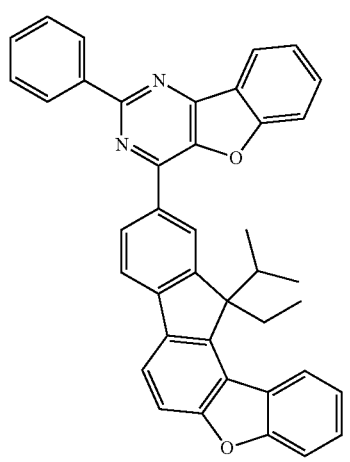
202
-continued
526
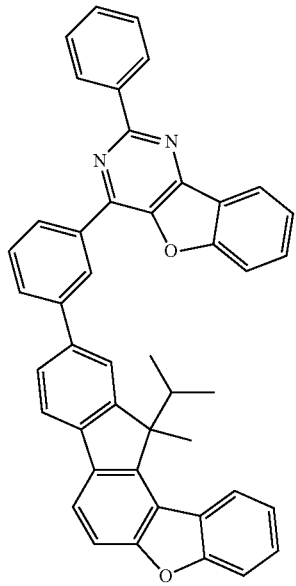
527
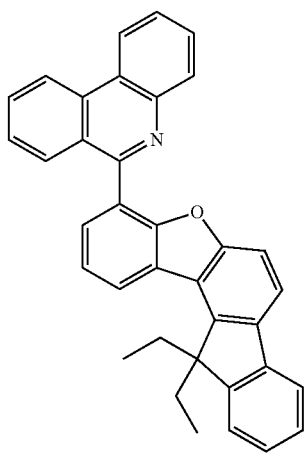
528
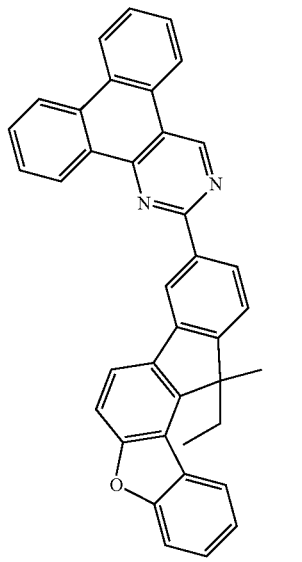

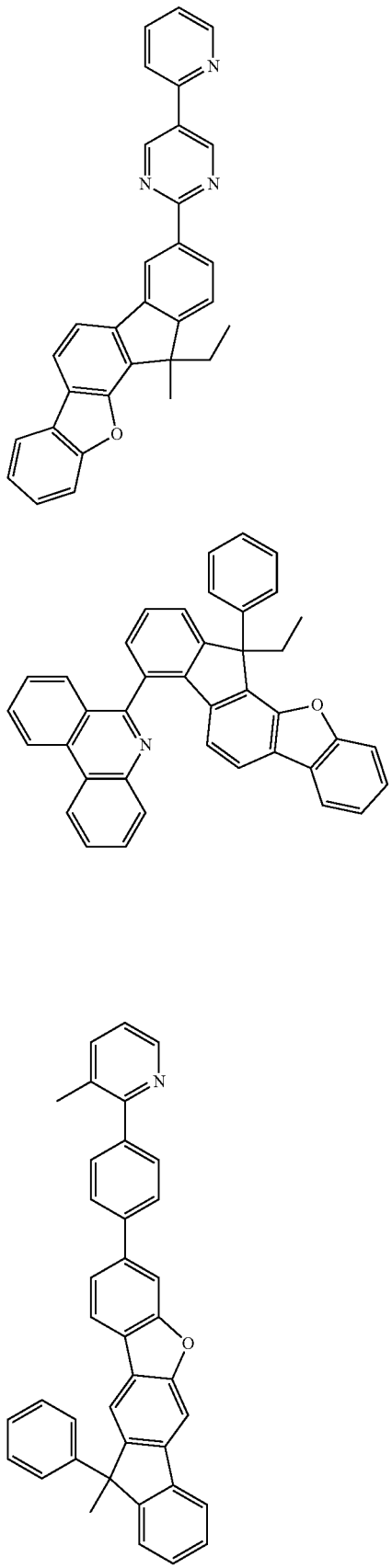
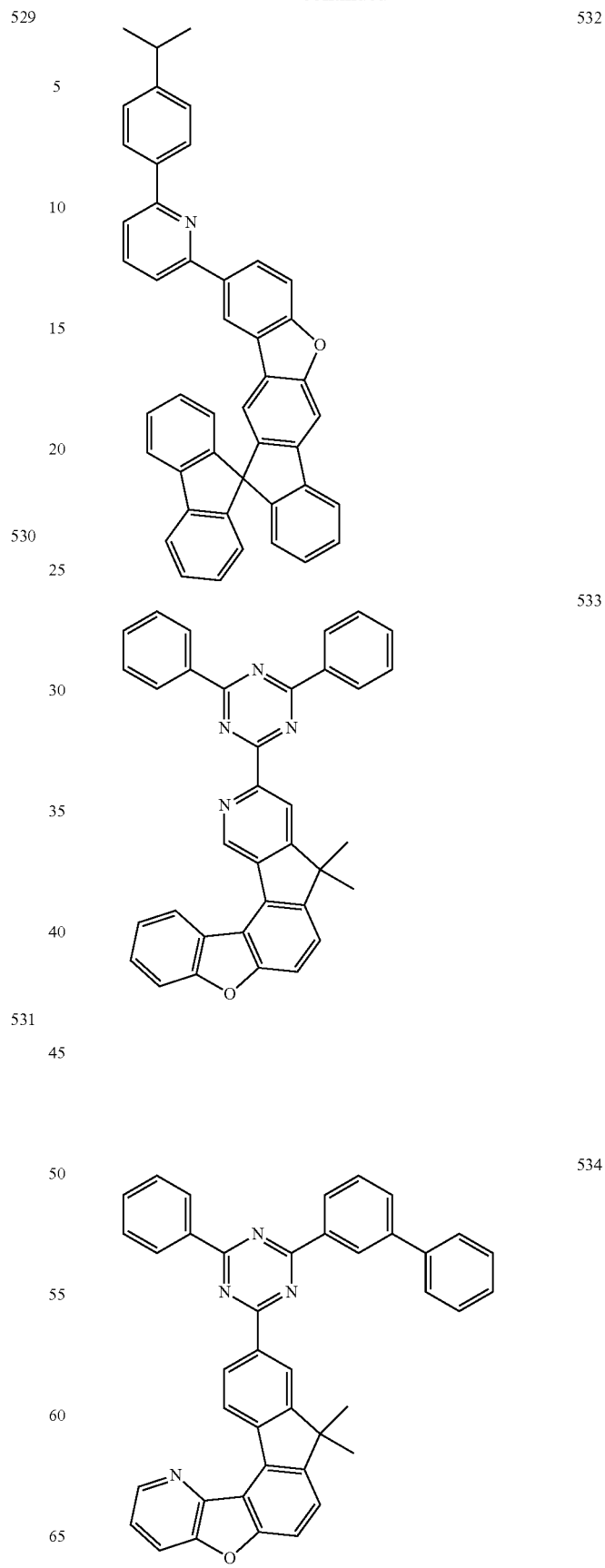

535
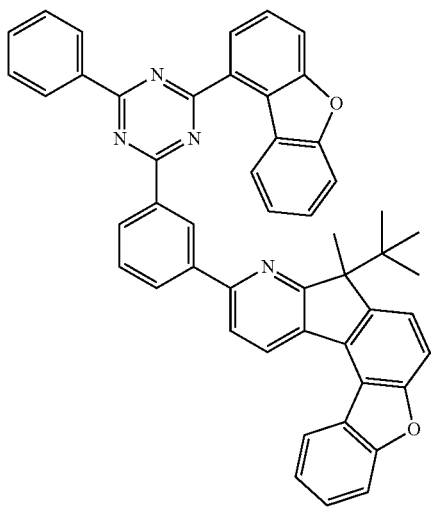
538
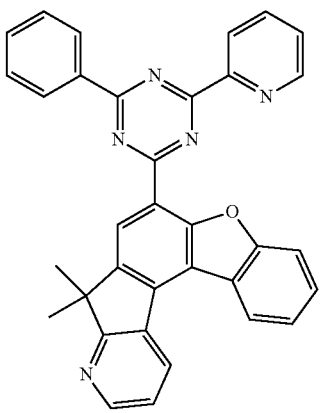
536
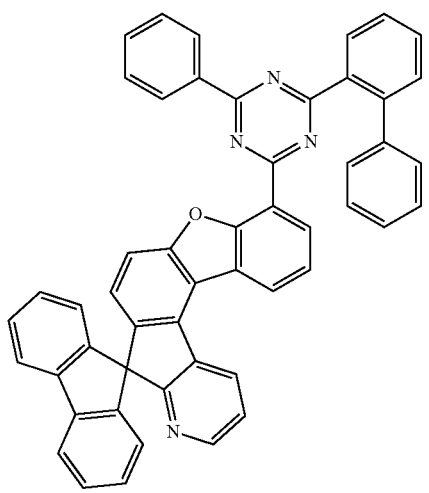
539
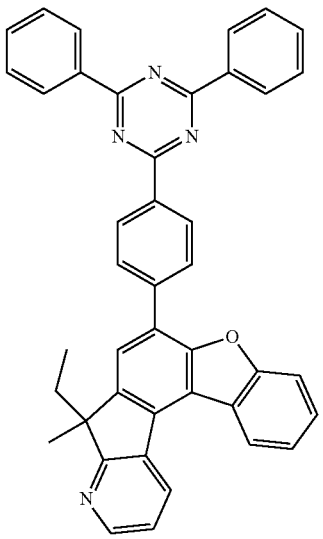
537
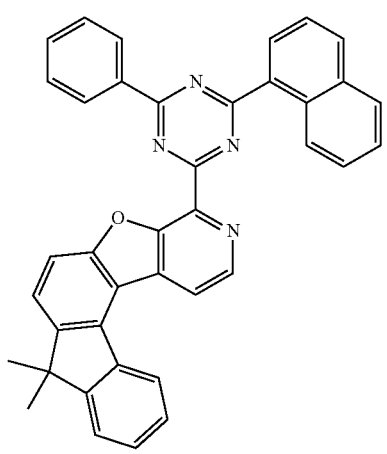
540
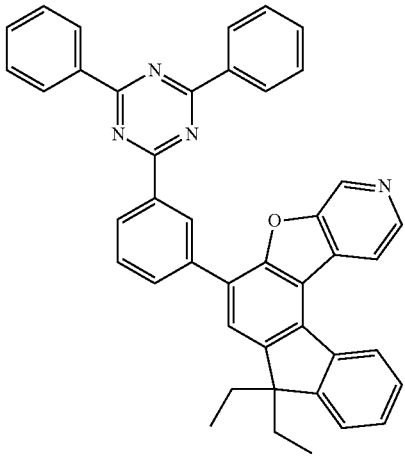

207
-continued
541
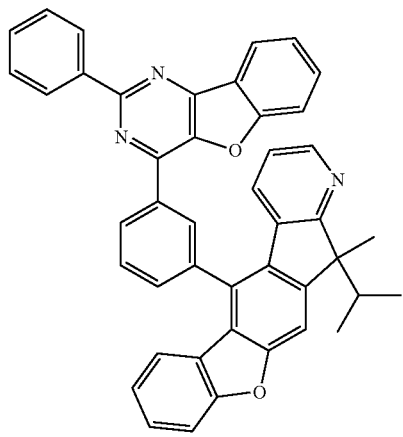
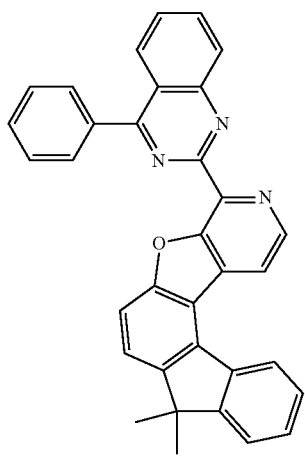
542
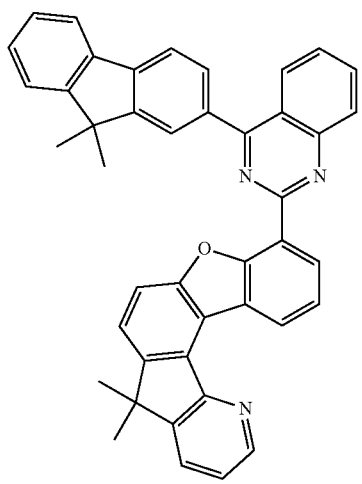
543
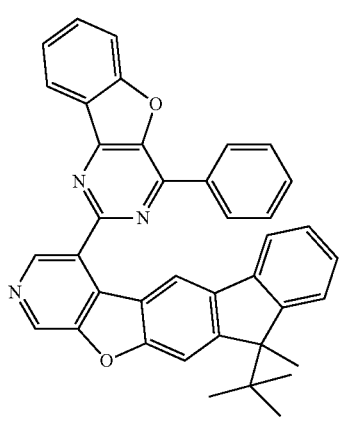
208
-continued
544
545
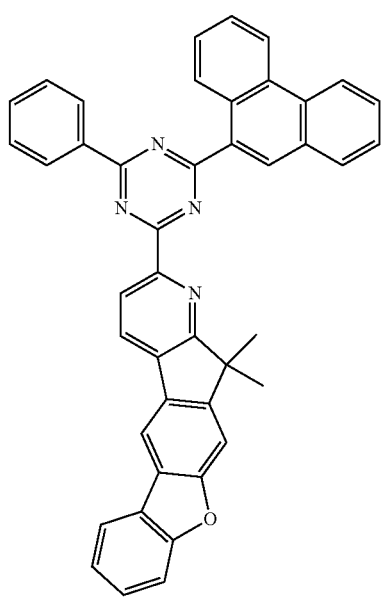
546
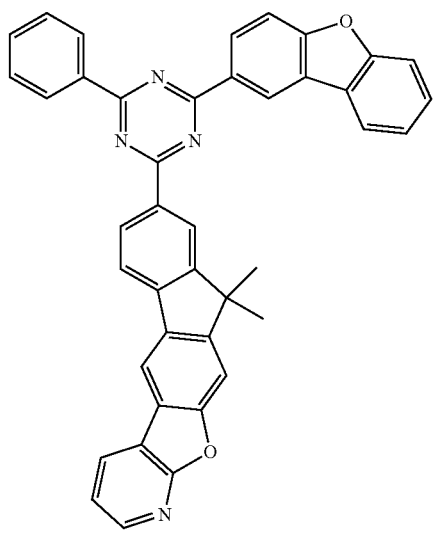

-continued
547
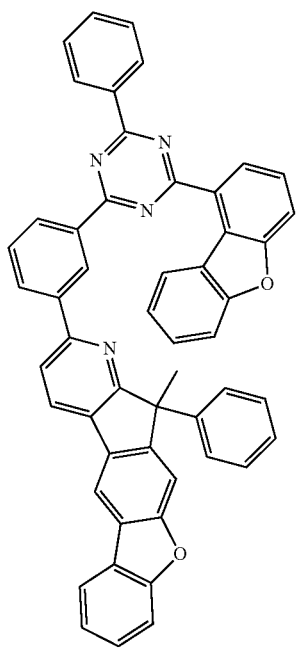
548
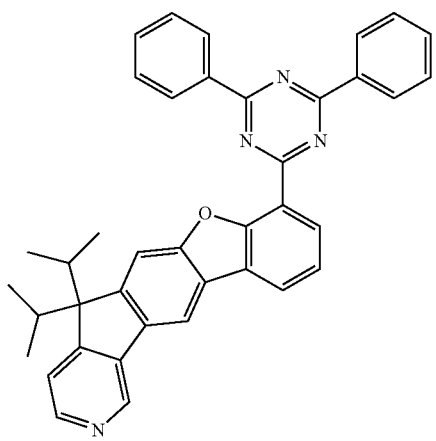
549
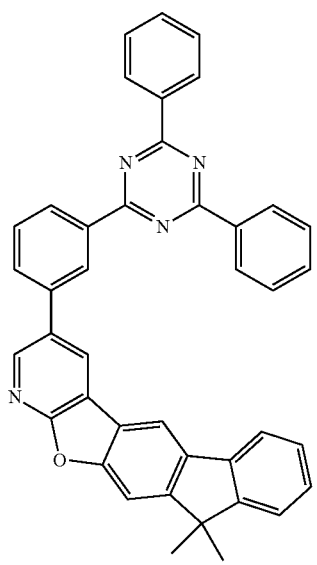
-continued
550
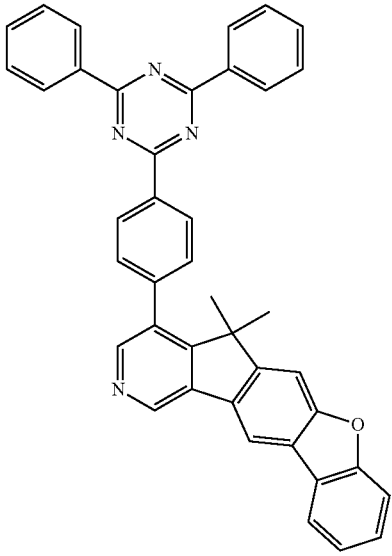
551
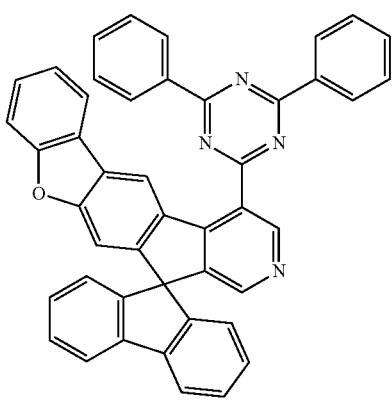
552
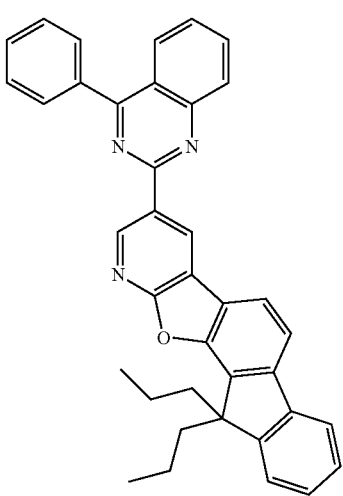

553
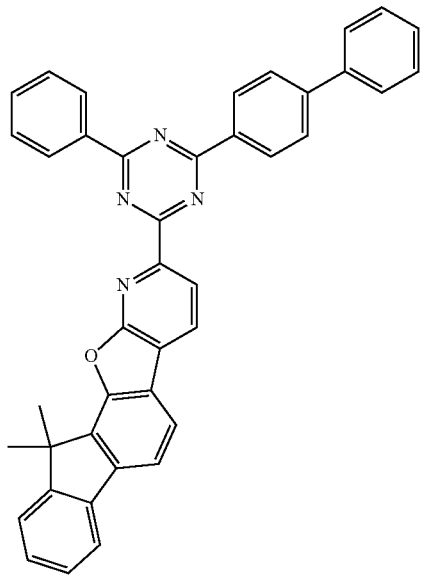
554
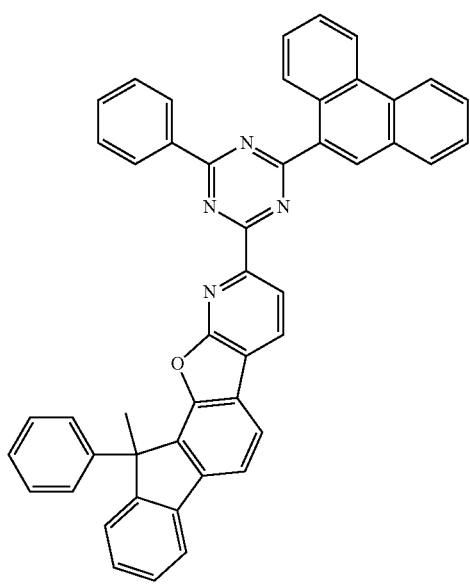
555
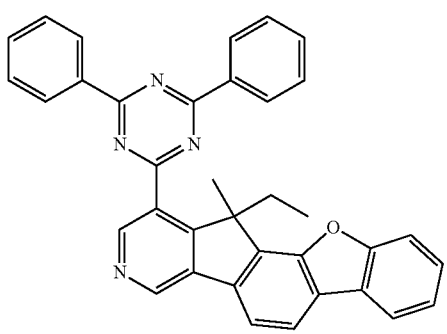
556
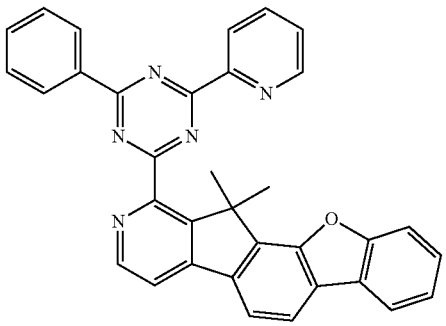
557
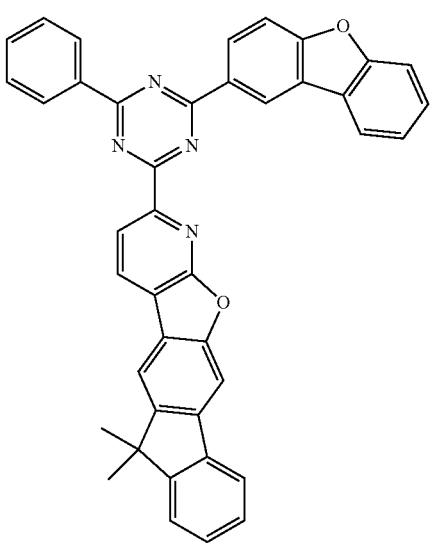
558
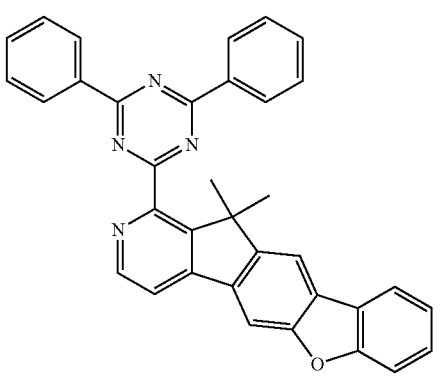
559
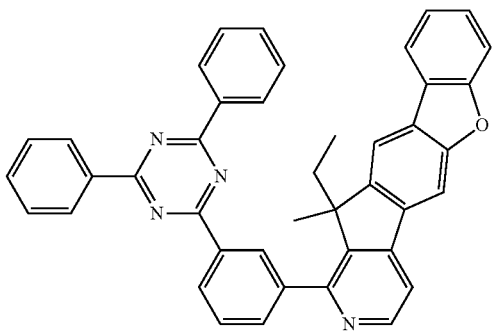

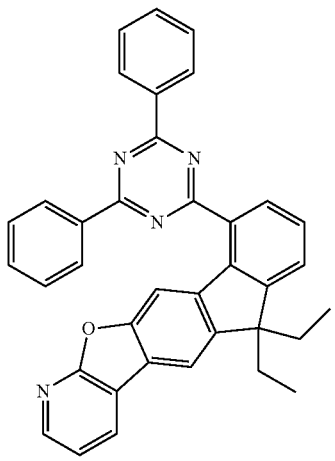

560

561

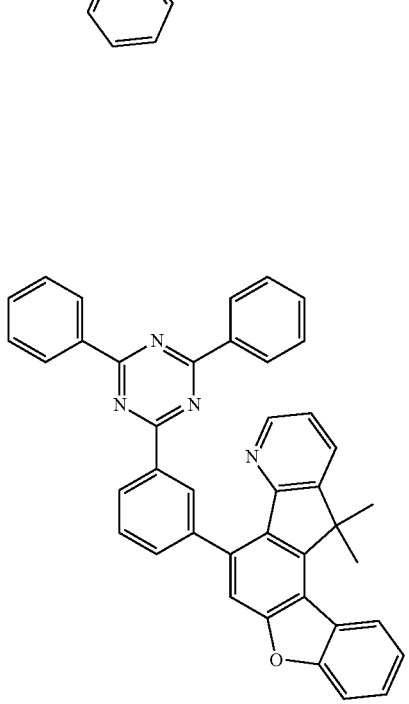

562

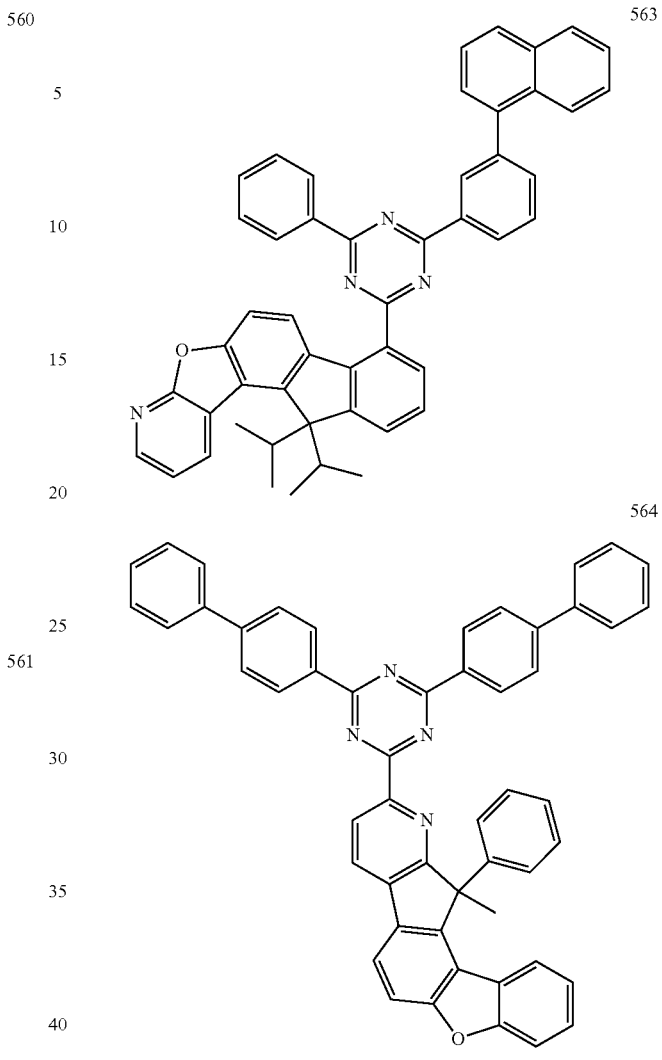

563

564

However, it is noted that the scope of Formula I is not limited to Compounds 1 to 564.

The present invention is also directed to an organic light emitting diode including the organic light emitting compound of Formula I. The organic light emitting diode of the present invention includes a first electrode, a second electrode opposite to the first electrode, and an organic layer interposed between the first and second electrodes. The organic layer includes one or more layers selected from a light emitting layer, an electron transport layer, a hole transport layer, an electron injecting layer, a hole injecting layer, a hole blocking layer, and an electron blocking layer. Particularly, the electron transport layer or the electron injecting layer includes the organic light emitting compound of Formula I.

The expression "including the organic light emitting compound" can be interpreted to mean that the organic layer may include the organic light emitting compound of Formula I or two or more different compounds falling within the scope of Formula I.

A more detailed description will be given concerning the organic light emitting diode of the present invention.

The organic light emitting diode of the present invention includes an anode, a hole transport layer, a light emitting layer, an electron transport layer, and a cathode. The organic light emitting diode of the present invention may optionally further include a hole injecting layer and an electron injecting layer. One or more intermediate layers may be further formed in the organic light emitting diode. A hole blocking layer or an electron blocking layer may be further formed in the organic light emitting diode. The diode may further include one or more organic layers with various functions depending on the desired characteristics thereof.

A description will be given concerning a method for fabricating the organic light emitting diode of the present invention. First, an electrode material for the anode is coated on a substrate to form the anode. The substrate may be any of those used in general organic light emitting diodes. The substrate is preferably an organic substrate or a transparent plastic substrate that is excellent in transparency, surface smoothness, ease of handling, and waterproofness. A highly transparent and conductive metal oxide, such as indium tin oxide (ITO), indium zinc oxide (IZO), tin oxide ($SnO_2$) or zinc oxide (ZnO), is used as the anode material.

A material for the hole injecting layer is coated on the anode by vacuum thermal evaporation or spin coating to form the hole injecting layer. Then, a material for the hole transport layer is coated on the hole injecting layer by vacuum thermal evaporation or spin coating to form the hole transport layer.

The material for the hole injecting layer is not specially limited so long as it is usually used in the art. Example of such materials include 4,4',4"-tris(2-naphthyl(phenyl)amino)triphenylamine (2-TNATA), N,N'-di(1-naphthyl)-N,N'-diphenylbenzidine) (NPD), N,N'-diphenyl-N,N'-bis(3-methylphenyl)-1,1'-biphenyl-4,4'-diamine (TPD), and N,N'-diphenyl-N,N'-bis[4-(phenyl-m-tolylamino)phenyl]biphenyl-4,4'-diamine (DNTPD).

The material for the hole transport layer is not specially limited so long as it is commonly used in the art. Example of such materials include N,N'-bis(3-methylphenyl)-N,N'-diphenyl-[1,1-biphenyl]-4,4'-diamine (TPD) and N,N'-di(naphthalen-1-yl)-N,N'-diphenylbenzidine (α-NPD).

Subsequently, the organic light emitting layer is laminated on the hole transport layer. A hole blocking layer may be optionally formed on the organic light emitting layer by vacuum thermal evaporation or spin coating. The hole blocking layer blocks holes from entering the cathode through the organic light emitting layer. This role of the hole blocking layer prevents the lifetime and efficiency of the diode from deteriorating. A material having a very low highest occupied molecular orbital (HOMO) energy level is used for the hole blocking layer. The hole blocking material is not particularly limited so long as it has the ability to transport electrons and a higher ionization potential than the light emitting compound. Representative examples of suitable hole blocking materials include BAlq, BCP, and TPBI.

The electron transport layer is deposited on the hole blocking layer by vacuum thermal evaporation or spin coating, and the electron injecting layer is formed thereon. A metal for the cathode is deposited on the electron injecting layer by vacuum thermal evaporation to form the cathode, completing the fabrication of the organic light emitting diode. As the metal for the cathode, there may be used, for example, lithium (Li), magnesium (Mg), aluminum (Al), aluminum-lithium (Al—Li), calcium (Ca), magnesium-indium (Mg—In) or magnesium-silver (Mg—Ag). The organic light emitting diode may be of top emission type. In this case, a transmissive material, such as ITO or IZO, may be used for the cathode.

The material for the electron transport layer functions to stably transport electrons injected from the electron injecting electrode (i.e. the cathode). The organic light emitting compound of Formula I is used as the material for the electron transport layer.

One or more layers selected from the hole injecting layer, the hole transport layer, the electron blocking layer, the light emitting layer, the hole blocking layer, the electron transport layer, and the electron injecting layer may be formed by a monomolecular deposition or solution process. According to the monomolecular deposition process, the material for each layer is evaporated under heat and vacuum or reduced pressure to form the layer in the form of a thin film. According to the solution process, the material for each layer is mixed with a suitable solvent, and then the mixture is formed into a thin film by a suitable method, such as ink-jet printing, roll-to-roll coating, screen printing, spray coating, dip coating or spin coating.

The organic light emitting diode of the present invention can be used in a variety of systems, such as flat panel displays, flexible displays, monochromatic flat panel lighting systems, white flat panel lighting systems, flexible monochromatic lighting systems, and flexible white lighting systems.

The present invention will be explained in more detail with reference to the following specific examples, including synthesis examples for synthesizing dye compounds, and examples and a comparative example for fabricating organic light emitting diodes. However, these examples are provided for illustrative purposes only and are not intended to limit the scope of the invention.

Synthesis Example 1: Synthesis of Compound 1

Synthesis Example 1-1: Synthesis of Intermediate 1-a

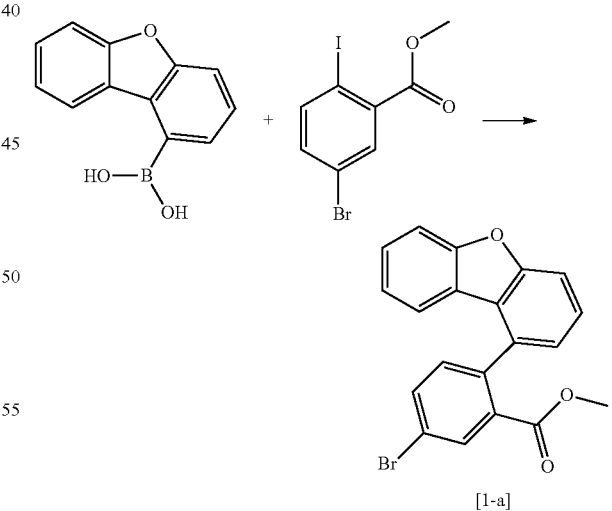

25 g (118 mmol) of dibenzofuran-1-boronic acid, 40.5 g (118 mmol) of methyl-5-bromo-2-iodobenzoate, 2.7 g (2.3 mmol) of tetrakis(triphenylphosphine)palladium, 33 g (237 mmol) of potassium carbonate, 200 ml of toluene, 200 ml of 1,4-dioxane, and 100 ml of water were placed in a round bottom flask under a nitrogen atmosphere. The mixture was refluxed for 12 h. After completion of the reaction, the reaction mixture was allowed to stand for phase separation. The organic layer was concentrated under reduced pressure and the resulting residue was purified by column chromatography to give Intermediate 1-a (33.5 g, yield 74%).

Synthesis Example 1-2: Synthesis of Intermediate 1-b

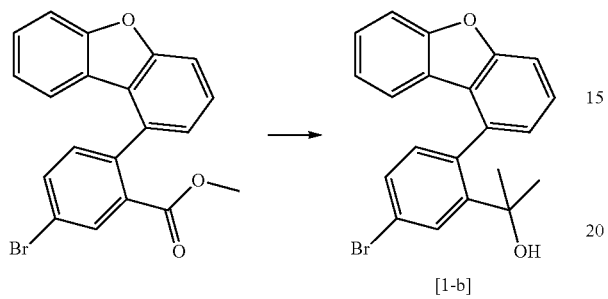

[1-b]

33.5 g (110 mmol) of Intermediate 1-a was added to 150 ml of tetrahydrofuran in a round bottom flask. After cooling to −10° C., 85 ml (254 mmol) of 3 M methylmagnesium bromide was slowly added dropwise to the flask. The mixture was heated to 40° C., followed by stirring for 4 h. Thereafter, the temperature was lowered to −10° C. 70 ml of 2 N hydrochloric acid was slowly added dropwise to the flask and 70 ml of an aqueous ammonium chloride solution was then added thereto. The temperature was allowed to rise to room temperature. After completion of the reaction, the reaction mixture was washed with water and concentrated under reduced pressure. The resulting residue was purified by column chromatography to give Intermediate 1-b (27 g, yield 80%).

Synthesis Example 1-3: Synthesis of Intermediate 1-c

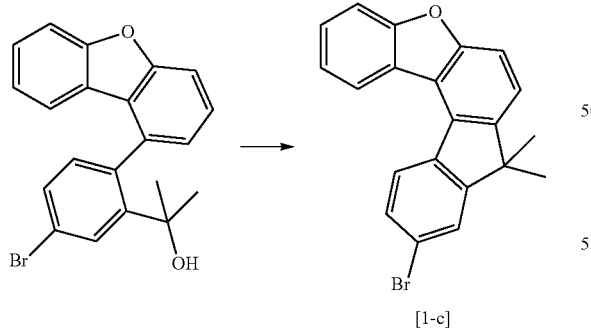

[1-c]

27 g (89.2 mmol) of Intermediate 1-b and 70 ml of phosphoric acid were placed in a round bottom flask under a nitrogen atmosphere. The mixture was stirred at room temperature for 12 h. After completion of the reaction, the reaction mixture was extracted and concentrated. The resulting residue was purified by column chromatography to give Intermediate 1-c (17.6 g, yield 70%).

Synthesis Example 1-4: Synthesis of Intermediate 1-d

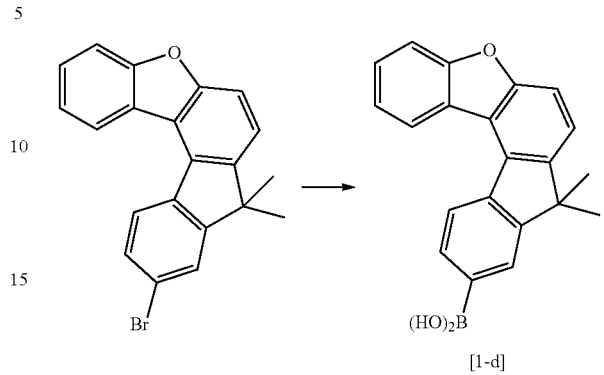

[1-d]

17.6 g (48.4 mmol) of Intermediate 1-c was placed in a round bottom flask and 200 ml of tetrahydrofuran was then added thereto under a nitrogen atmosphere. After cooling to −78° C., 36.3 ml (58.1 mmol) of 1.6 M butyllithium was slowly added dropwise to the flask. 1 h after the addition, 7.0 ml (62.9 mmol) of trimethyl borate was slowly added to the flask while maintaining the same temperature. Thereafter, the resulting mixture was stirred at room temperature. After completion of the reaction, the organic layer was concentrated under reduced pressure and recrystallized from hexane to give Intermediate 1-d (13 g, yield 82%).

Synthesis Example 1-5: Synthesis of Compound 1

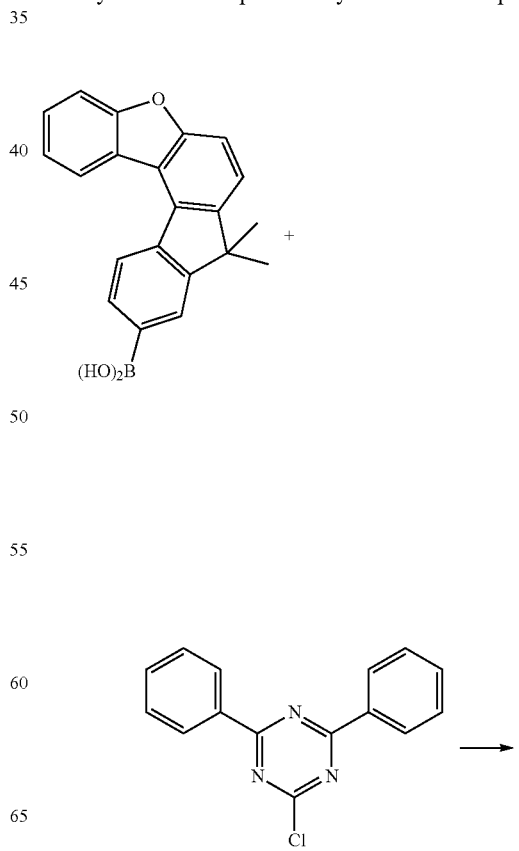

-continued

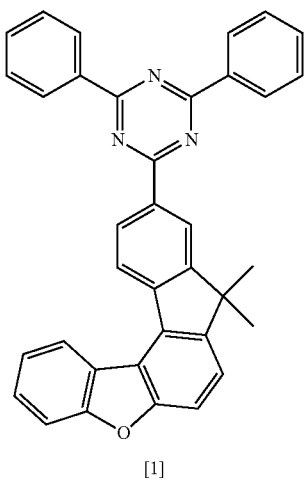

[1]

5 g (15.2 mmol) of Intermediate 1-d, 6.5 g (16.7 mmol) of 2-chloro-4,6-diphenyl-1,3,5-triazine, 0.3 g (0.3 mmol) of tetrakis(triphenylphosphine)palladium, 4.2 g (30.4 mmol) of potassium carbonate, 25 ml of toluene, 25 ml of 1,4-dioxane, and 15 ml of water were placed in a round bottom flask under a nitrogen atmosphere. The mixture was refluxed for 12 h. After completion of the reaction, the organic layer was concentrated under reduced pressure and the resulting residue was purified by column chromatography to give Compound 1 (6.8 g, yield 76%).

MS (MALDI-TOF): m/z 515.20 [M]$^+$

Synthesis Example 2: Synthesis of Compound 5

Synthesis Example 2-1: Synthesis of Intermediate 2-a

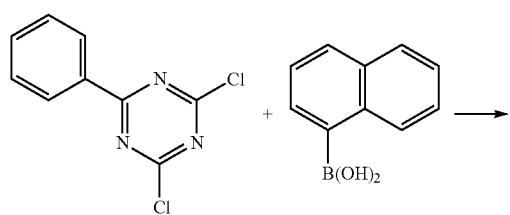

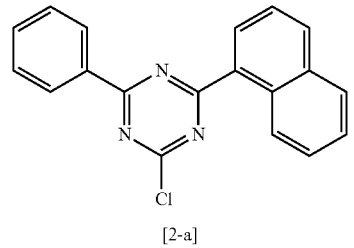

[2-a]

Intermediate 2-a (yield 42%) was synthesized in the same manner as in Synthesis Example 1-5, except that 2,4-dichloro-6-phenyl-1,3,5-triazine and 1-naphthaleneboronic acid were used instead of 2-chloro-4,6-diphenyl-1,3,5-triazine and Intermediate 1-d, respectively.

Synthesis Example 2-2: Synthesis of Compound 5

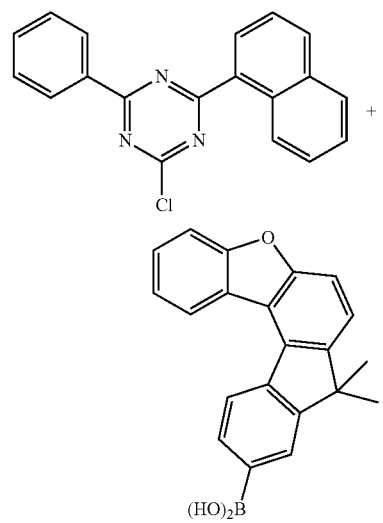

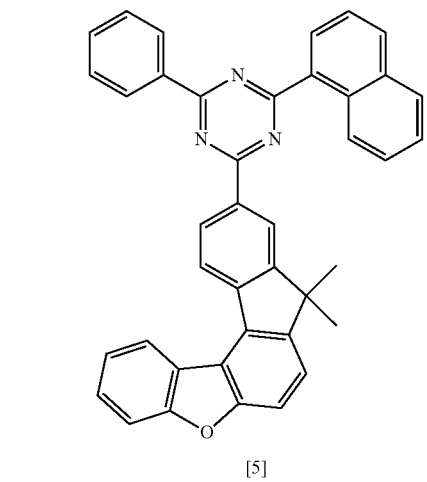

[5]

Compound 5 (yield 72%) was synthesized in the same manner as in Synthesis Example 1-5, except that Intermediate 2-a was used instead of 2-chloro-4,6-diphenyl-1,3,5-triazine.

MS (MALDI-TOF): m/z 565.22 [M]$^+$

Synthesis Example 3: Synthesis of Compound 71

Synthesis Example 3-1: Synthesis of Intermediate 3-a

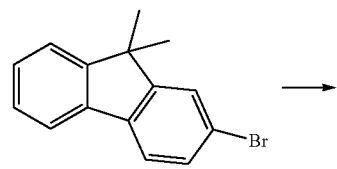

-continued

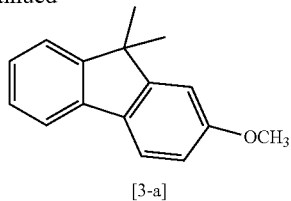

[3-a]

50 g (183 mmol) of 2-bromo-9,9-dimethylfluorene, 59.3 g (1098 mmol) of an aqueous sodium methoxide solution, 10.4 g (54.9 mmol) of copper iodide, and 200 ml of methanol were placed in a round bottom flask under a nitrogen atmosphere. The mixture was refluxed for 12 h. After completion of the reaction, the organic layer was concentrated under reduced pressure and the resulting residue was purified by column chromatography to give Intermediate 3-a (33.2 g, yield 81%).

Synthesis Example 3-2: Synthesis of Intermediate 3-b

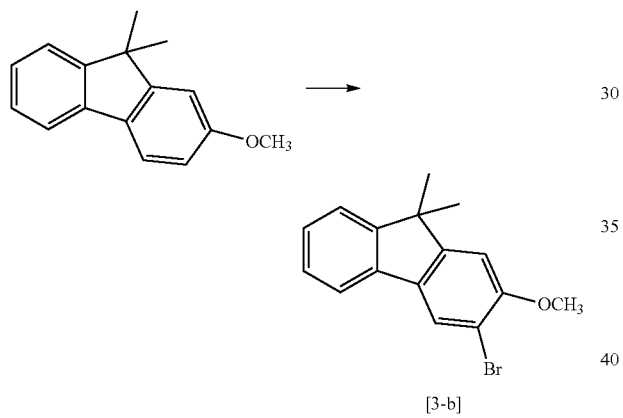

[3-b]

30 g (133 mmol) of Intermediate 3-a, 23.8 g (133 mmol) of N-bromosuccinimide, and 600 ml of dimethylformamide were placed in a round bottom flask under a nitrogen atmosphere. The mixture was stirred at 50° C. for 12 h. After completion of the reaction, the organic layer was concentrated under reduced pressure and the resulting residue was purified by column chromatography to give Intermediate 3-b (28 g, yield 70%).

Synthesis Example 3-3: Synthesis of Intermediate 3-c

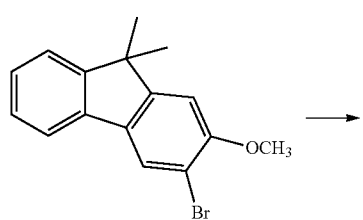

-continued

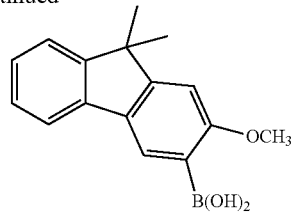

[3-c]

Intermediate 3-c (yield 77%) was synthesized in the same manner as in Synthesis Example 1-4, except that Intermediate 3-b was used instead of Intermediate 1-c.

Synthesis Example 3-4: Synthesis of Intermediate 3-d

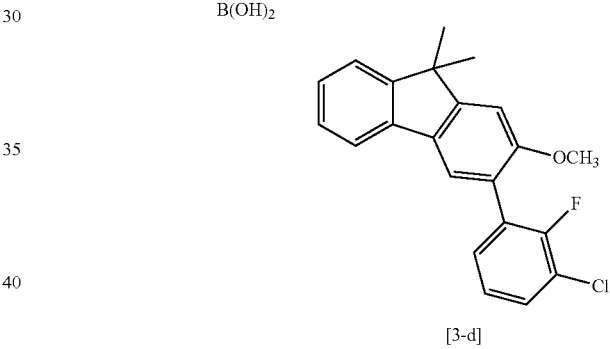

[3-d]

Intermediate 3-d (yield 52%) was synthesized in the same manner as in Synthesis Example 1-5, except that 1-bromo-3-chloro-2-fluorobenzene and to Intermediate 3-c were used instead of 2-chloro-4,6-diphenyl-1,3,5-triazine and Intermediate 1-d, respectively.

Synthesis Example 3-5: Synthesis of Intermediate 3-e

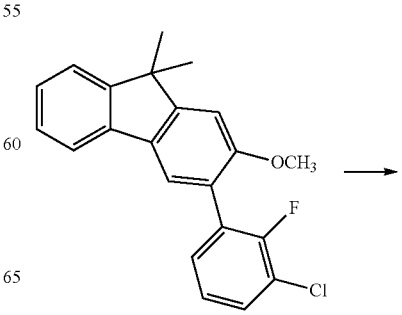

-continued

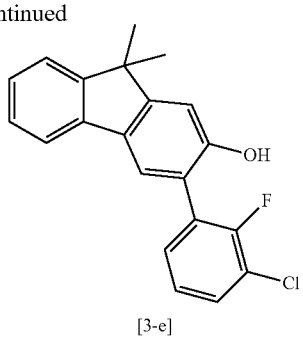

[3-e]

30 g (85 mmol) of Intermediate 3-d and 300 ml of dichloromethane were placed in a round bottom flask under a nitrogen atmosphere. After cooling to 0° C., a dilute solution of 63.9 g (255 mmol) of boron tribromide in 150 ml of dichloromethane was slowly added dropwise to the flask. The temperature was allowed to rise to room temperature. The mixture was stirred for 6 h. After completion of the reaction, the organic layer was concentrated under reduced pressure and the resulting residue was purified by column chromatography to give Intermediate 3-e (21.3 g, yield 74%).

Synthesis Example 3-6: Synthesis of Intermediate 3-f

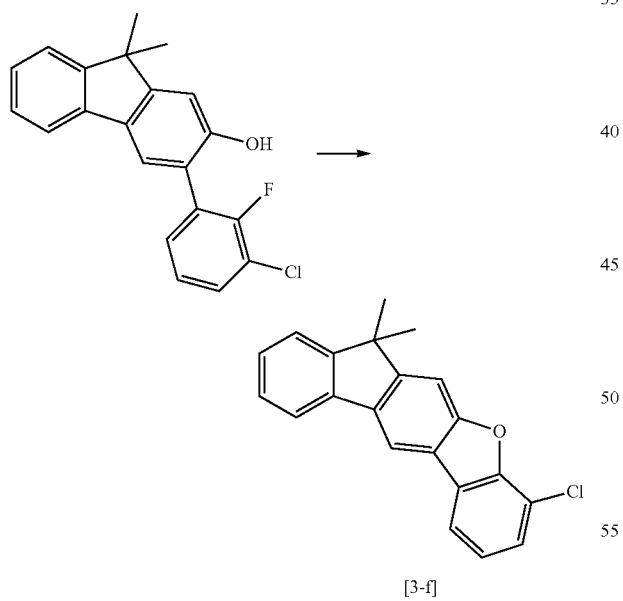

[3-f]

20 g (59 mmol) of Intermediate 3-e, 13 g (94.5 mmol) of potassium carbonate, and 200 ml of 1-methyl-2-pyrrolidinone were placed in a round bottom flask under a nitrogen atmosphere. The mixture was stirred at 150° C. for 12 h. After completion of the reaction, the organic layer was concentrated under reduced pressure and the resulting residue was purified by column chromatography to give Intermediate 3-f (13.5 g, yield 72%).

Synthesis Example 3-7: Synthesis of Intermediate 3-g

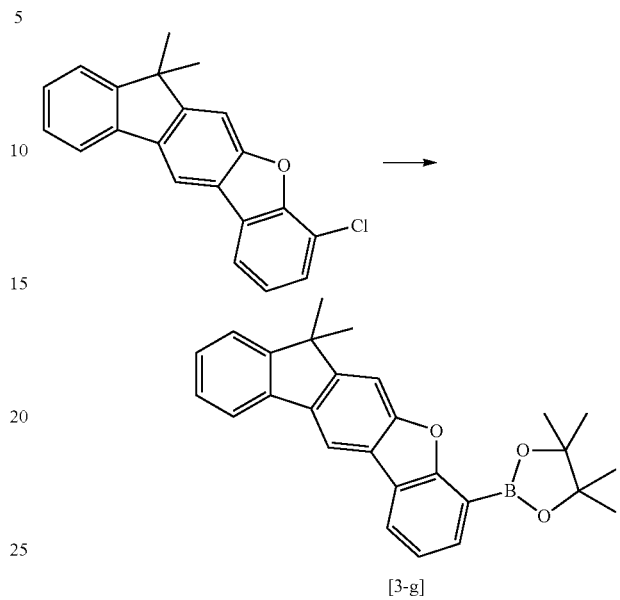

[3-g]

13 g (40.8 mmol) of Intermediate 3-f, 12.4 g (48.9 mmol) of bis(pinacolato)diborane, 2 g (2.4 mmol) of tris(dibenzylideneacetone)palladium, 11.6 g (122 mmol) of potassium acetate, 2.7 g (9.8 mmol) of tricyclohexylphosphine, and 150 ml of N-dimethylformamide were placed in a round bottom flask under a nitrogen atmosphere. The mixture was refluxed. After completion of the reaction, the organic layer was concentrated under reduced pressure and the resulting residue was purified by column chromatography to give Intermediate 3-g (10.8 g, yield 65%).

Synthesis Example 3-8: Synthesis of Compound 71

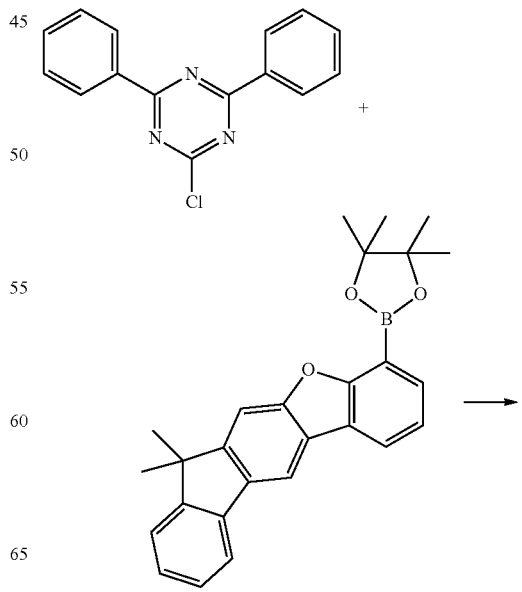

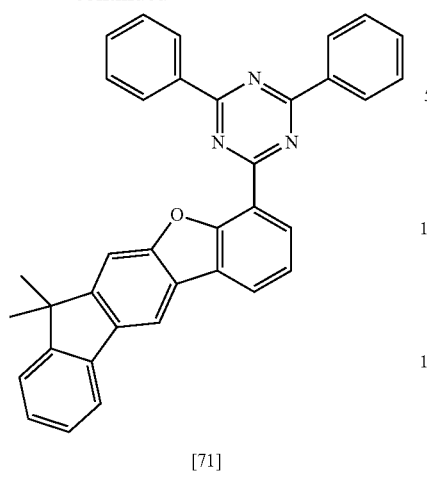

[71]

Compound 71 (yield 69%) was synthesized in the same manner as in Synthesis Example 1-5, except that Intermediate 3-g was used instead of Intermediate 1-d.

MS (MALDI-TOF): m/z 515.20 [M]$^+$

Synthesis Example 4: Synthesis of Compound 72

Synthesis Example 4-1: Synthesis of Compound 72

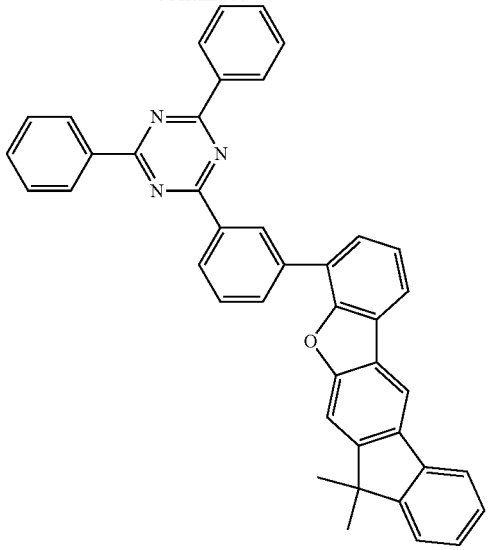

[72]

Compound 72 (yield 46%) was synthesized in the same manner as in Synthesis Example 1-5, except that 2-(3-bromophenyl)-4,6-diphenyl-1,3,5-triazine and Intermediate 3-g were used instead of 2-chloro-4,6-diphenyl-1,3,5-triazine and Intermediate 1-d, respectively.

MS (MALDI-TOF): m/z 591.23 [M]$^+$

Synthesis Example 5: Synthesis of Compound 164

Synthesis Example 5-1: Synthesis of Intermediate 5-a

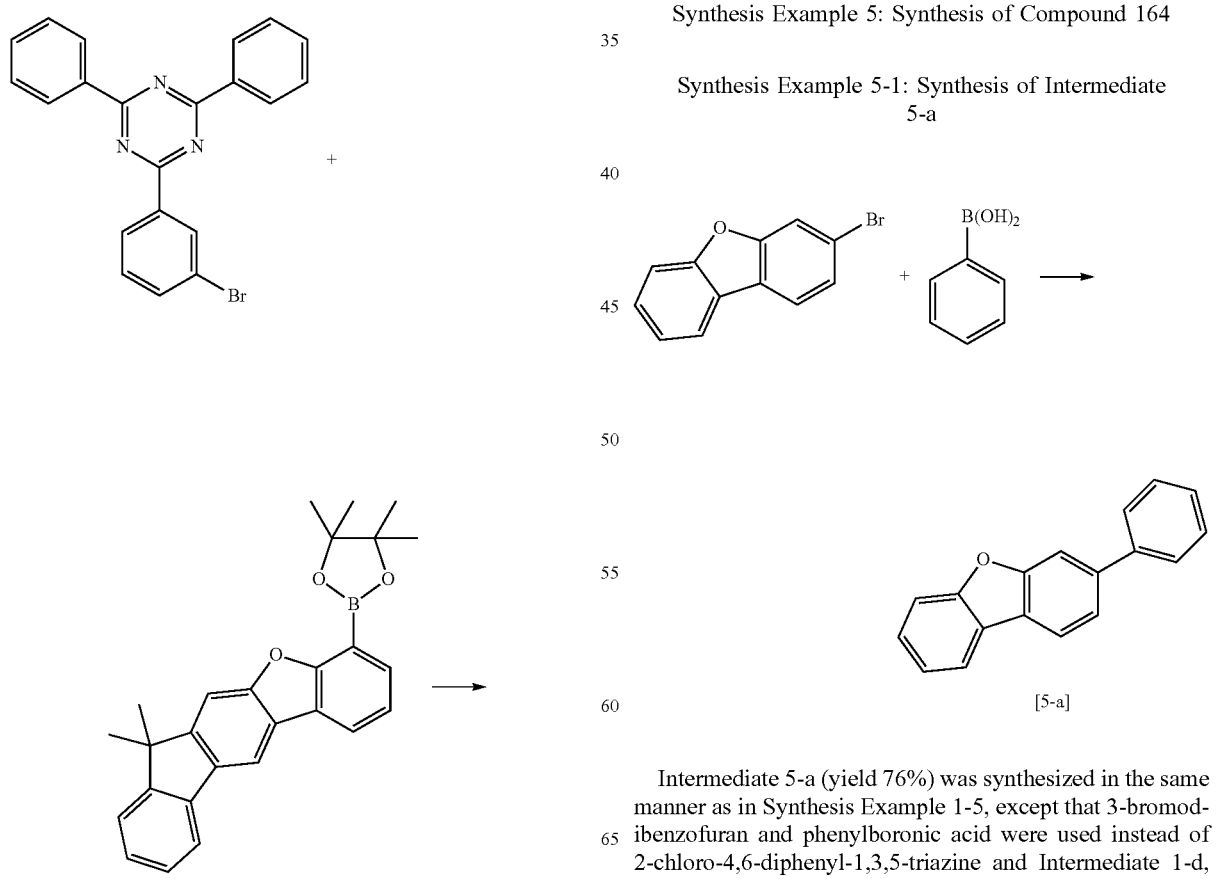

[5-a]

Intermediate 5-a (yield 76%) was synthesized in the same manner as in Synthesis Example 1-5, except that 3-bromodibenzofuran and phenylboronic acid were used instead of 2-chloro-4,6-diphenyl-1,3,5-triazine and Intermediate 1-d, respectively.

Synthesis Example 5-2: Synthesis of Intermediate 5-b

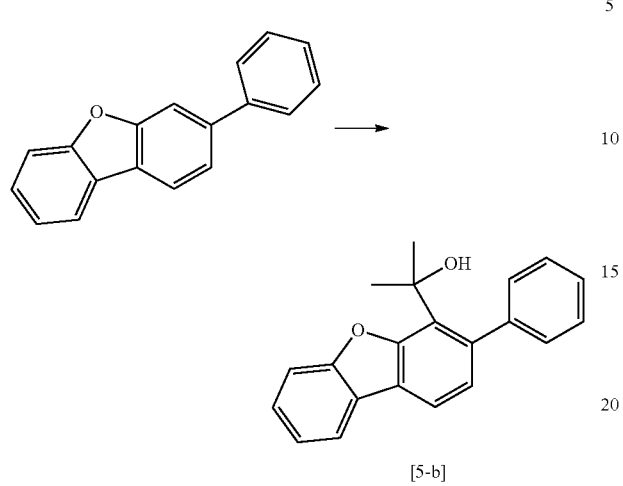

[5-b]

50 g (204 mmol) of Intermediate 5-a and 500 ml of tetrahydrofuran were placed in a round bottom flask under a nitrogen atmosphere. After cooling to −78° C., 128 ml (204 mmol) of 1.6 M butyllithium was slowly added dropwise to the flask. The mixture was stirred for 1 h. To the mixture slowly added dropwise 14.3 g (245 mmol) of acetone. The resulting mixture was stirred at room temperature for 6 h. After completion of the reaction, 50 ml of an aqueous ammonium chloride solution was added for phase separation. The organic layer was concentrated under reduced pressure and the resulting residue was purified by column chromatography to give Intermediate 5-b (38.3 g, yield 62%).

Synthesis Example 5-3: Synthesis of Intermediate 5-c

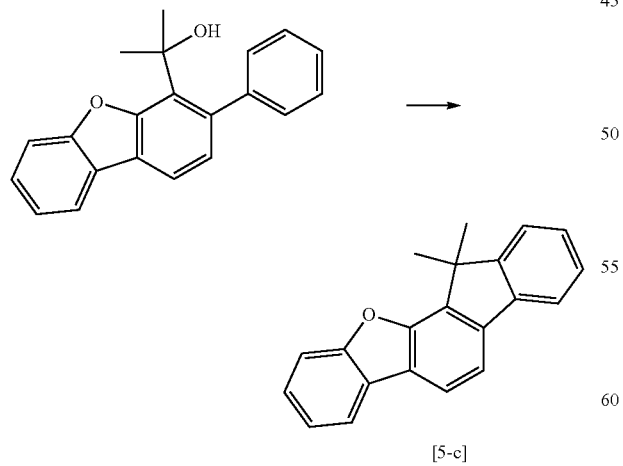

[5-c]

Intermediate 5-c (yield 69%) was synthesized in the same manner as in Synthesis Example 1-3, except that Intermediate 5-b was used instead of Intermediate 1-b.

Synthesis Example 5-4: Synthesis of Intermediate 5-d

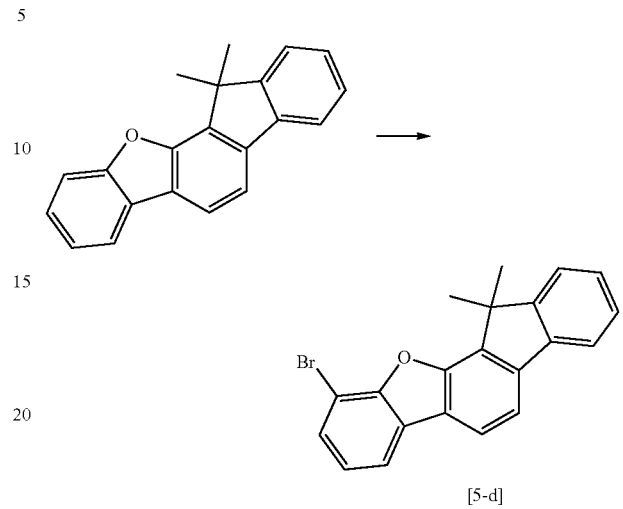

[5-d]

14.5 g (50.9 mmol) of Intermediate 5-c and 150 ml of dichloromethane were stirred in a 1 L reactor. To the mixture was slowly added dropwise 8.9 g (56 mmol) at room temperature. The resulting mixture was stirred for 5 h. After completion of the reaction, the reaction mixture was precipitated by adding methanol. Filtration of the precipitate gave Intermediate 5-d (9.4 g, yield 51%).

Synthesis Example 5-5: Synthesis of Intermediate 5-e

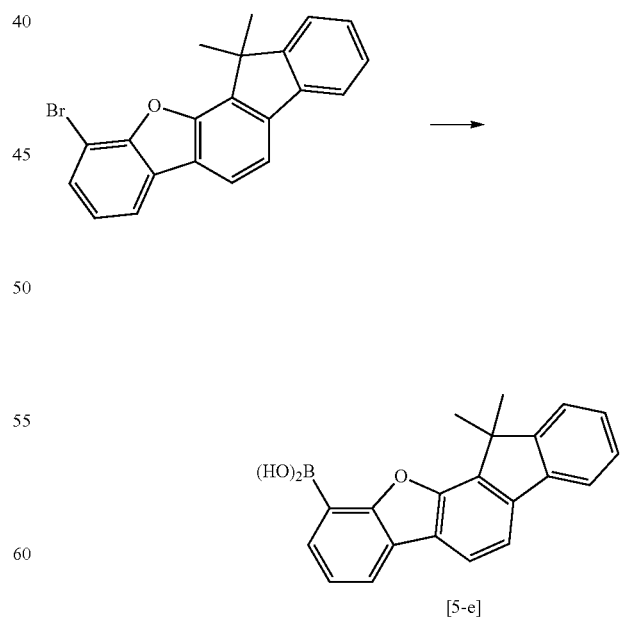

[5-e]

Intermediate 5-e (yield 65%) was synthesized in the same manner as in Synthesis Example 1-4, except that Intermediate 5-d was used instead of Intermediate 1-c.

Synthesis Example 5-6: Synthesis of Compound 164

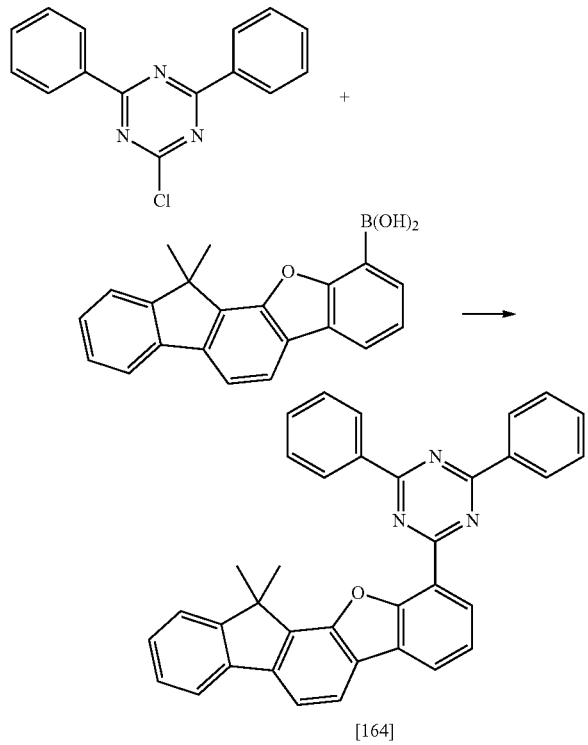

[164]

Compound 164 (yield 73%) was synthesized in the same manner as in Synthesis Example 1-5, except that Intermediate 5-e was used instead of Intermediate 1-d.

MS (MALDI-TOF): m/z 515.20 $[M]^+$

Synthesis Example 6: Synthesis of Compound 167

Synthesis Example 6-1: Synthesis of Compound 167

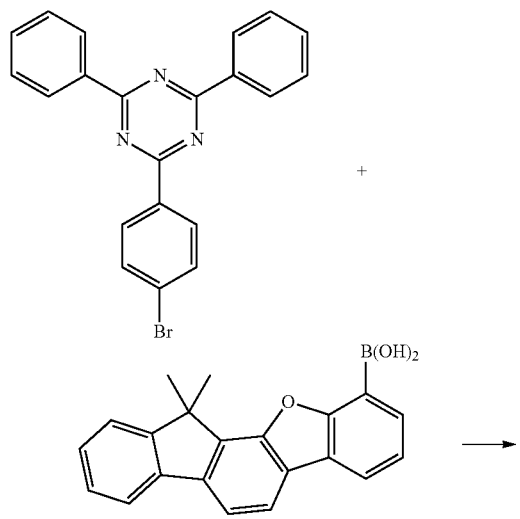

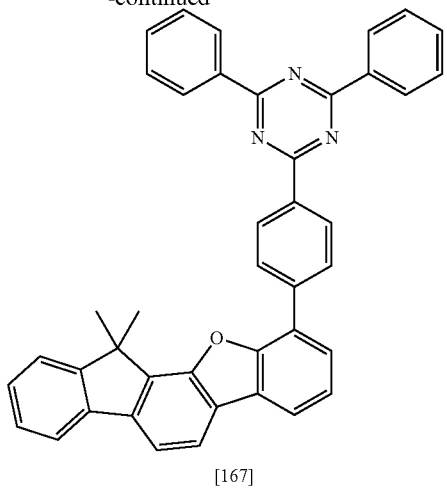

[167]

Compound 167 (yield 48%) was synthesized in the same manner as in Synthesis Example 1-5, except that 2-(4-bromophenyl)-4,6-diphenyl-1,3,5-triazine and Intermediate 5-e were used instead of 2-chloro-4,6-diphenyl-1,3,5-triazine and Intermediate 1-d, respectively.

MS (MALDI-TOF): m/z 591.23 $[M]^+$

Synthesis Example 7: Synthesis of Compound 197

Synthesis Example 7-1: Synthesis of Intermediate 7-a

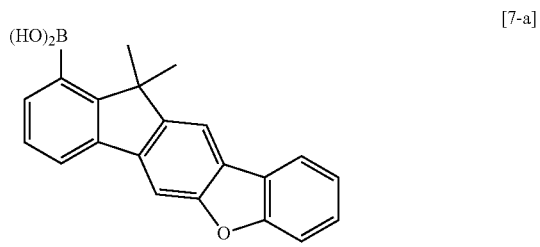 [SMILES: CC1(C)c2cc3c(cc2-c2cccc(B(O)O)c21)oc1ccccc13]

[7-a]

Intermediate 7-a (yield 66%) was synthesized in the same manner as in Synthesis Examples 1-1 to 1-4, except that dibenzofuran-3-boronic acid and methyl-5-bromo-1-iodobenzoate were used instead of dibenzofuran-1-boronic acid and methyl-5-bromo-2-iodobenzoate in Synthesis Example 1-1, respectively.

Synthesis Example 7-2: Synthesis of Compound 197

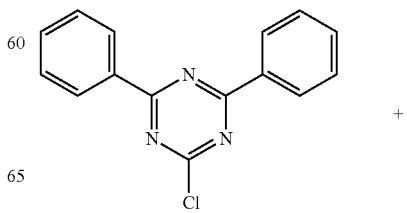

-continued

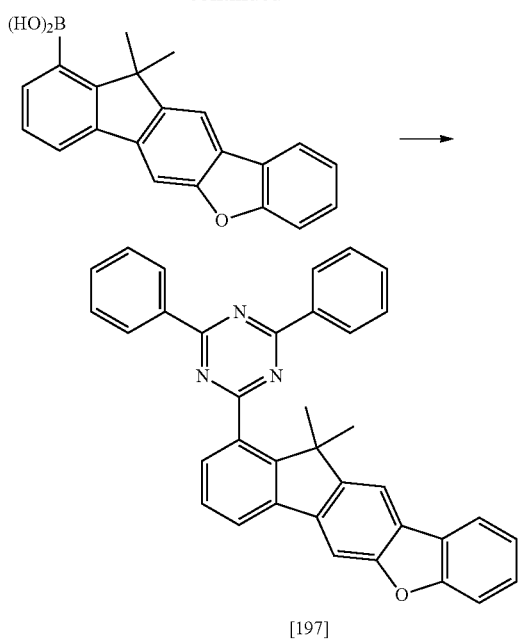

[197]

Compound 197 (yield 63%) was synthesized in the same manner as in Synthesis Example 1-5, except that Intermediate 7-a was used instead of Intermediate 1-d.

MS (MALDI-TOF): m/z 515.20 [M]$^+$

Synthesis Example 8: Synthesis of Compound 200

Synthesis Example 8-1: Synthesis of Compound 200

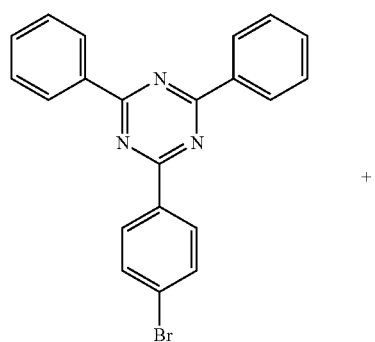

-continued

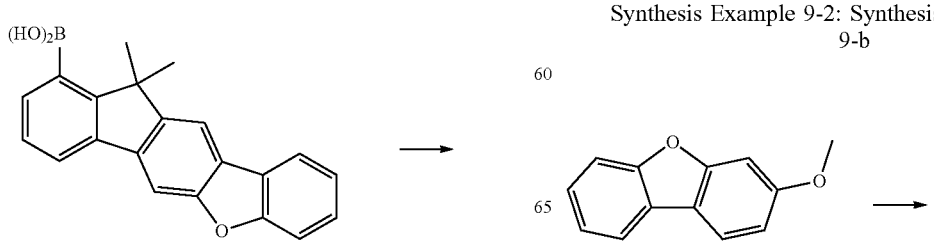

[200]

Compound 200 (yield 68%) was synthesized in the same manner as in Synthesis Example 1-5, except that 2-(4-bromophenyl)-4,6-diphenyl-1,3,5-triazine and Intermediate 7-a were used instead of 2-chloro-4,6-diphenyl-1,3,5-triazine and Intermediate 1-d, respectively.

MS (MALDI-TOF): m/z 591.23 [M]$^+$

Synthesis Example 9: Synthesis of Compound 233

Synthesis Example 9-1: Synthesis of Intermediate 9-a

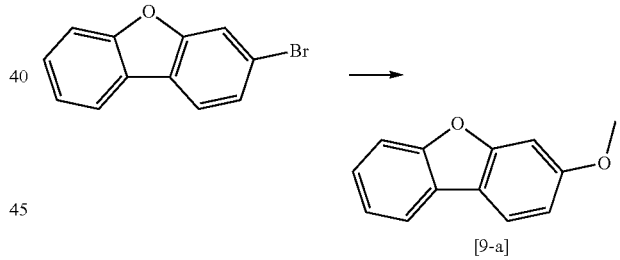

[9-a]

50 g (202 mmol) of 3-bromodibenzofuran, 54.6 g (1214 mmol) of an aqueous sodium methoxide solution, 11.5 g (60.7 mmol) of copper iodide, and 200 ml of methanol were placed in a round bottom flask under a nitrogen atmosphere. The mixture was refluxed for 12 h. After completion of the reaction, the organic layer was concentrated under reduced pressure and the resulting residue was purified by column chromatography to give Intermediate 9-a (36 g, yield 90%).

Synthesis Example 9-2: Synthesis of Intermediate 9-b

-continued

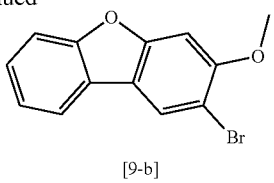

[9-b]

36 g (181 mmol) of Intermediate 9-a, 32.3 g (181 mmol) of N-bromosuccinimide, and 700 ml of dimethylformamide were placed in a round bottom flask under a nitrogen atmosphere. The mixture was stirred at 50° C. for 12 h. After completion of the reaction, the organic layer was concentrated under reduced pressure and the resulting residue was purified by column chromatography to give Intermediate 9-b (35 g, yield 70%).

Synthesis Example 9-3: Synthesis of Intermediate 9-c

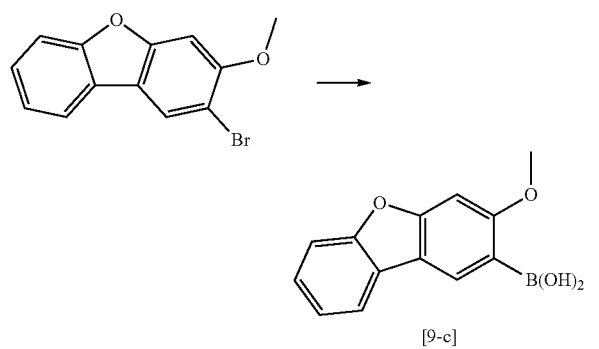

[9-c]

Intermediate 9-c (yield 71%) was synthesized in the same manner as in Synthesis Example 1-4, except that Intermediate 9-b was used instead of Intermediate 1-c.

Synthesis Example 9-4: Synthesis of Intermediate 9-d

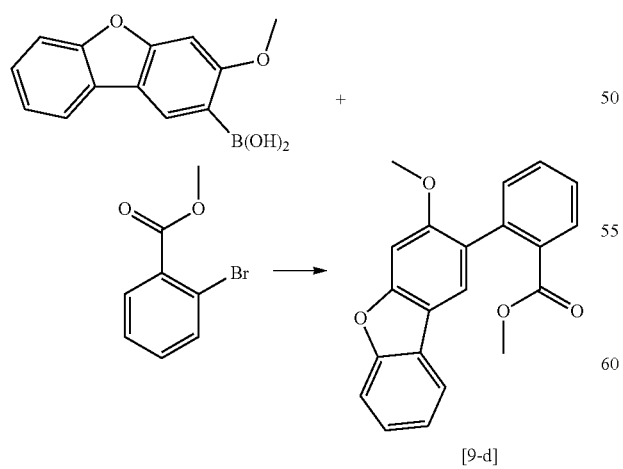

[9-d]

Intermediate 9-d (yield 64%) was synthesized in the same manner as in Synthesis Example 1-5, except that methyl-2-bromobenzoate and Intermediate 9-c were used instead of 2-chloro-4,6-diphenyl-1,3,5-triazine and Intermediate 1-d, respectively.

Synthesis Example 9-5: Synthesis of Intermediate 9-e

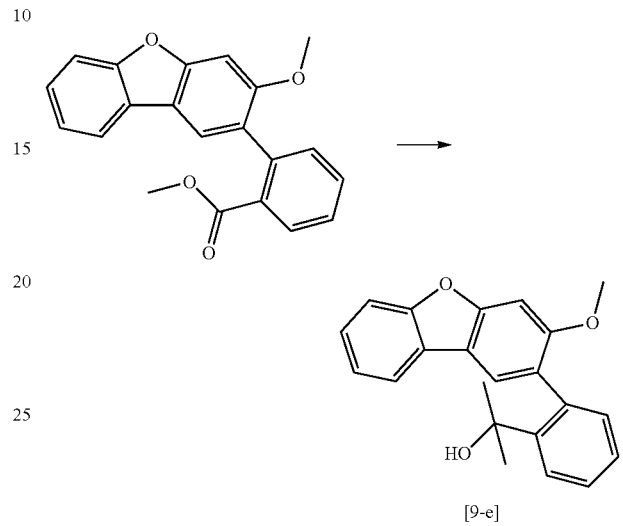

[9-e]

Intermediate 9-e (yield 77%) was synthesized in the same manner as in Synthesis Example 1-2, except that Intermediate 9-d was used instead of Intermediate 1-a.

Synthesis Example 9-6: Synthesis of Intermediate 9-f

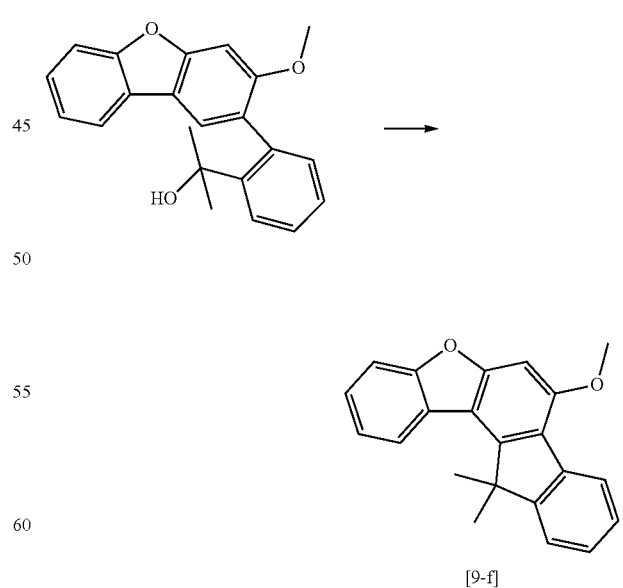

[9-f]

Intermediate 9-f was synthesized in a yield of 67% in the same manner as in Synthesis Example 1-3, except that Intermediate 9-e was used instead of Intermediate 1-b.

Synthesis Example 9-7: Synthesis of Intermediate 9-g

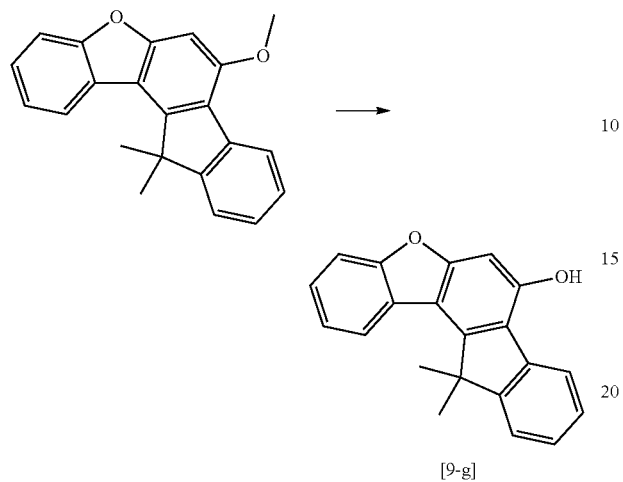

[9-g]

30 g (95.4 mmol) of Intermediate 9-f and 200 ml of dichloromethane were placed in a round bottom flask under a nitrogen atmosphere. The temperature was lowered to 0° C. A dilute solution of 120 g (143 mmol) of boron tribromide in 300 ml of dichloromethane was slowly added dropwise to the flask. The mixture was stirred at room temperature for 3 h. After completion of the reaction, the reaction solution was added to 1 L of distilled water. The organic layer was concentrated under reduced pressure and the resulting residue was purified by column chromatography to give Intermediate 9-g (19.2 g, yield 67%).

Synthesis Example 9-8: Synthesis of Intermediate 9-h

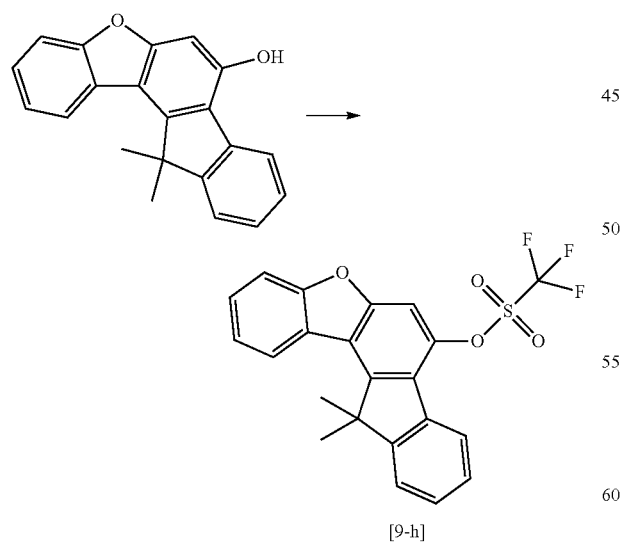

[9-h]

10 g (33.2 mmol) of Intermediate 9-g was placed in a round bottom flask under a nitrogen atmosphere. The temperature was lowered to 0° C. 3.2 ml (39.9 mmol) of pyridine and 7.3 ml (43.2 mmol) of trifluoromethanesulfonic anhydride were slowly added dropwise to the flask. The mixture was stirred at room temperature for 2 h. After completion of the reaction, the organic layer was concentrated under reduced pressure and the resulting residue was purified by column chromatography to give Intermediate 9-h (12.2 g, yield 85%).

Synthesis Example 9-9: Synthesis of Intermediate 9-i

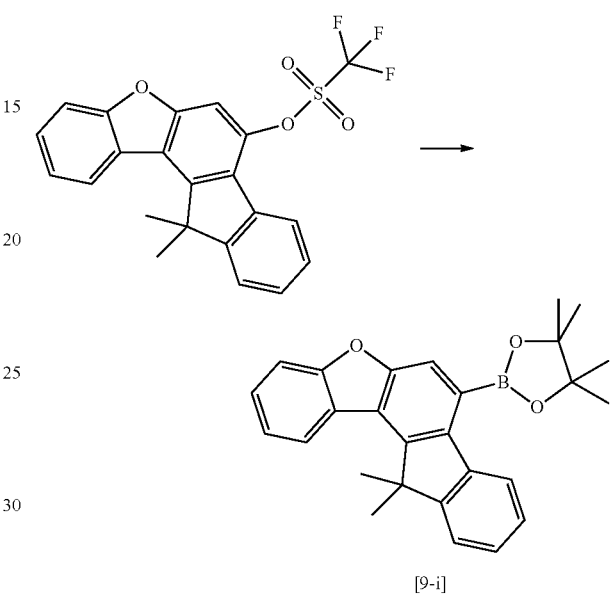

[9-i]

8.5 g (26.7 mmol) of Intermediate 9-h, 8.8 g (34.7 mmol) of bis(pinacolato)diborane, 1 g (1.3 mmol) of (diphenylphosphinoferrocene)palladium dichloride, 7.6 g (80 mmol) of potassium acetate, and 90 ml of toluene were placed in a round bottom flask under a nitrogen atmosphere. The mixture was refluxed for 12 h. After completion of the reaction, the organic layer was concentrated under reduced pressure and the resulting residue was purified by column chromatography to give Intermediate 9-i (8 g, yield 75%).

Synthesis Example 9-10: Synthesis of Compound 233

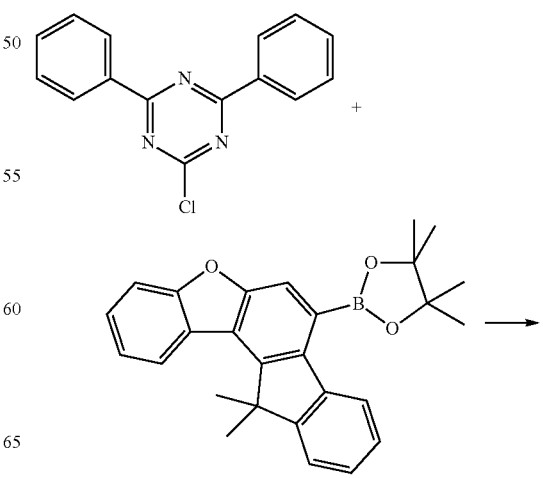

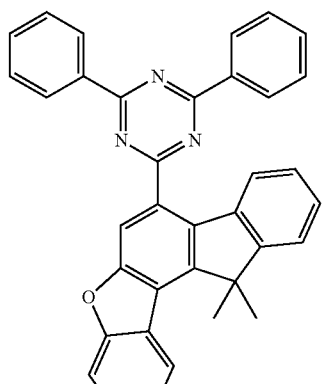

[233]

Compound 233 (yield 78%) was synthesized in the same manner as in Synthesis Example 1-5, except that Intermediate 9-i was used instead of Intermediate 1-d.

MS (MALDI-TOF): m/z 515.20 [M]+

Synthesis Example 10: Synthesis of Compound 234

Synthesis Example 10-1: Synthesis of Compound 234

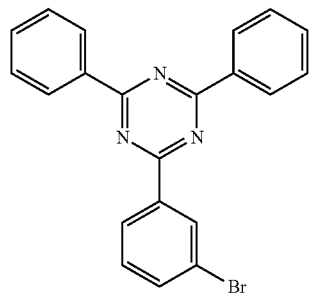

+

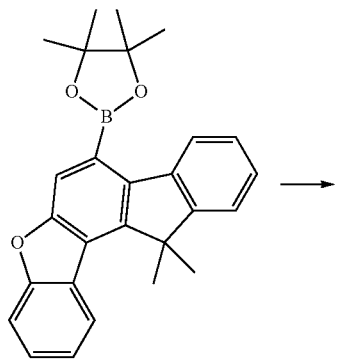

→

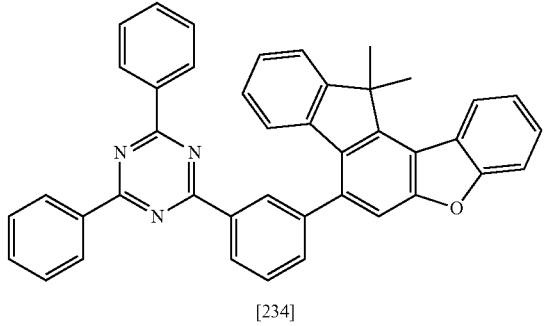

[234]

Compound 234 (yield 52%) was synthesized in the same manner as in Synthesis Example 1-5, except that 2-(3-bromophenyl)-4,6-diphenyl-1,3,5-triazine and Intermediate 9-i were used instead of 2-chloro-4,6-diphenyl-1,3,5-triazine and Intermediate 1-d, respectively.

MS (MALDI-TOF): m/z 591.23 [M]+

Synthesis Example 11: Synthesis of Compound 293

Synthesis Example 11-1: Synthesis of Intermediate 11-a

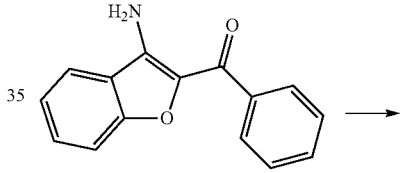

→

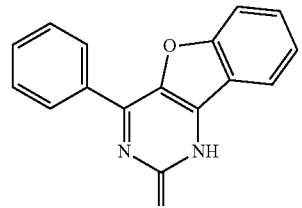

[11-a]

37 g (156 mmol) of (3-amino-benzofuran-2-yl)-phenyl-methanone, 16.9 g (281 mmol) of urea, and 185 mL of acetic acid were placed in a 500 mL reactor. The mixture was refluxed with stirring for 12 h. After completion of the reaction, the reaction mixture was precipitated by adding excess water. The precipitate was collected by filtration, slurried with hot methanol, filtered, slurried with hot toluene, filtered, and dried to obtain Intermediate 11-a (24 g, yield 59%).

Synthesis Example 11-2: Synthesis of Intermediate 11-b

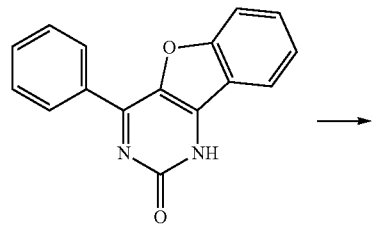 

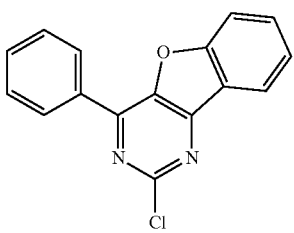

[11-b]

15 g (44 mmol) of Intermediate 11-a and 150 mL of phosphorus oxychloride were placed in a 500 mL reactor. The mixture was refluxed with stirring for 3 h. After completion of the reaction, the reaction mixture was precipitated by slowly adding excess water at 0° C. The precipitate was collected by filtration and purified by column chromatography to give 21 g (yield 81%) of Intermediate 11-b.

Synthesis Example 11-3: Synthesis of Compound 293

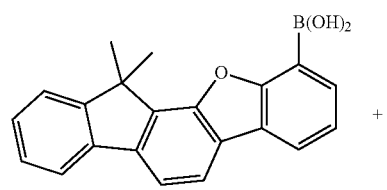

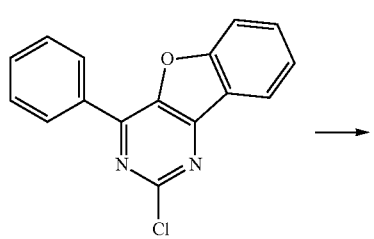

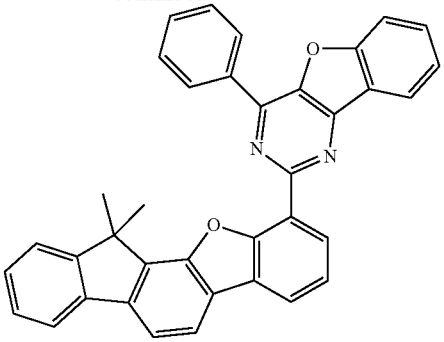

[293]

Compound 293 (yield 57%) was synthesized in the same manner as in Synthesis Example 1-5, except that Intermediate 11-b and Intermediate 5-e were used instead of 2-chloro-4,6-diphenyl-1,3,5-triazine and Intermediate 1-d, respectively.

MS (MALDI-TOF): m/z 528.18 [M]$^+$

Synthesis Example 12: Synthesis of Compound 313

Synthesis Example 12-1: Synthesis of Intermediate 12-a

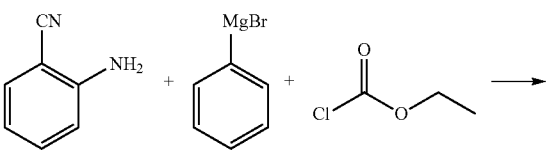

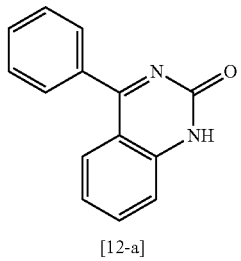

[12-a]

27.4 g (232 mmol) of 2-aminobenzonitrile and 300 mL of tetrahydrofuran were stirred in a 1 L reactor. After cooling to 0° C., 88.2 mL (487 mmol) of 3 M phenylmagnesium bromide was added dropwise to the flask. The mixture was refluxed for 3 h. After cooling to 0° C., a solution of 44.3 g (732 mmol) of ethyl chloroformate in 200 mL of tetrahydrofuran was added dropwise to the reaction mixture. The resulting mixture was refluxed for 2 h. After cooling to 0° C., to the reaction mixture was added a saturated aqueous solution of ammonium chloride. The organic layer was extracted and concentrated under reduced pressure. The resulting residue was purified by column chromatography to give Intermediate 12-a (40 g, yield 78%).

Synthesis Example 12-2: Synthesis of Intermediate 12-b

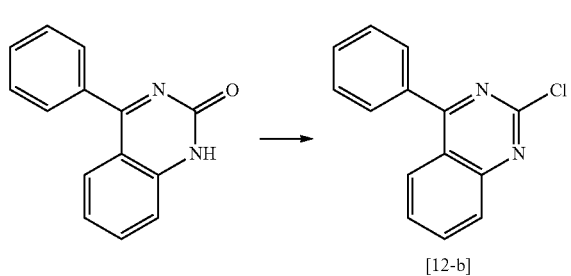 [SMILES: O=c1nc(-c2ccccc2)c2ccccc2[nH]1 ; Clc1nc(-c2ccccc2)c2ccccc2n1]

[12-b]

40 g (181 mmol) of Intermediate 12-a and 400 mL of phosphorus oxychloride were placed in a 1 L reactor. The mixture was refluxed for 5 h. After cooling to 0° C., distilled water was added dropwise to the reactor. The reaction mixture was filtered and the resulting residue was purified by column chromatography to give Intermediate 12-b (29.5 g, yield 68%).

Synthesis Example 12-3: Synthesis of Compound 313

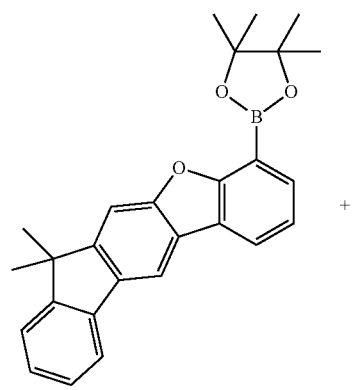

+

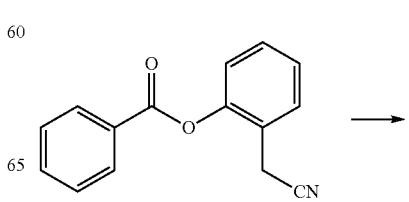

→

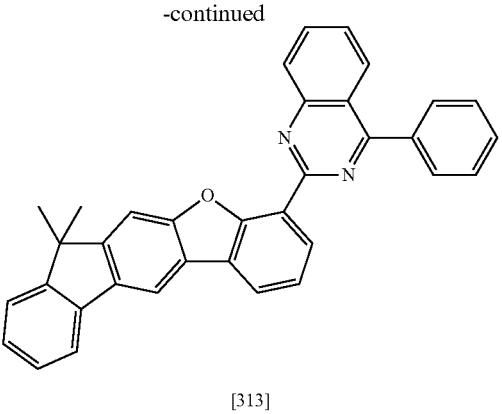

[313]

Compound 313 (yield 54%) was synthesized in the same manner as in Synthesis Example 1-5, except that Intermediate 12-b and Intermediate 3-g were used instead of 2-chloro-4,6-diphenyl-1,3,5-triazine and Intermediate 1-d, respectively.

MS (MALDI-TOF): m/z 488.19 [M]$^+$

Synthesis Example 13: Synthesis of Compound 329

Synthesis Example 13-1: Synthesis of Intermediate 13-a

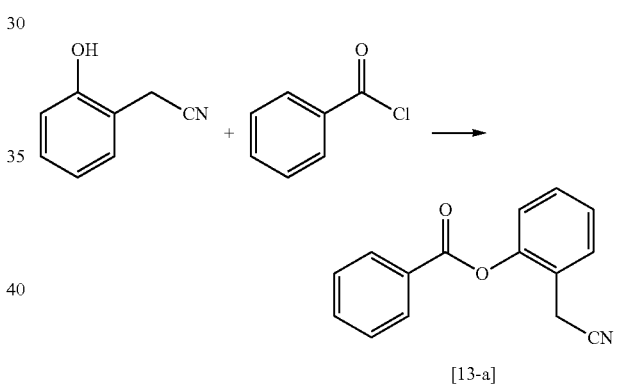

[13-a]

90 g (676 mmol) of 2-hydroxyphenylacetonitrile, 68.8 g (338 mmol) of 4-dimethylaminopyridine, 137 g (1352 mmol) of triethylamine, and 900 mL of methylene chloride were placed in a 2 L reactor and 82.4 g (676 mmol) of benzoyl chloride was then added dropwise thereto at 0° C. Thereafter, the mixture was stirred at room temperature for 4 h. After completion of the reaction, the reaction mixture was concentrated and the resulting residue was purified by column chromatography to give Intermediate 13-a (40 g, yield 61%).

Synthesis Example 13-2: Synthesis of Intermediate 13-b

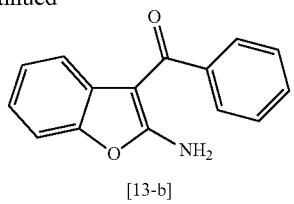

[13-b]

40 g (169 mmol) of Intermediate 13-a, 9.5 g (34 mmol) of tricyclohexylphosphine, 1.9 g (17 mmol) of zinc, 3.8 g (17 mmol) of palladium acetate, and 400 mL of dimethylformamide were placed in a 1 L reactor. The mixture was refluxed with stirring under a nitrogen atmosphere for 12 h. After completion of the reaction, the reaction mixture was added to excess water at room temperature. The resulting brown crystal was collected by filtration and purified by column chromatography to give Intermediate 13-b (20 g, yield 52%).

Synthesis Example 13-3: Synthesis of Intermediate 13-c

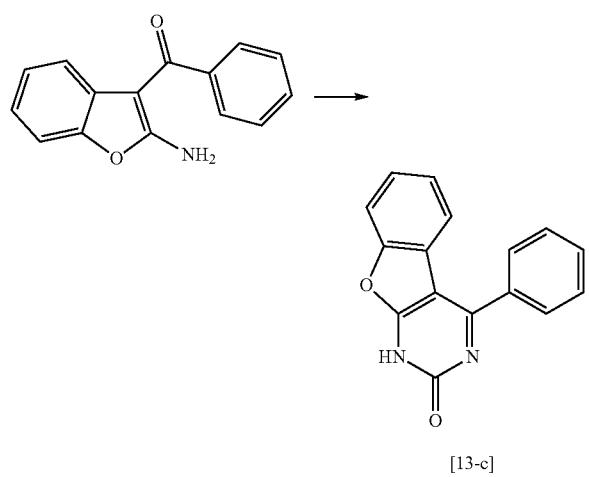

[13-c]

Intermediate 13-c (10 g, yield 62%) was synthesized in the same manner as in Synthesis Example 11-1, except that Intermediate 13-b was used instead of (3-amino-benzofuran-2-yl)-phenylmethanone.

Synthesis Example 13-4: Synthesis of Intermediate 13-d

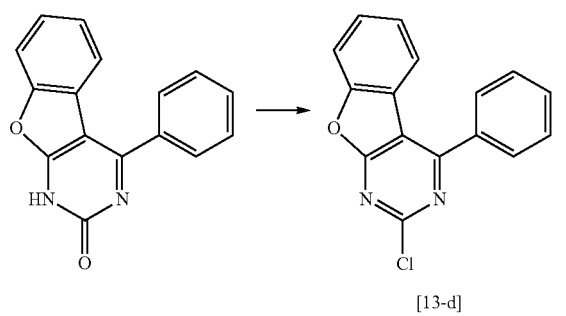 [SMILES: O=c1nc(-c2ccccc2)c2c([nH]1)oc1ccccc12 ; Clc1nc(-c2ccccc2)c2c(n1)oc1ccccc12]

[13-d]

Intermediate 13-d (yield 77%) was synthesized in the same manner as in Synthesis Example 11-2, except that Intermediate 13-c was used instead of Intermediate 11-a.

Synthesis Example 13-6: Synthesis of Compound 329

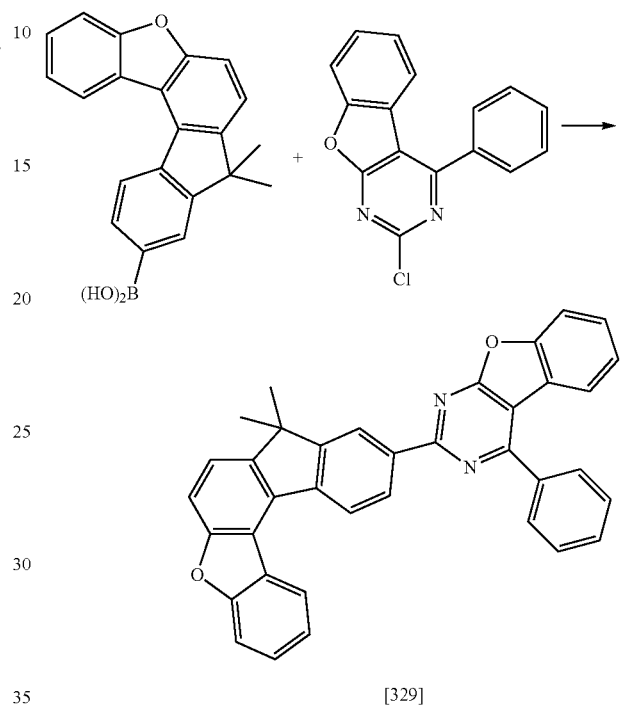

[329]

Compound 329 (yield 54%) was synthesized in the same manner as in Synthesis Example 1-5, except that Intermediate 13-d was used instead of 2-chloro-4,6-diphenyl-1,3,5-triazine.

MS (MALDI-TOF): m/z 528.18 [M]$^+$

Synthesis Example 14: Synthesis of Compound 341

Synthesis Example 14-1: Synthesis of Compound 341

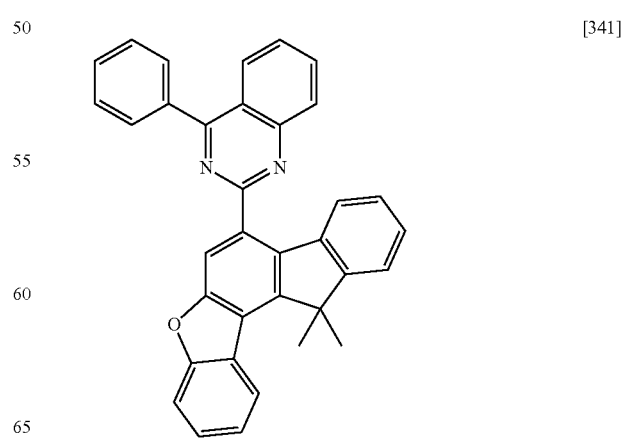

[341]

Compound 341 (yield 58%) was synthesized in the same manner as in Synthesis Example 1-5, except that Intermediate 12-b and Intermediate 9-i were used instead of 2-chloro-4,6-diphenyl-1,3,5-triazine and Intermediate 1-d, respectively.

MS (MALDI-TOF): m/z 488.19 [M]$^+$

Synthesis Example 15: Synthesis of Compound 370

Synthesis Example 15-1: Synthesis of Intermediate 15-a

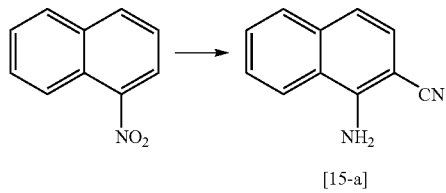

[15-a]

Ethyl cyanoacetate (139.8 g, 1.236 mol), potassium cyanide (29.5 g, 0.453 mol), and potassium hydroxide (46.2 g, 0.824 mol) were dissolved in 920 mL of dimethylformamide in a 2 L round bottom flask under a nitrogen atmosphere. The solution was stirred at 10° C. for 20 min. Thereafter, the solution was added with 1-nitronaphthalene (92 g, 531 mol), followed by stirring at 60° C. for 4 h. After completion of the reaction, the reaction mixture was concentrated and 600 mL of a 10% aqueous sodium hydroxide solution was added thereto. The resulting mixture was refluxed with stirring. The solid was collected by filtration and purified by column chromatography to give Intermediate 15-a (50 g, yield 56%).

Synthesis Example 15-2: Synthesis of Intermediate 15-b

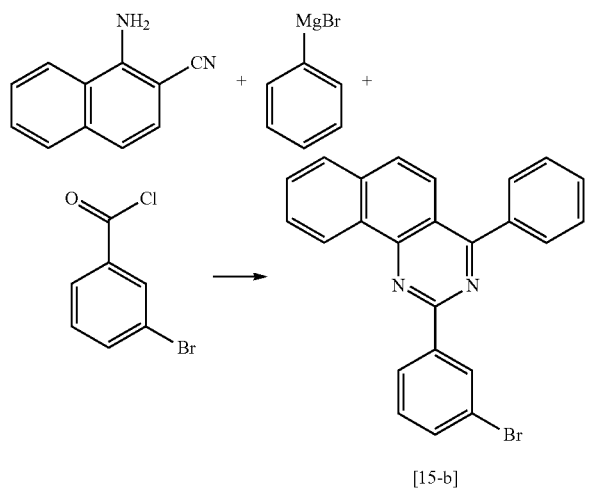

[15-b]

Intermediate 15-a (20.0 g, 169 mmol) and tetrahydrofuran (200 mL) were placed in a 1 L round bottom flask filled with nitrogen and 3 M phenylmagnesium bromide (113 mL, 623 mmol) was slowly added dropwise thereto at 0° C. The mixture was refluxed with stirring for 3 h. When the starting material disappeared, the temperature was again lowered. A solution of 3-bromobenzoyl chloride (44.58 g, 0.203 mmol) in 200 mL of tetrahydrofuran was slowly added dropwise to the flask. The resulting mixture was refluxed with stirring for 2 h. The reaction was quenched with an aqueous ammonium chloride solution. The reaction mixture was extracted with ethyl acetate and water. The organic layer was concentrated under reduced pressure and the resulting residue was purified by column chromatography to give Intermediate 15-b (37 g, yield 30%).

Synthesis Example 15-3: Synthesis of Compound 370

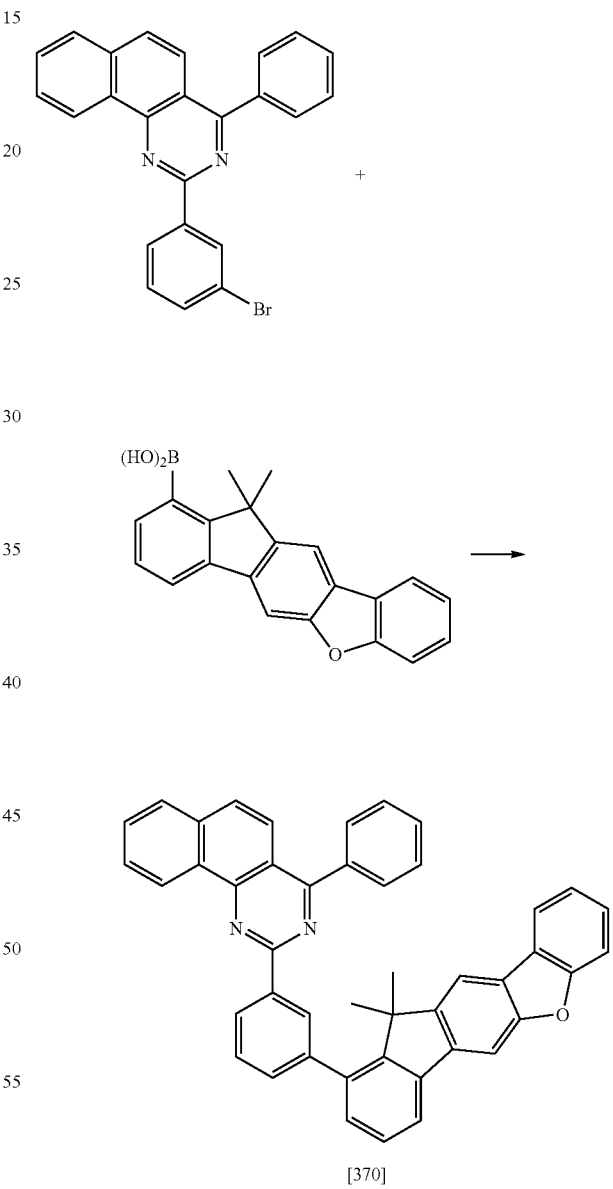

[370]

Compound 370 (yield 57%) was synthesized in the same manner as in Synthesis Example 1-5, except that Intermediate 15-b and Intermediate 7-a were used instead of 2-chloro-4,6-diphenyl-1,3,5-triazine and Intermediate 1-d, respectively.

MS (MALDI-TOF): m/z 614.24 [M]$^+$

Synthesis Example 16: Synthesis of Compound 375

Synthesis Example 16-1: Synthesis of Intermediate 16-a

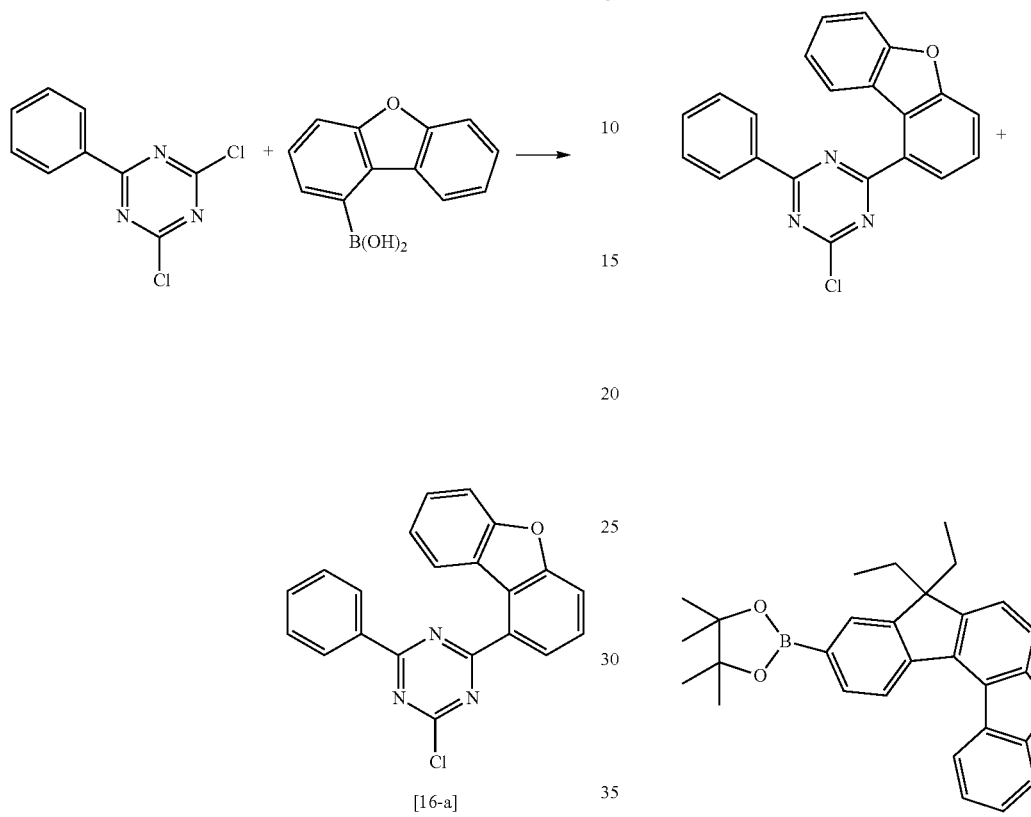

[16-a]

Intermediate 16-a (yield 42%) was synthesized in the same manner as in Synthesis Example 1-5, except that 2,4-dichloro-6-phenyl-1,3,5-triazine and benzofuran-1-boronic acid were used instead of 2-chloro-4,6-diphenyl-1,3,5-triazine and Intermediate 1-d, respectively.

Synthesis Example 16-2: Synthesis of Intermediate 16-b

[16-b]

Intermediate 16-b (yield 55%) was synthesized in the same manner as in Synthesis Examples 1-2 to 1-4, except that 3 M ethylmagnesium bromide was used instead of 3 M methylmagnesium bromide in Synthesis Example 1-2.

Synthesis Example 16-3: Synthesis of Compound 375

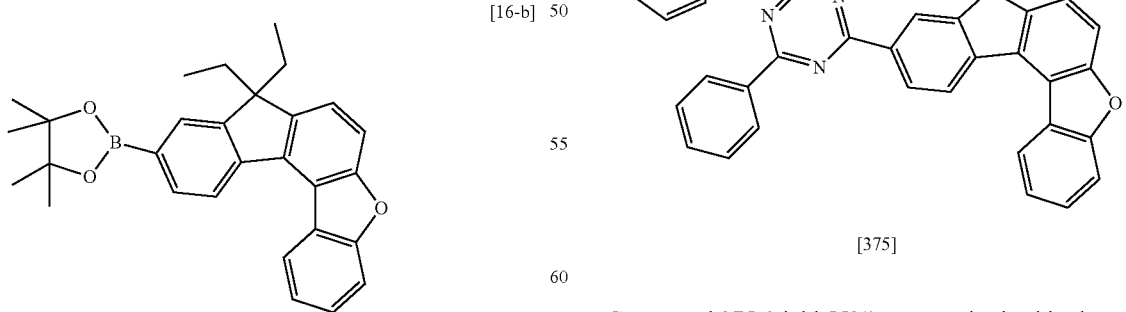

[375]

Compound 375 (yield 55%) was synthesized in the same manner as in Synthesis Example 1-5, except that Intermediate 16-a and Intermediate 16-b were used instead of 2-chloro-4,6-diphenyl-1,3,5-triazine and Intermediate 1-d, respectively.

MS (MALDI-TOF): m/z 633.24 $[M]^+$

Synthesis Example 17: Synthesis of Compound 414

Synthesis Example 17-1: Synthesis of Intermediate 17-a

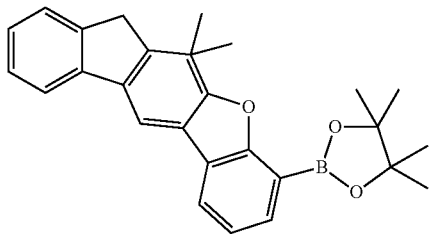

[17-a]

Intermediate 17-a (yield 57%) was synthesized in the same manner as in Synthesis Examples 3-1 to 3-7, except that 2-bromo-9,9-diethylfluorene was used instead of 2-bromo-9,9-dimethylfluorene in Synthesis Example 3-1.

Synthesis Example 17-2: Synthesis of Compound 414

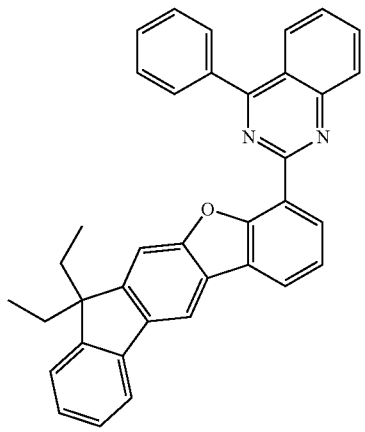

[414]

Compound 414 (yield 54%) was synthesized in the same manner as in Synthesis Example 1-5, except that Intermediate 12-b and Intermediate 17-a were used instead of 2-chloro-4,6-diphenyl-1,3,5-triazine and Intermediate 1-d, respectively.

MS (MALDI-TOF): m/z 516.22 [M]$^+$

Synthesis Example 18: Synthesis of Compound 443

Synthesis Example 18-1: Synthesis of Intermediate 18-a

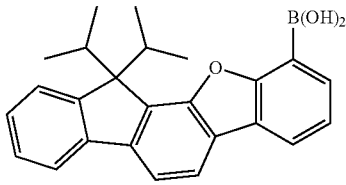

[18-a]

Intermediate 18-a (yield 52%) was synthesized in the same manner as in Synthesis Examples 5-2 to 5-5, except that 2,4-dimethyl-3-pentanone was used instead of acetone in Synthesis Example 5-2.

Synthesis Example 18-2: Synthesis of Compound 443

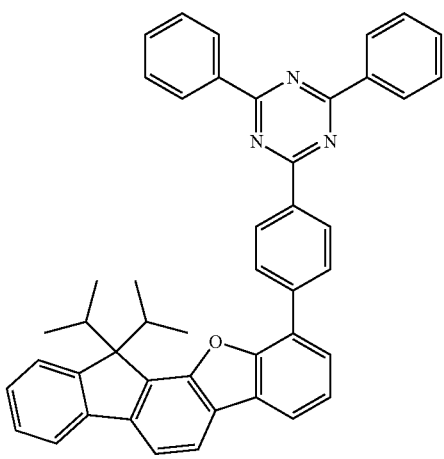

[443]

Compound 443 (yield 55%) was synthesized in the same manner as in Synthesis Example 1-5, except that 2-(4-bromophenyl)-4,6-diphenyl-1,3,5-triazine and Intermediate 18-a were used instead of 2-chloro-4,6-diphenyl-1,3,5-triazine and Intermediate 1-d, respectively.

MS (MALDI-TOF): m/z 647.29 [M]$^+$

Synthesis Example 19: Synthesis of Compound 474

Synthesis Example 19-1: Synthesis of Intermediate 19-a

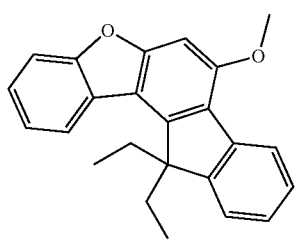

[19-a]

Intermediate 19-a (yield 55%) was synthesized in the same manner as in Synthesis Examples 1-2 and 1-3, except that 3 M ethylmagnesium bromide and Intermediate 9-d were used instead of 3 M methylmagnesium bromide and Intermediate 1-a in Synthesis Example 1-2, respectively.

Synthesis Example 19-2: Synthesis of Intermediate 19-b

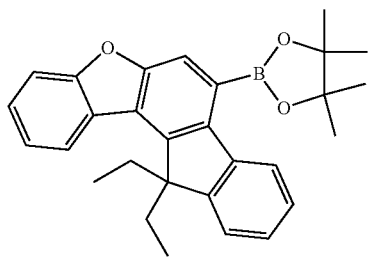

[19-b]

Intermediate 19-b (yield 67%) was synthesized in the same manner as in Synthesis Examples 9-7 to 9-9, except that Intermediate 19-a was used instead of Intermediate 9-f in Synthesis Example 9-7.

Synthesis Example 19-2: Synthesis of Compound 474

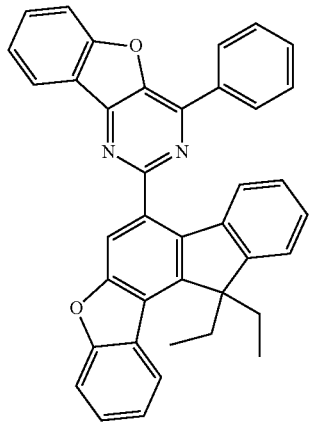

[474]

Compound 474 (yield 60%) was synthesized in the same manner as in Synthesis Example 1-5, except that Intermediate 11-b and Intermediate 19-b were used instead of 2-chloro-4,6-diphenyl-1,3,5-triazine and Intermediate 1-d, respectively.

MS (MALDI-TOF): m/z 556.22 [M]$^+$

Examples 1 to 19: Fabrication of Organic Light Emitting Diodes

ITO glass was patterned to have a light emitting area of 2 mm×2 mm, followed by cleaning. After the cleaned ITO glass was mounted in a vacuum chamber, the base pressure was adjusted to $1\times10^{-6}$ torr. HATCN (50 Å), NPD (650 Å), [BH]+Blue dopant (BD) 5% (200 Å), the corresponding compound shown in Table 1 (300 Å), Liq (10 Å), and Al (1,000 Å) were deposited in this order on the ITO glass to fabricate an organic light emitting diode. The luminescent properties of the organic light emitting diode were measured at 0.4 mA.

The structures of HATCN, NPD, BD, BH, and Liq are as follows:

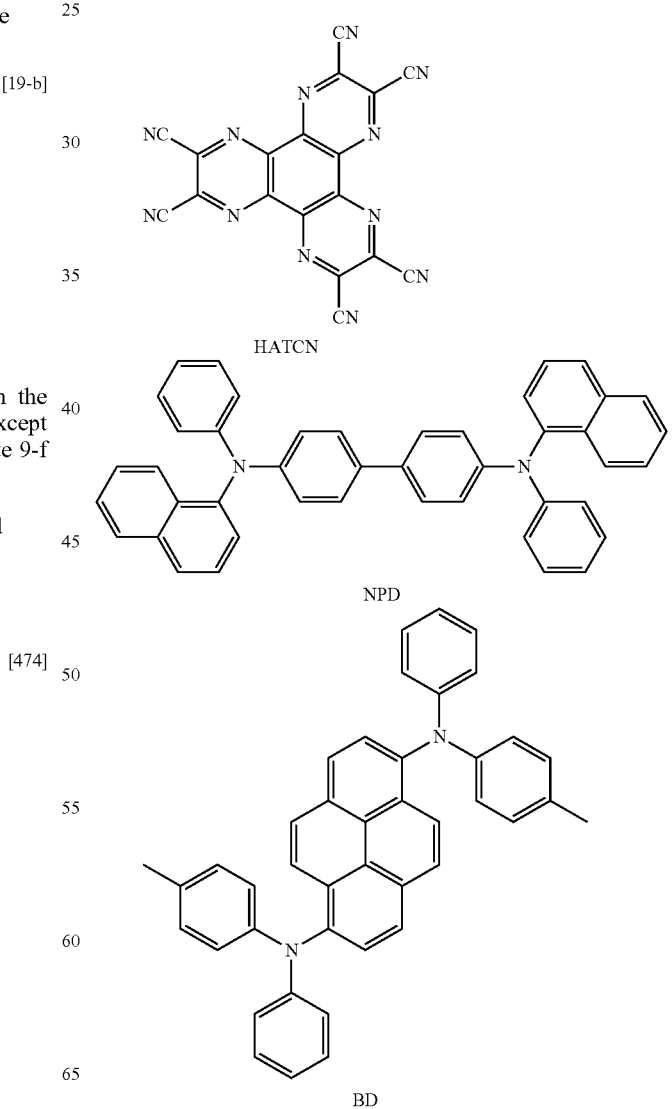

HATCN

NPD

BD

-continued

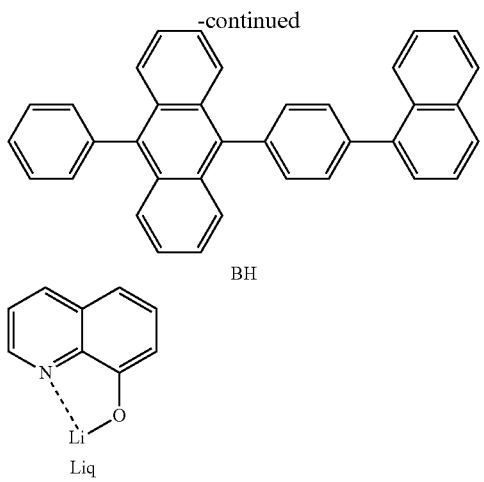

BH

Liq

Comparative Example 1

An organic light emitting diode was fabricated in the same manner as in Examples 1-19, except that ET was used instead of the compounds shown in Table 1. ET is widely used as an electron transport material and its structure is as follows.

[ET]

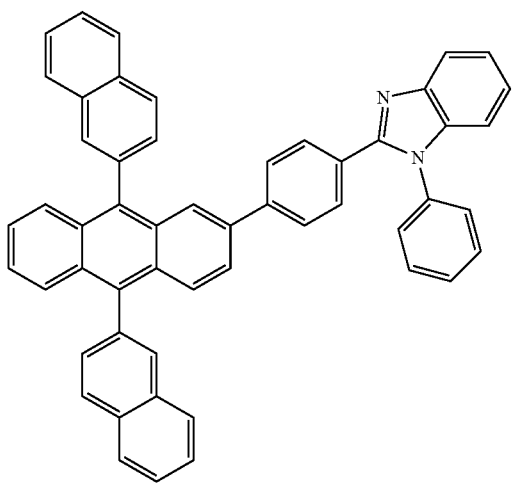

The organic electroluminescence diodes fabricated in Examples 1-19 and Comparative Example 1 were measured for voltage, luminance, color coordinates, and lifetime. The results are shown in Table 1. $T_{95}$ indicates the time at which the luminance of each diode was decreased to 95% of the initial luminance (2000 cd/m$^2$).

TABLE 1

| Properties | ETL | V | Cd/A | CIEx | CIEy | $T_{95}$ (Hrs) |
|---|---|---|---|---|---|---|
| Comparative Example 1 | ET | 4.2 | 6.4 | 0.133 | 0.129 | 16 |
| Example 1 | Compound 1 | 3.6 | 8.0 | 0.132 | 0.130 | 35 |
| Example 2 | Compound 5 | 3.6 | 7.9 | 0.133 | 0.128 | 43 |
| Example 3 | Compound 71 | 3.4 | 8.0 | 0.132 | 0.126 | 40 |
| Example 4 | Compound 72 | 3.8 | 7.9 | 0.133 | 0.125 | 36 |

TABLE 1-continued

| Properties | ETL | V | Cd/A | CIEx | CIEy | $T_{95}$ (Hrs) |
|---|---|---|---|---|---|---|
| Example 5 | Compound 164 | 3.3 | 7.6 | 0.132 | 0.126 | 34 |
| Example 6 | Compound 167 | 3.9 | 7.6 | 0.133 | 0.125 | 45 |
| Example 7 | Compound 197 | 4.0 | 7.5 | 0.133 | 0.125 | 42 |
| Example 8 | Compound 200 | 3.6 | 8.1 | 0.132 | 0.130 | 37 |
| Example 9 | Compound 233 | 3.4 | 8.0 | 0.133 | 0.128 | 37 |
| Example 10 | Compound 234 | 3.6 | 7.8 | 0.133 | 0.127 | 34 |
| Example 11 | Compound 293 | 3.6 | 8.0 | 0.132 | 0.130 | 45 |
| Example 12 | Compound 313 | 3.6 | 7.9 | 0.133 | 0.128 | 42 |
| Example 13 | Compound 329 | 3.4 | 8.0 | 0.132 | 0.126 | 40 |
| Example 14 | Compound 341 | 3.8 | 7.9 | 0.133 | 0.125 | 34 |
| Example 15 | Compound 370 | 3.3 | 8.0 | 0.132 | 0.126 | 38 |
| Example 16 | Compound 375 | 3.9 | 7.9 | 0.133 | 0.125 | 40 |
| Example 17 | Compound 414 | 4.0 | 7.6 | 0.132 | 0.126 | 33 |
| Example 18 | Compound 443 | 3.6 | 7.6 | 0.133 | 0.125 | 37 |
| Example 19 | Compound 474 | 3.7 | 7.5 | 0.133 | 0.125 | 41 |

As can be seen from the results in Table 1, the inventive organic compounds had higher efficiencies, lower driving voltages, and longer lifetimes than ET, which is widely used as an electron transport material. Therefore, it can be concluded that the inventive compounds are suitable for the fabrication of organic light emitting diodes with improved characteristics.

What is claimed is:

1. An organic light emitting compound selected from the group consisting of Compounds 1 to 564:

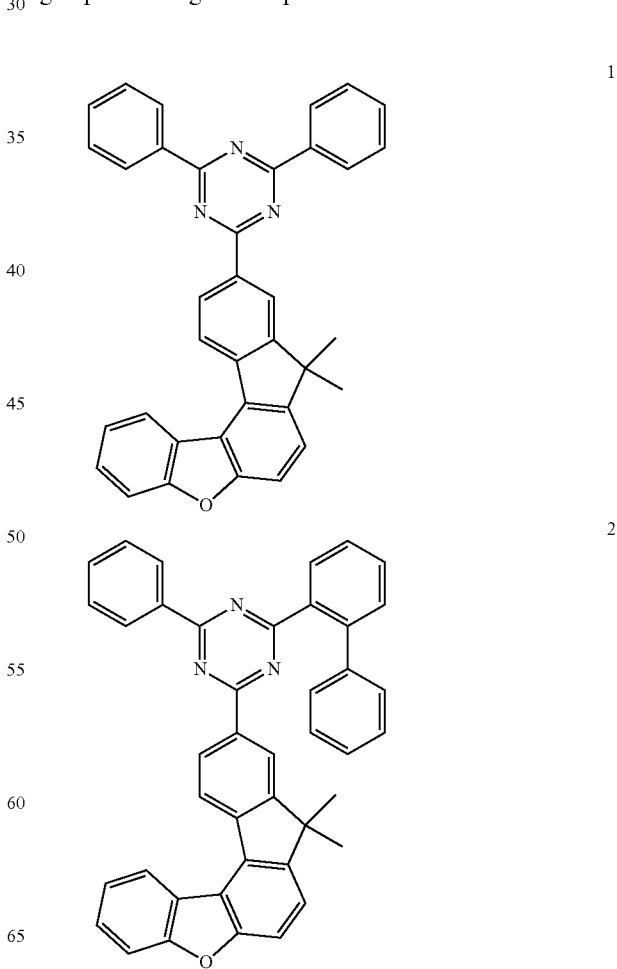

255
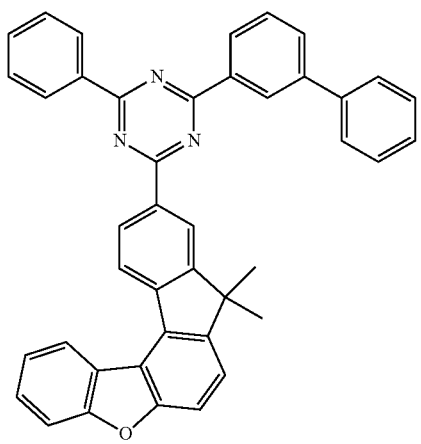
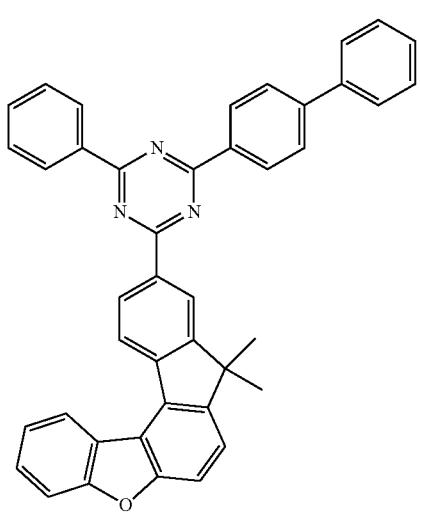
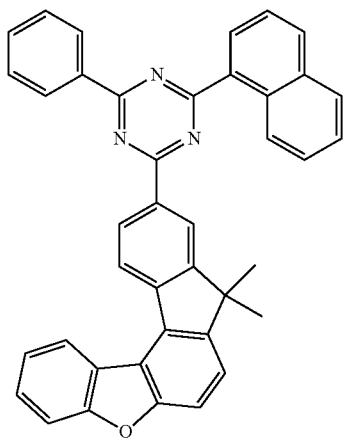
256
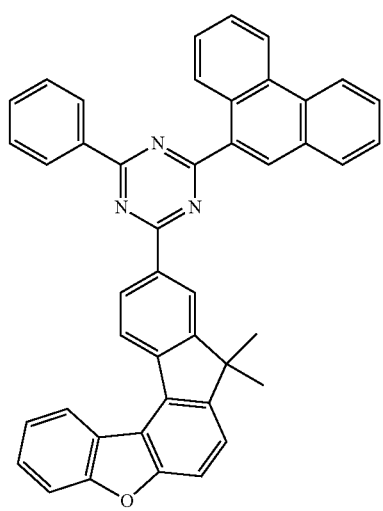
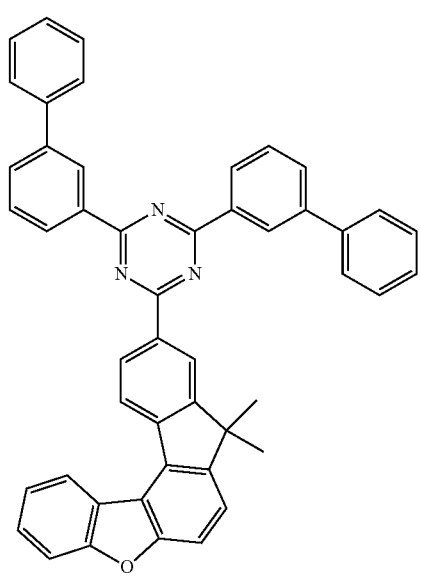
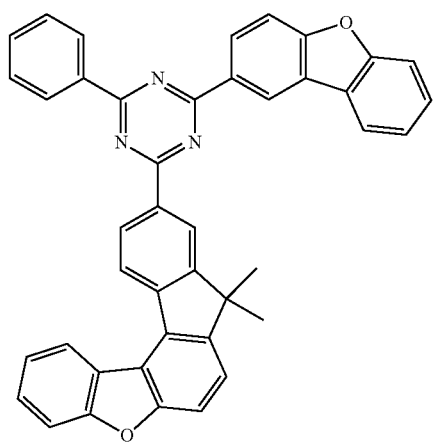

9
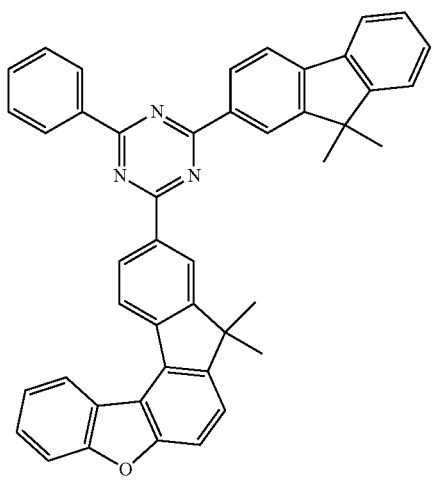
10
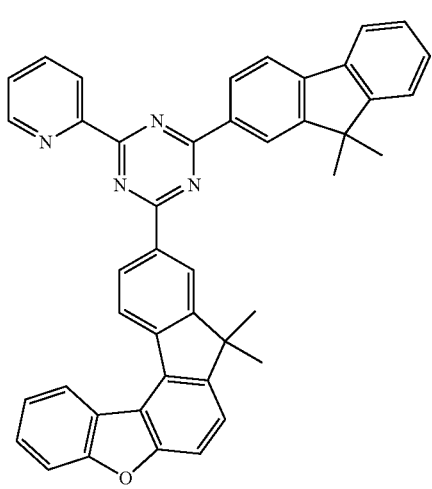
11
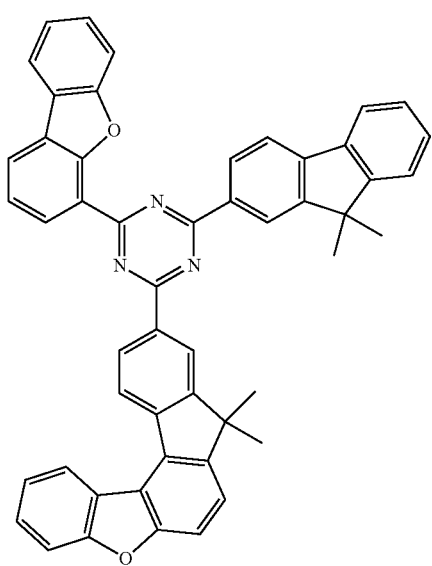
12
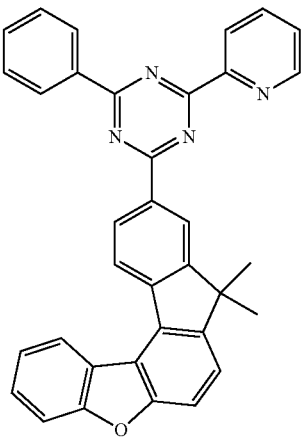
13
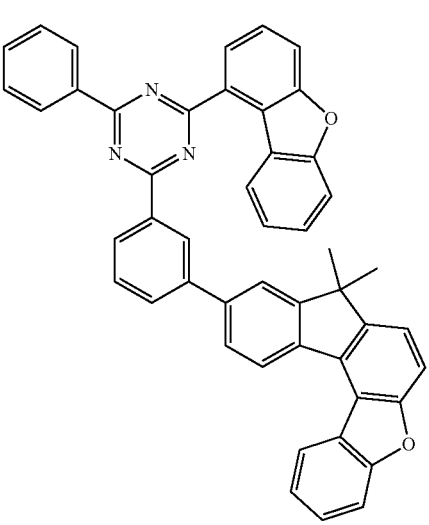
14
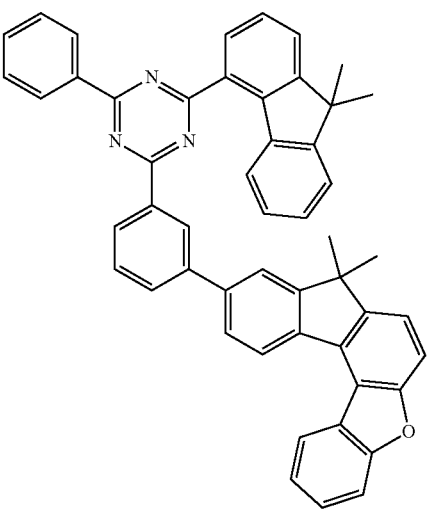

259
-continued
15
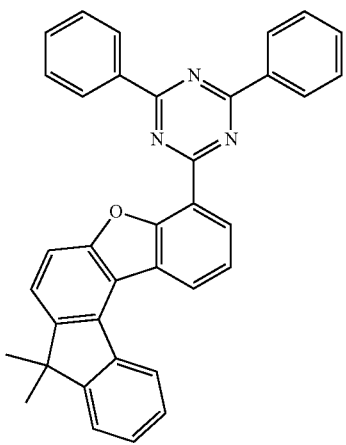
16
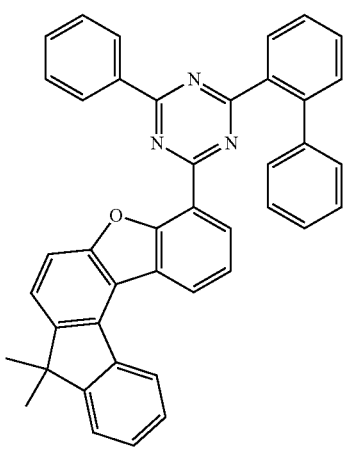
17
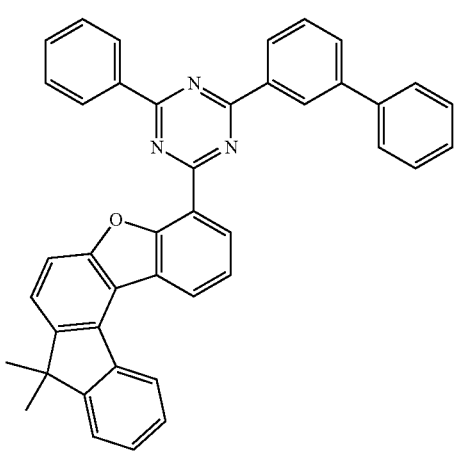
260
-continued
18
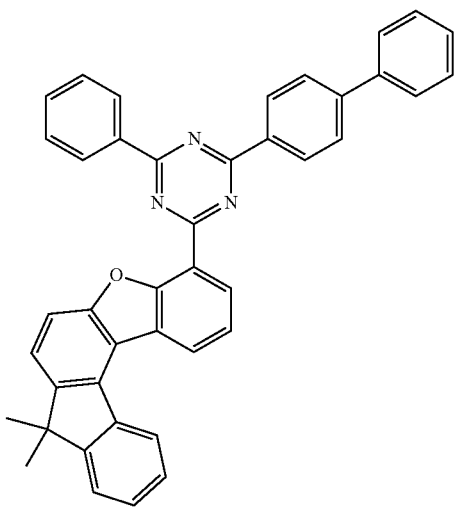
19
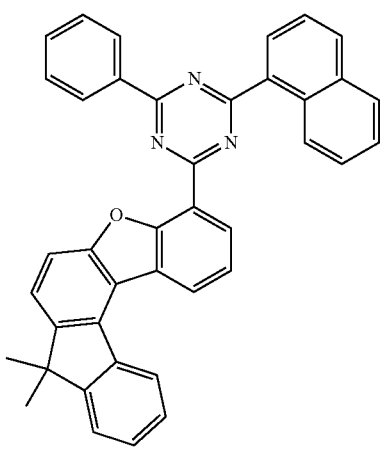
20
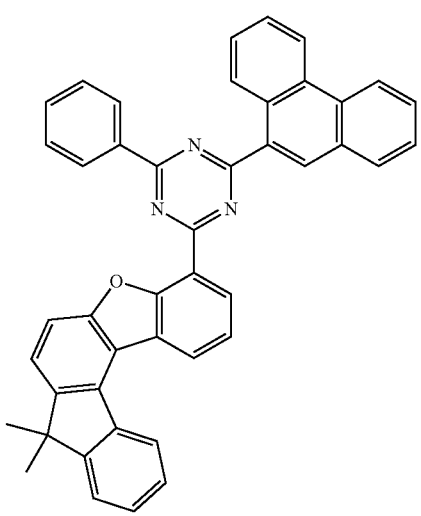

261
-continued
21
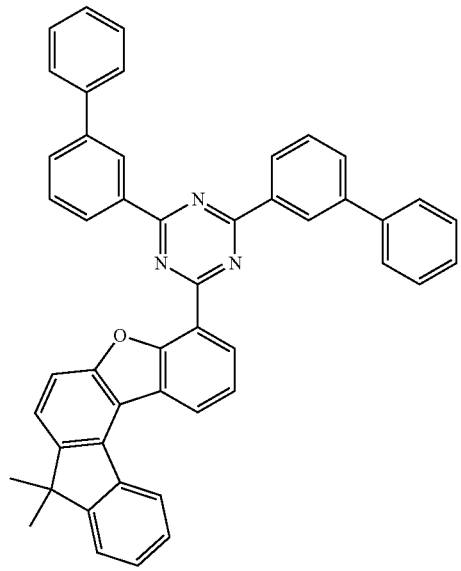
22
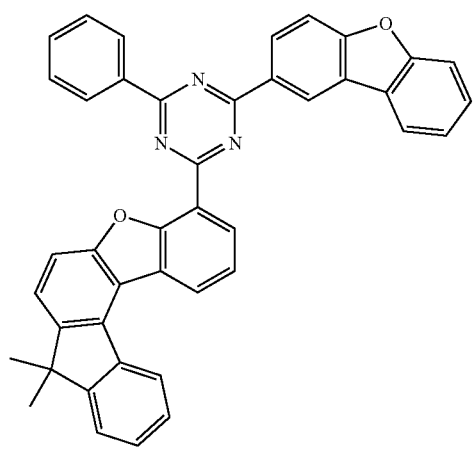
23
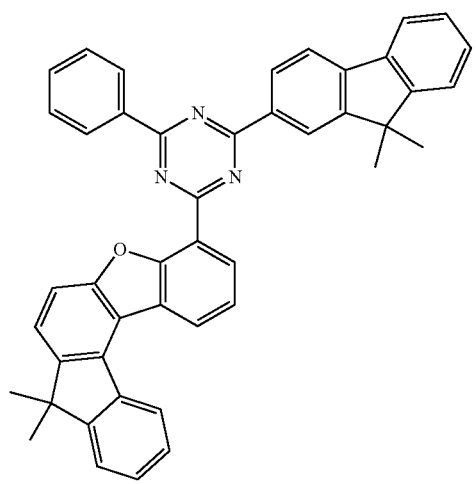
262
-continued
24
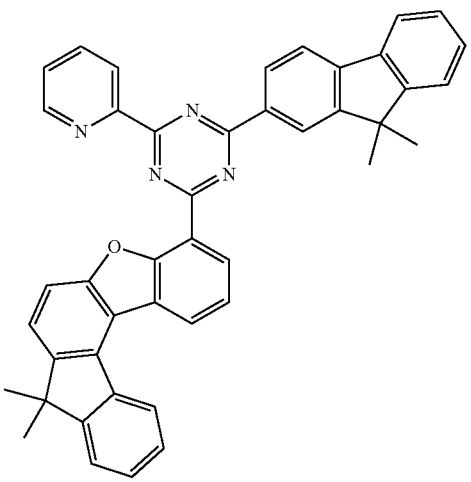
25
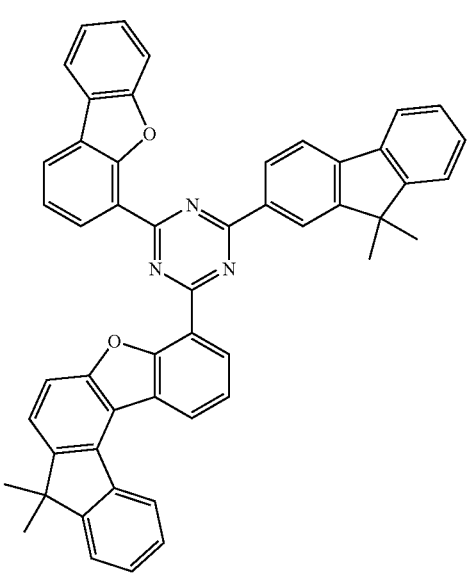
26
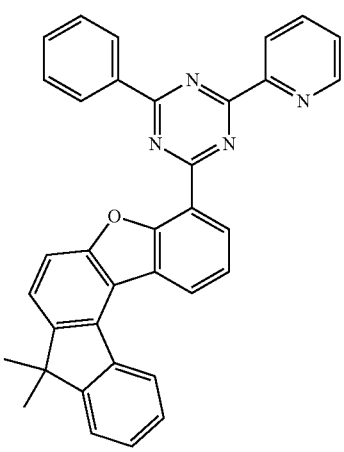

-continued
27
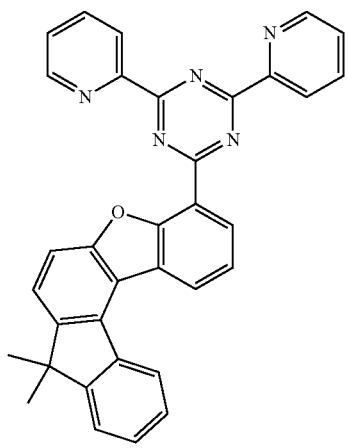
28
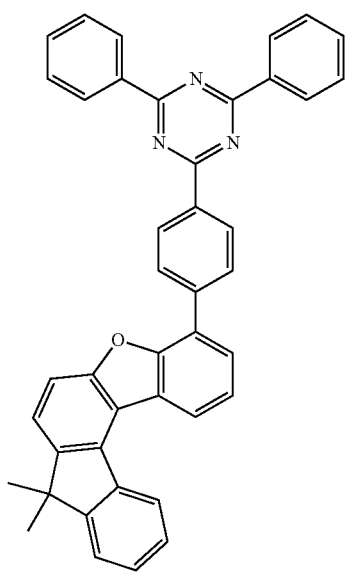
29
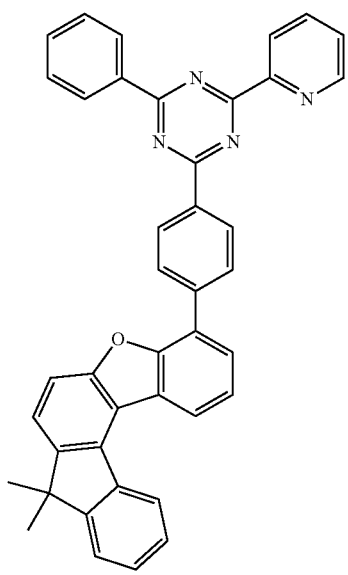
-continued
30
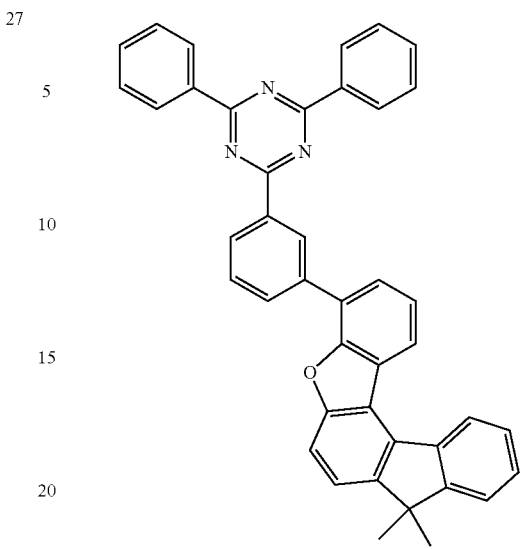
31
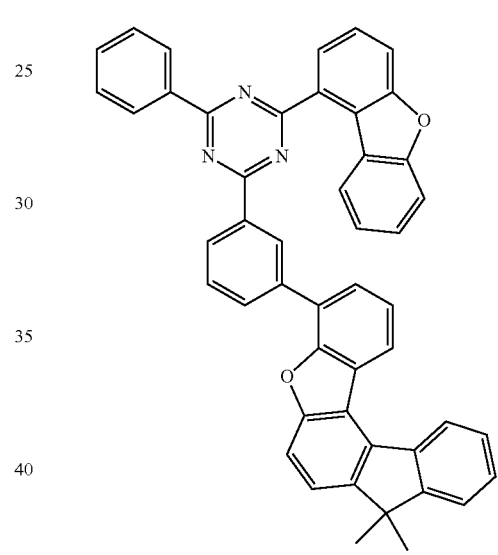
32
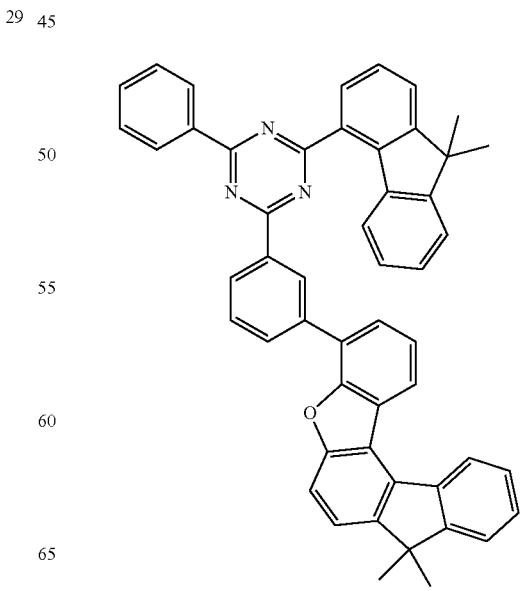

33
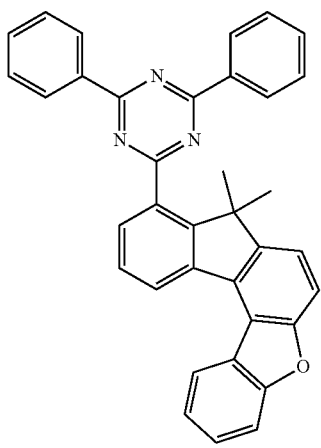
34
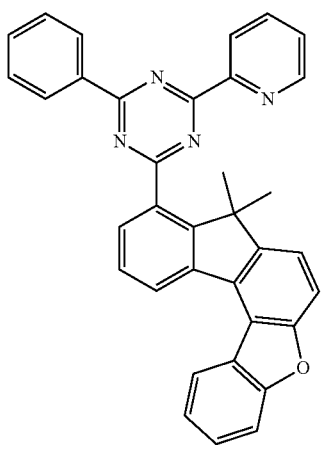
35
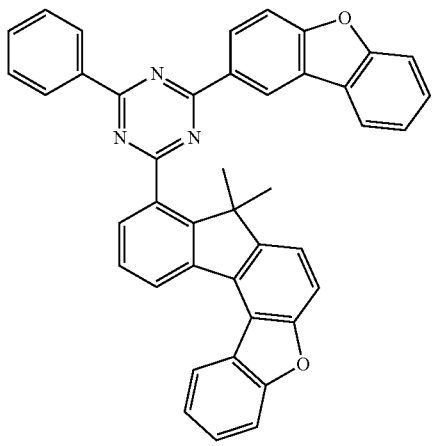
36
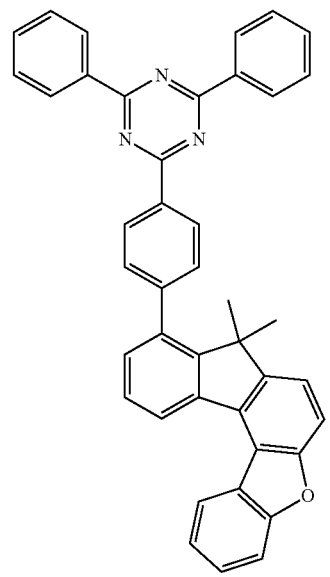
37
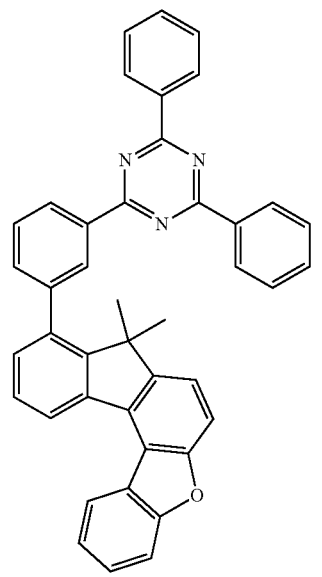
38
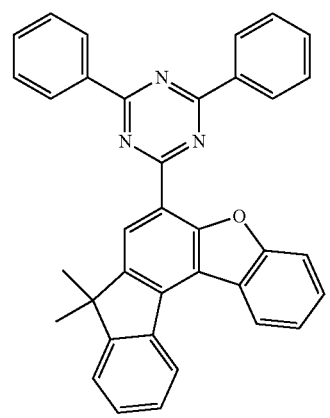

39
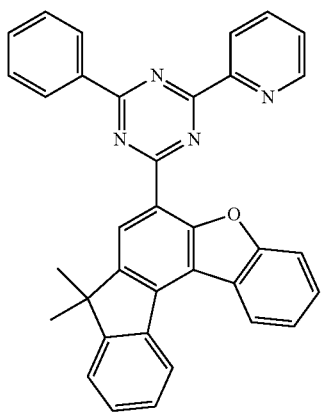
40
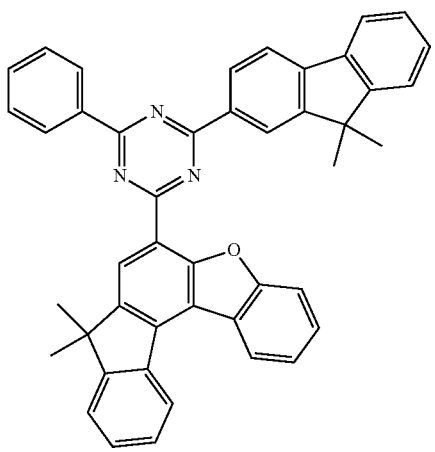
41
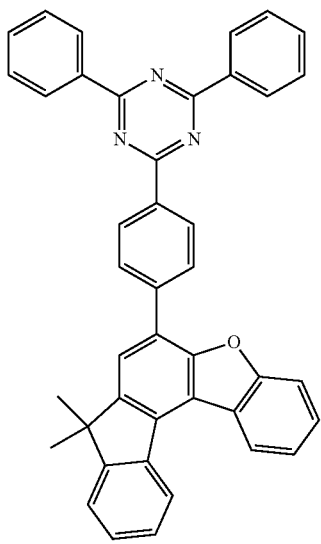
42
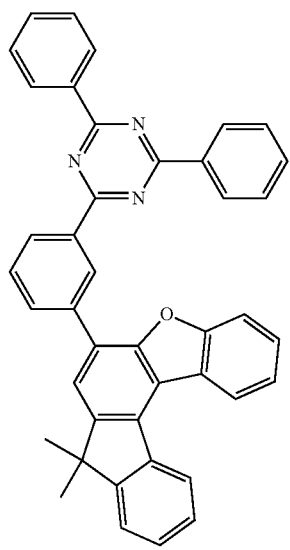
43
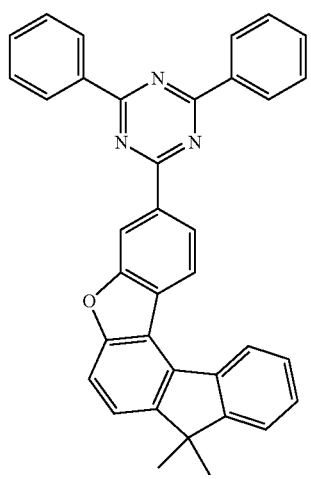
44
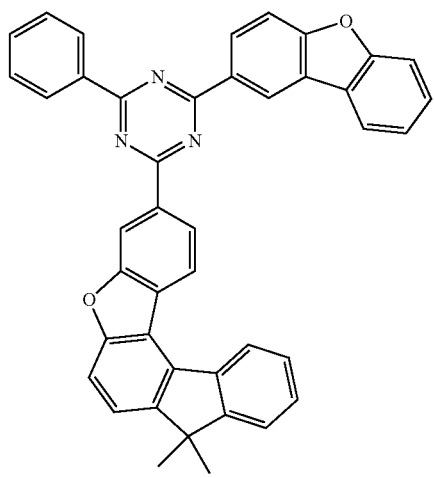

269
-continued
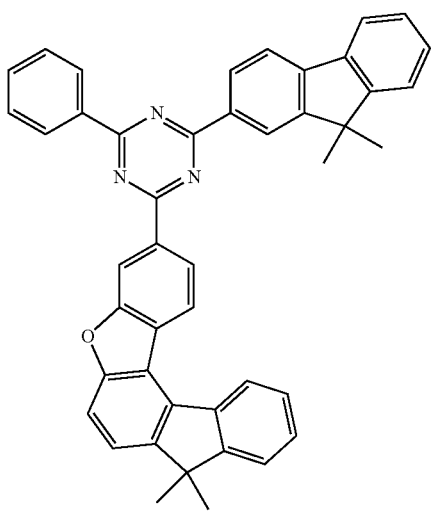
45
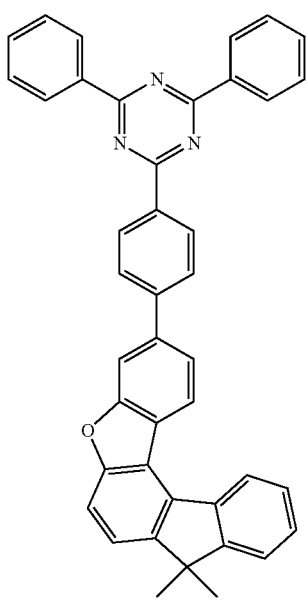
46
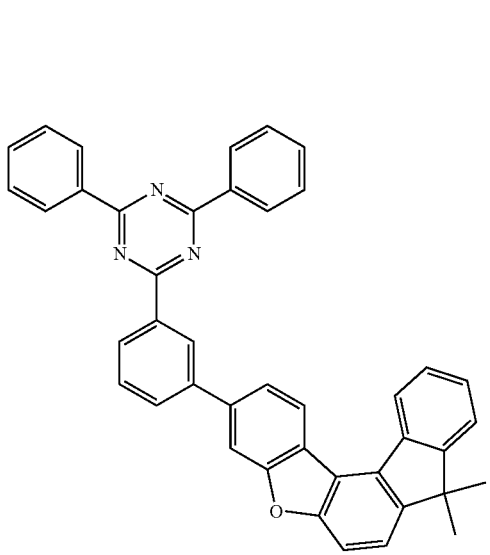
47
270
-continued
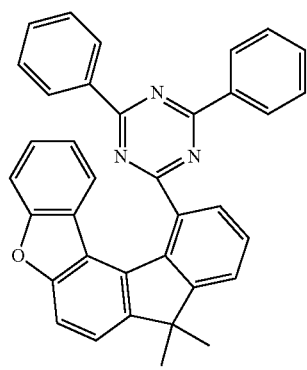
48
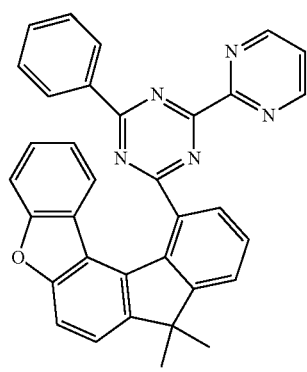
49
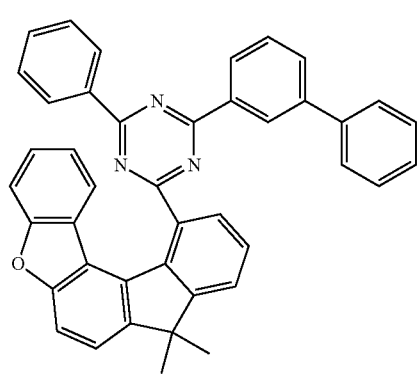
50
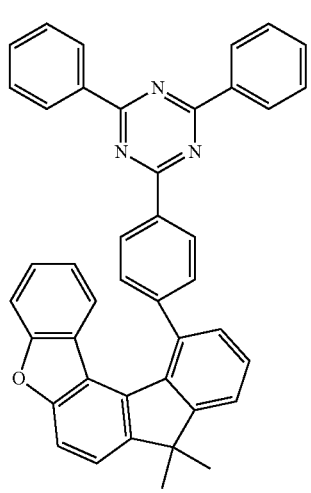
51

-continued
271
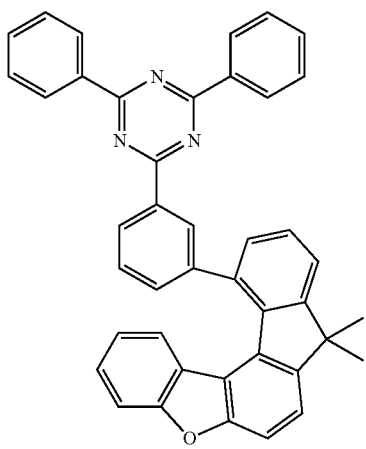
52
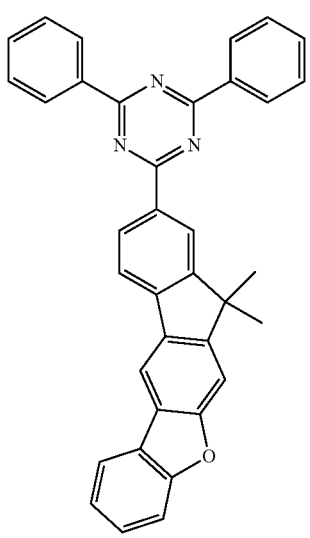
53
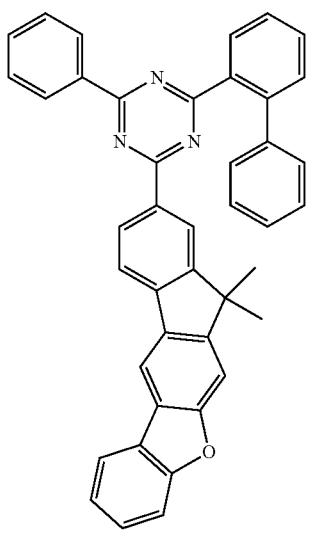
54
272
-continued
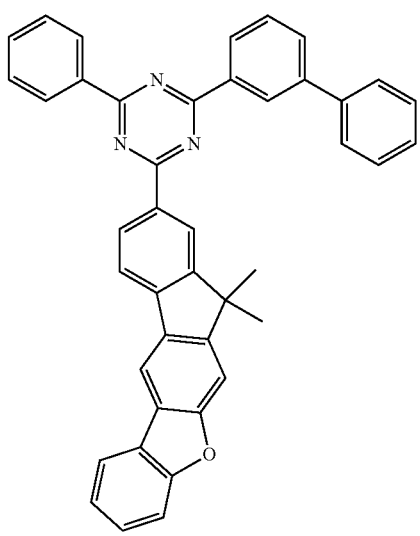
55
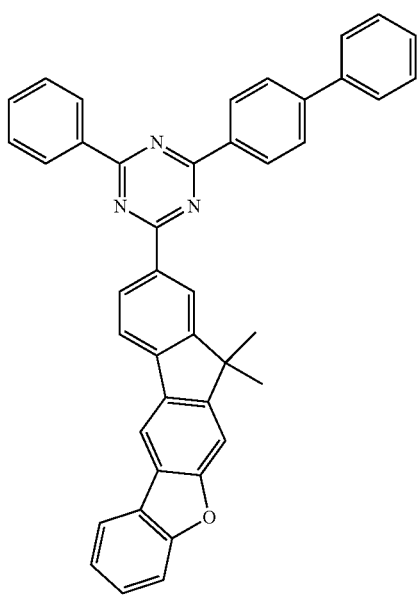
56
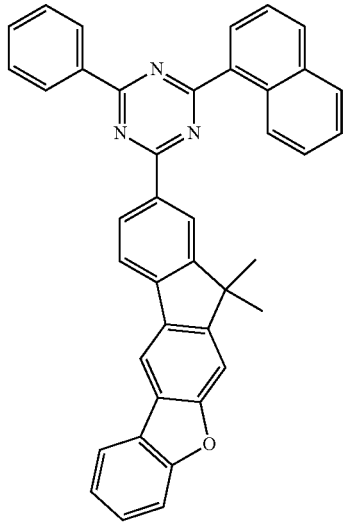
57

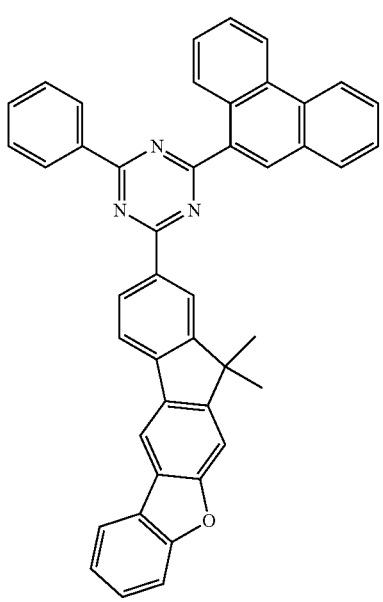
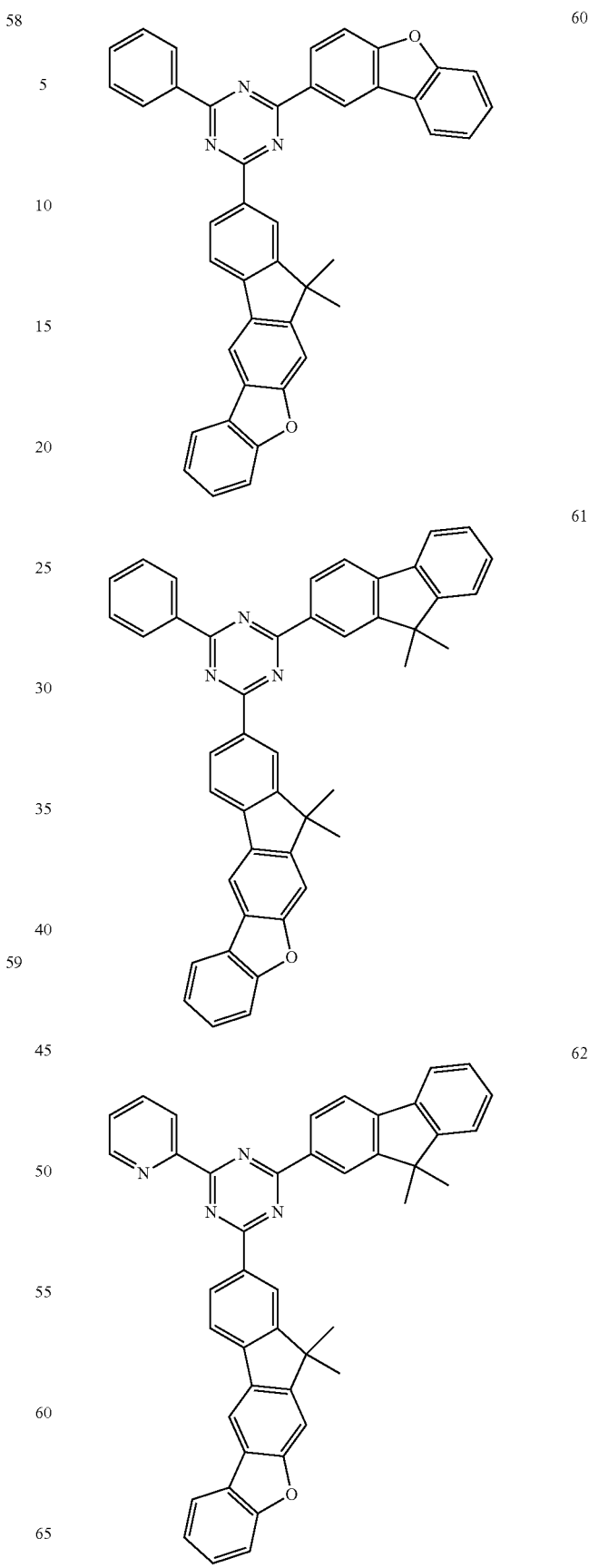

275
-continued
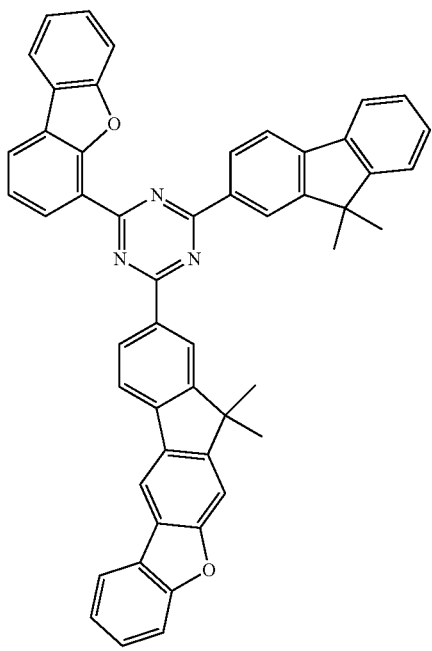
63
276
-continued
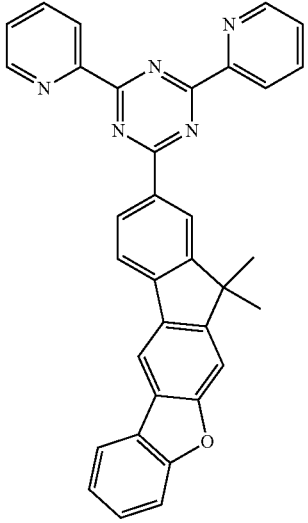
65
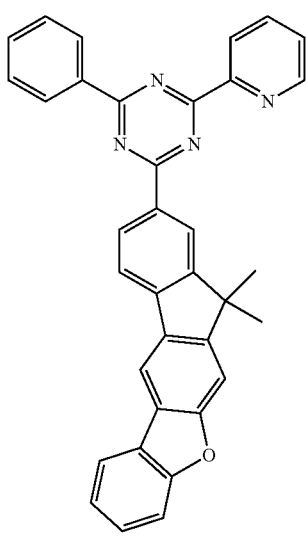
64
66

277
-continued
67
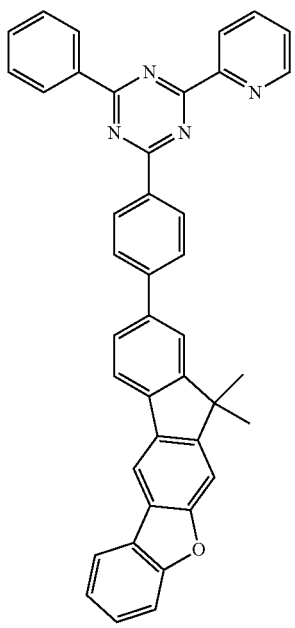
68
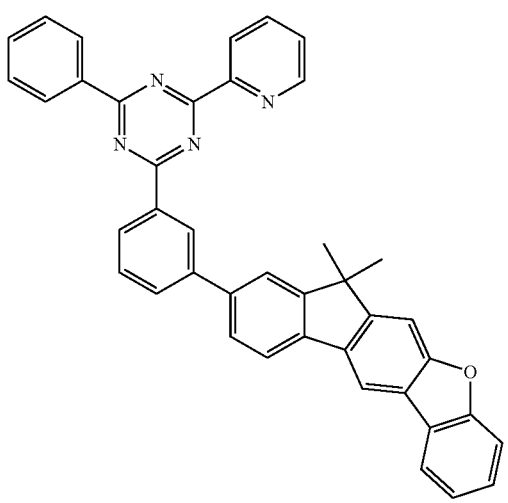
69
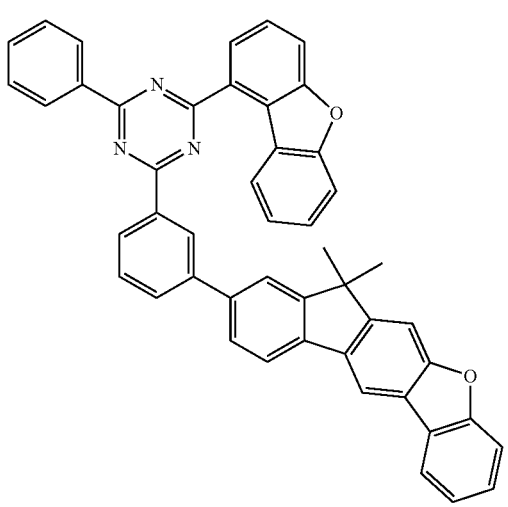
278
-continued
70
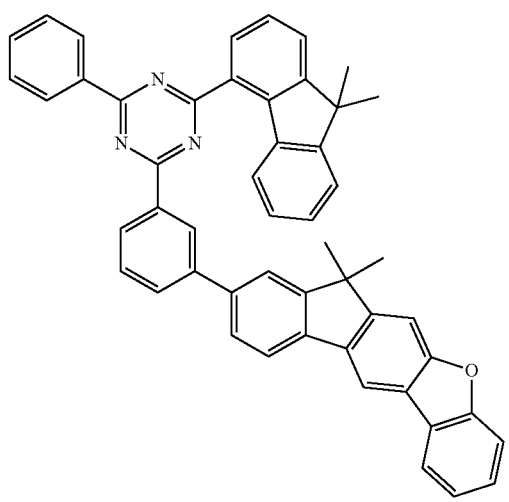
71
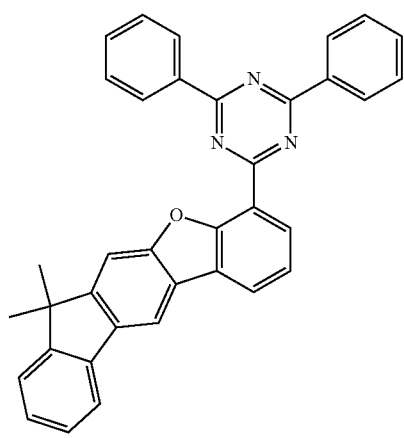
72
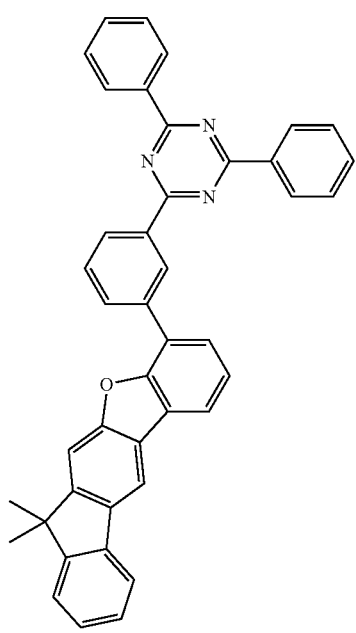

-continued
73
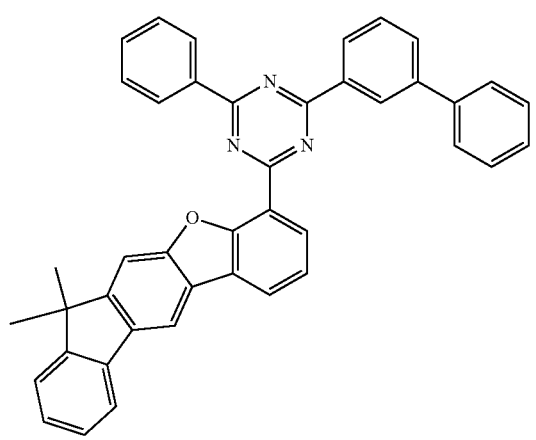
74
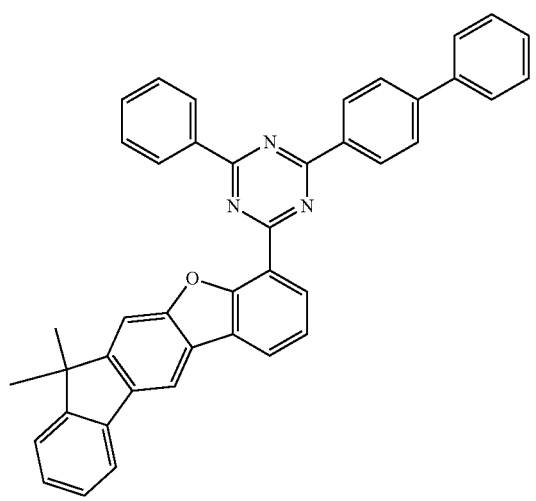
75
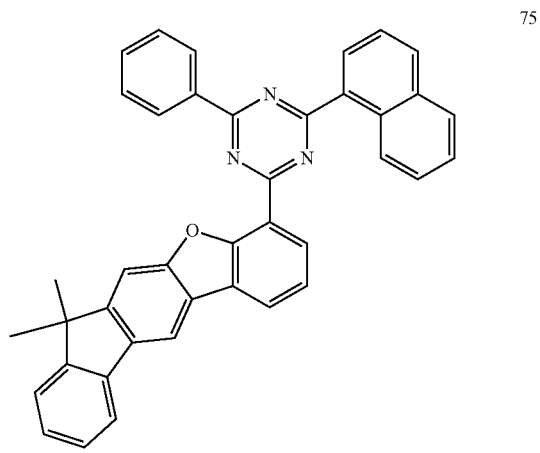
-continued
76
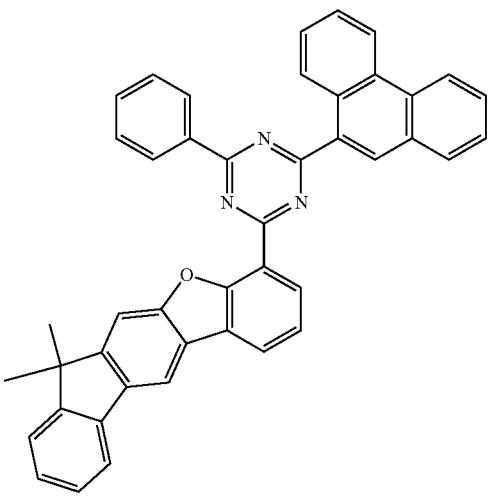
77
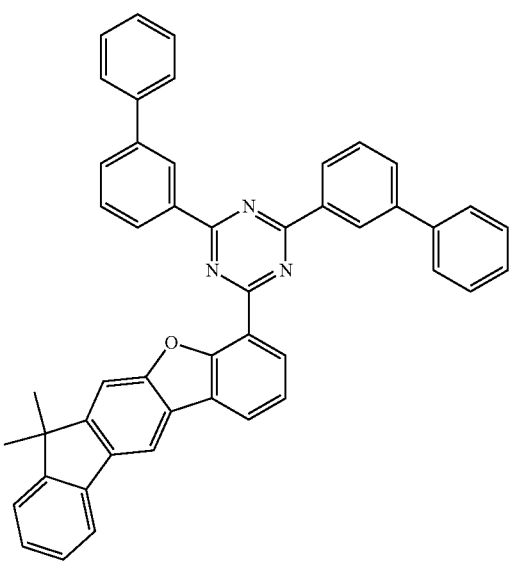
78

281
79
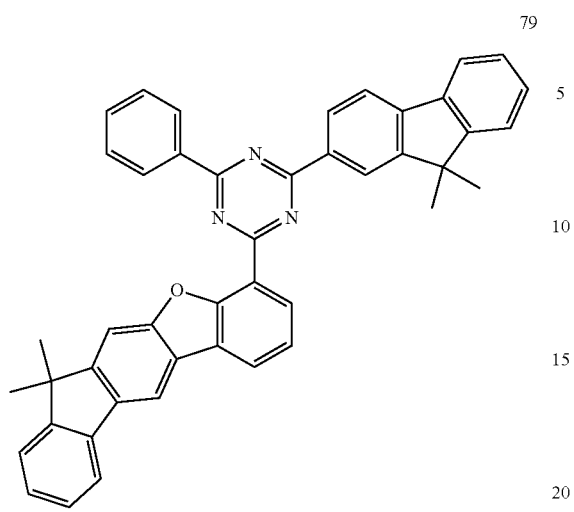
80
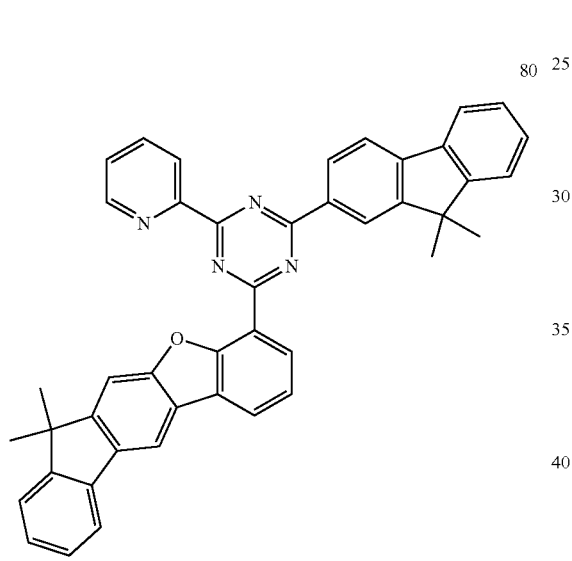
81
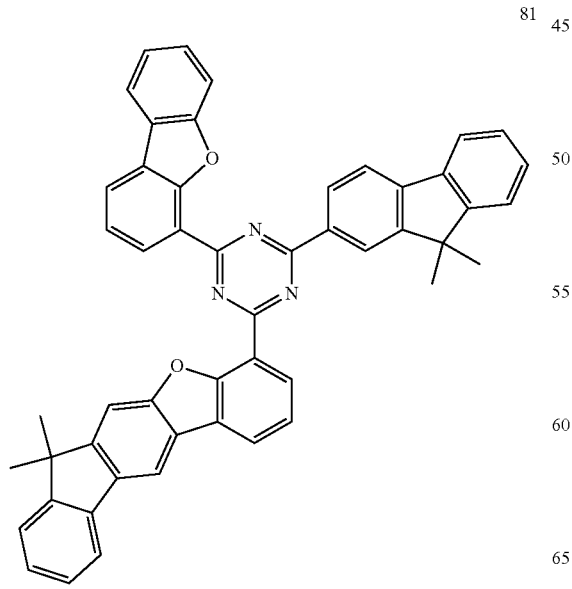
282
82
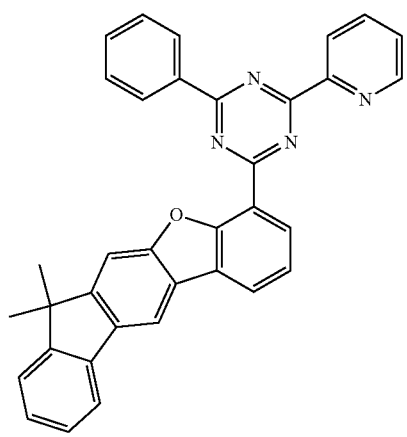
83
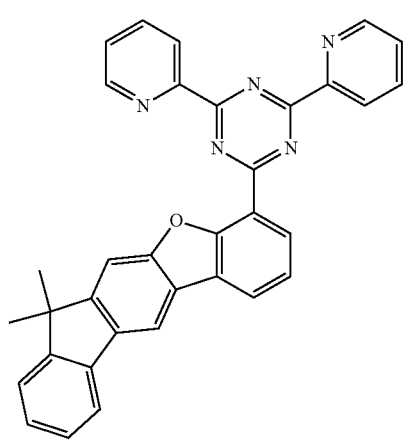
84
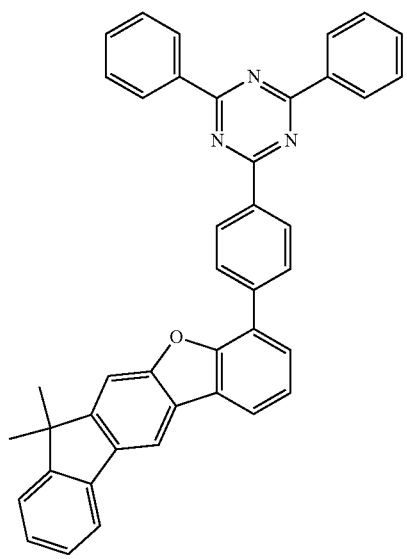

283
-continued
85
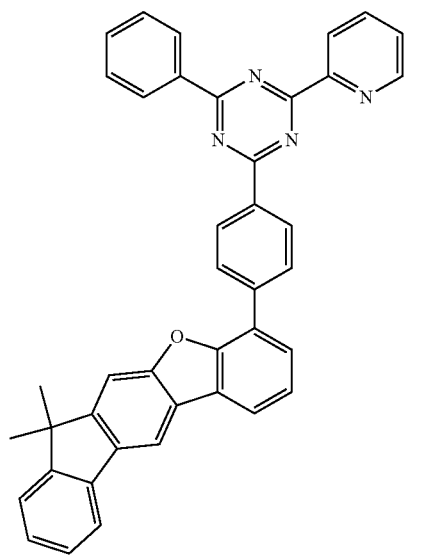
86
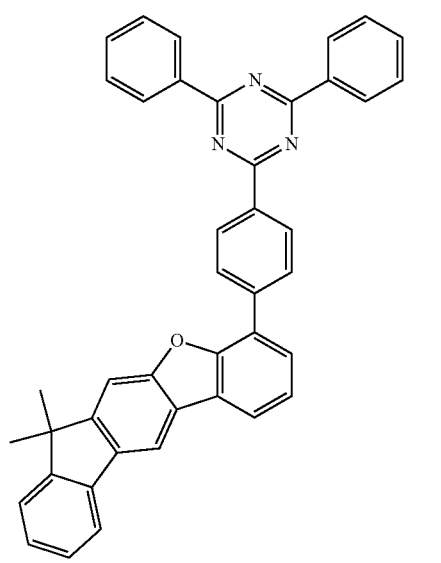
87
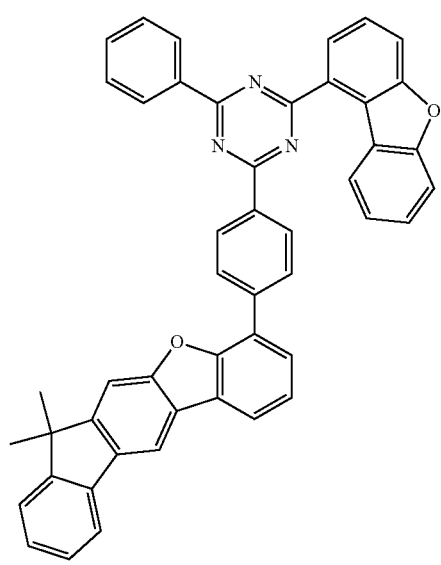
284
-continued
88
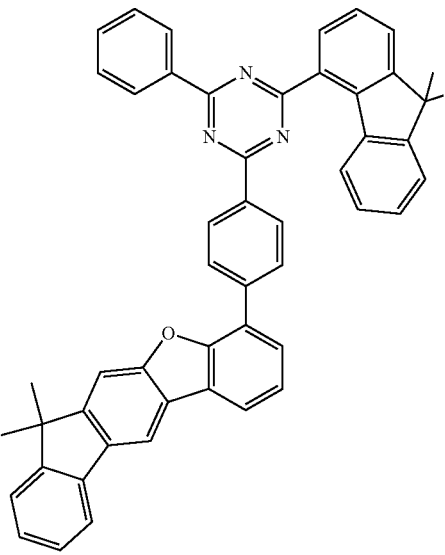
89
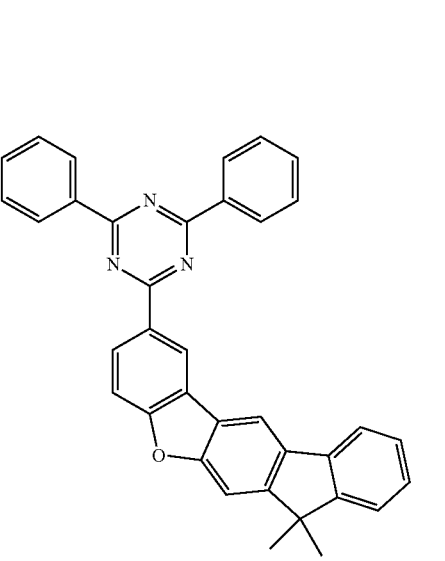
90
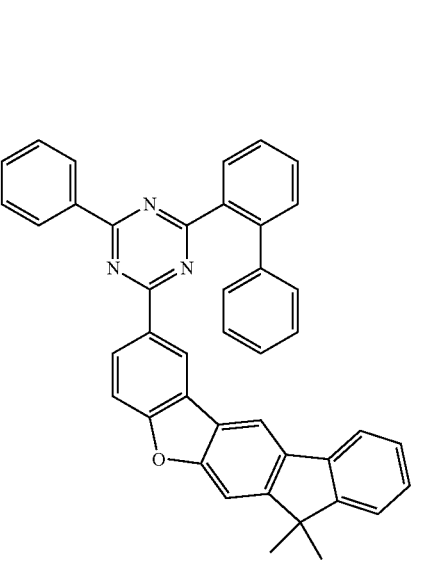

285
91
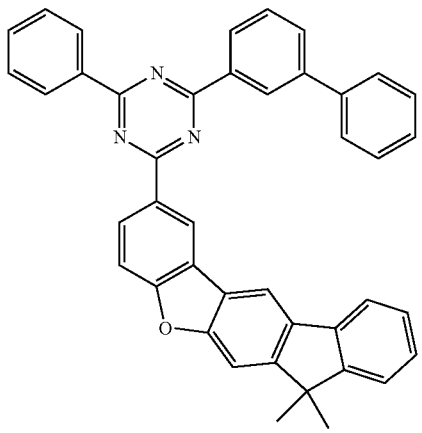
92
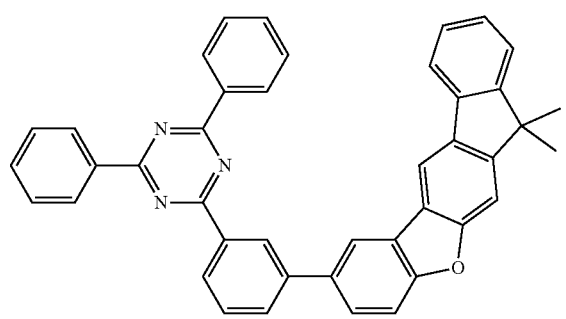
93
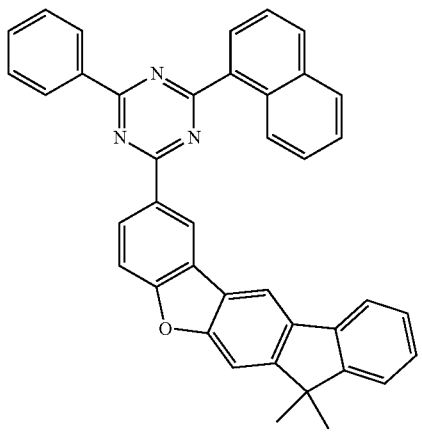
286
94
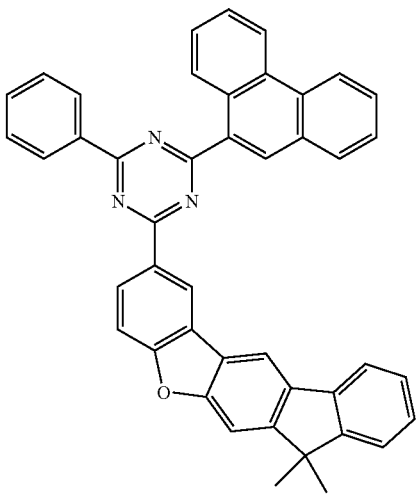
95
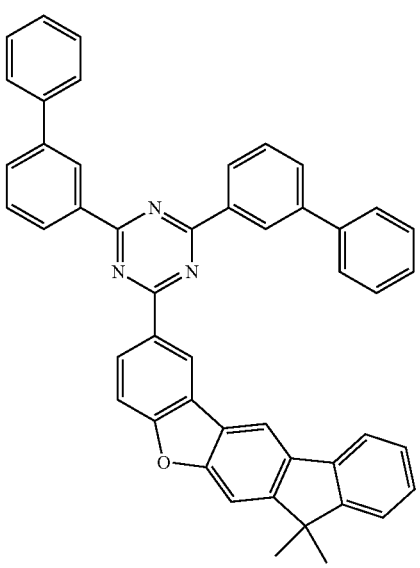
96
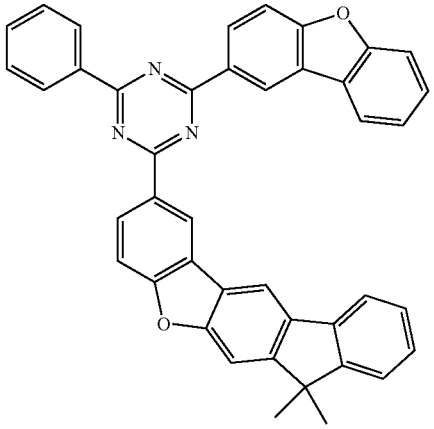

97
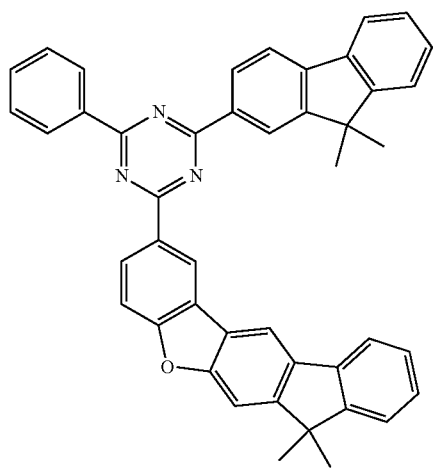
98
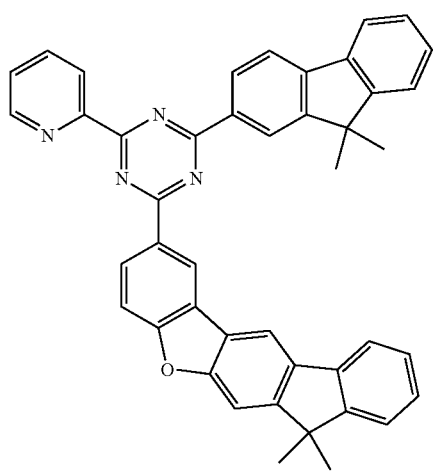
99
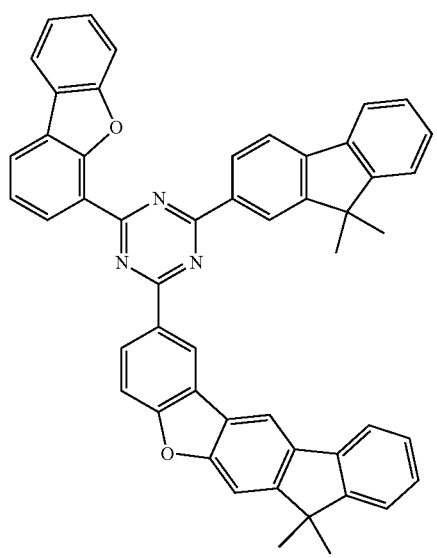
100
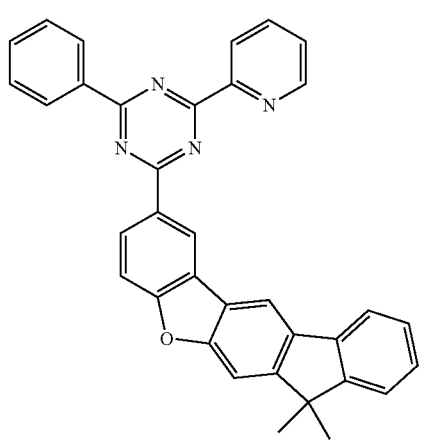
101
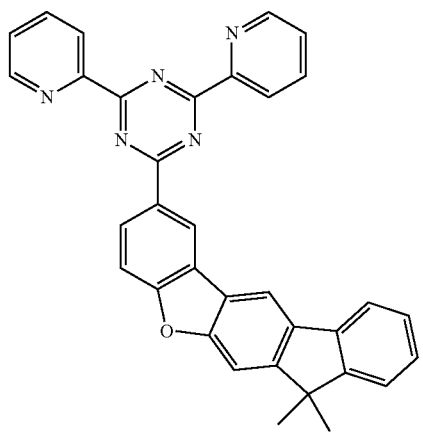
102
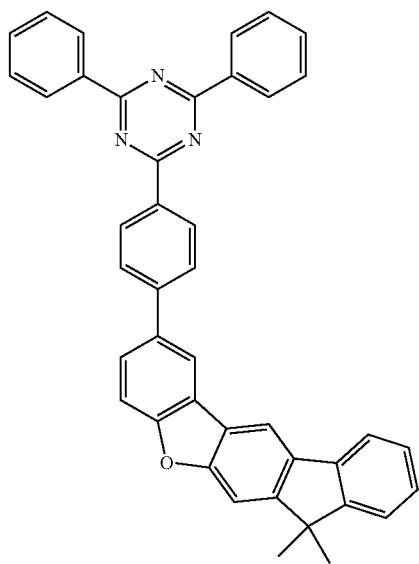

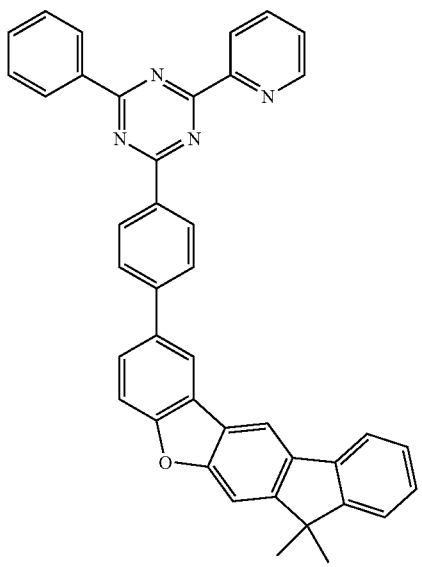
103
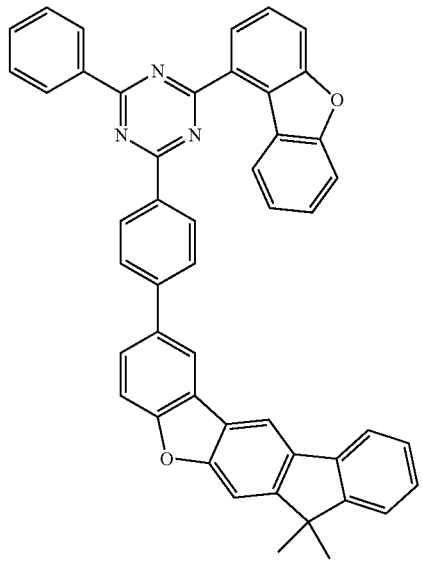
105
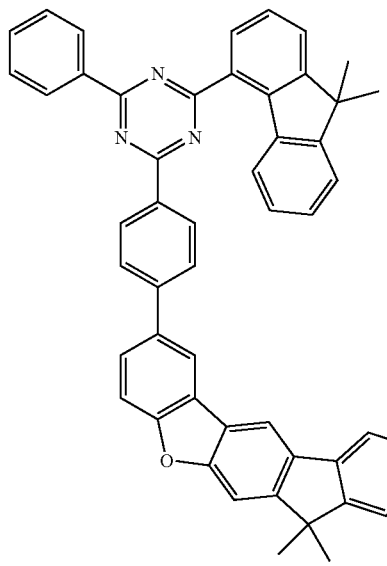
106
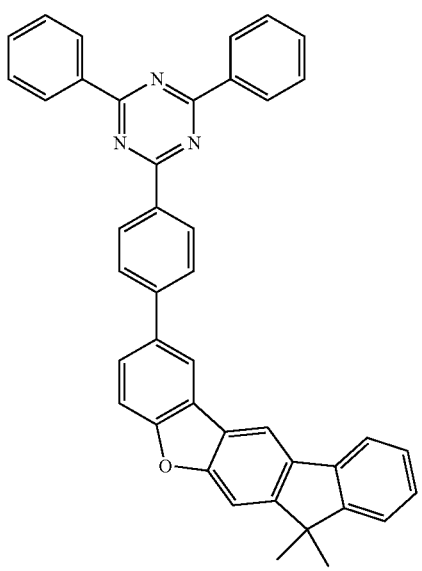
104
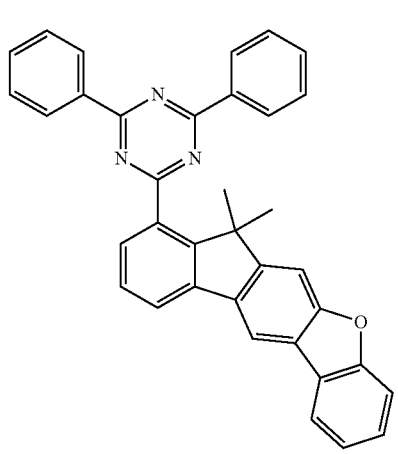
107

291
-continued
108
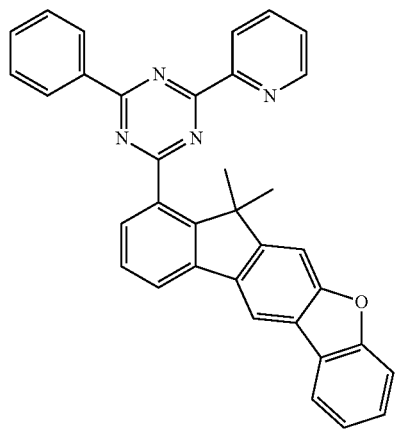
109
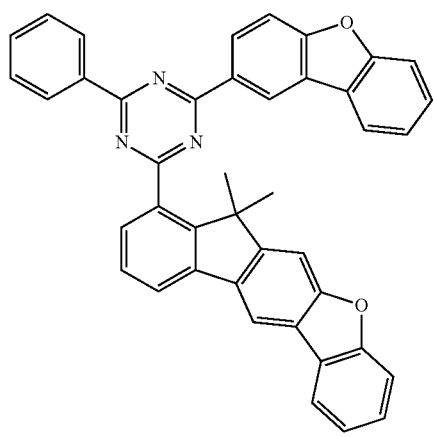
110
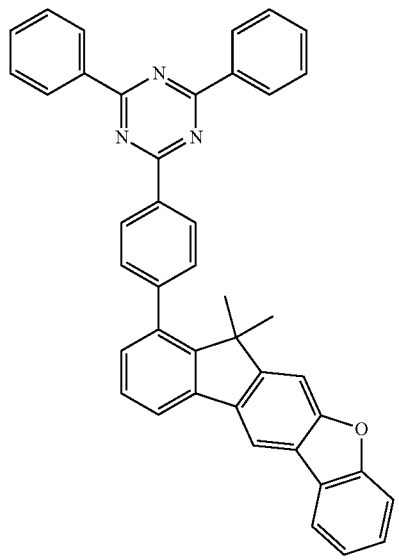
292
-continued
111
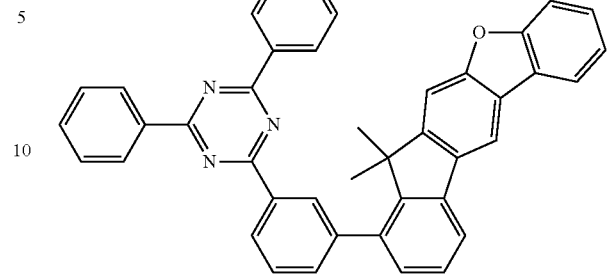
112
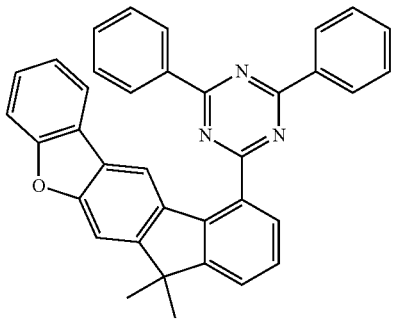
113
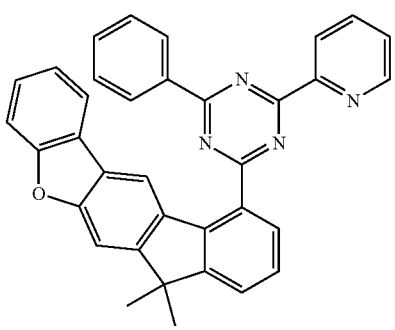
114
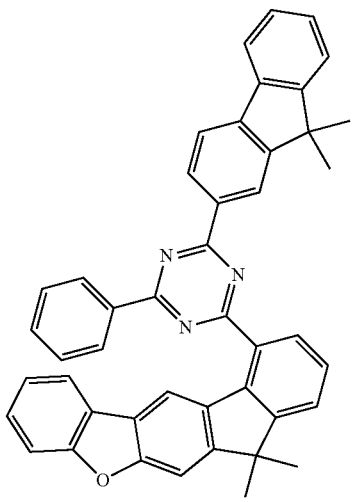

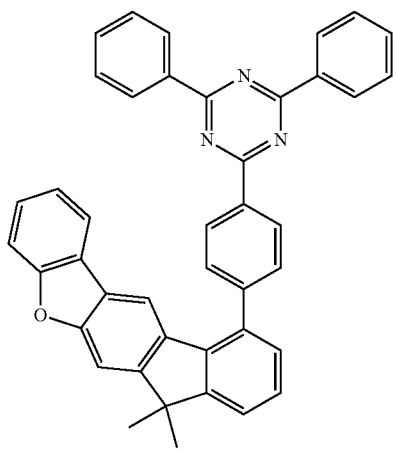
115
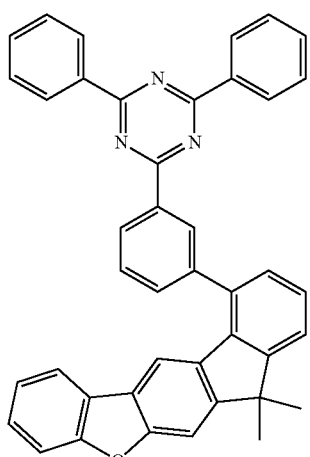
116
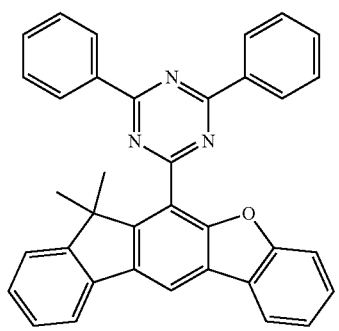
117
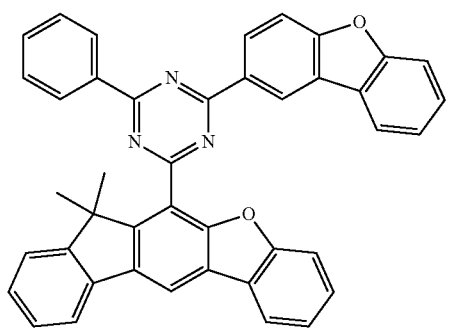
118
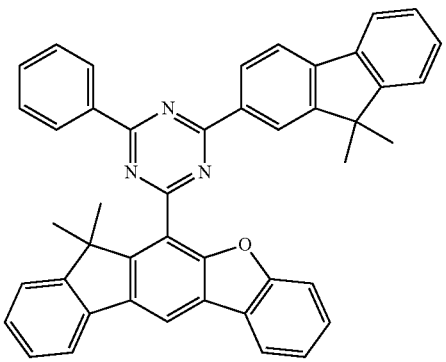
119
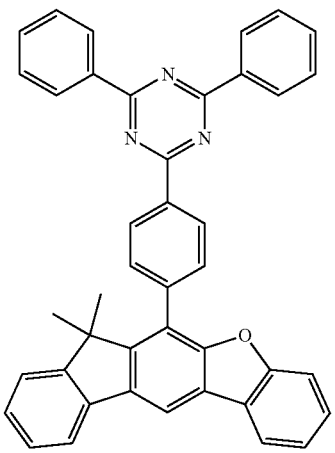
120
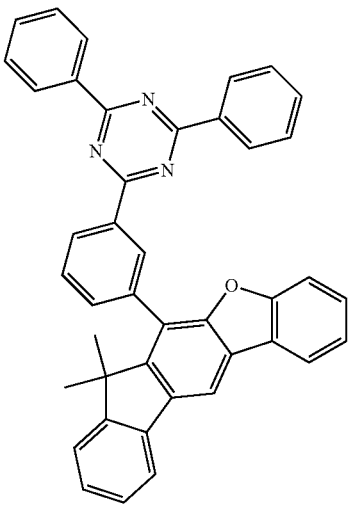
121

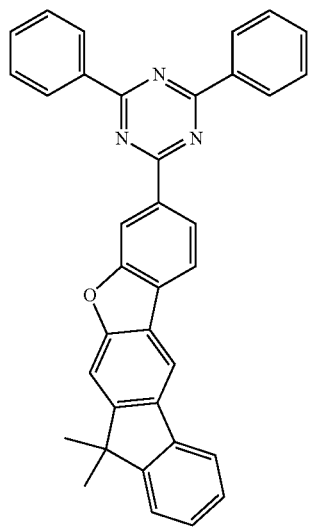
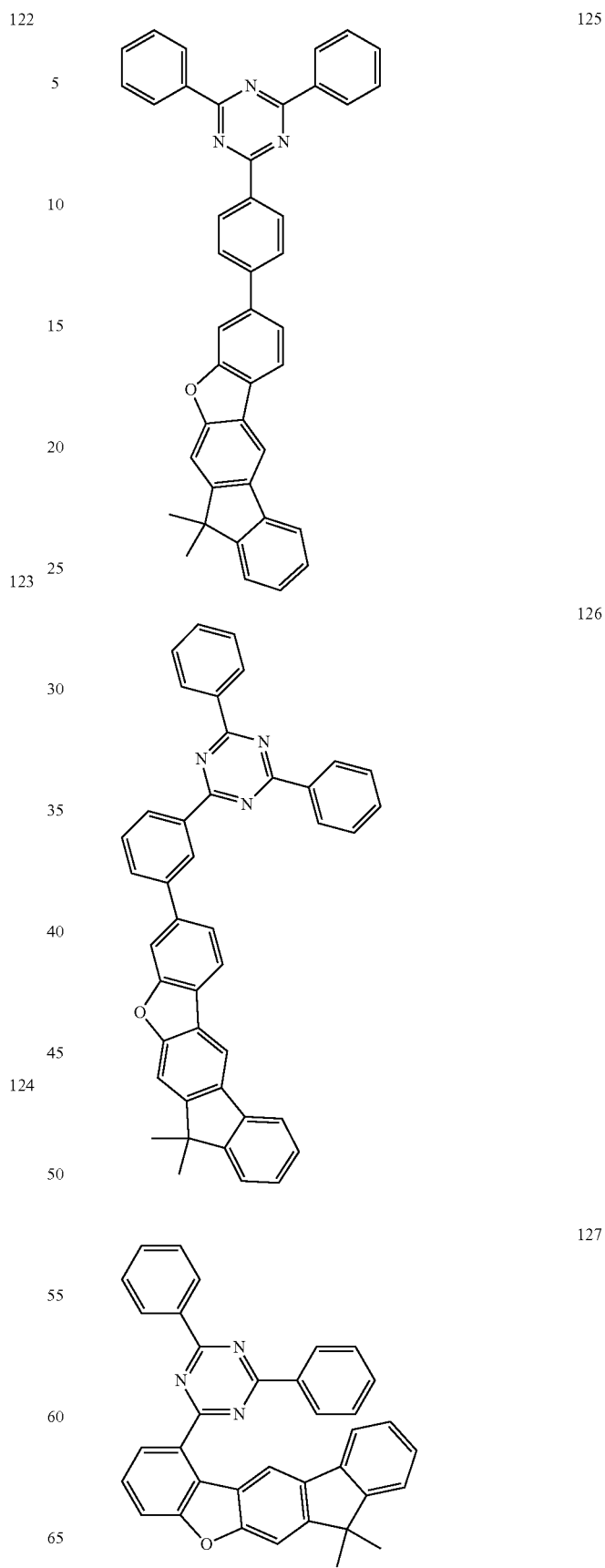

297
-continued
128
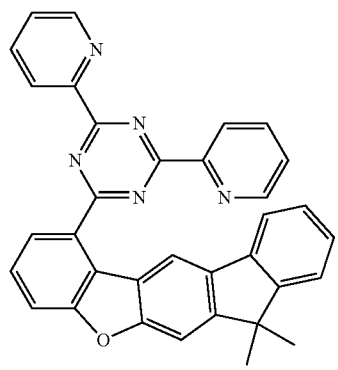
129
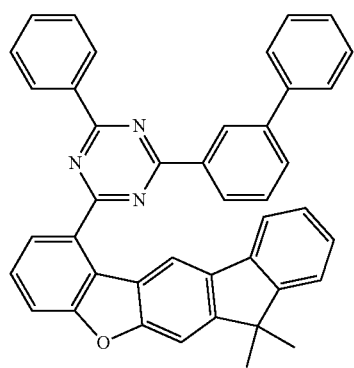
130
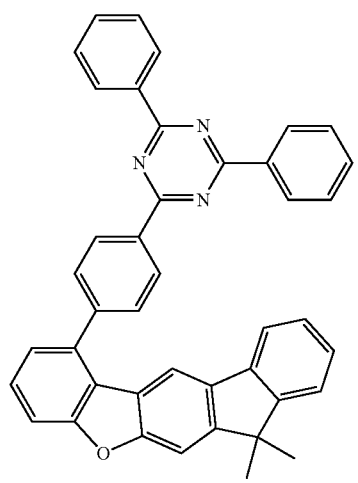
298
-continued
131
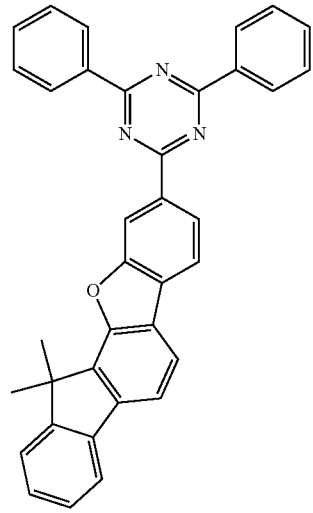
132
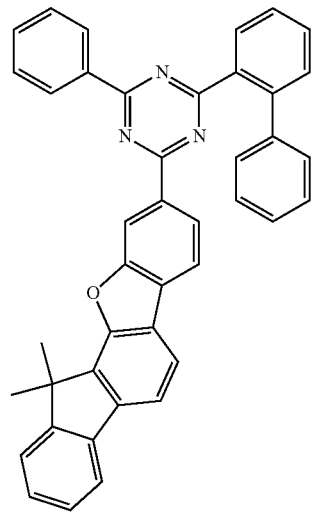
133
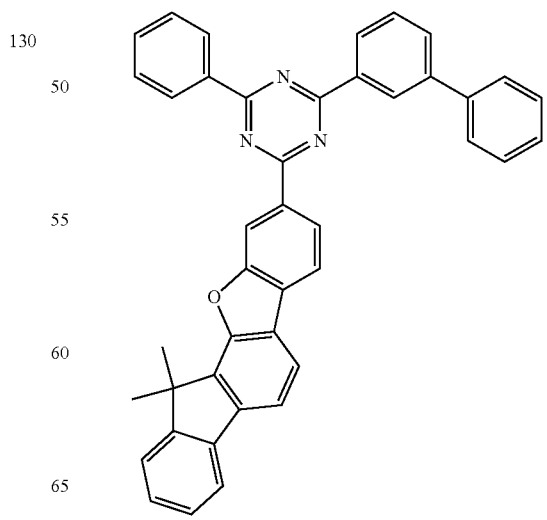

134
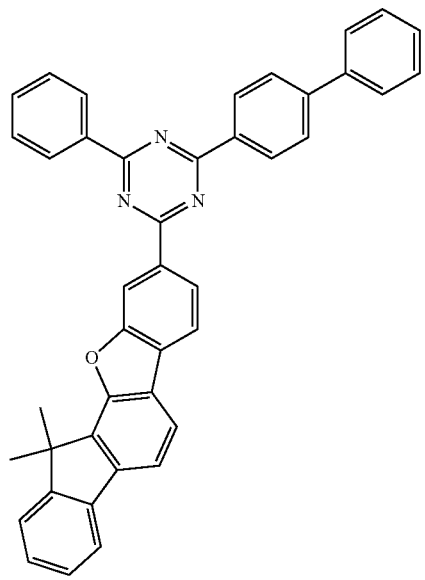
135
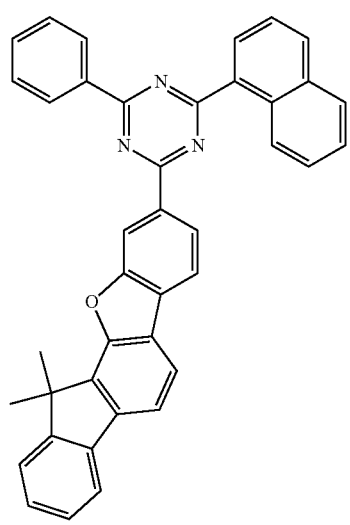
136
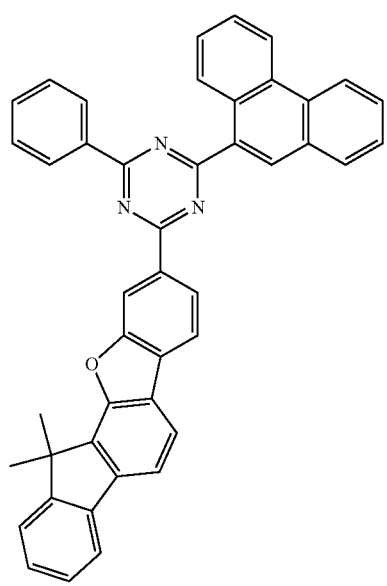
137
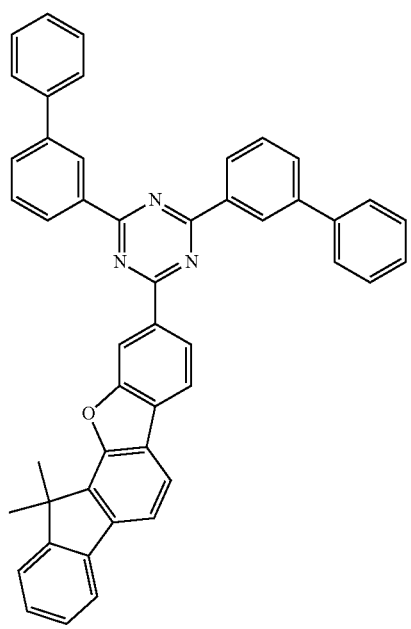
138
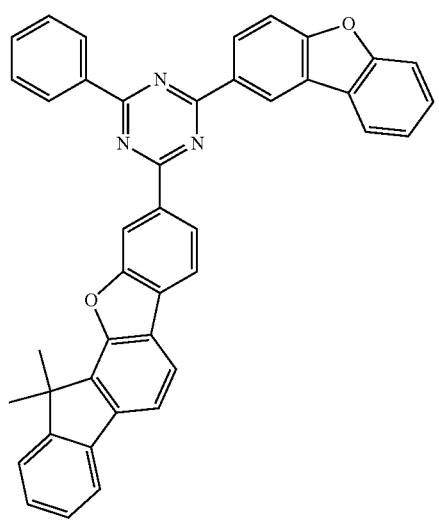

301
-continued
139
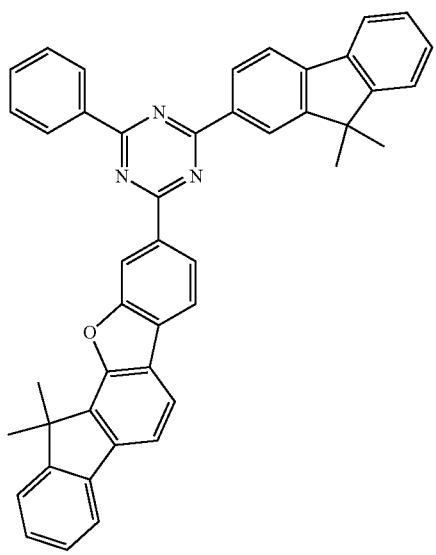
302
-continued
141
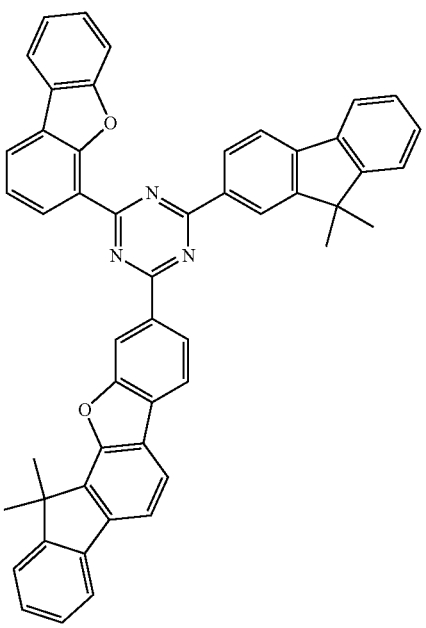
142
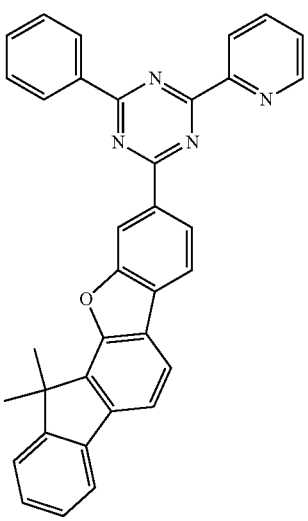
140
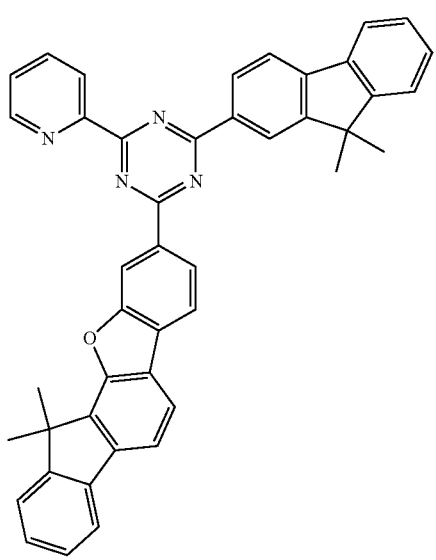
143
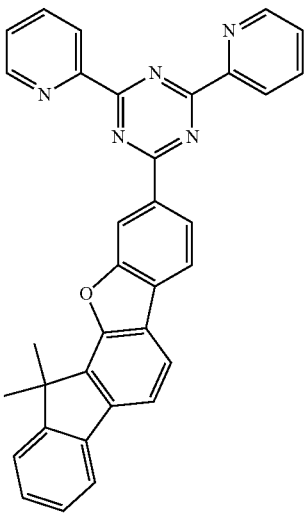

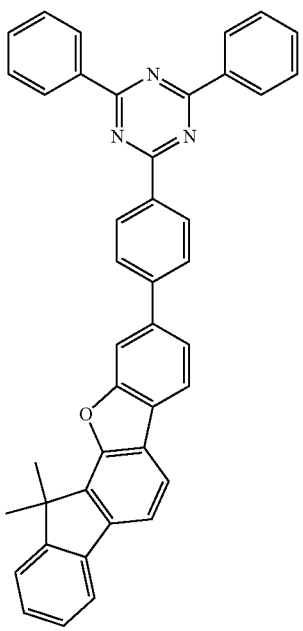
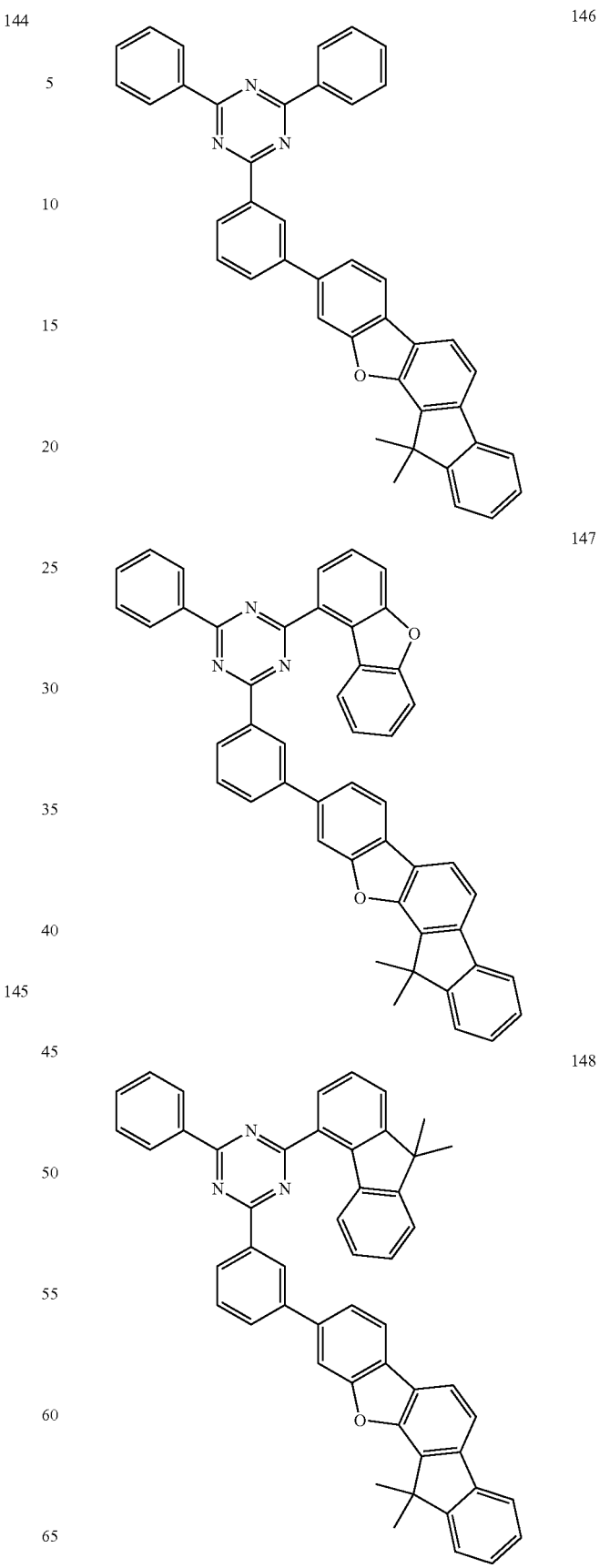

305
-continued
149
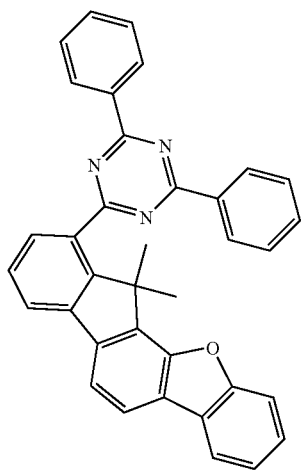
150
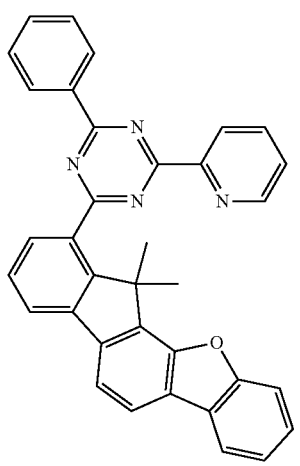
151
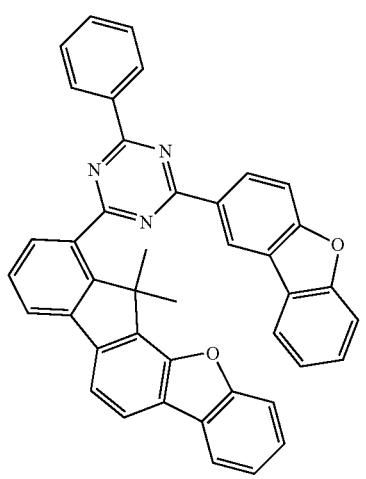
306
-continued
152
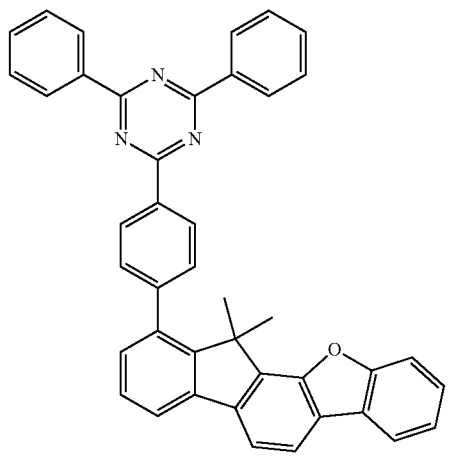
153
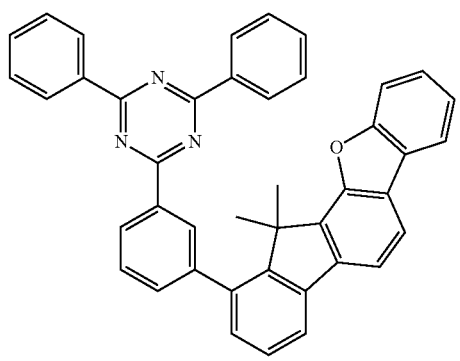
154
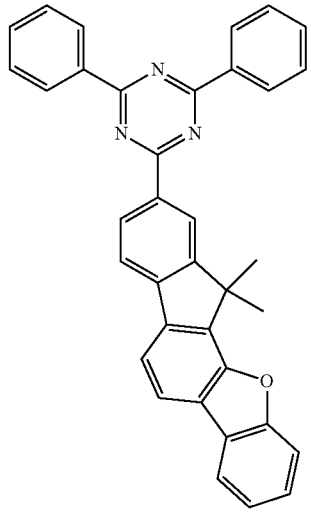

307
155
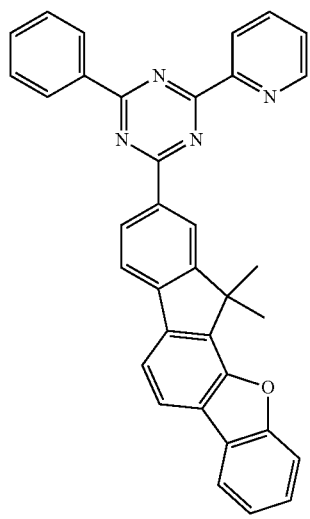
156
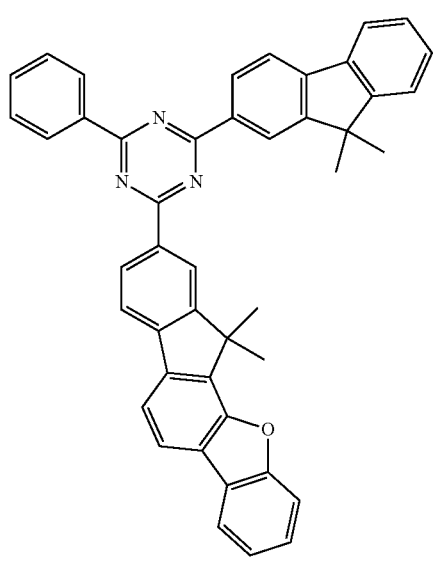
157
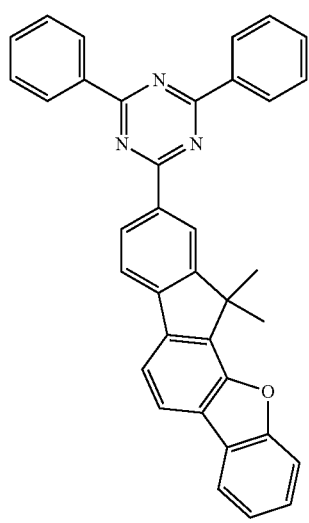
308
158
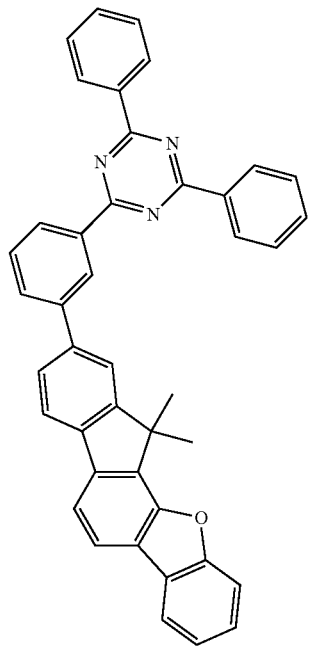
159
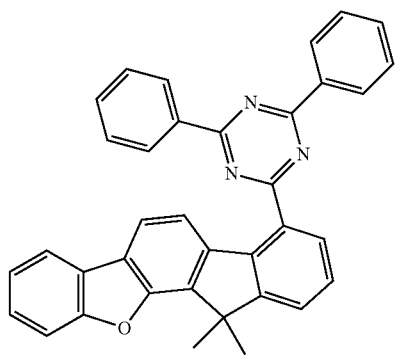
160
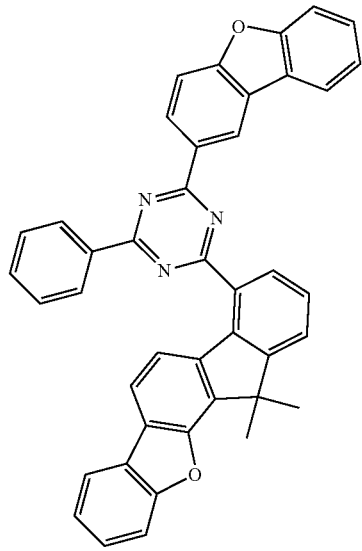

309
-continued
161
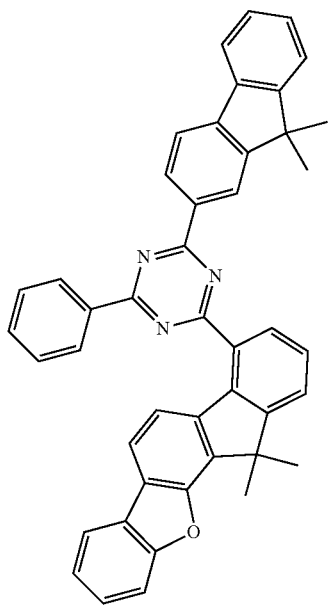
162
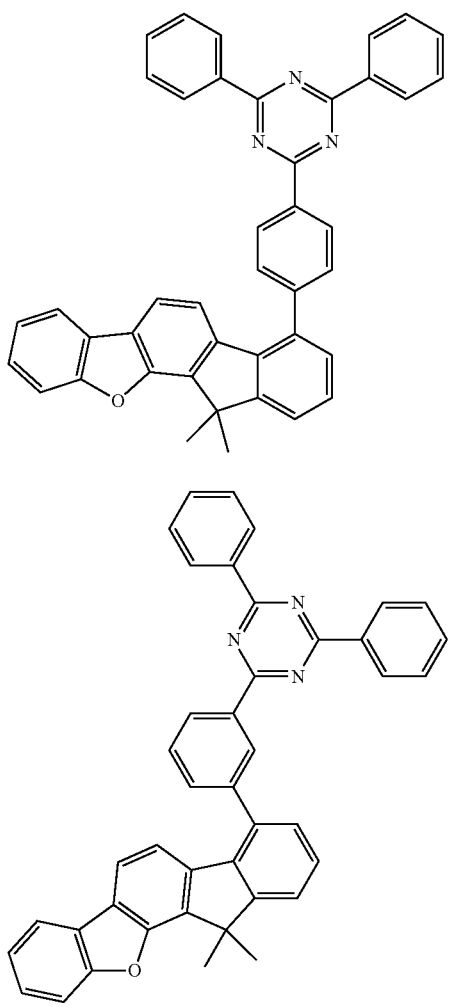
163
310
-continued
164
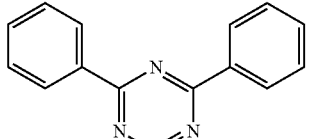
165
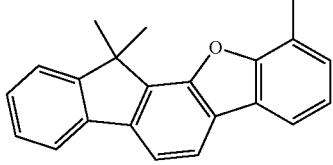
166
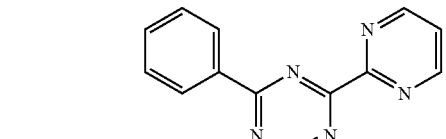
167
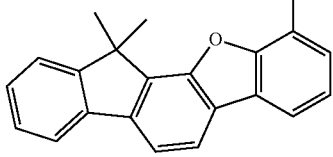

311
-continued
312
-continued
168
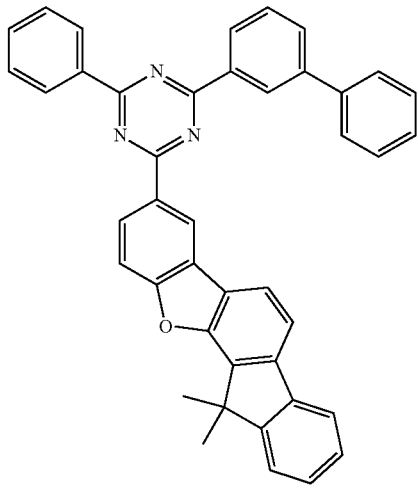
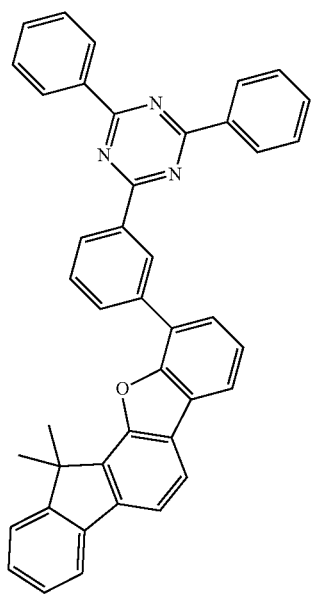
169
170
171
172
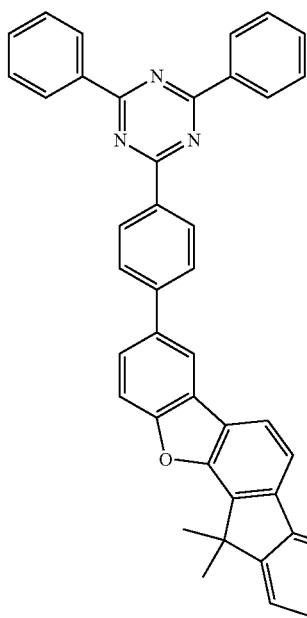
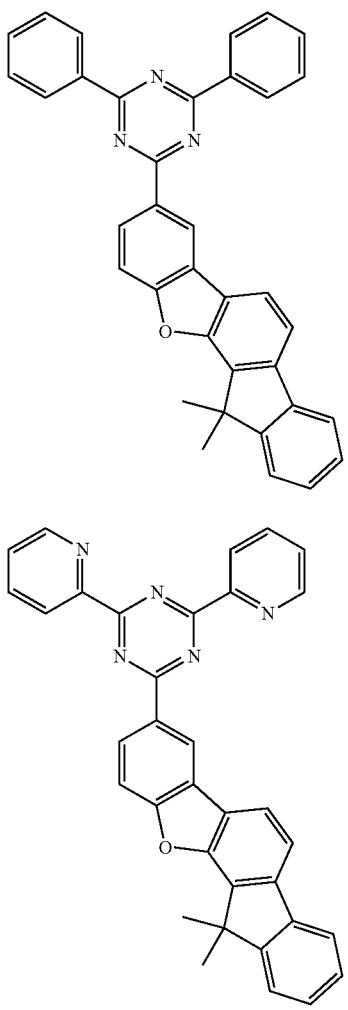

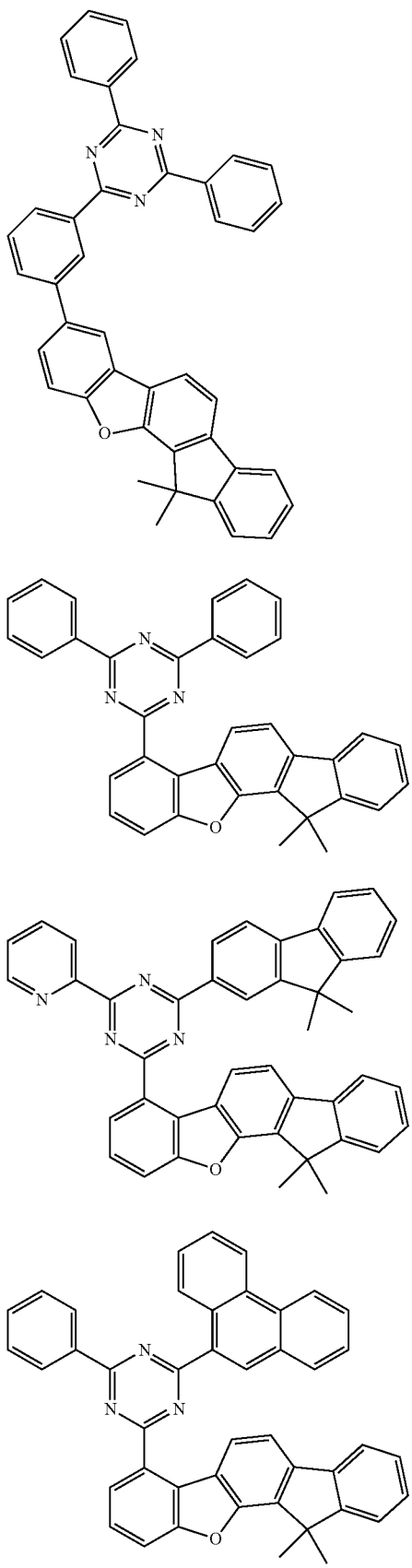
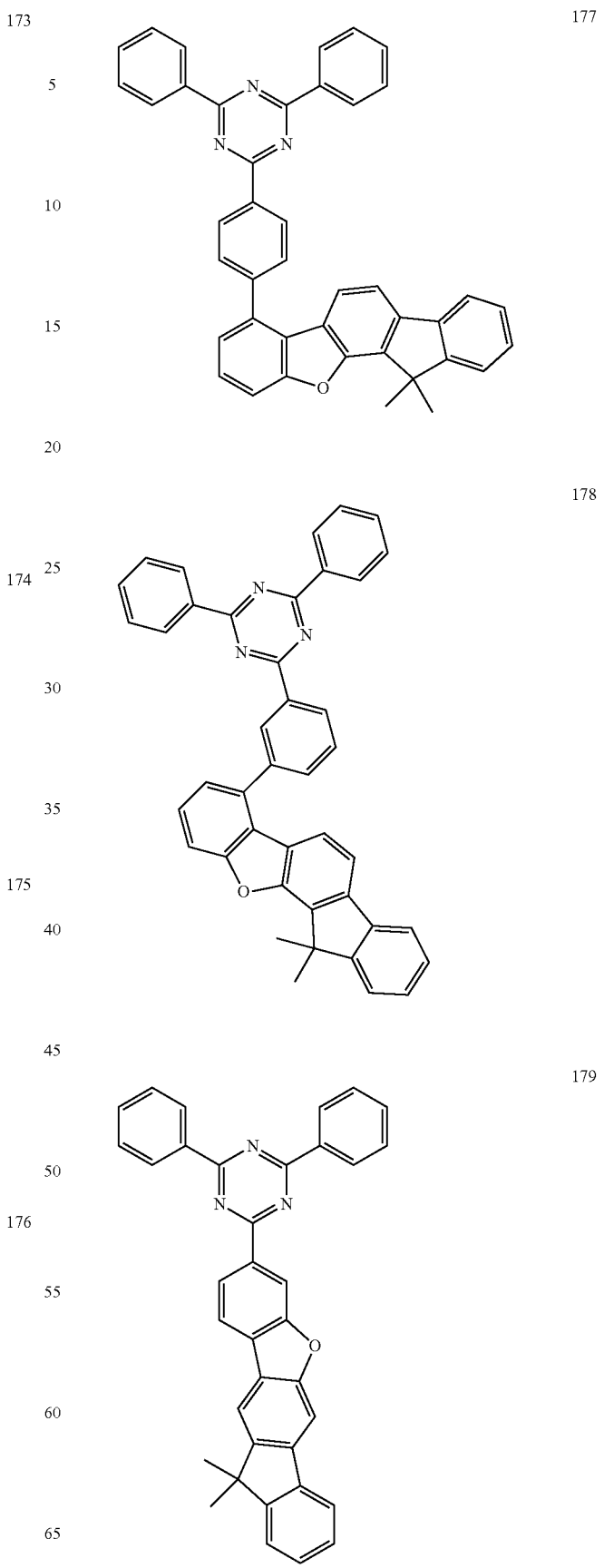

315
-continued
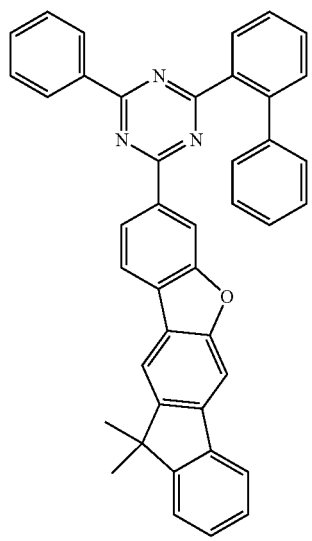
180
316
-continued
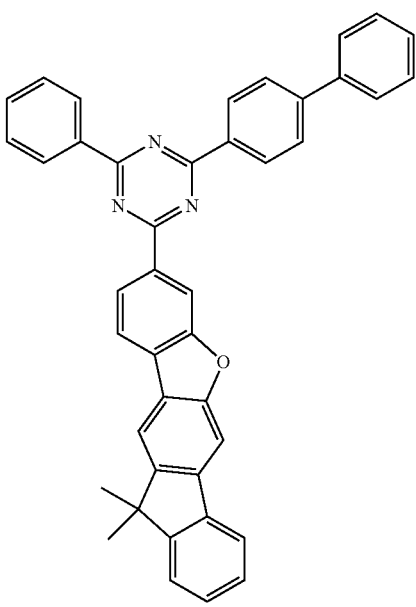
182
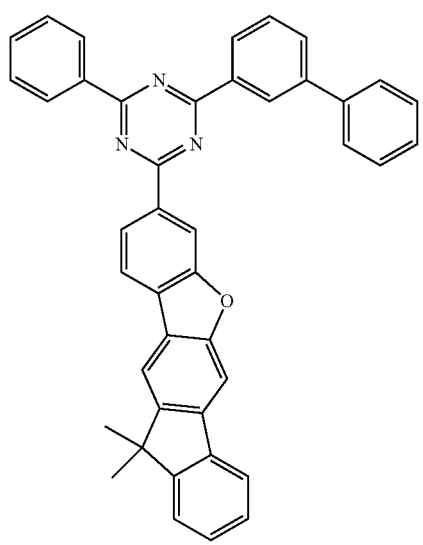
181
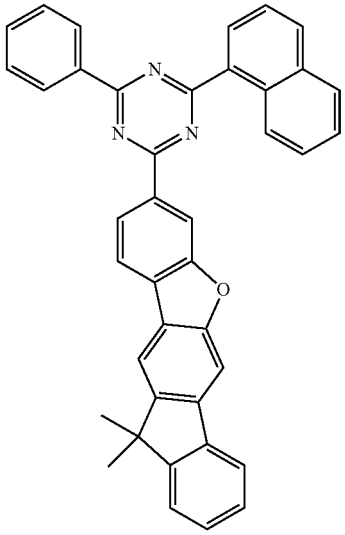
183

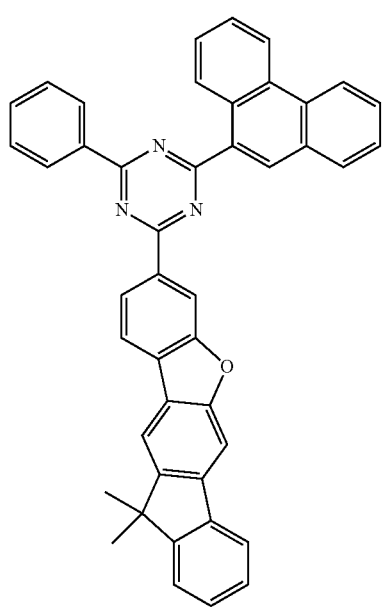
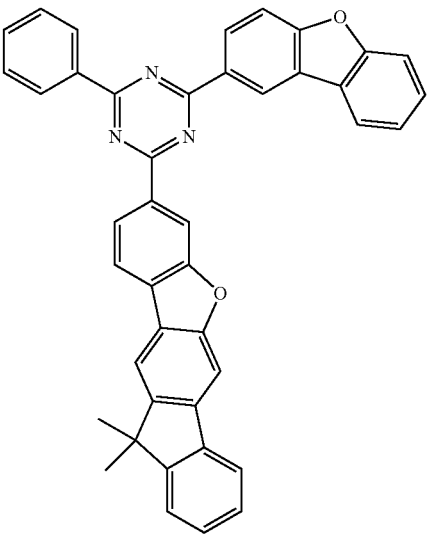
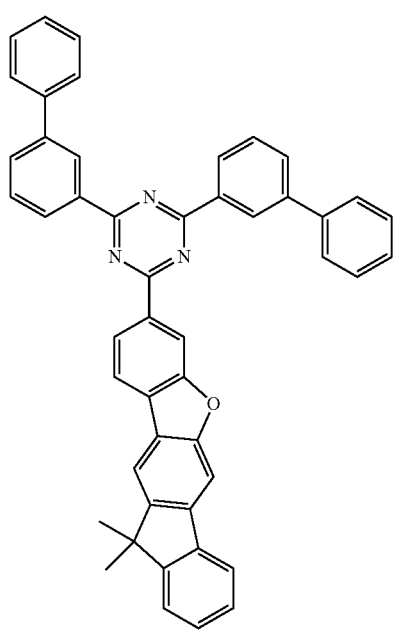
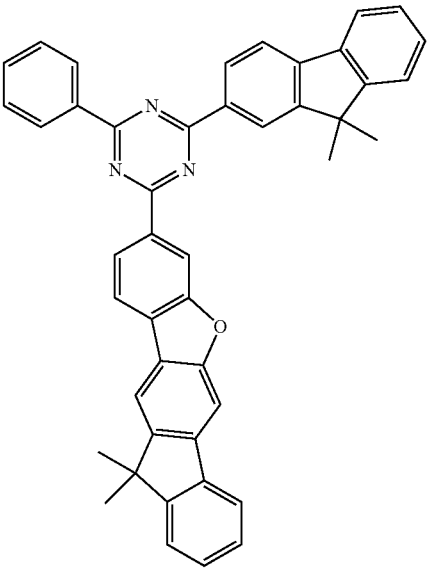

188
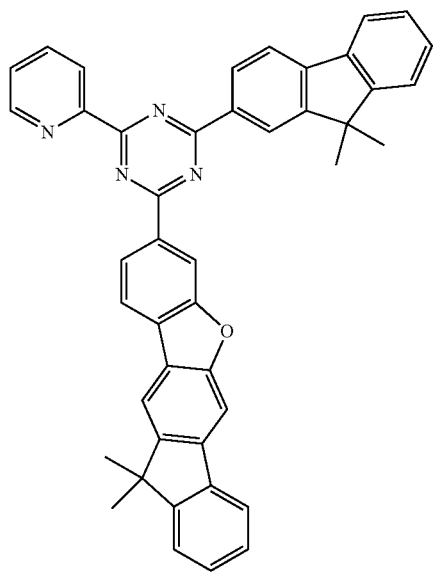
190
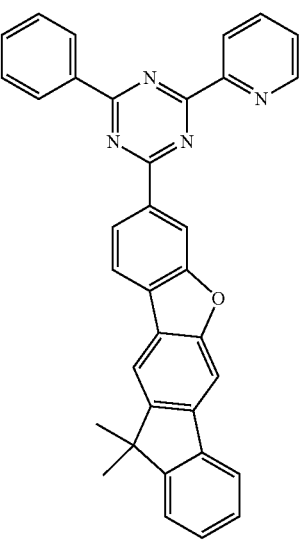
189
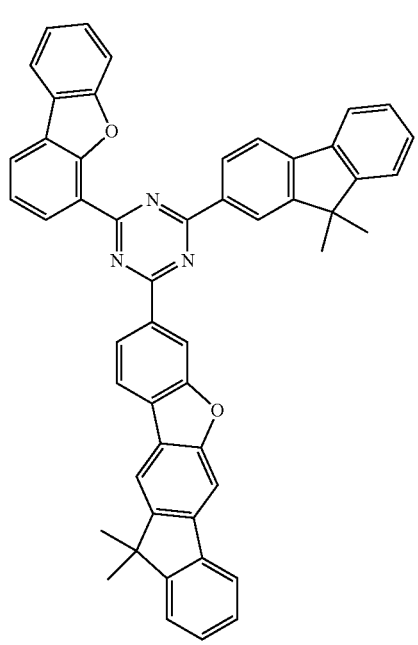
191
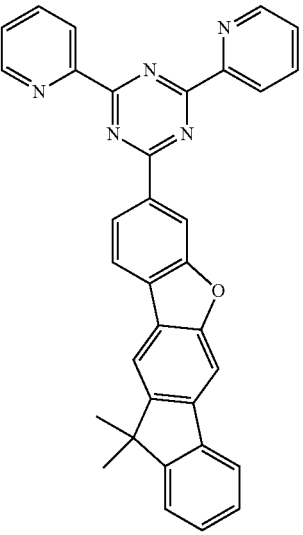

321
-continued
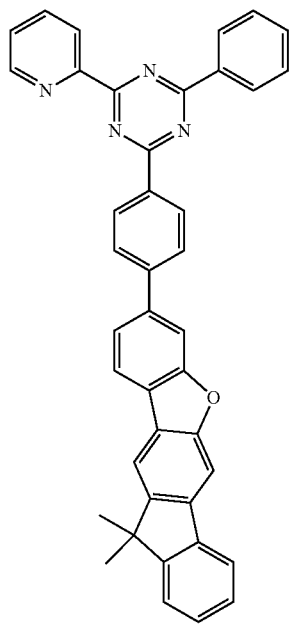
322
-continued
192
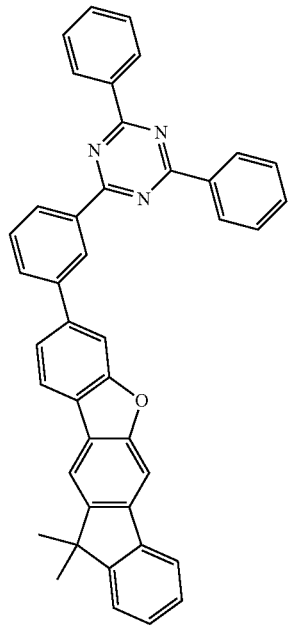
194
193
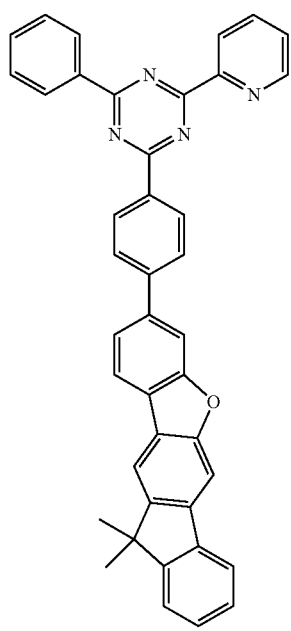
195
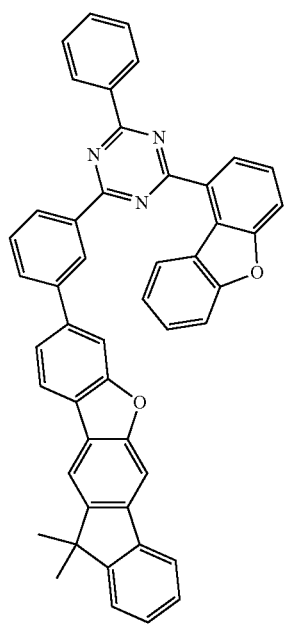

323
-continued
196
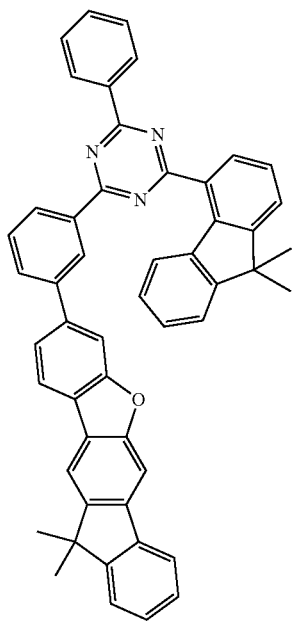
197
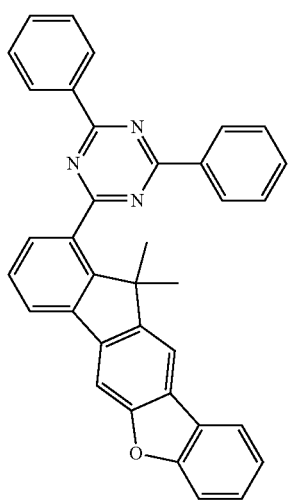
198
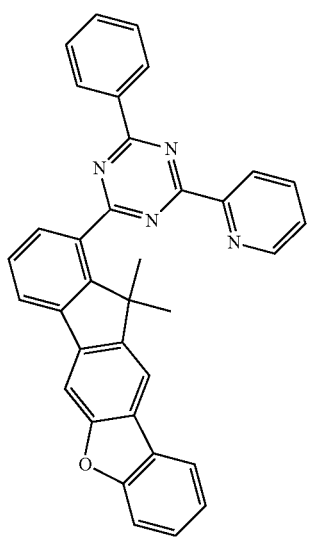
324
-continued
199
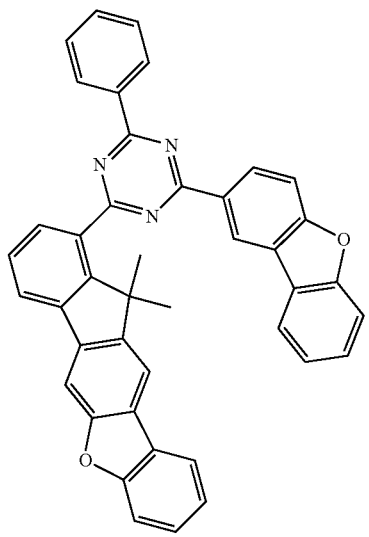
200
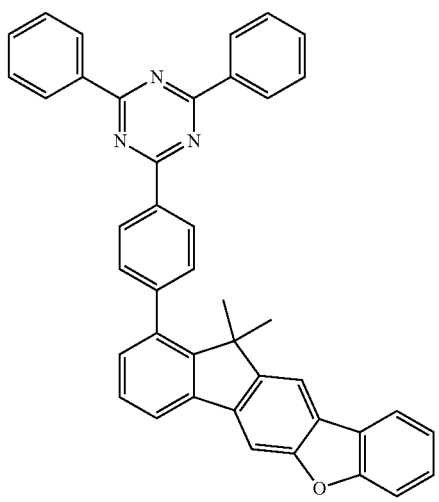
201
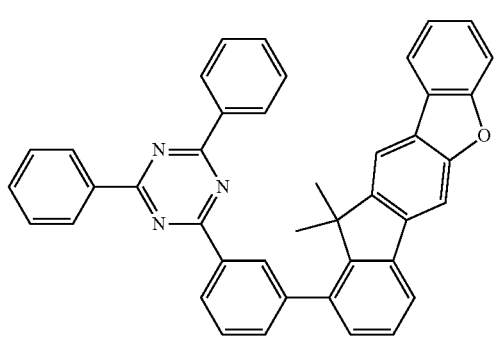

-continued
202
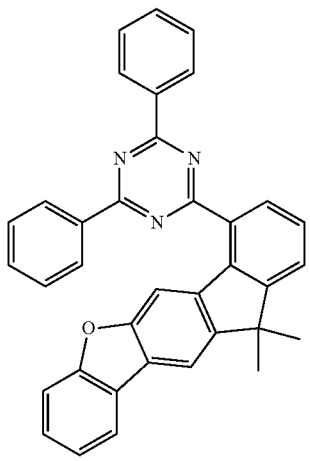
205
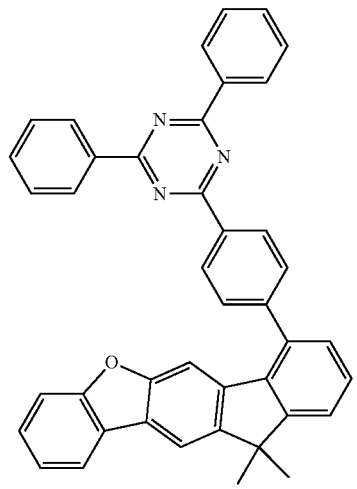
203
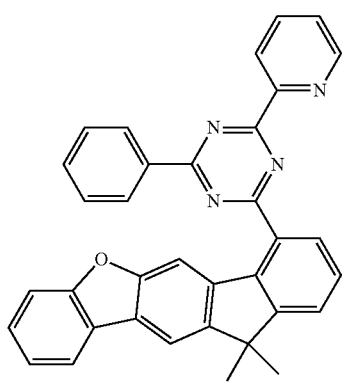
206
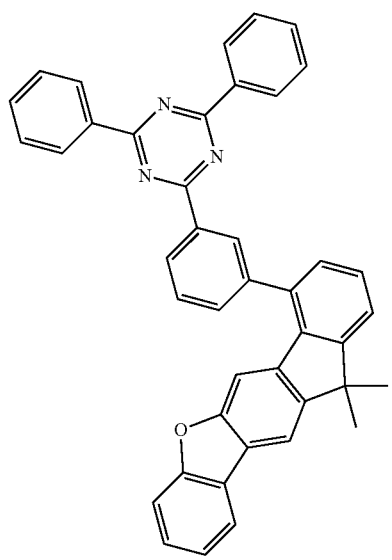
204
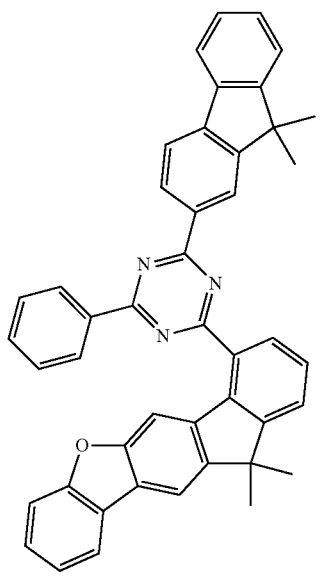
207
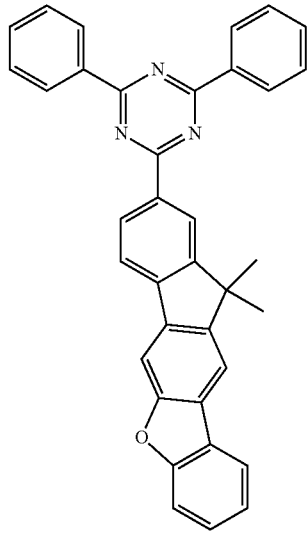

327
-continued
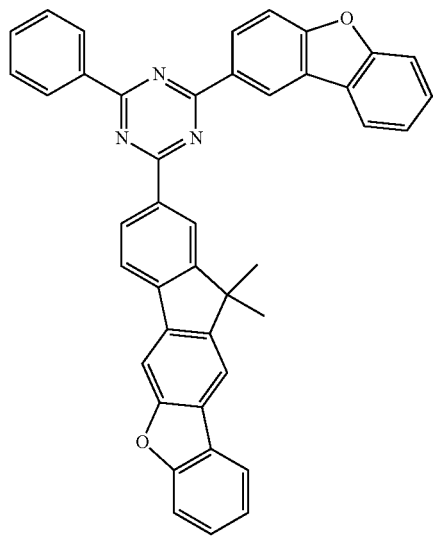
208
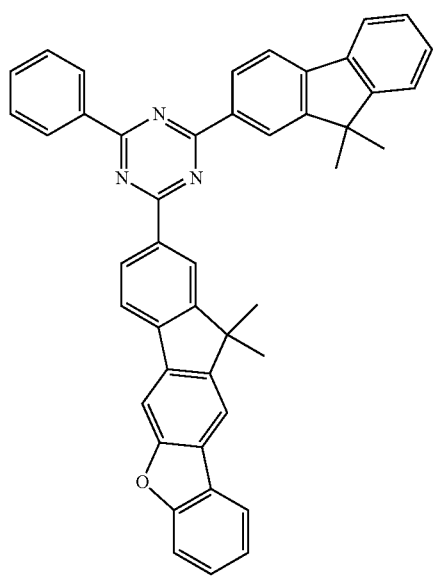
209
328
-continued
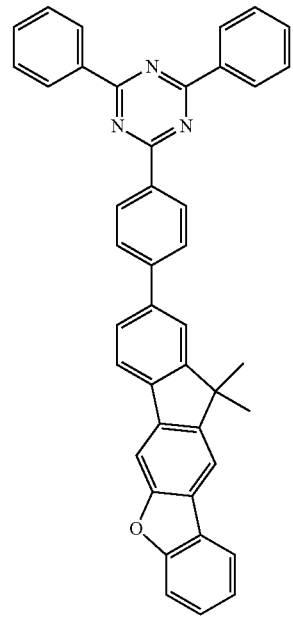
210
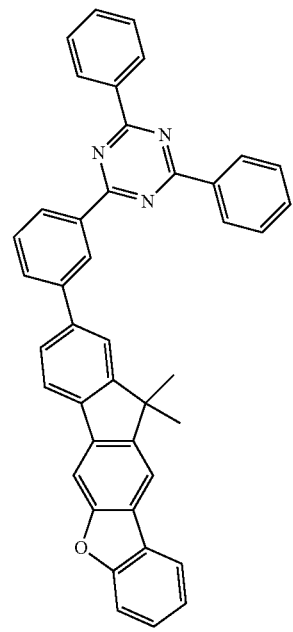
211
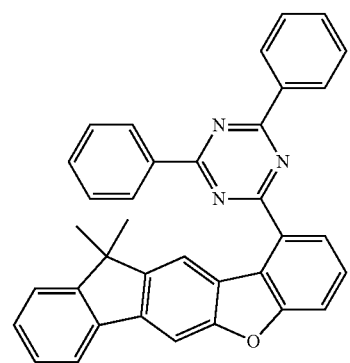
212

213
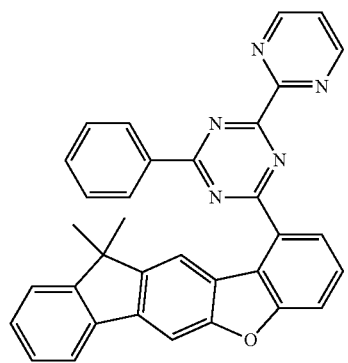
214
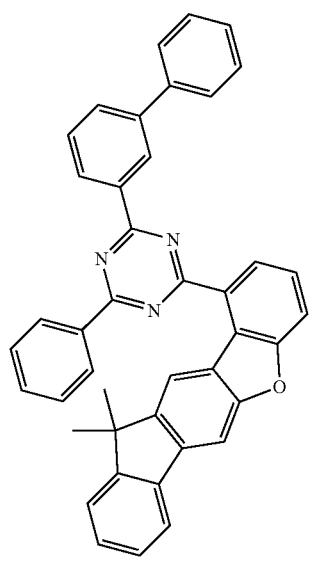
215
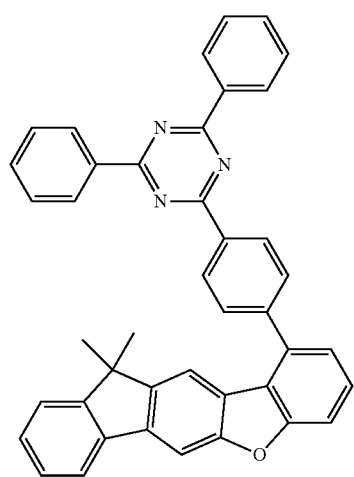
216
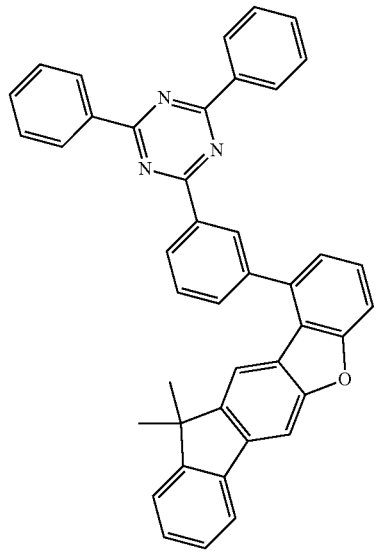
217
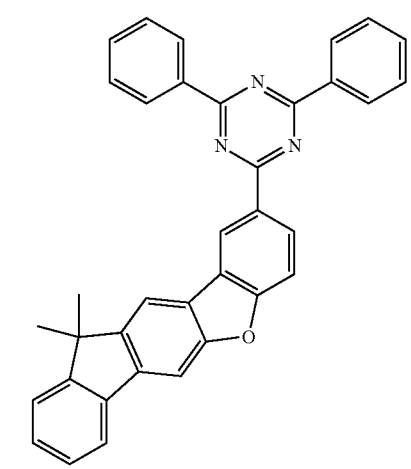
218
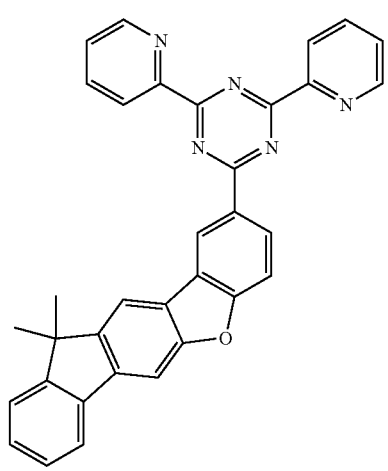

331
219
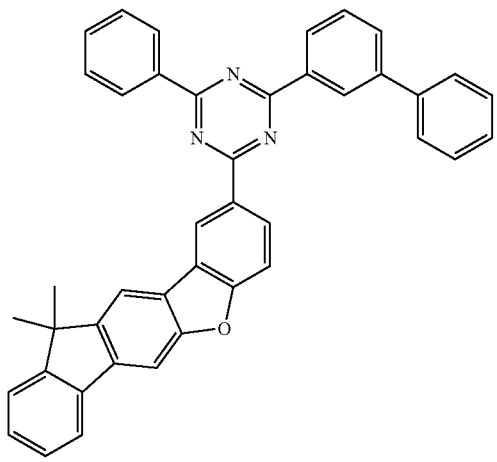
220
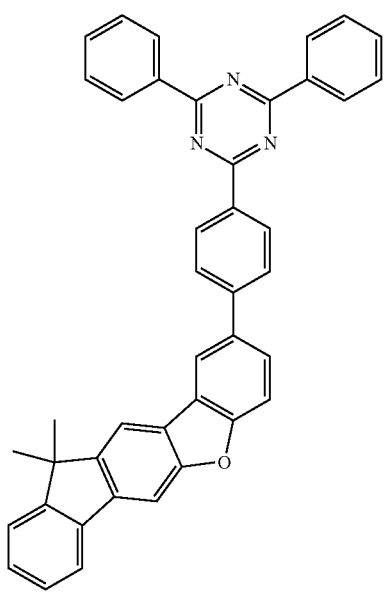
221
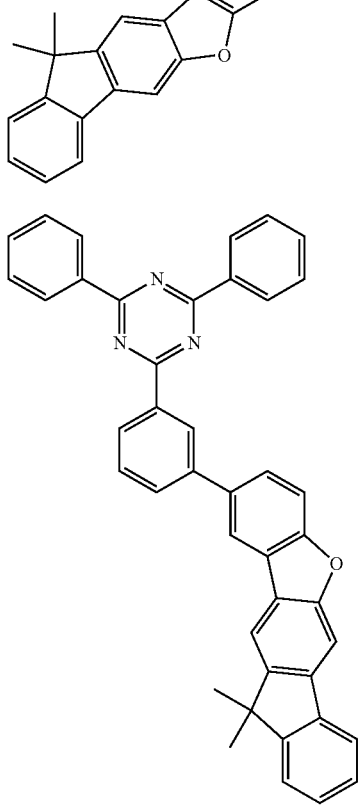
332
222
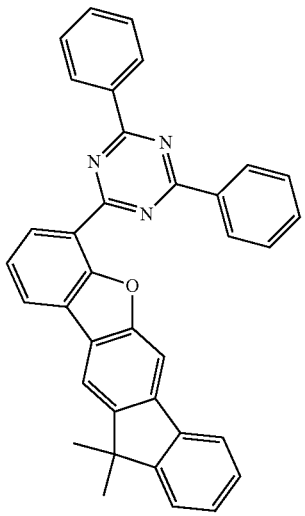
223
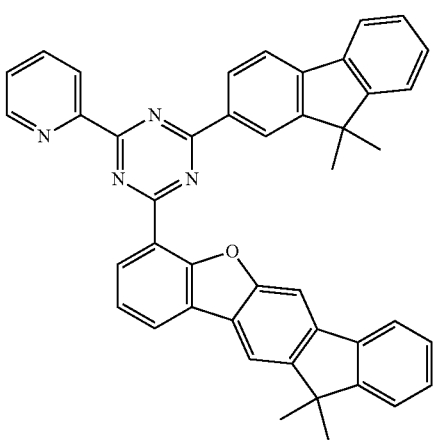
224
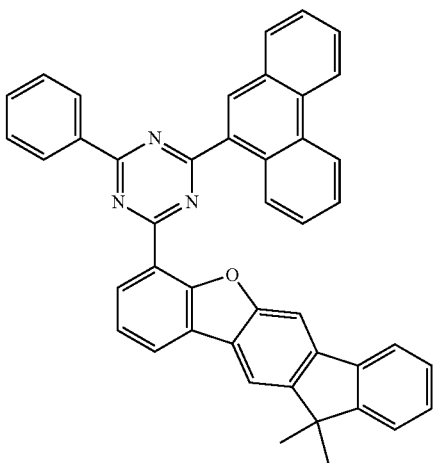

333
-continued
225
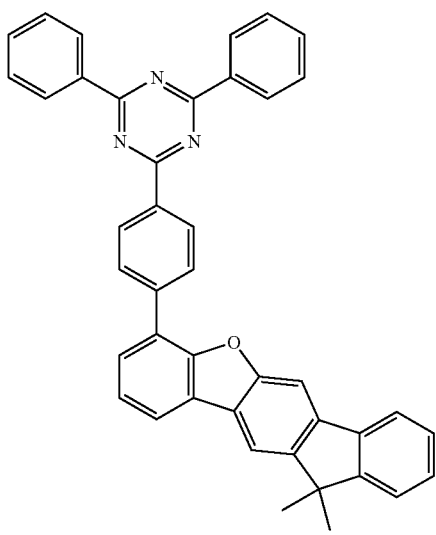
226
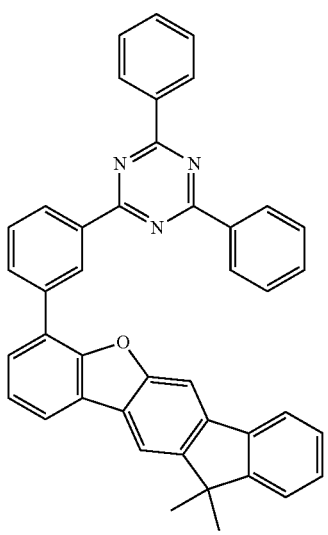
227
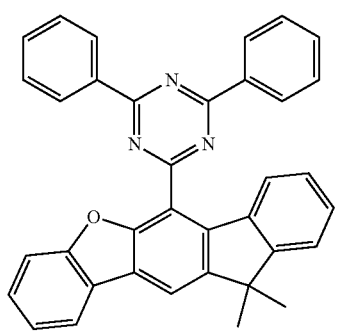
334
-continued
228
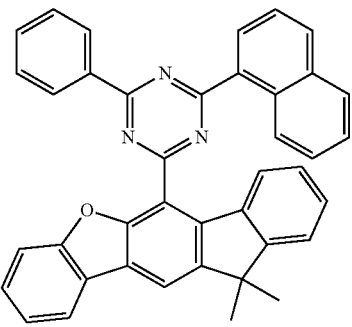
229
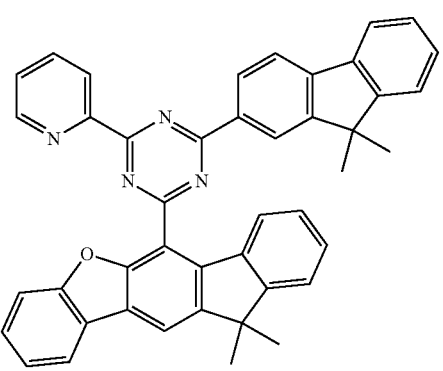
230
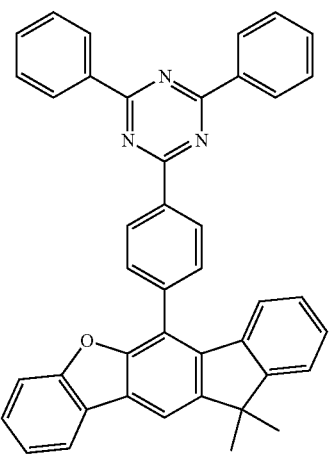

335
-continued
231
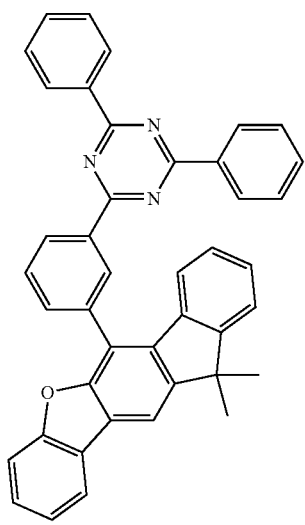
232
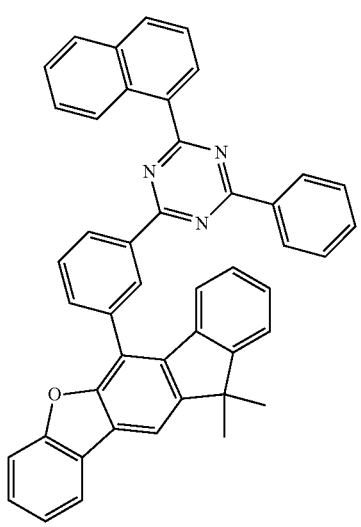
233
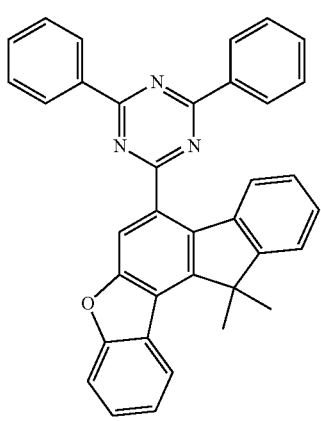
336
-continued
234
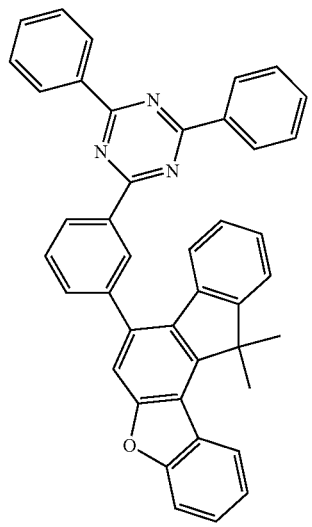
235
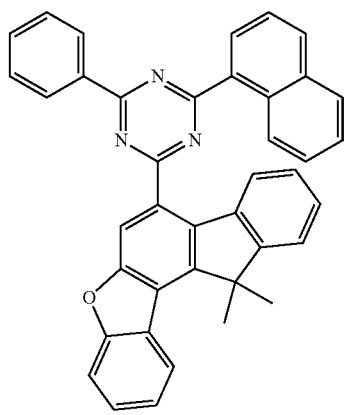
236
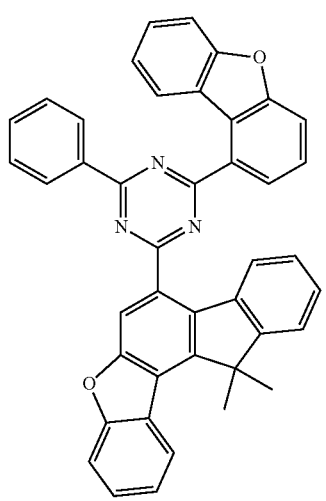

237
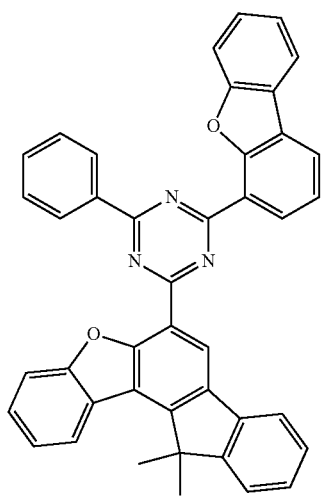
238
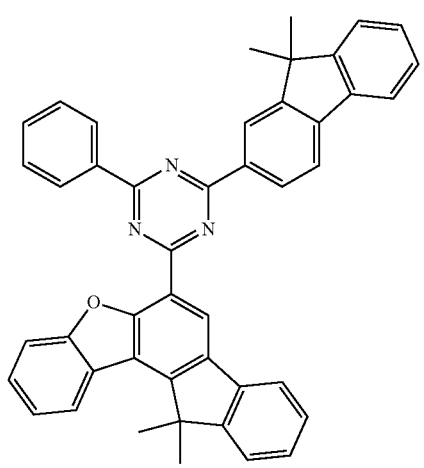
239
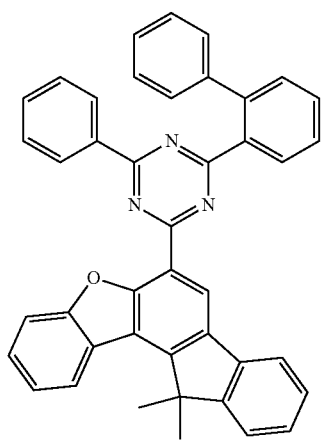
240
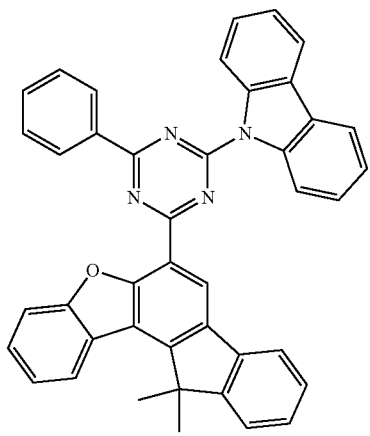
241
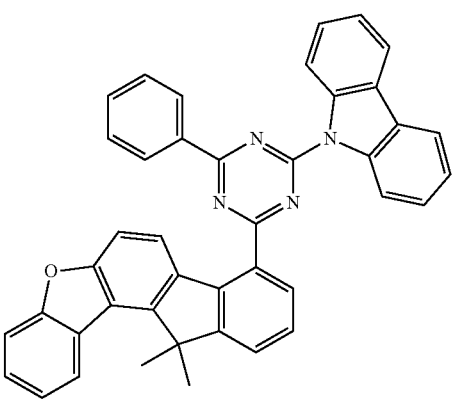
242
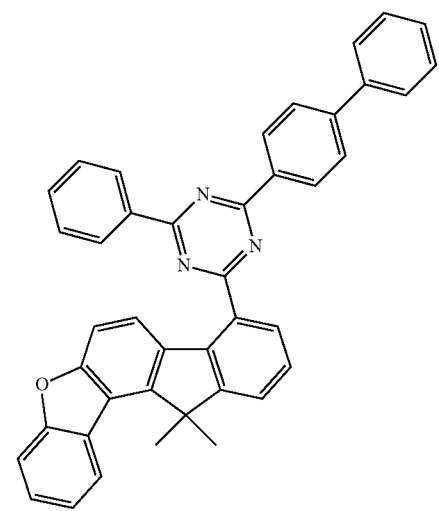

243
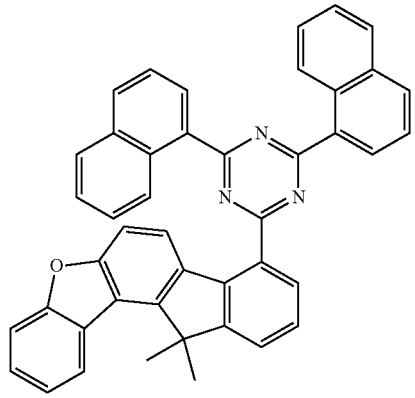
244
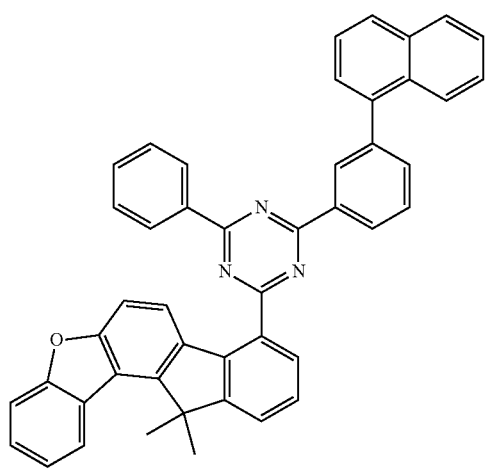
245
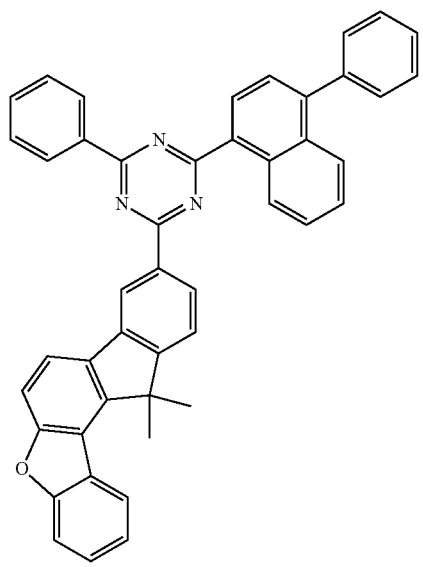
246
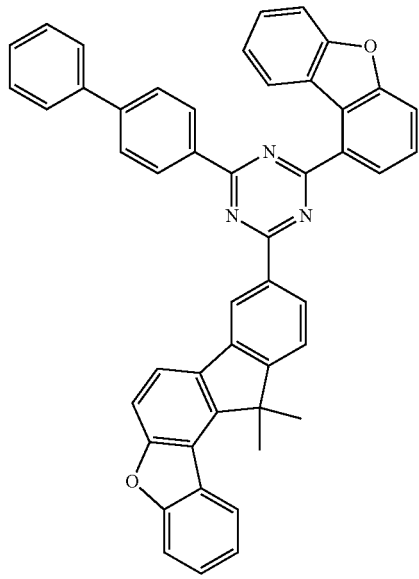
247
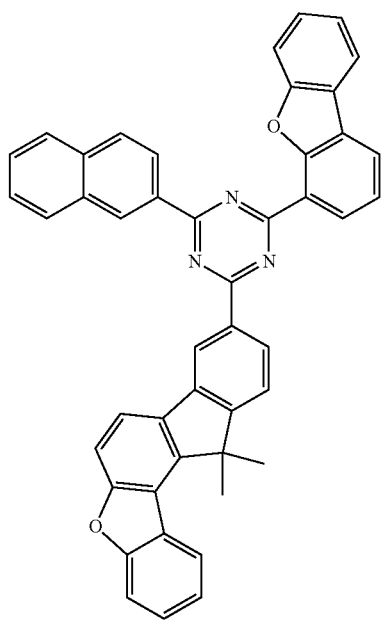

-continued
248
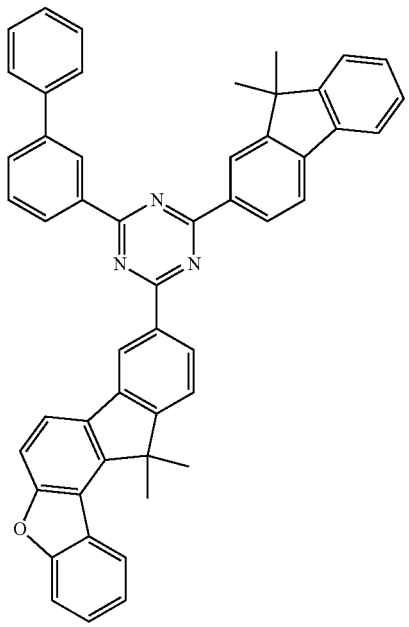
250
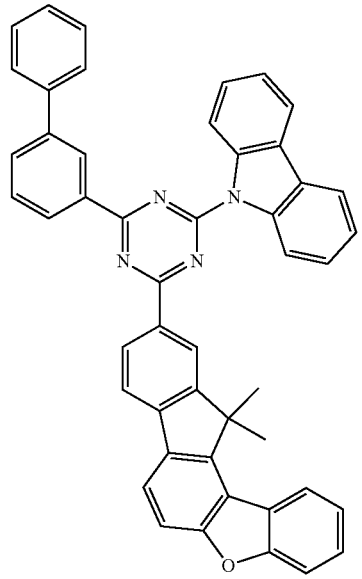
251
249
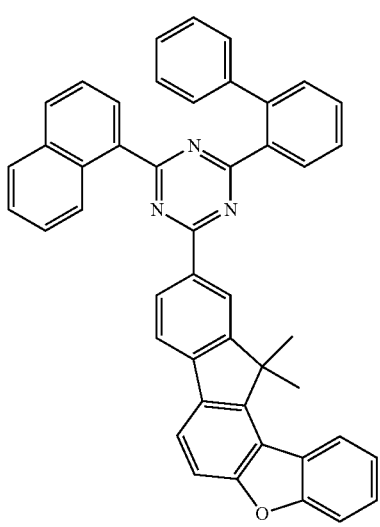
252
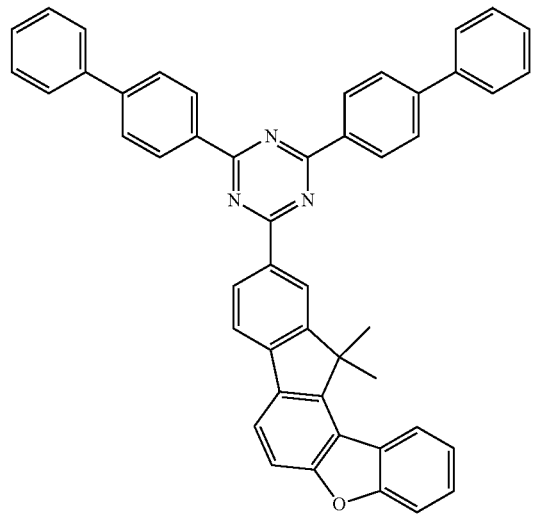

343
-continued
253
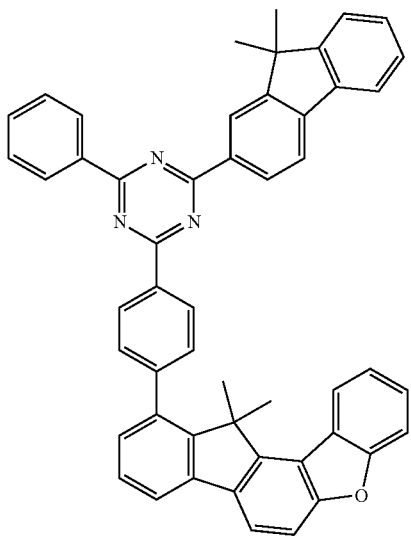
254
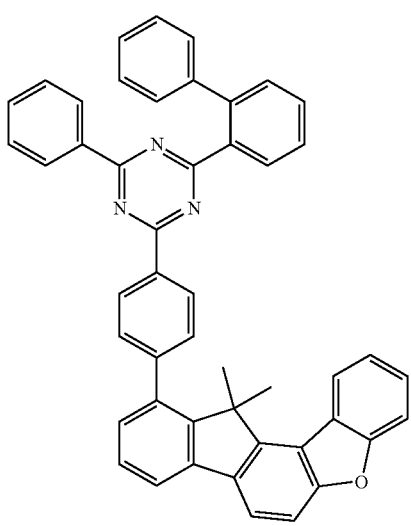
255
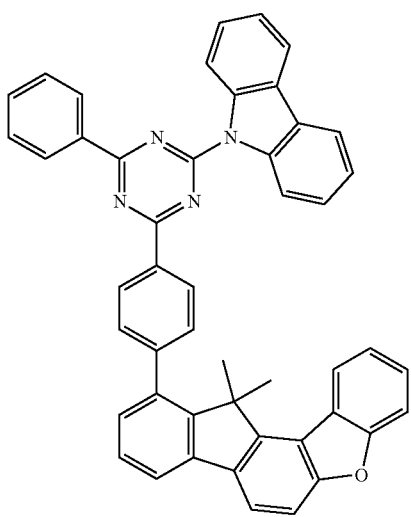
344
-continued
256
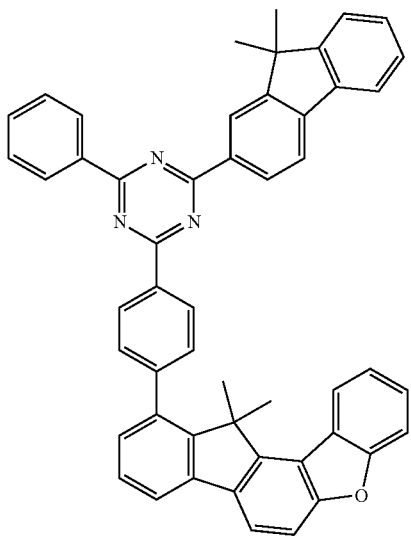
257
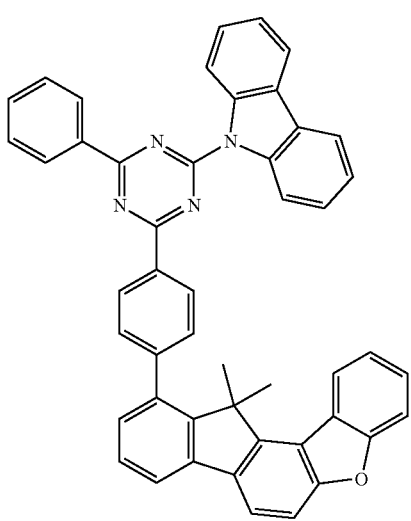

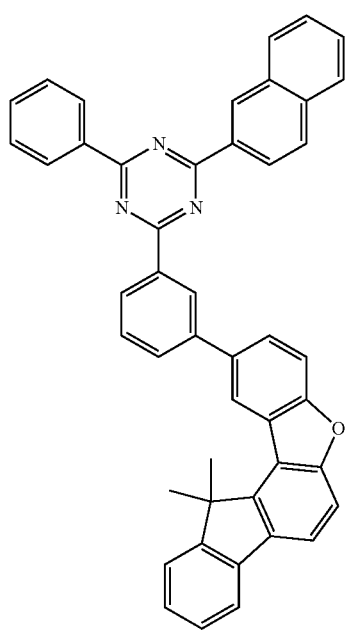
258
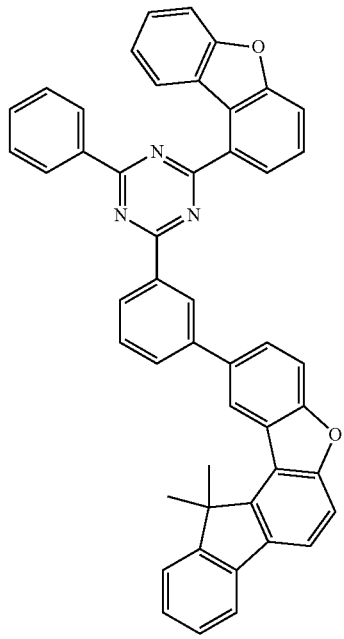
260
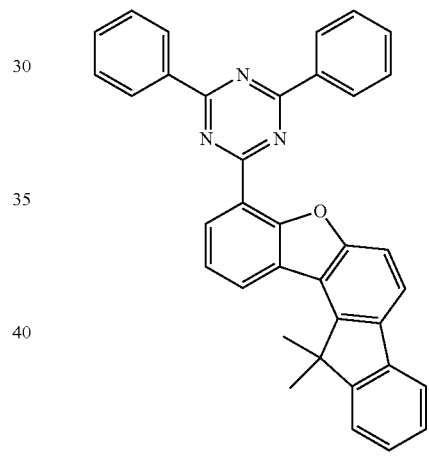
261
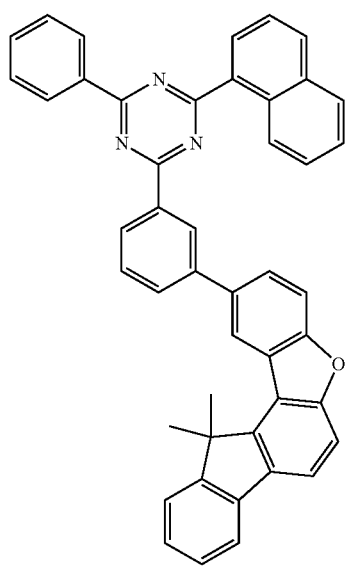
259
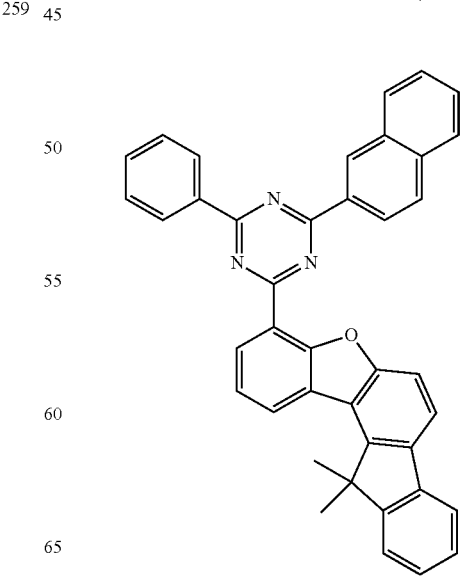
262

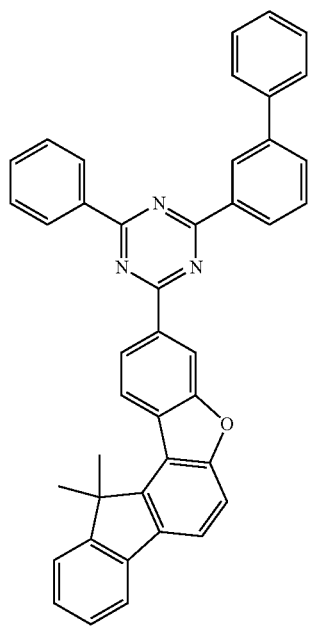
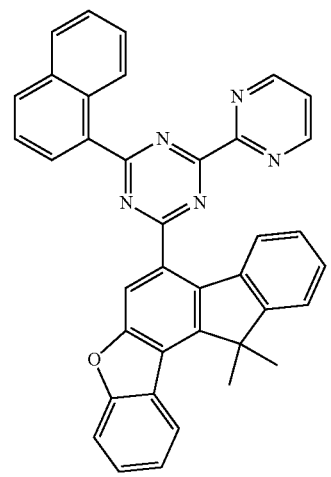
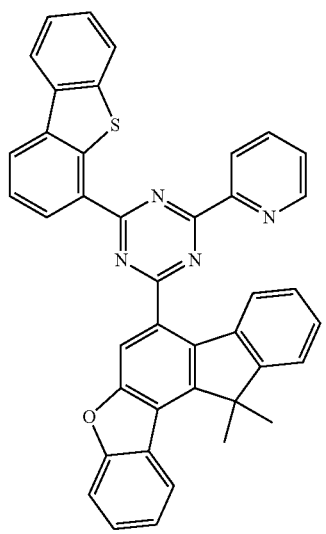
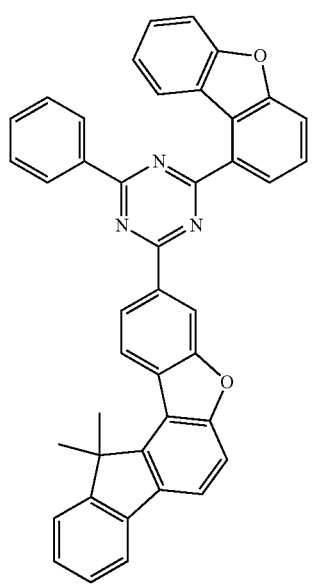
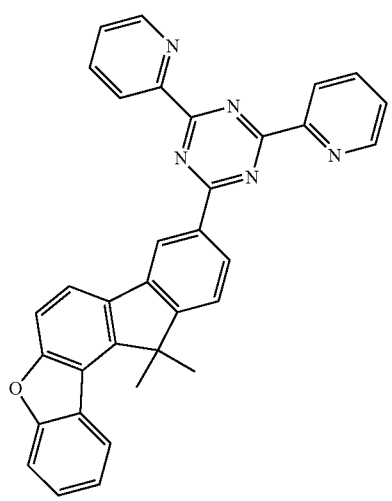

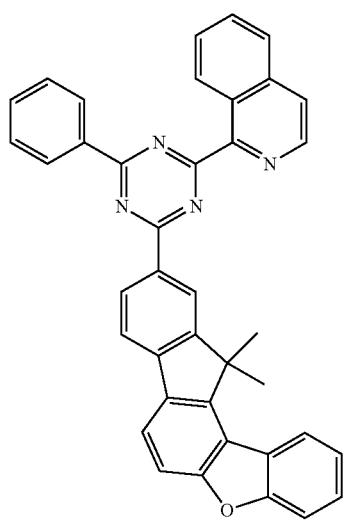
268
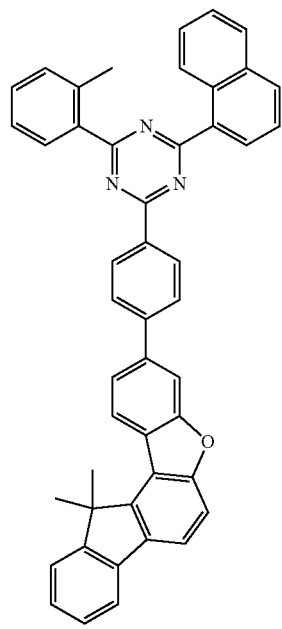
270
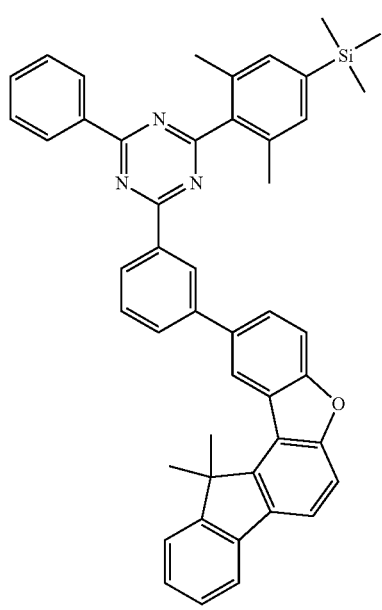
269
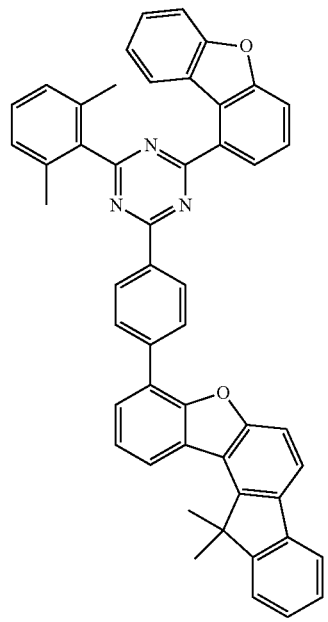
271

351
-continued
352
-continued
272
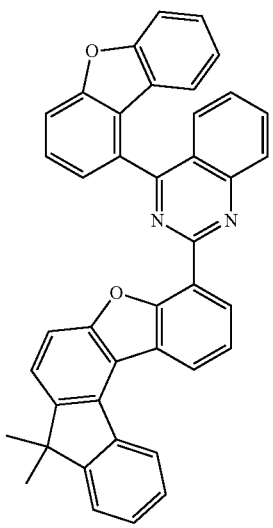
275
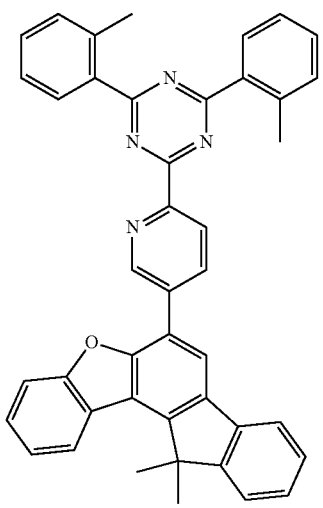
273
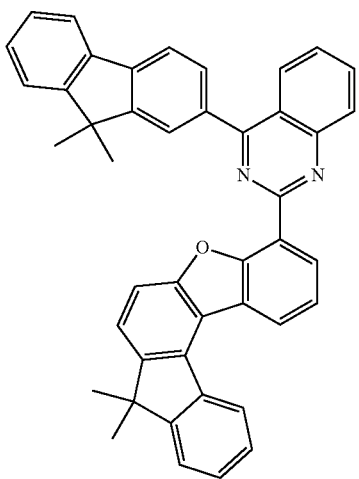
276
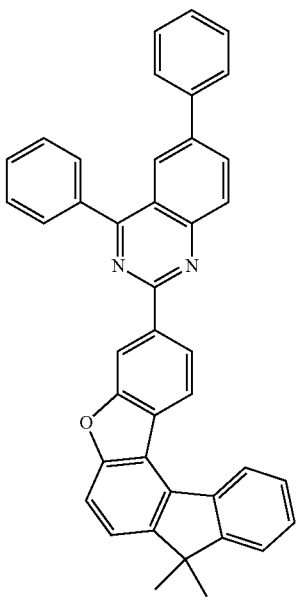
274
277
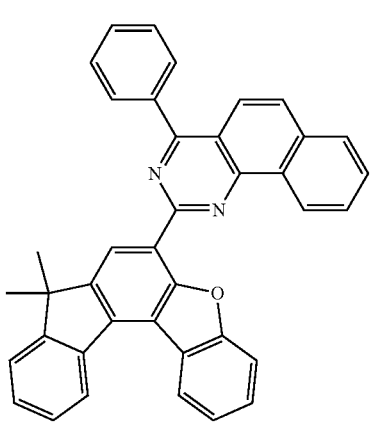

353
-continued
354
-continued
278
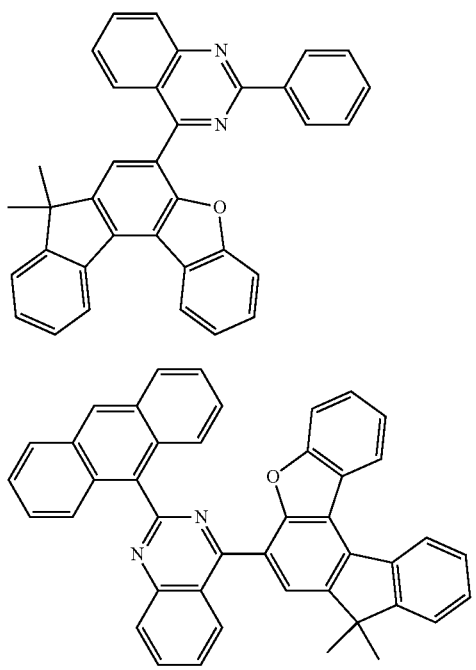
279
280
281
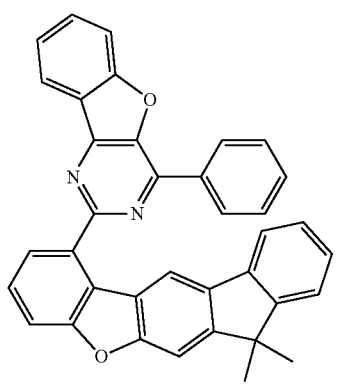
282
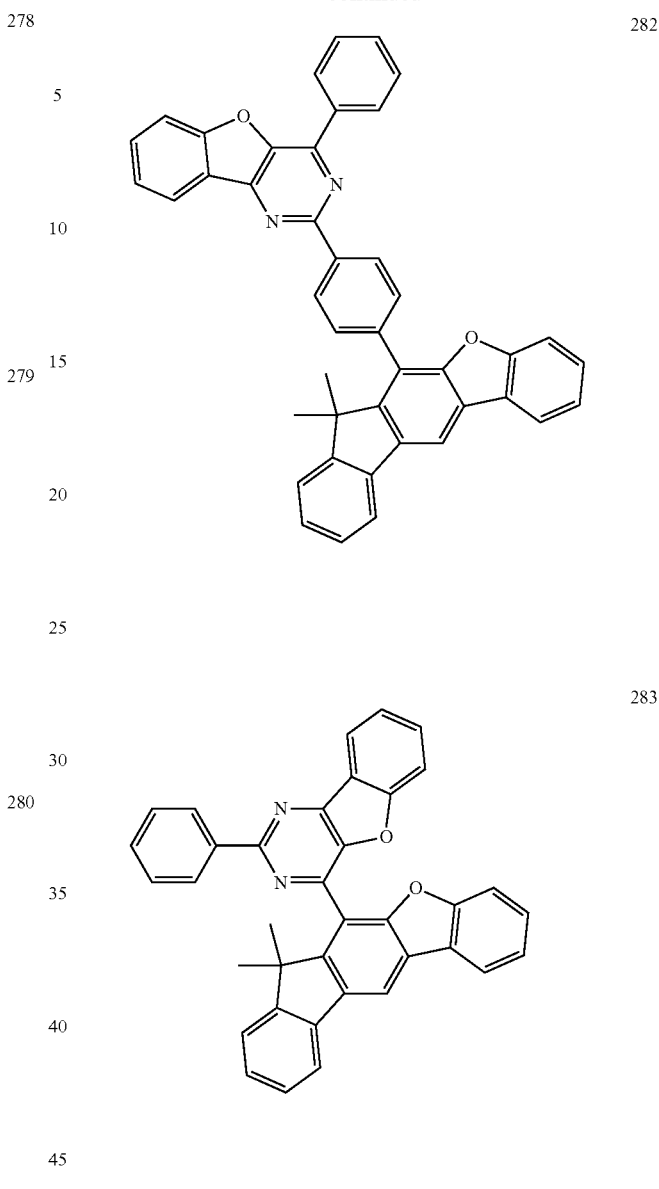
283
284

355
-continued
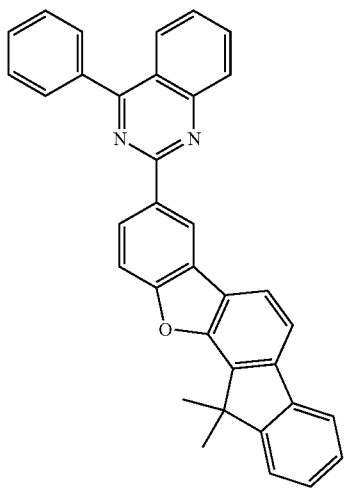
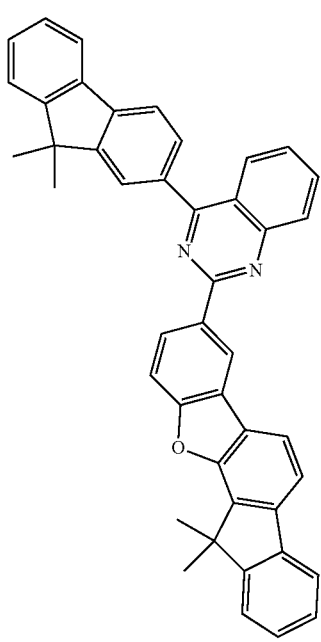
356
-continued
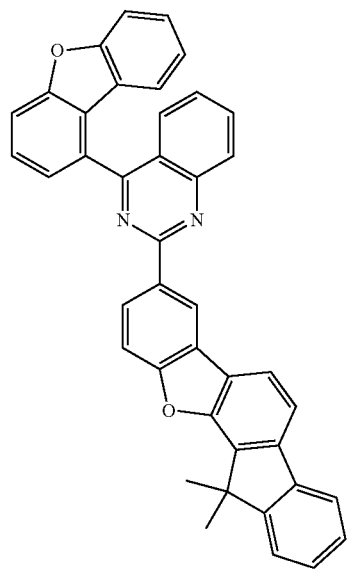
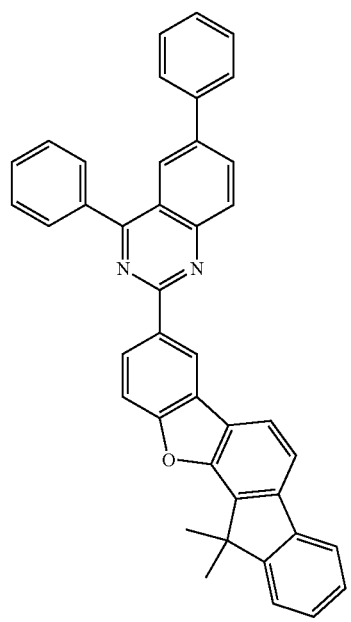

289 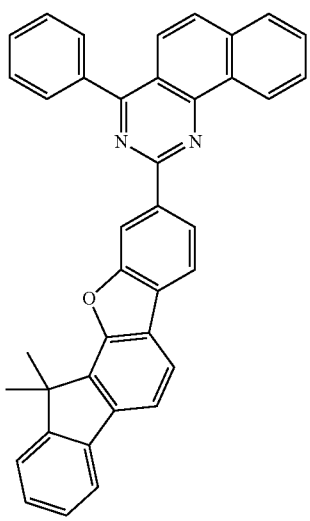
290 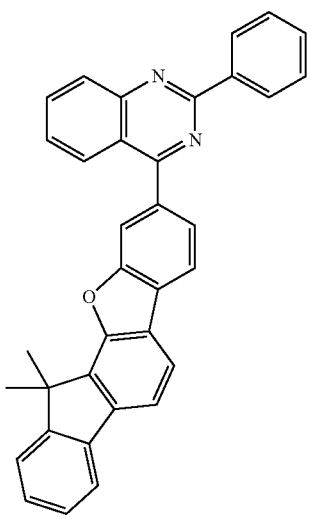
291 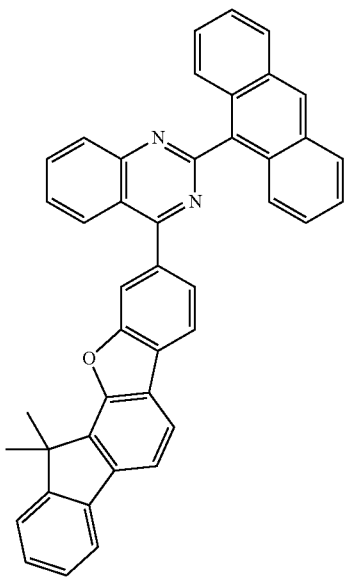
292 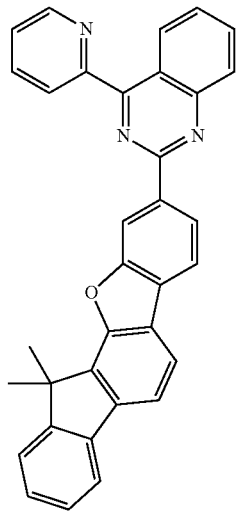
293 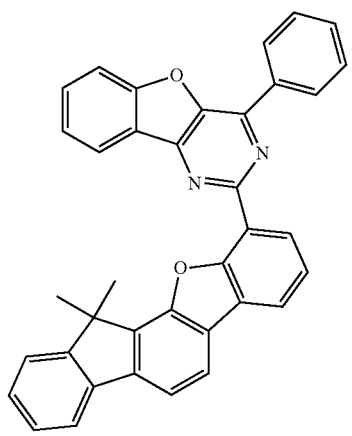
294

359
-continued
295 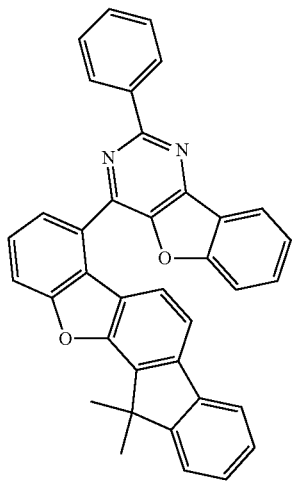
296 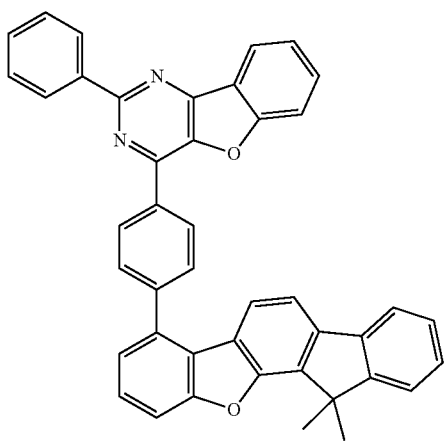
297 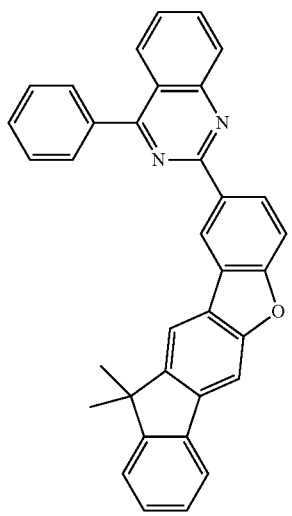
360
-continued
298 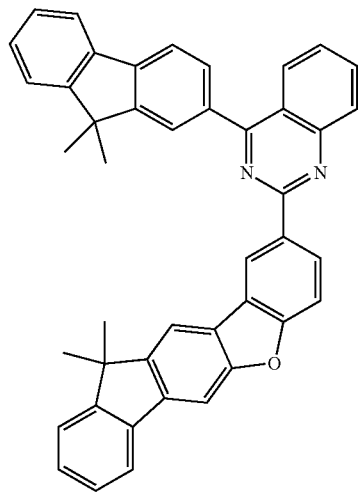
299 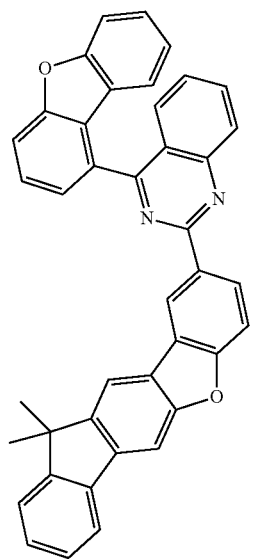

361
-continued
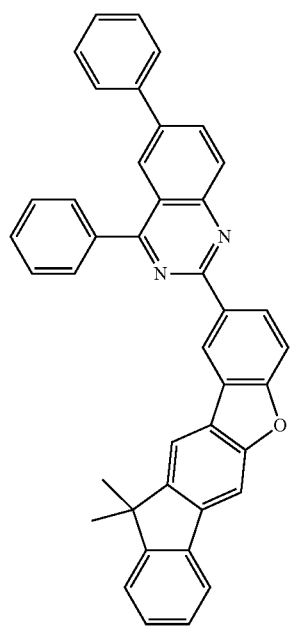
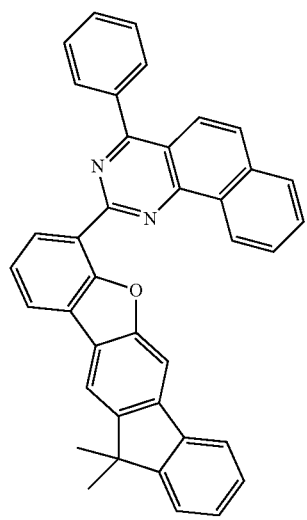
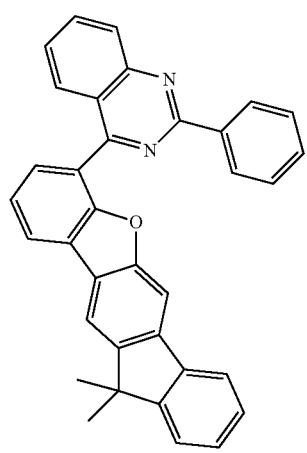
362
-continued
300
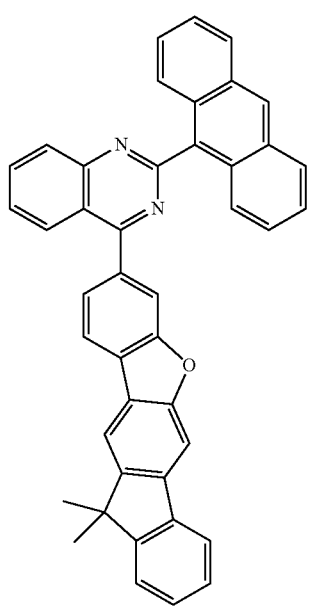
301
302
304
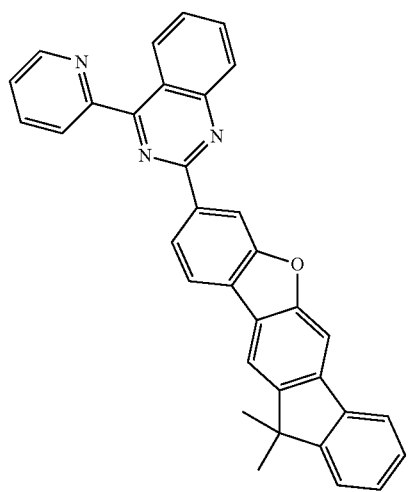
303

363
-continued
305
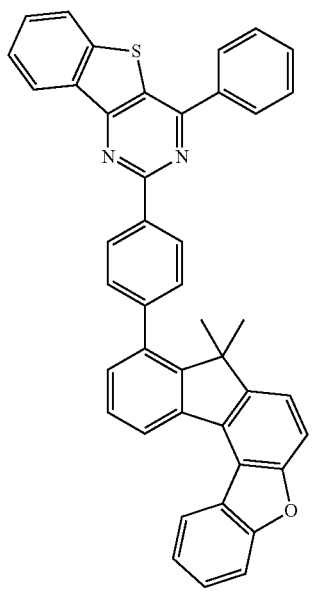
306
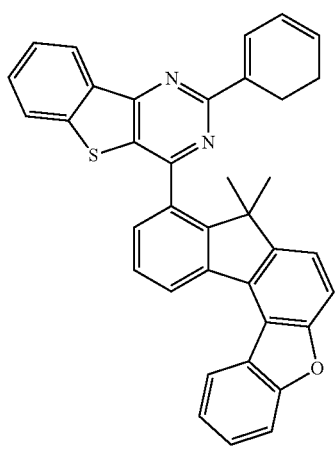
307
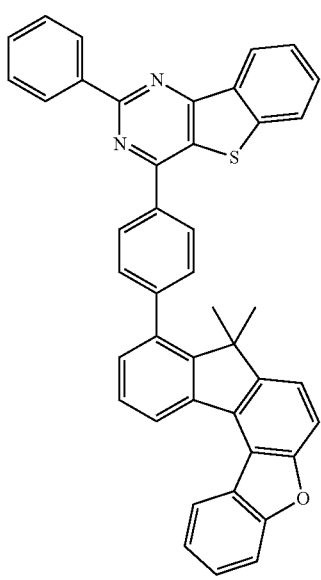
364
-continued
308
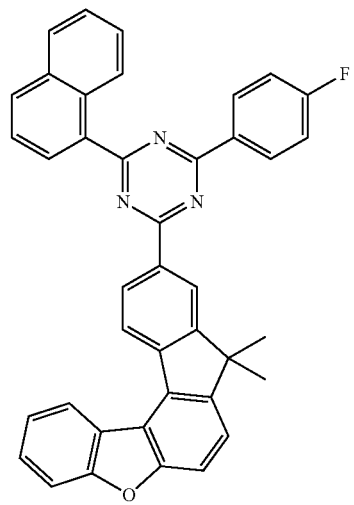
309
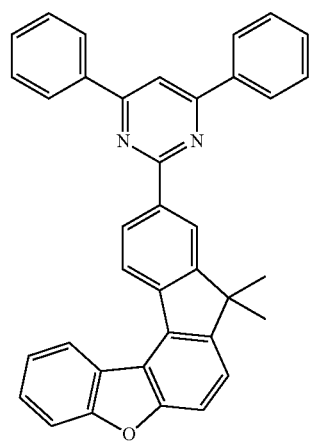
310
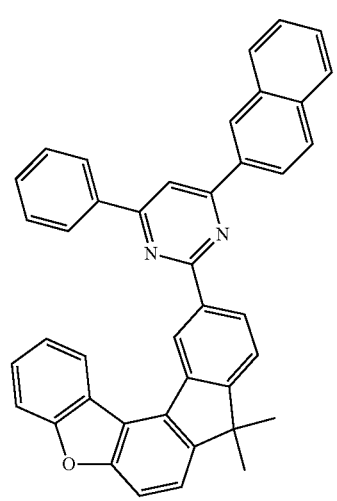

311 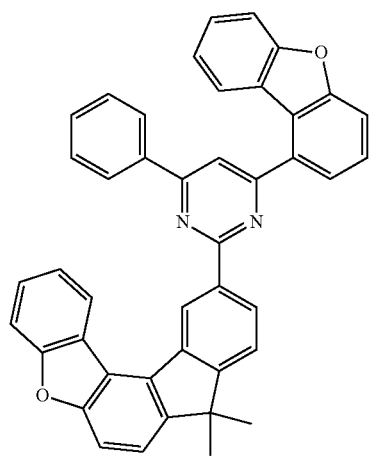
312 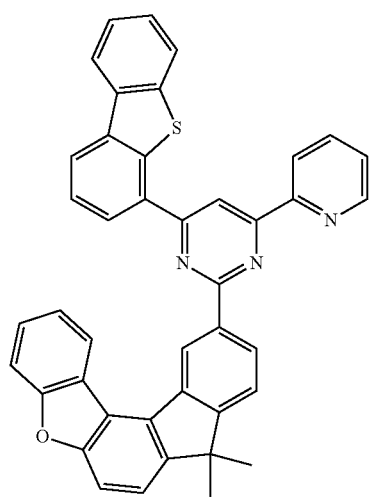
313 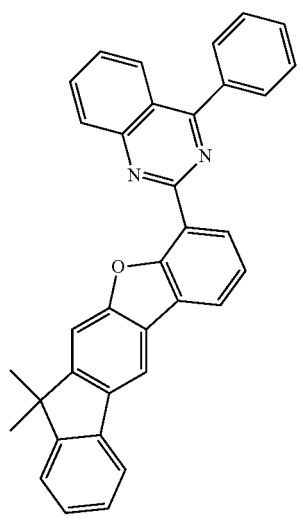
314 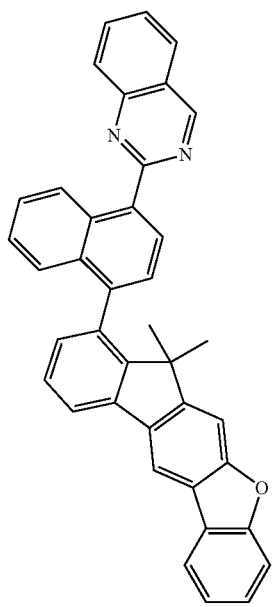
315 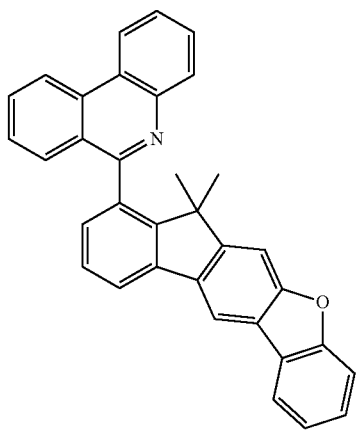
316 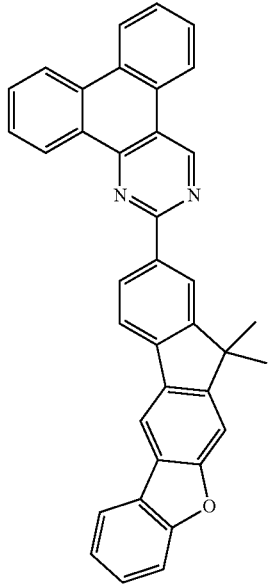

367
-continued
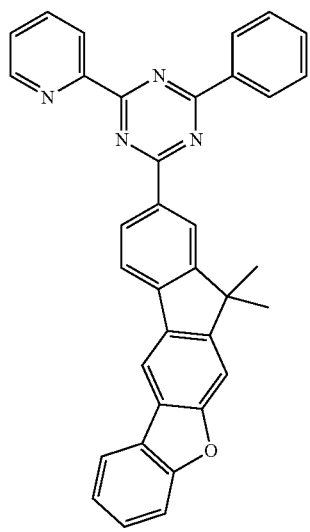
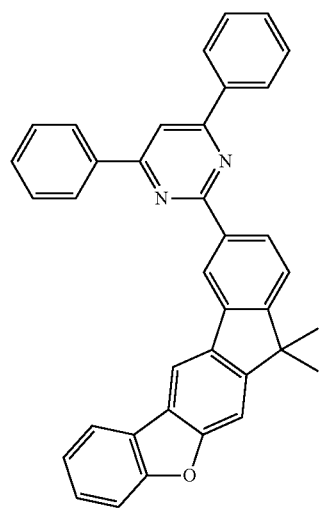
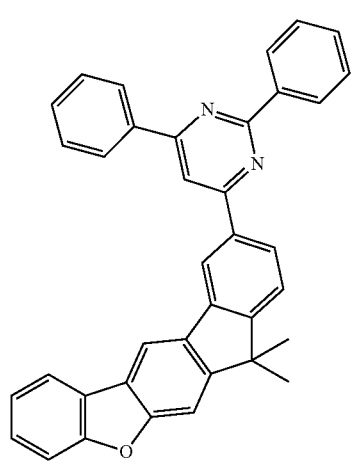
368
-continued
317
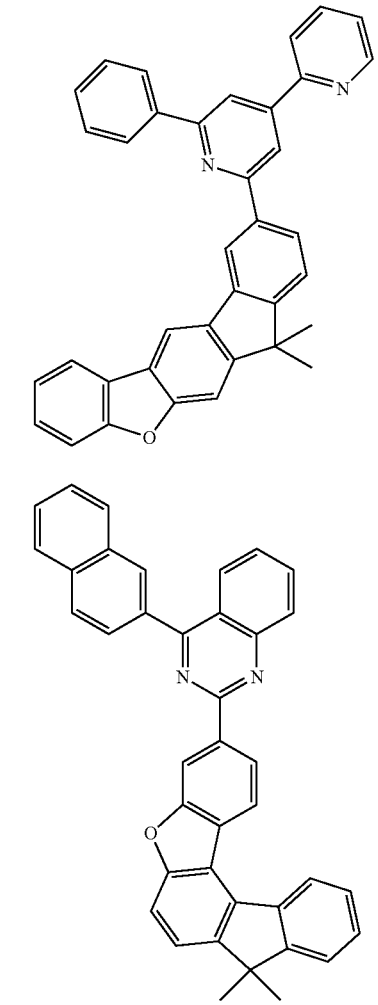
318
319
320
321
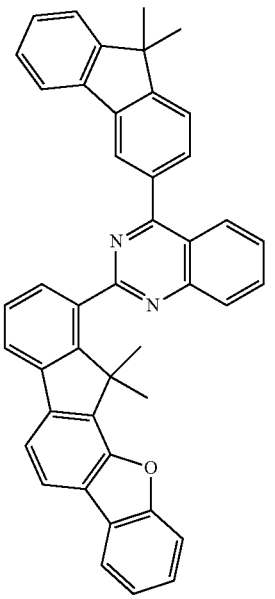
322

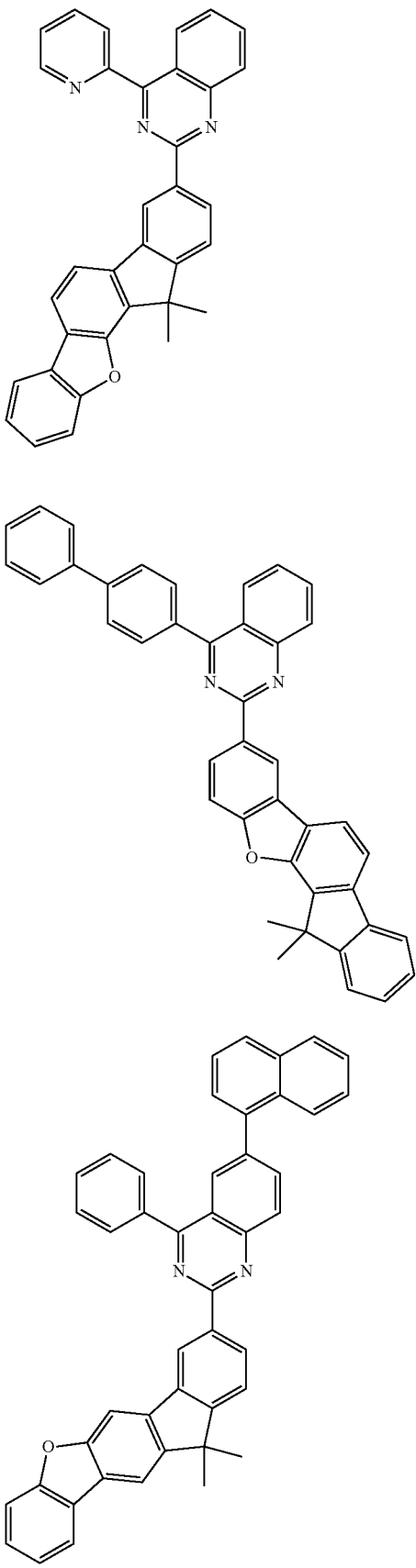
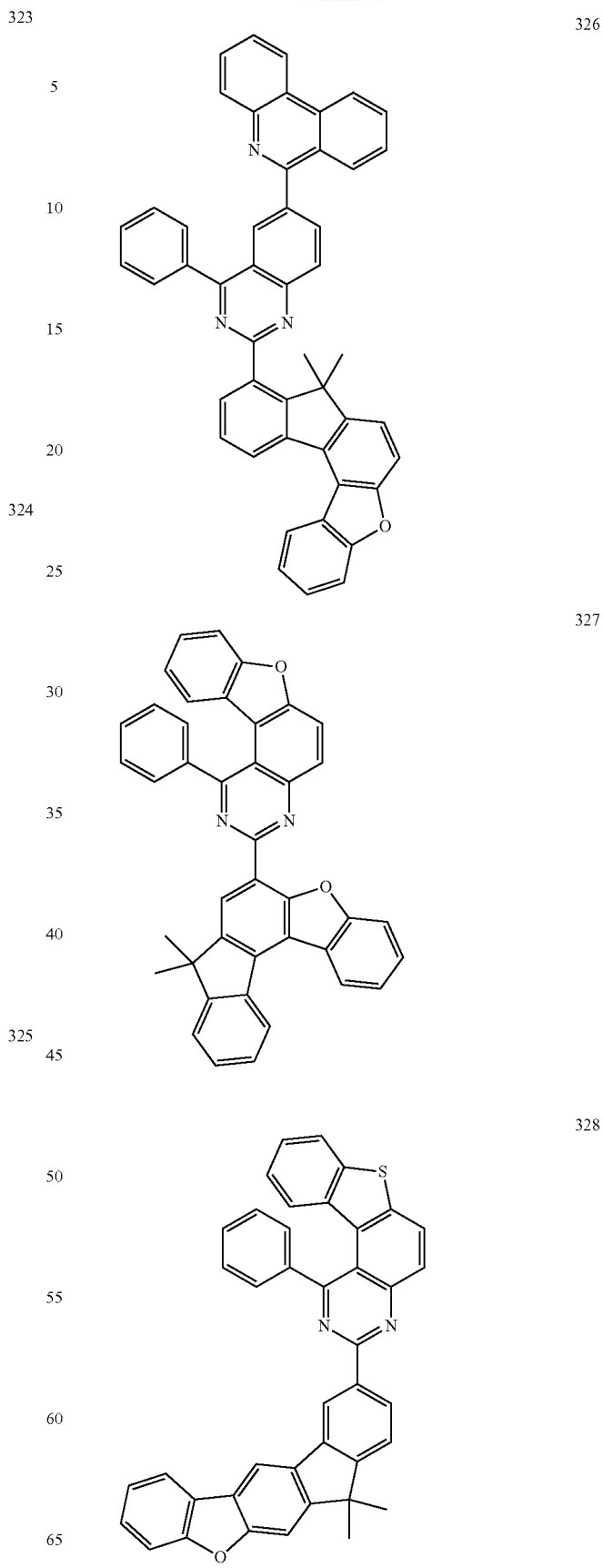

329
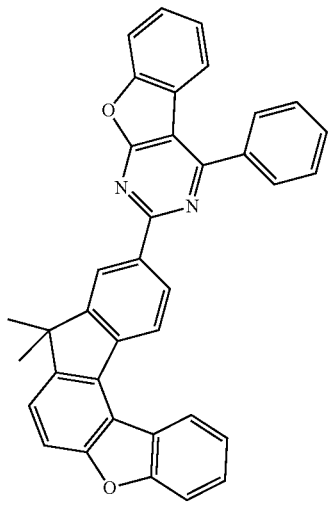
332
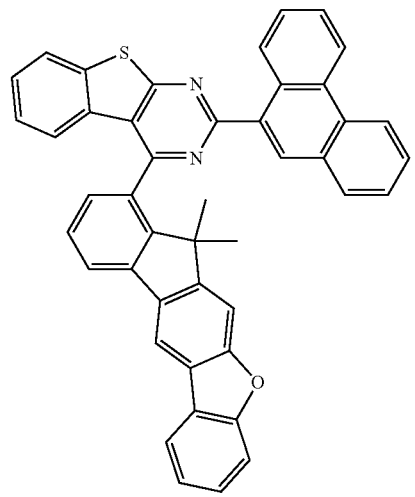
330
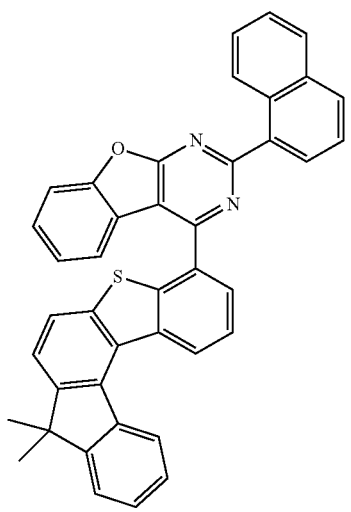
333
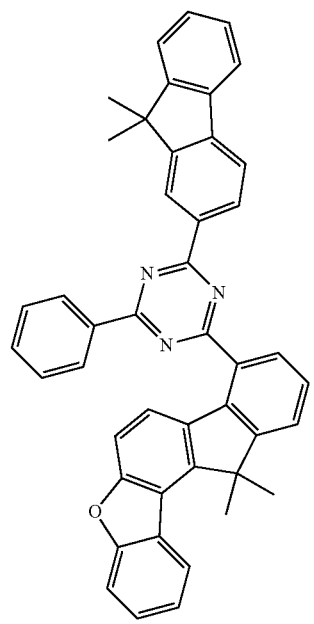
331
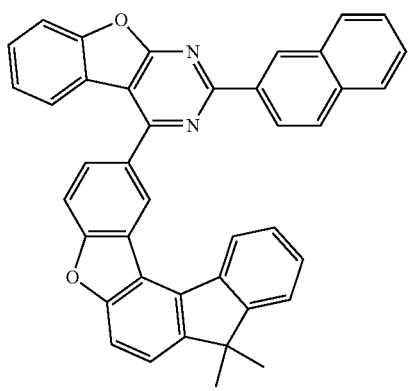
334
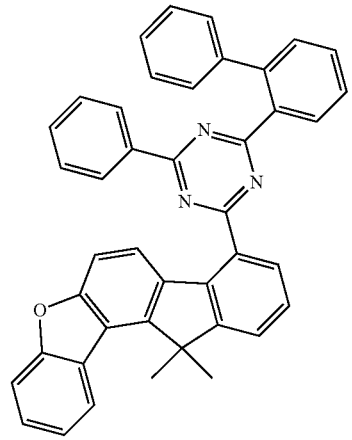

335
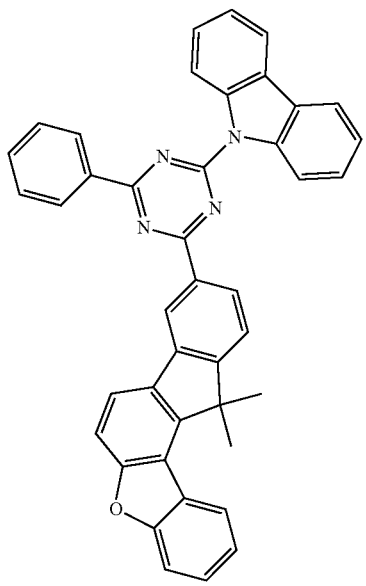
336
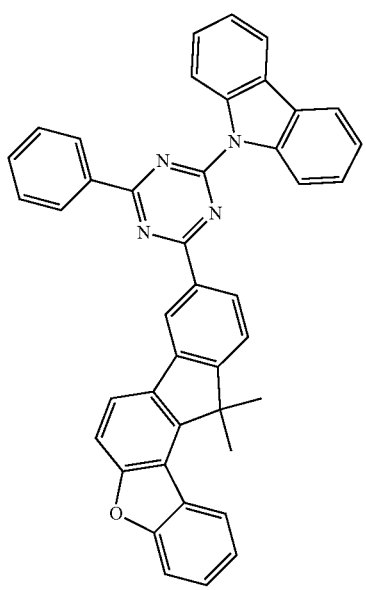
337
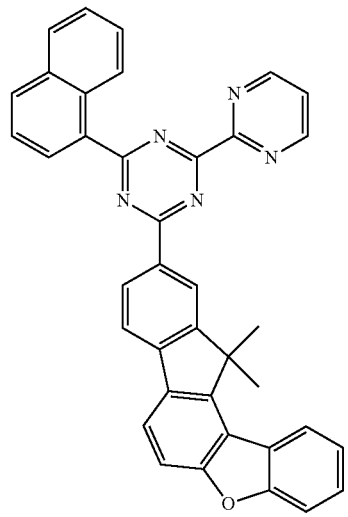
338
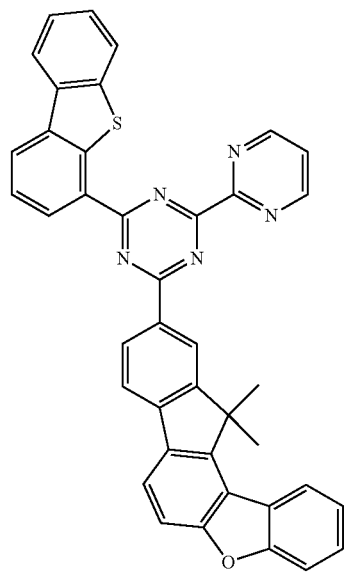
339

375
-continued
340 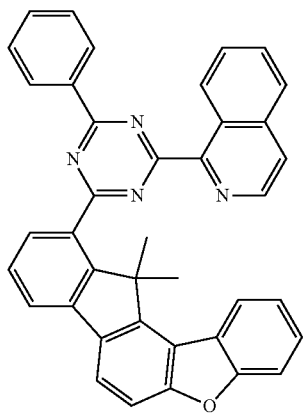
341 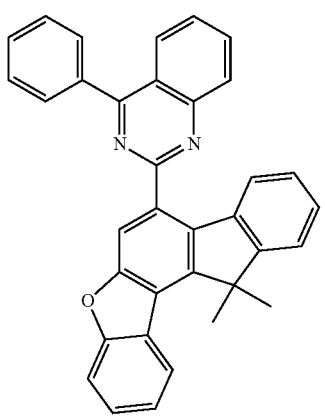
342 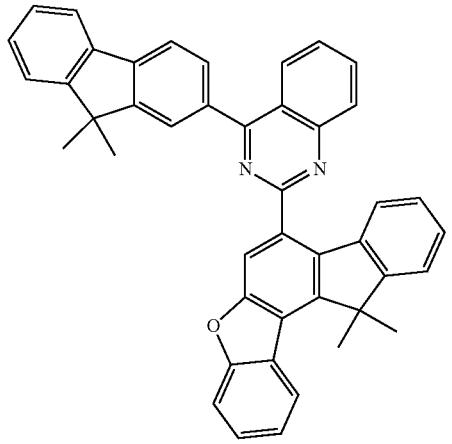
376
-continued
343 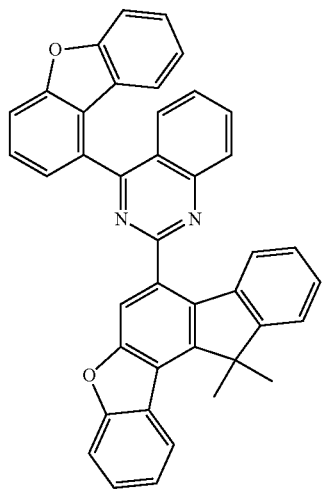
344 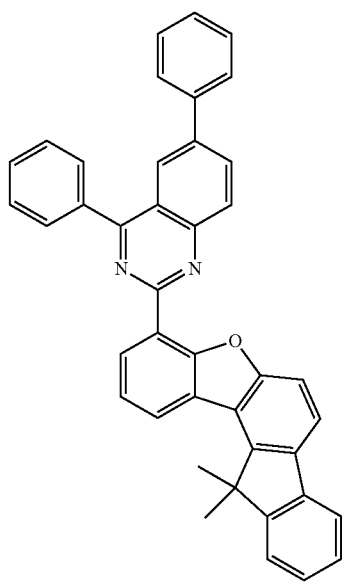
345 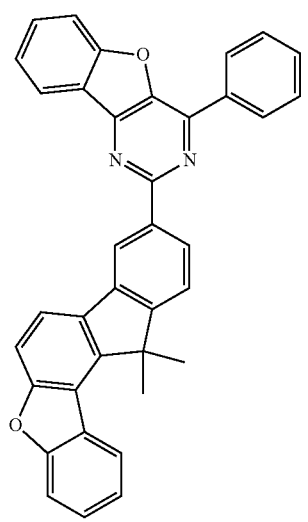

377
-continued
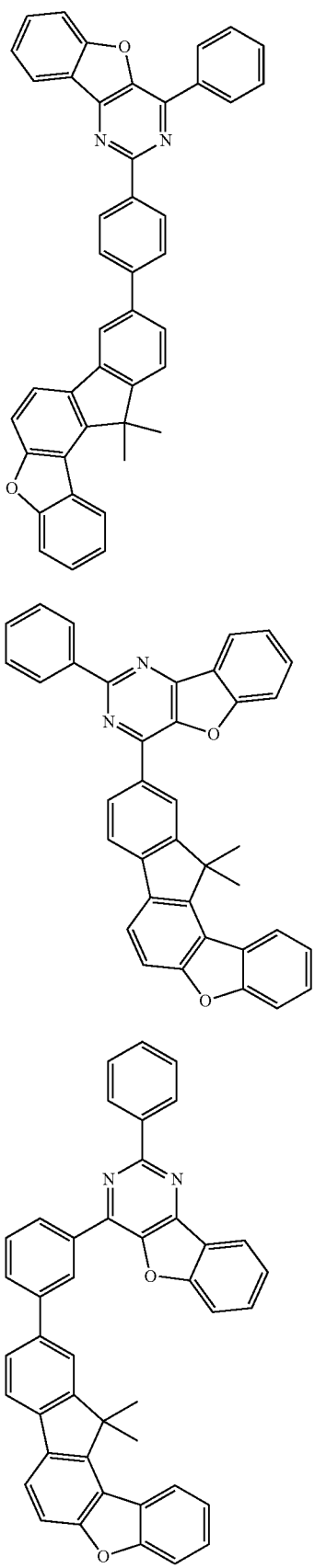
378
-continued
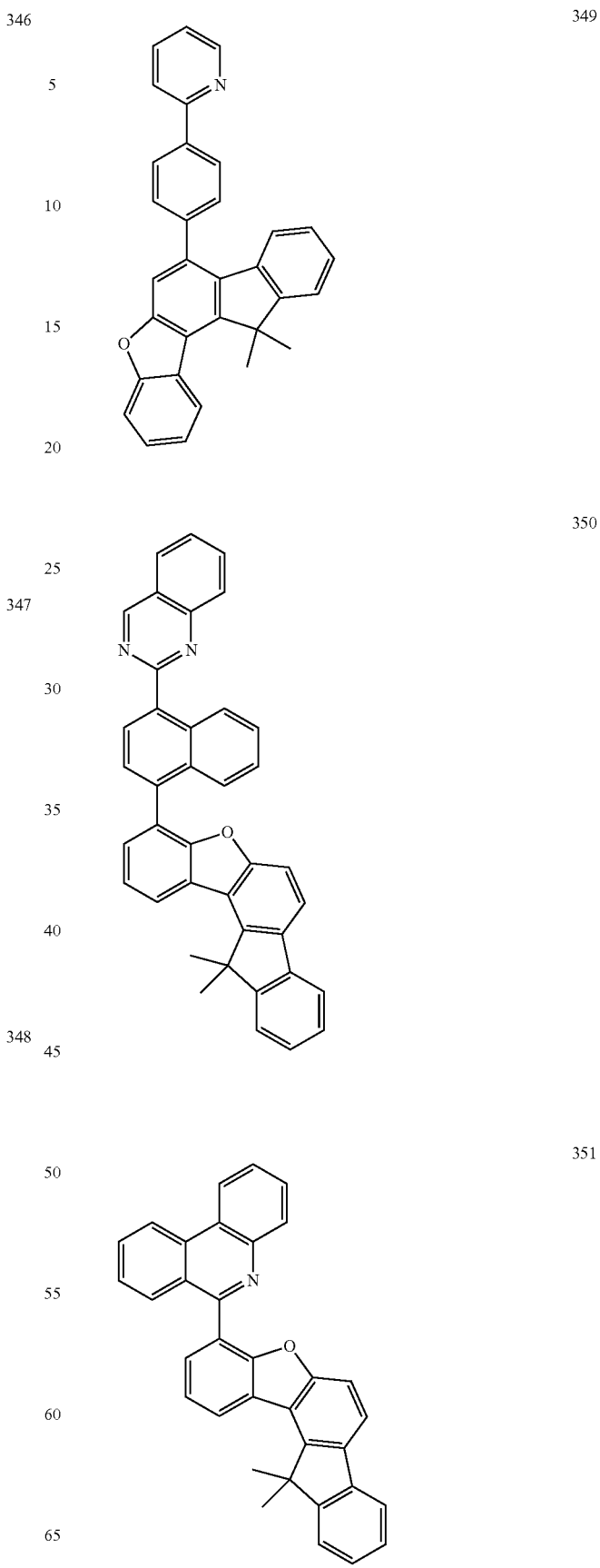

379
-continued
352
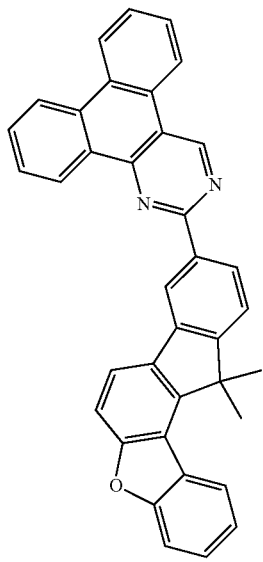
353
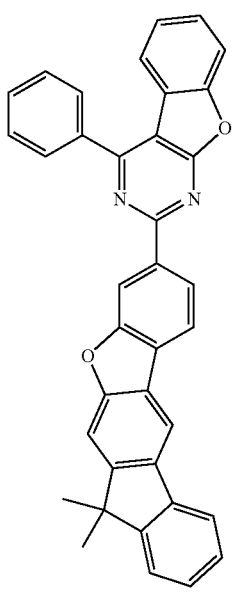
380
-continued
354
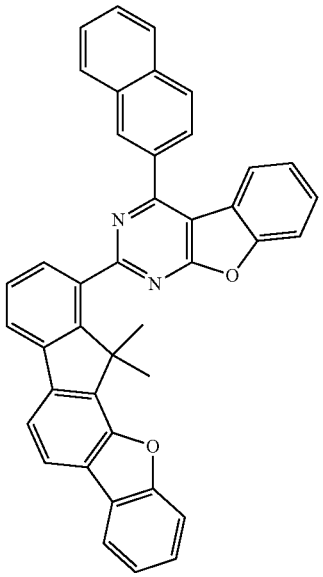
355
356

357
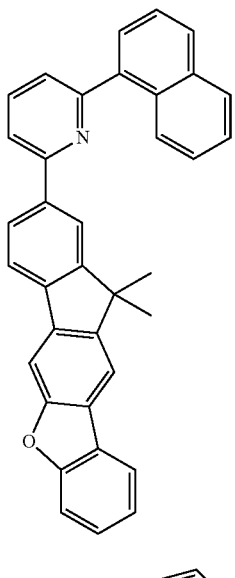
358
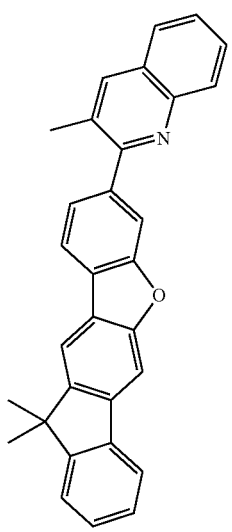
359
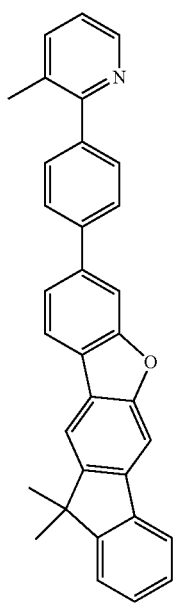
360
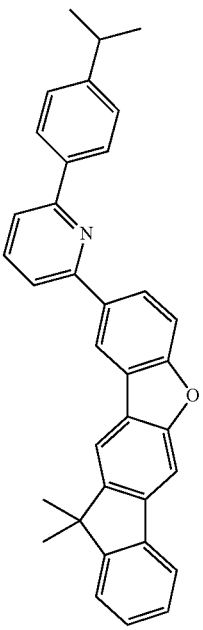
361
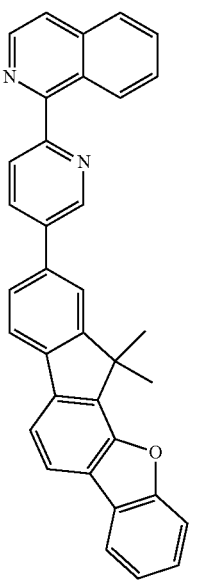

383
-continued
362
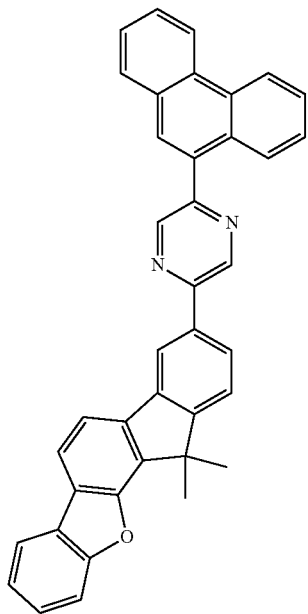
363
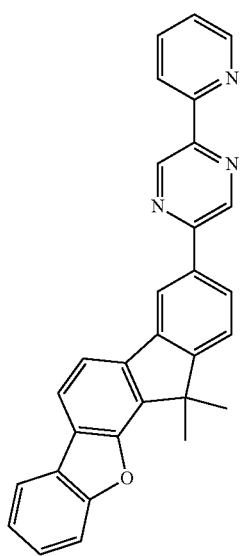
364
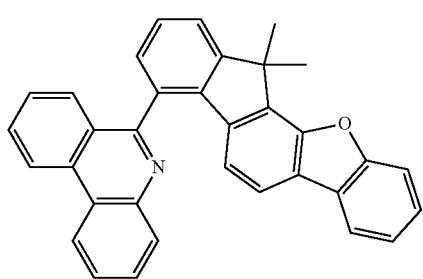
384
-continued
365
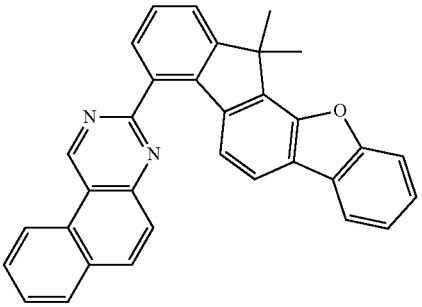
366
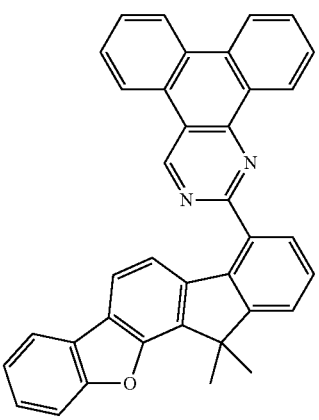
367
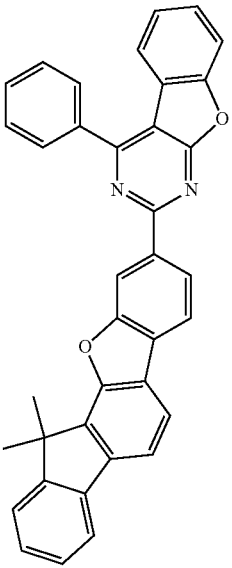

385
-continued
368
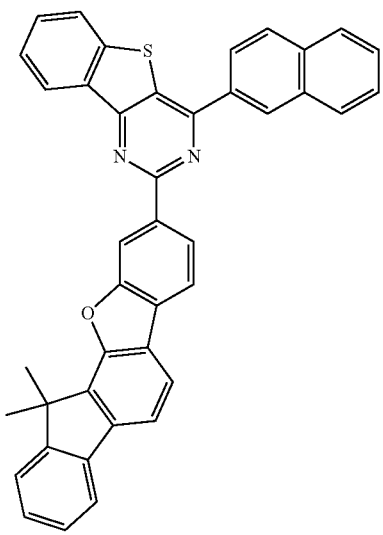
369
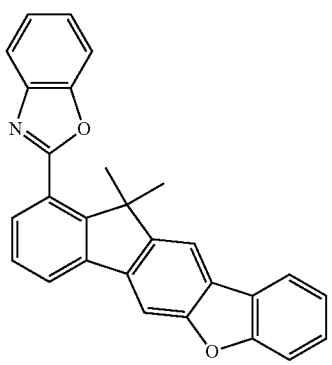
370
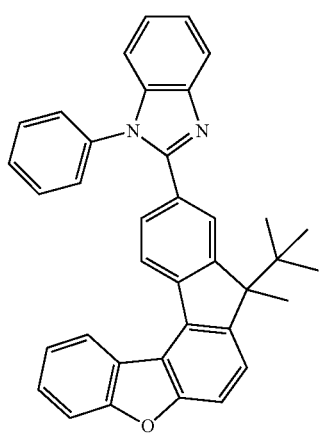
386
-continued
371
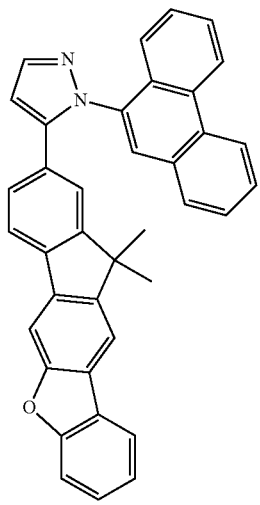
372
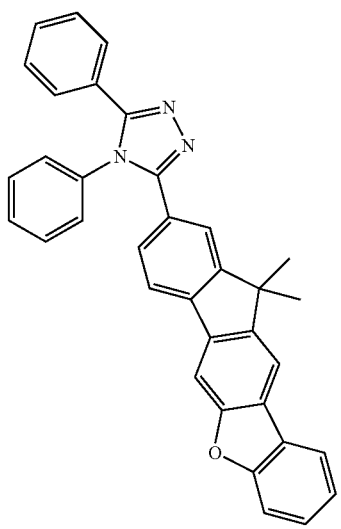
373

387
-continued
374
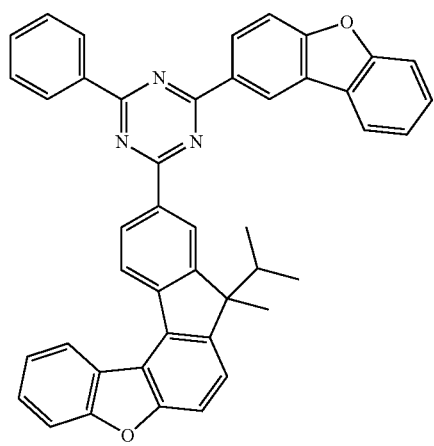
375
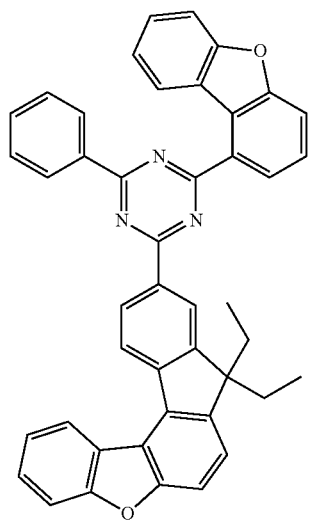
376
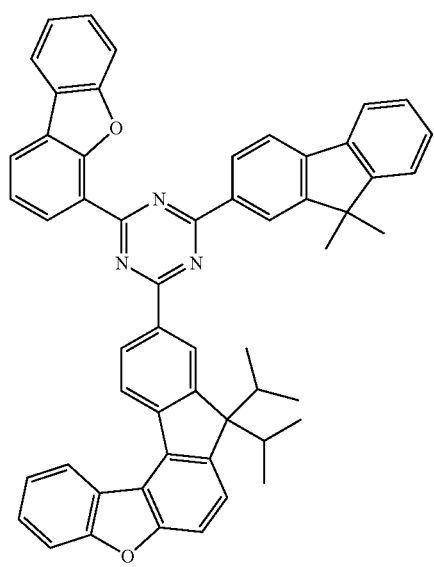
388
-continued
377
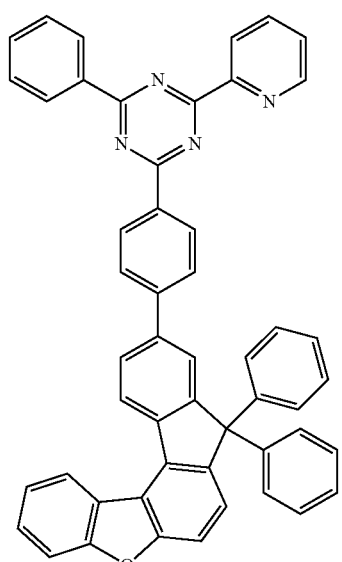
378
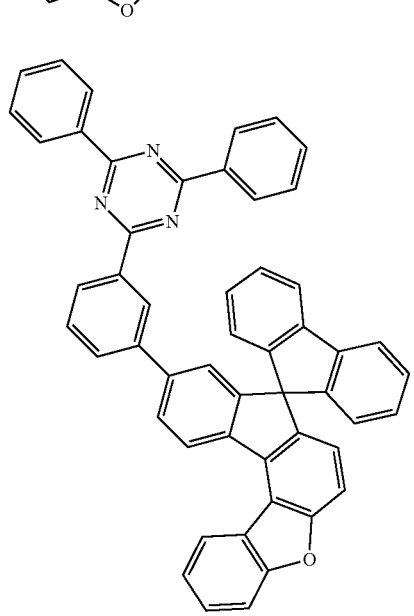
379
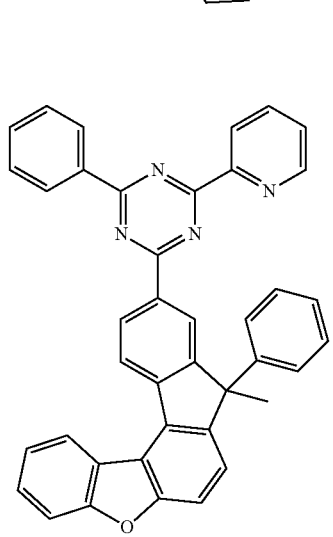

380
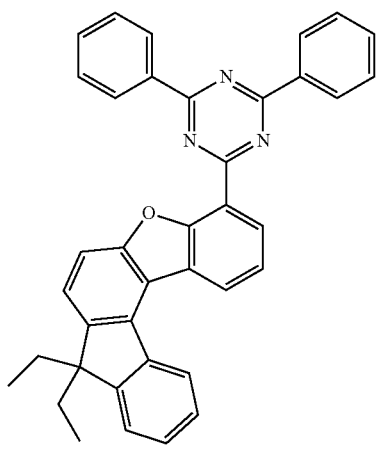
381
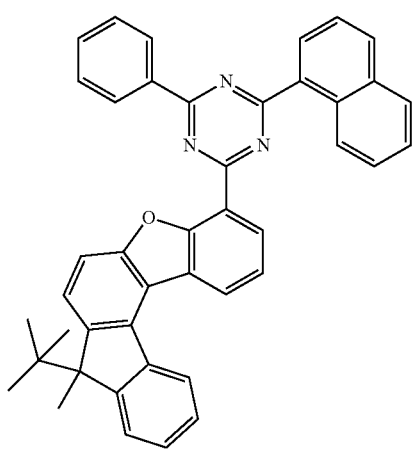
382
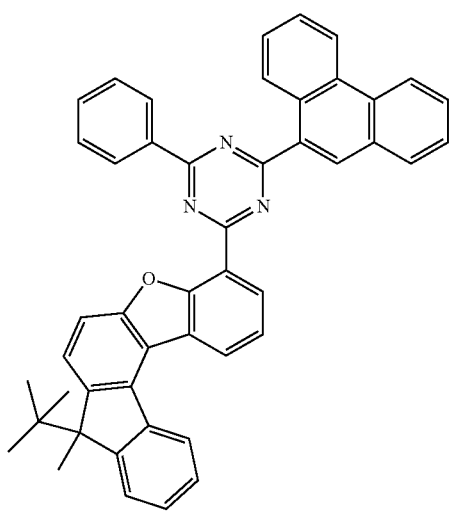
383
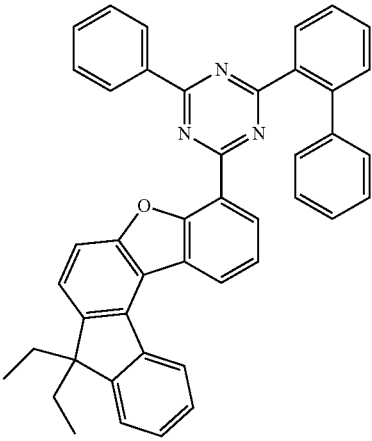
384
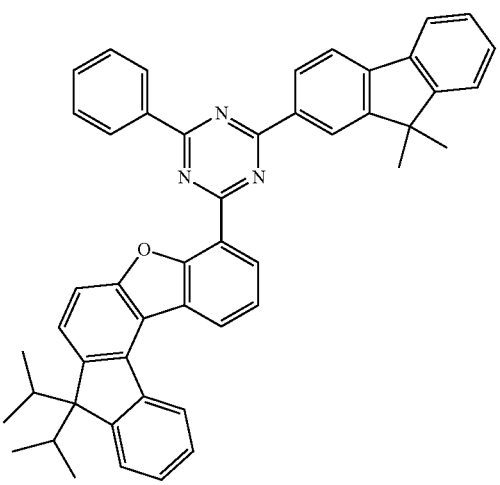
385
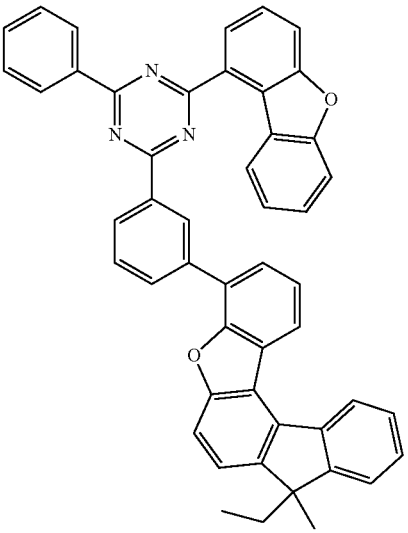

391
-continued
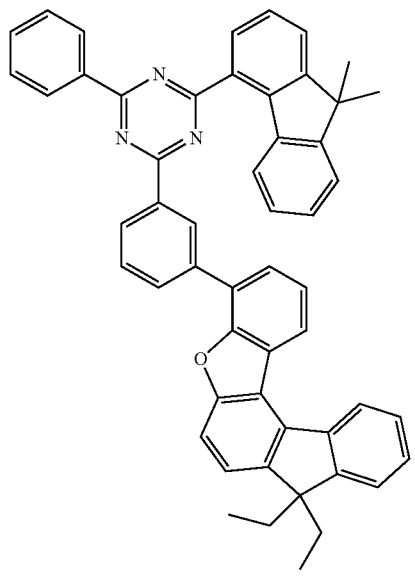
386
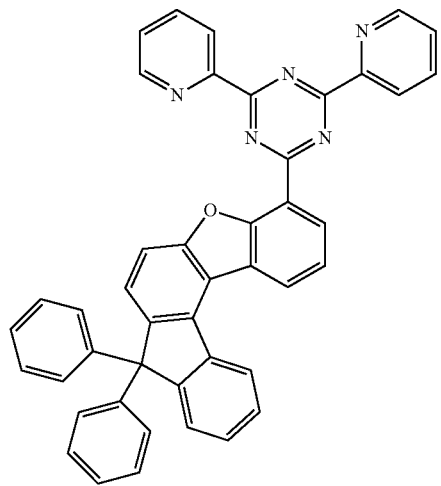
387
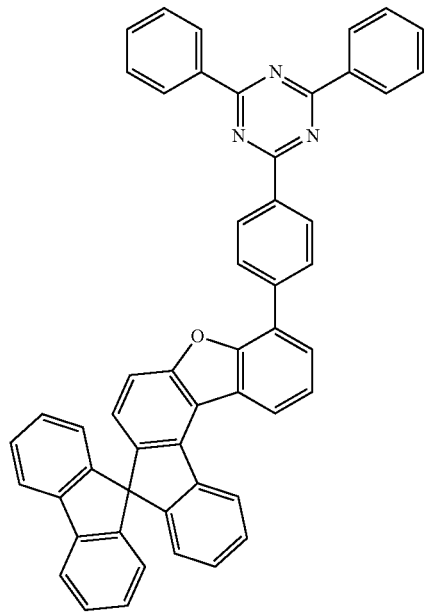
388
392
-continued
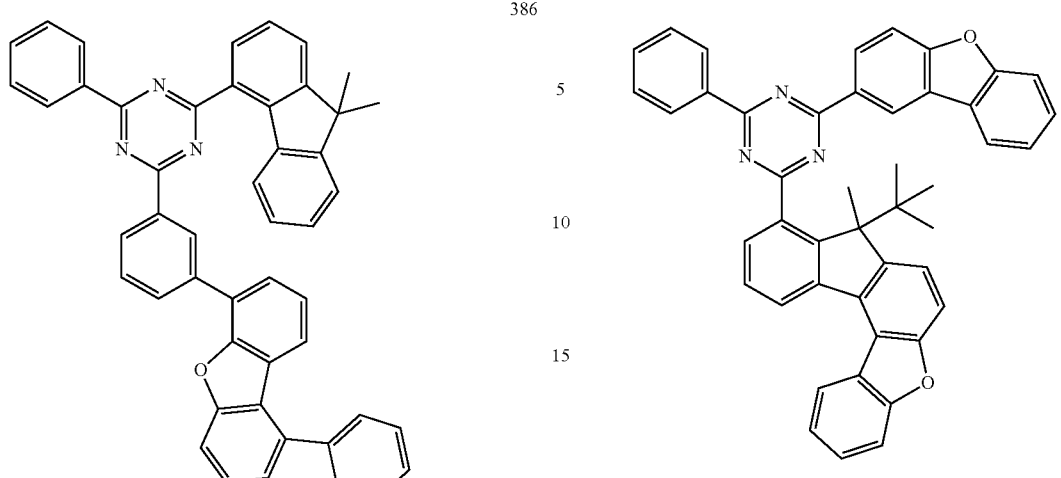
389
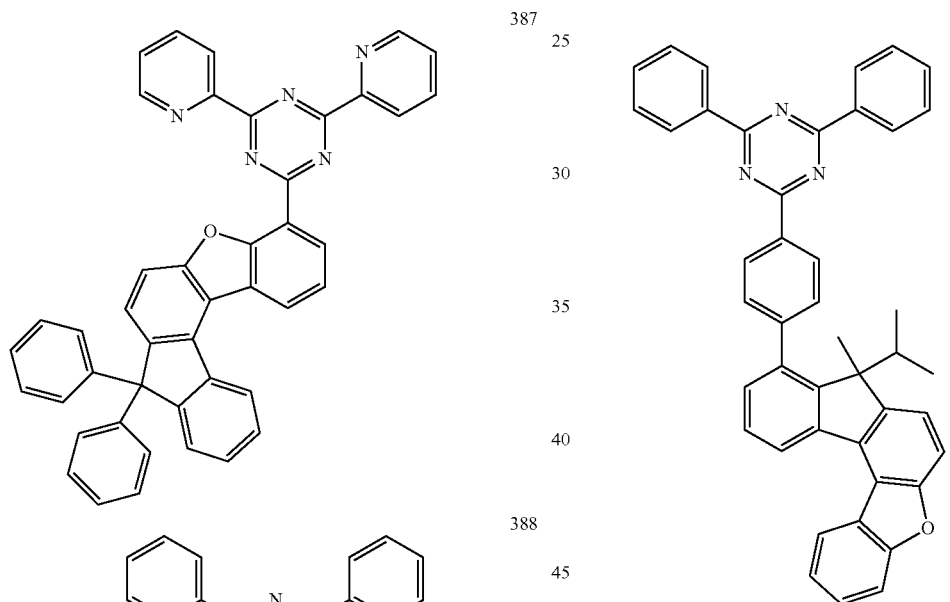
390
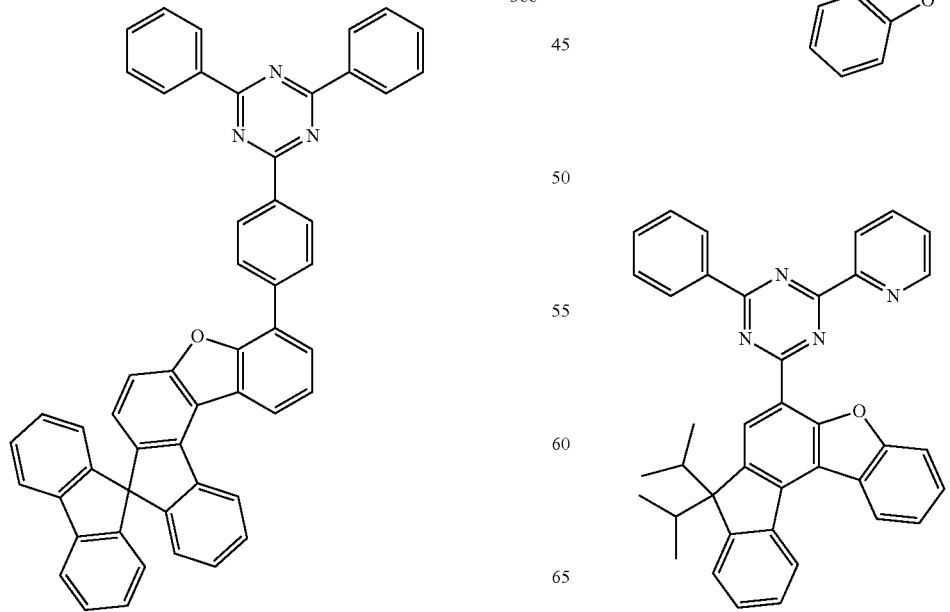
391

392
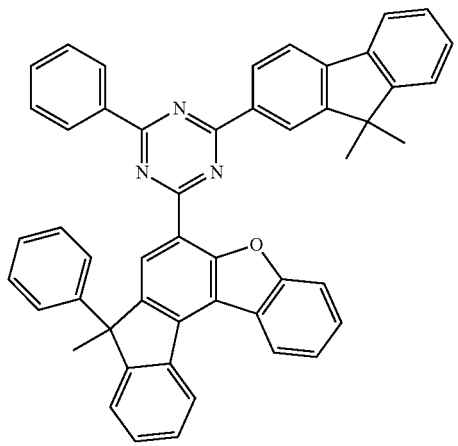
393
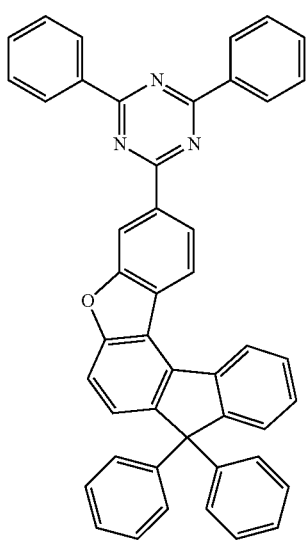
394
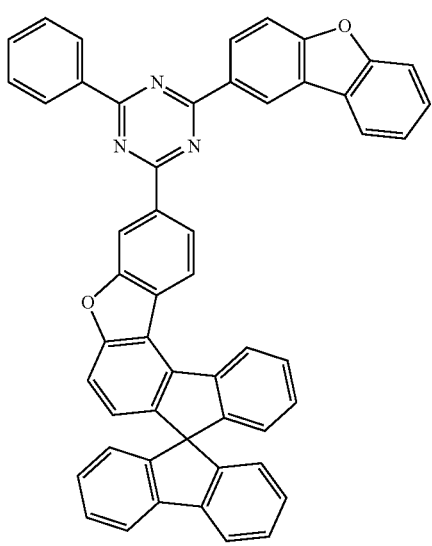
395
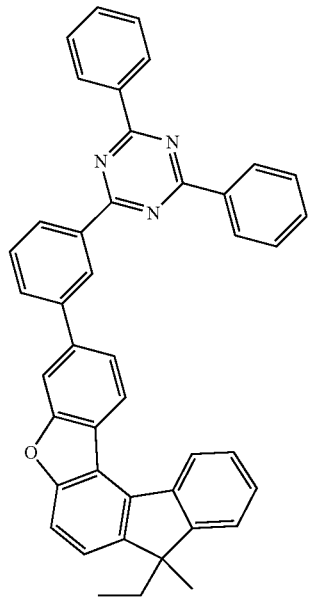
396
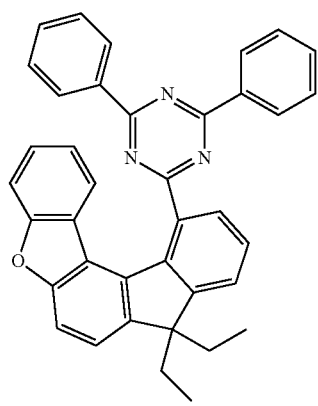
397
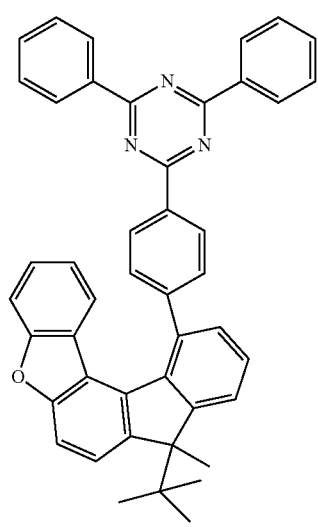

395
-continued
398
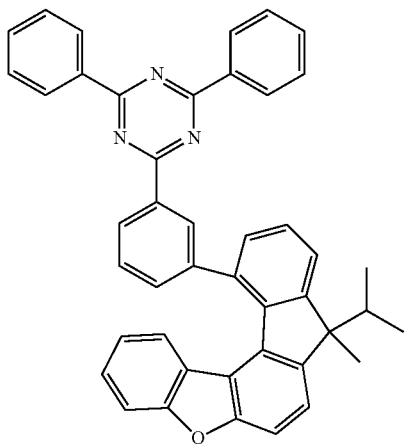
399
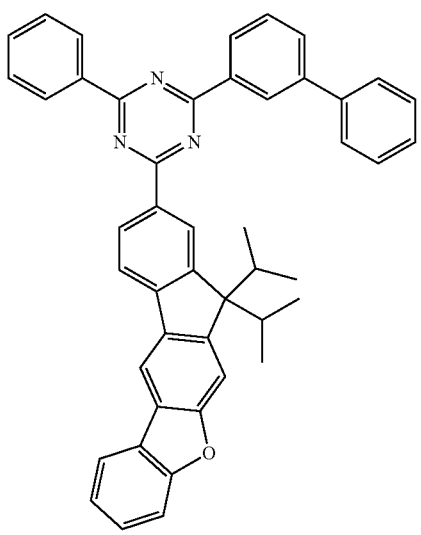
400
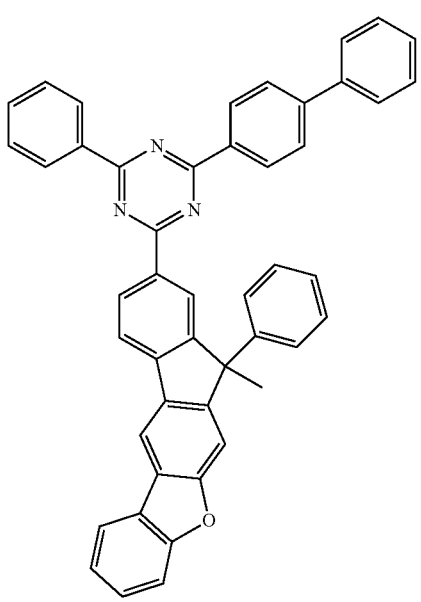
396
-continued
401
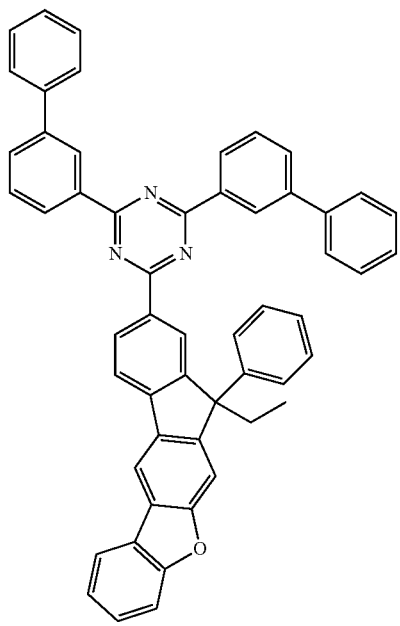
402
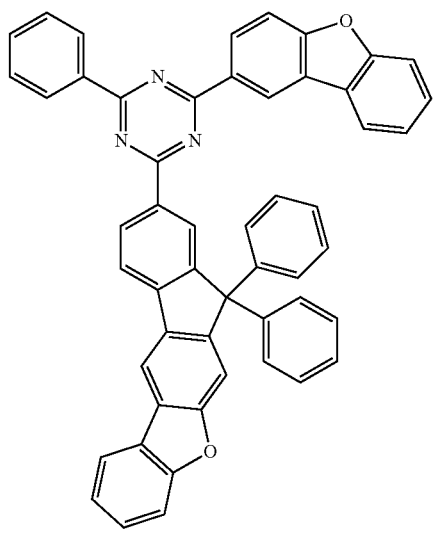

397
-continued
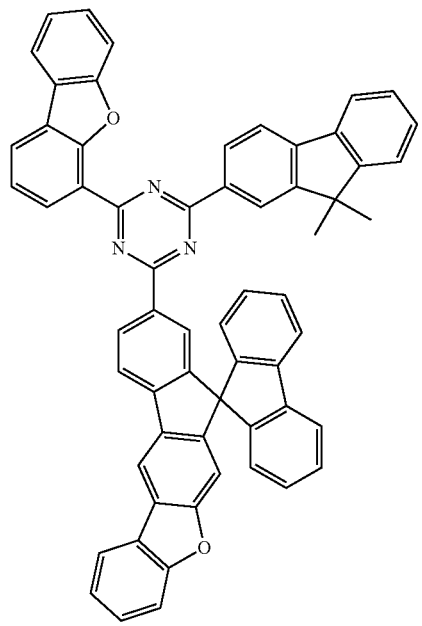
403
398
-continued
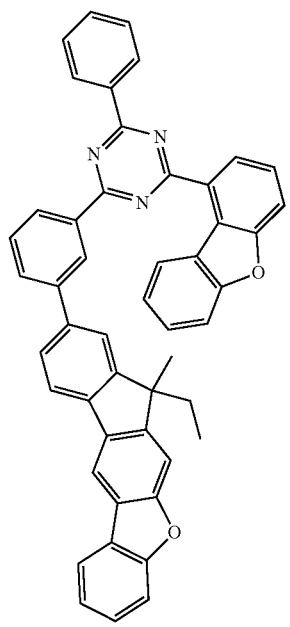
405
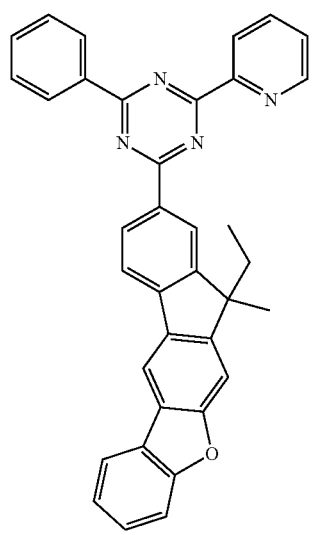
404
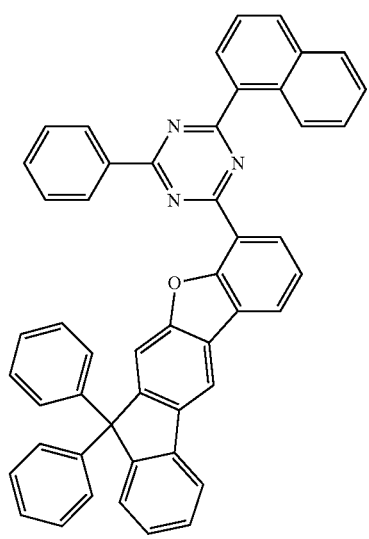
406

399
-continued
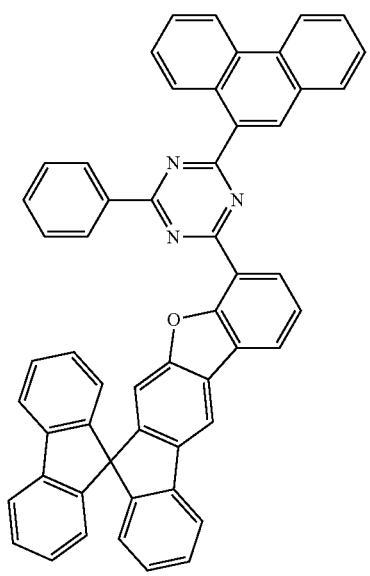
400
-continued
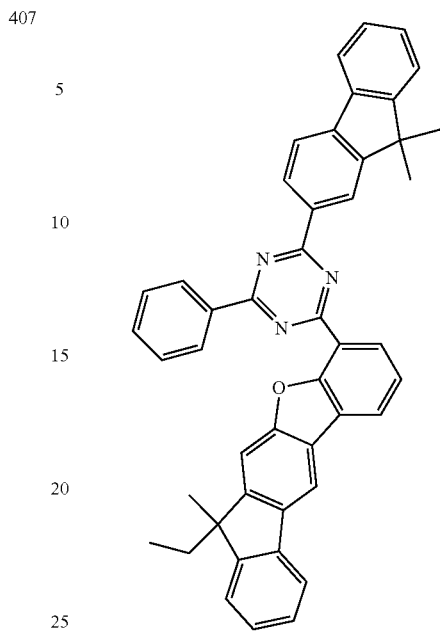
407
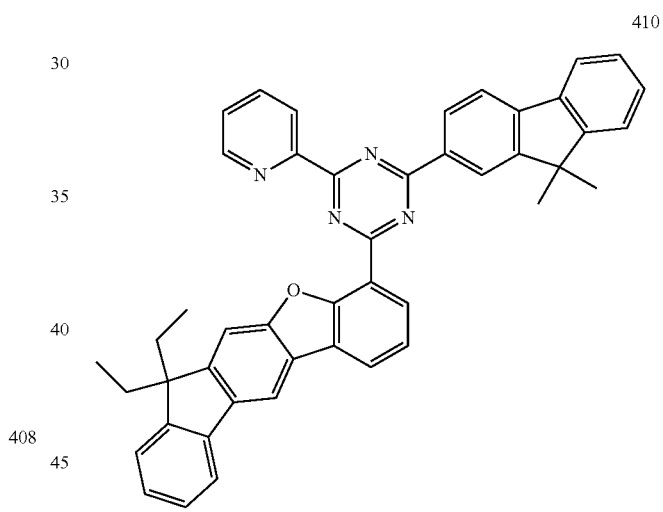
408
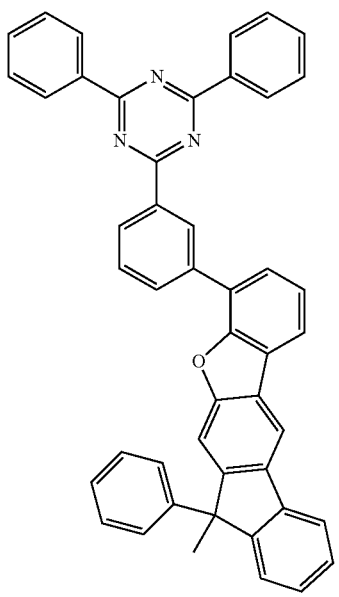
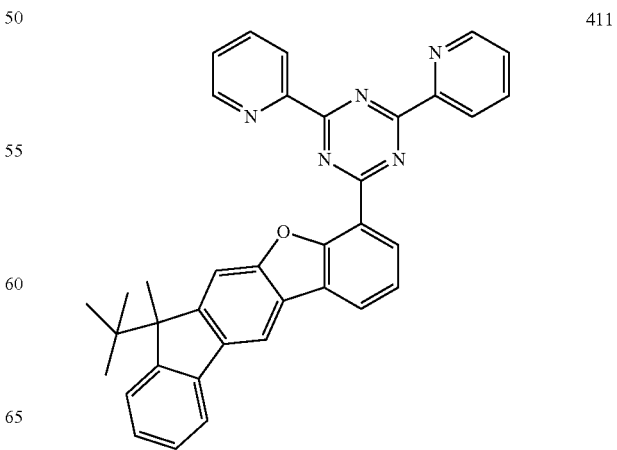
409
410
411

-continued
412
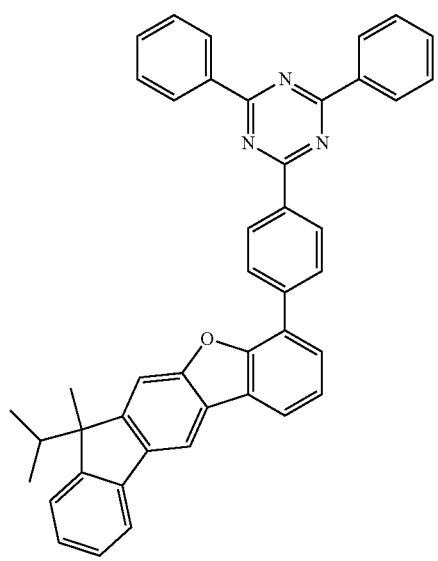
413
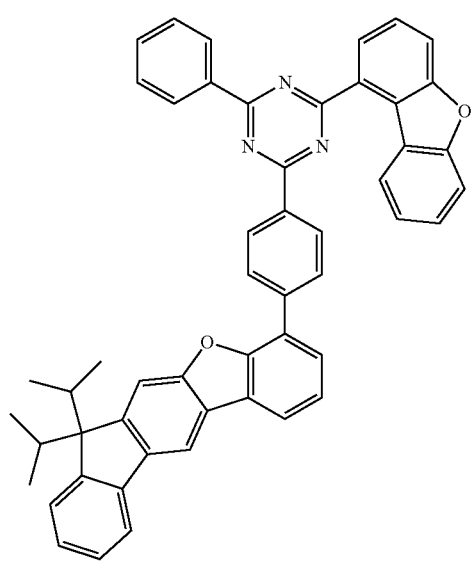
414
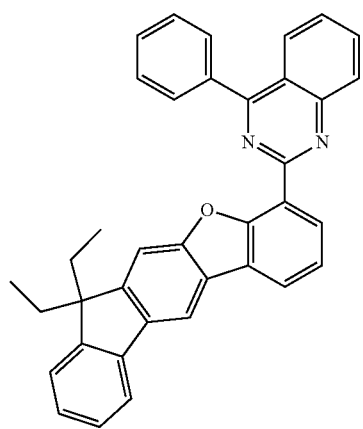
-continued
415
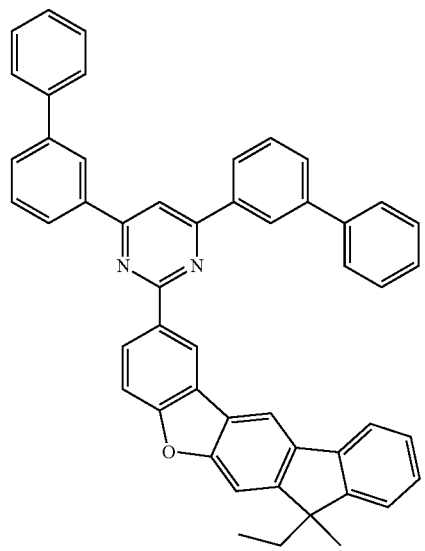
416
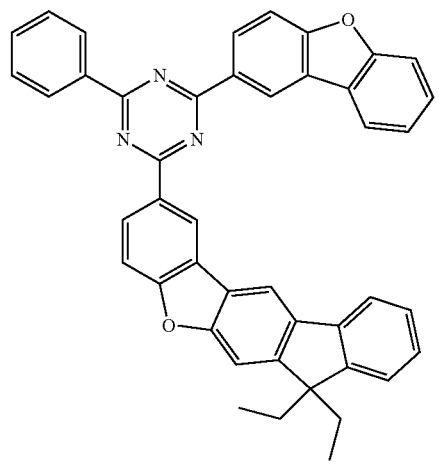
417
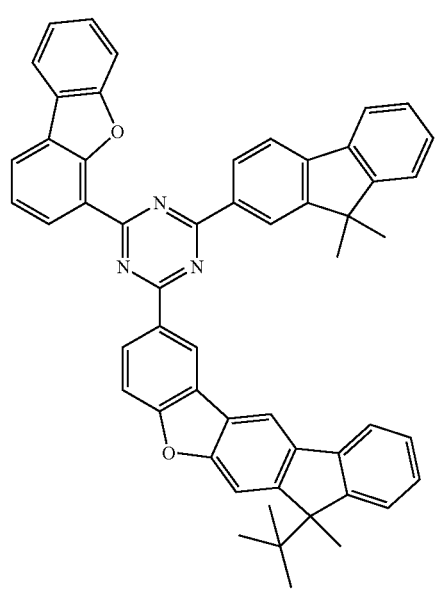

403
-continued
418
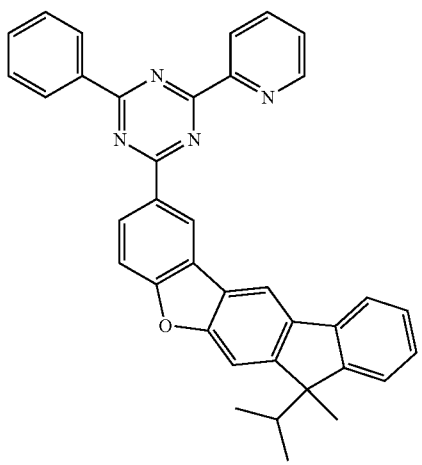
419
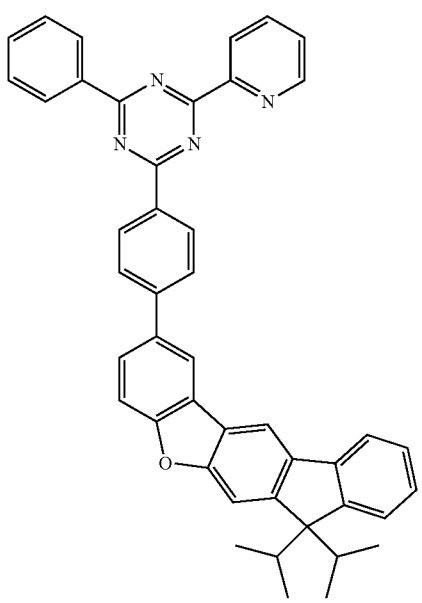
404
-continued
420
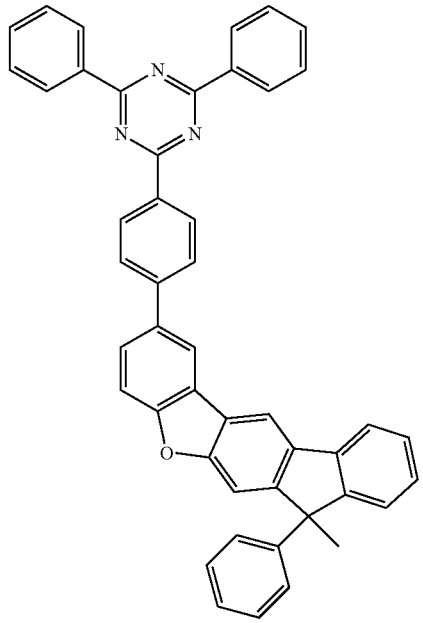
421
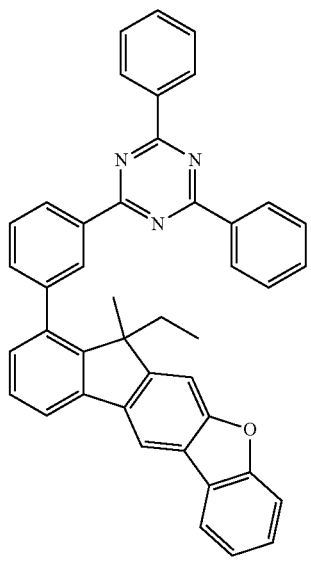
422
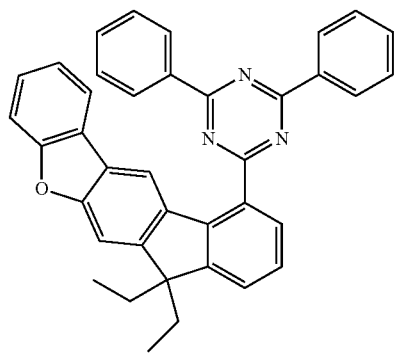

405
-continued
423
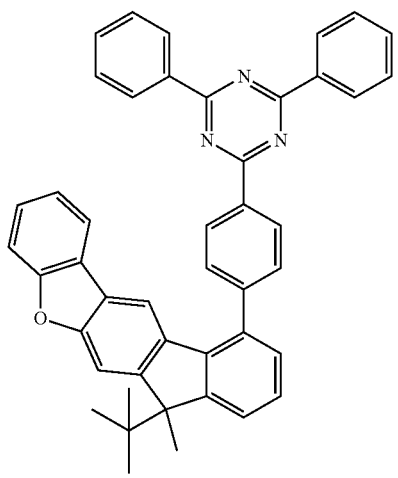
424
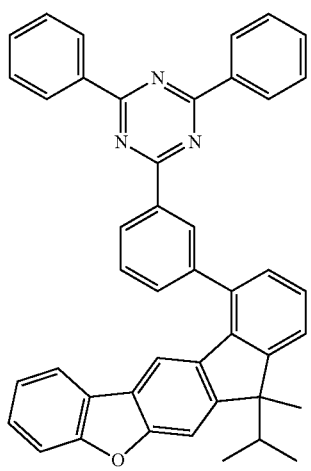
425
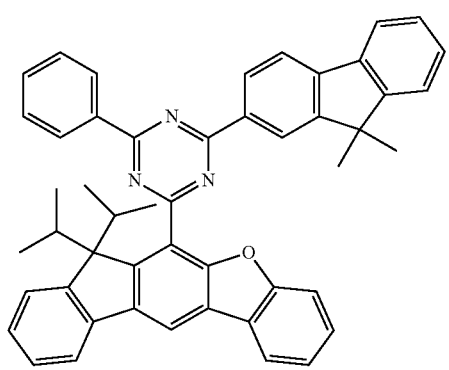
406
-continued
426
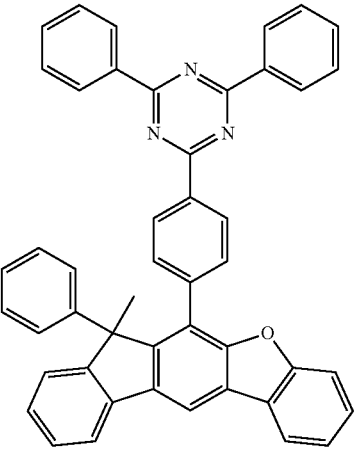
427
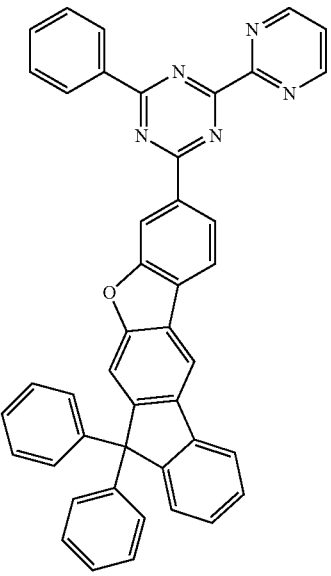
428
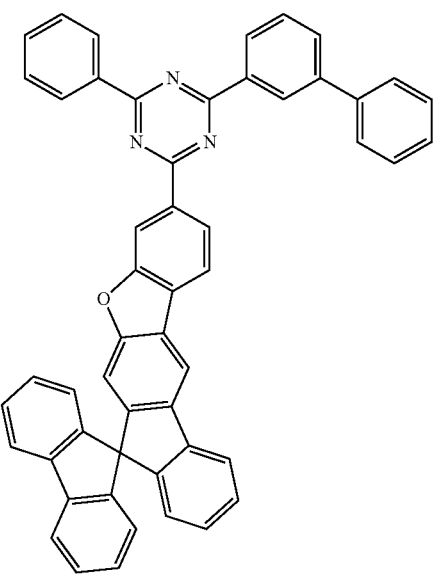

407
-continued
429
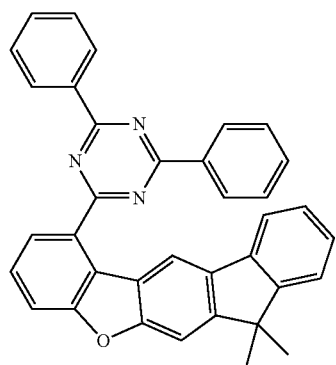
430
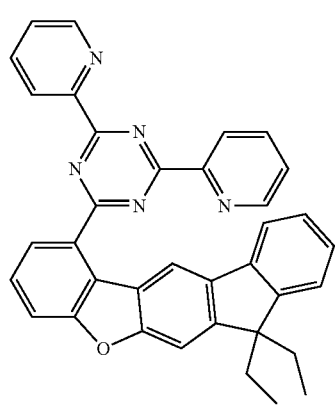
431
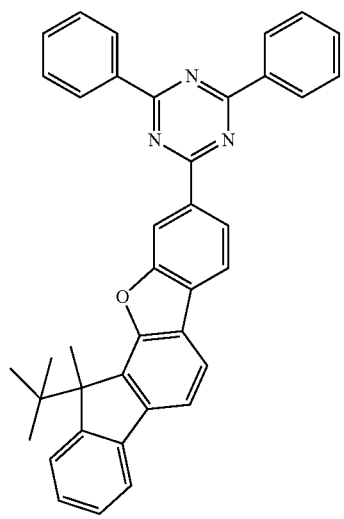
408
-continued
432
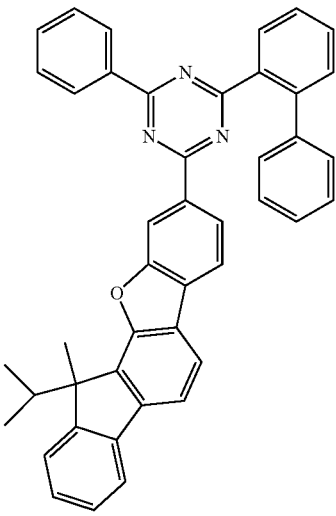
433
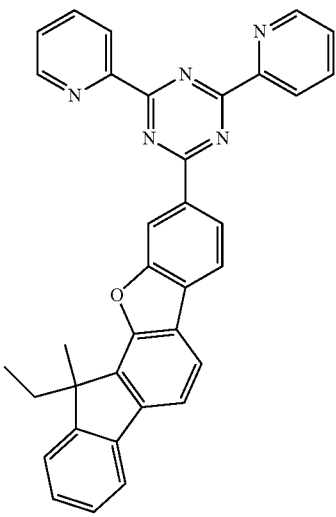
434
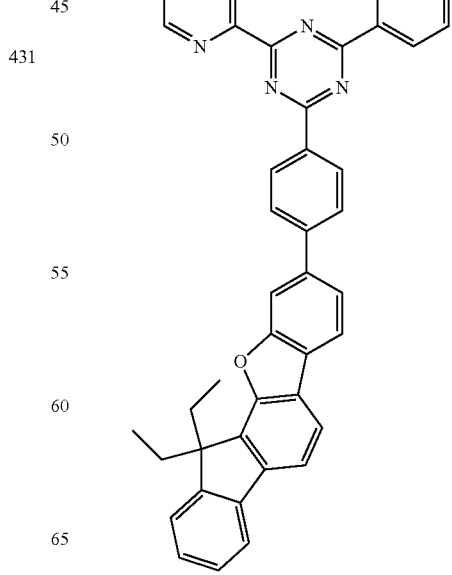

409
-continued
435
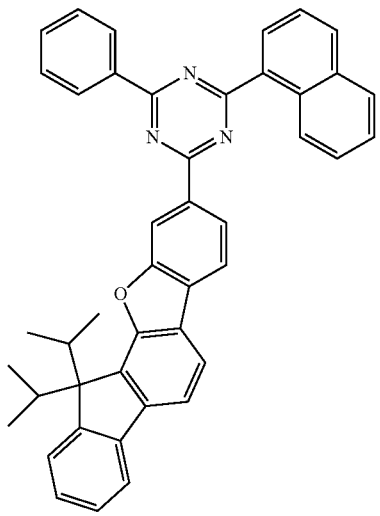
436
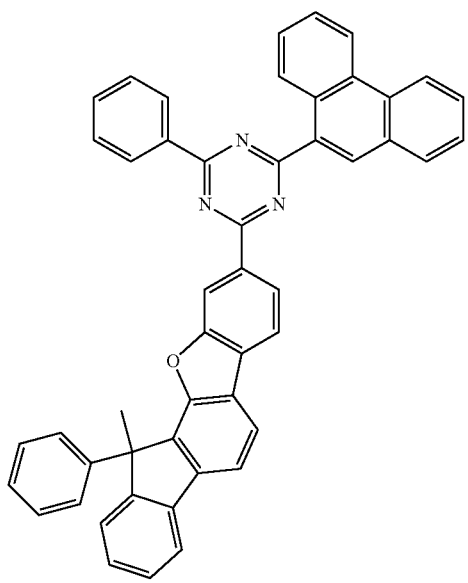
437
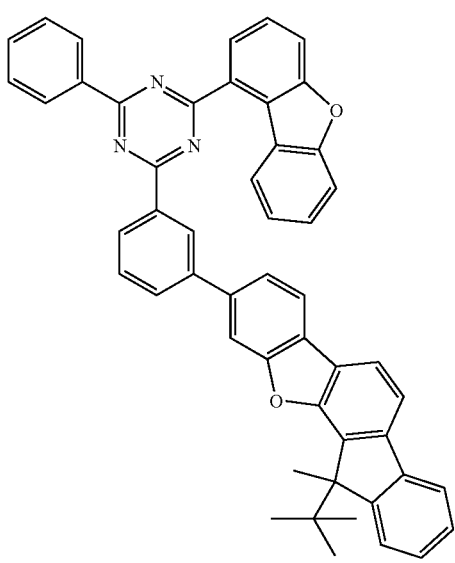
410
-continued
438
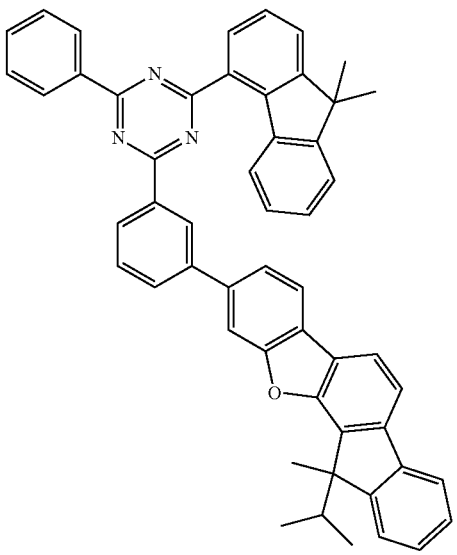
439
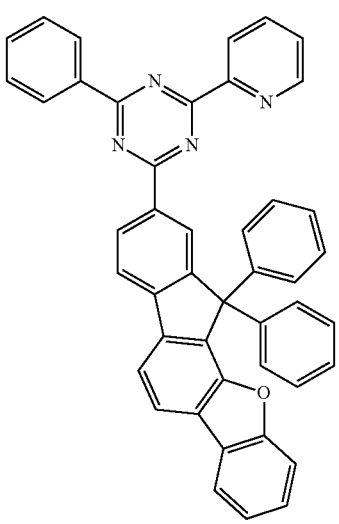
440
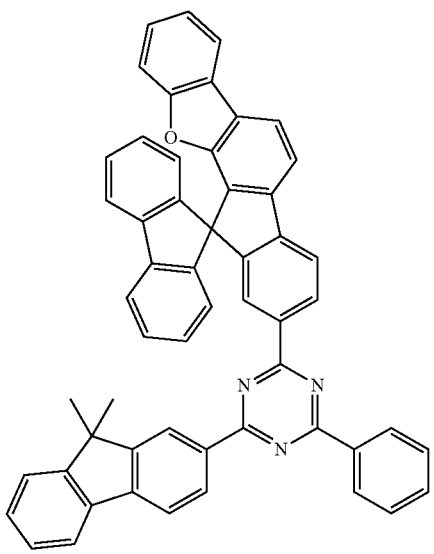

411
-continued
441
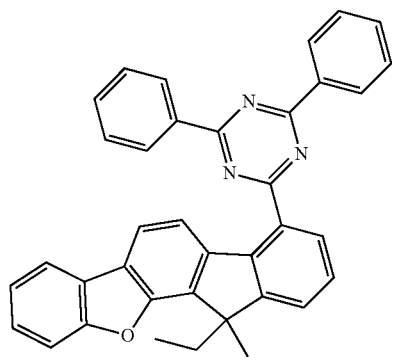
442
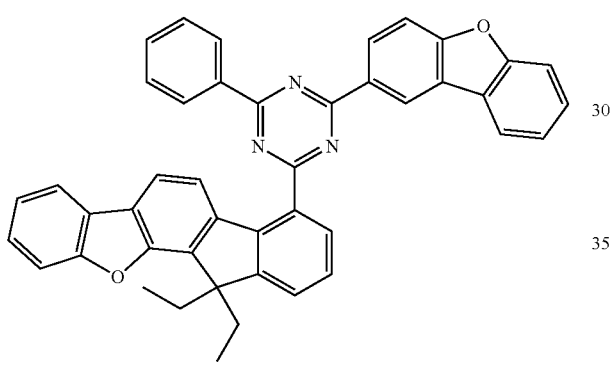
443
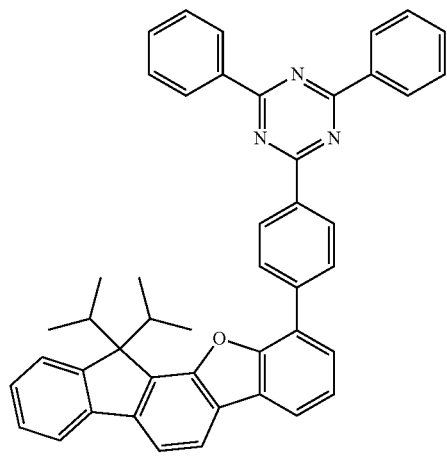
412
-continued
444
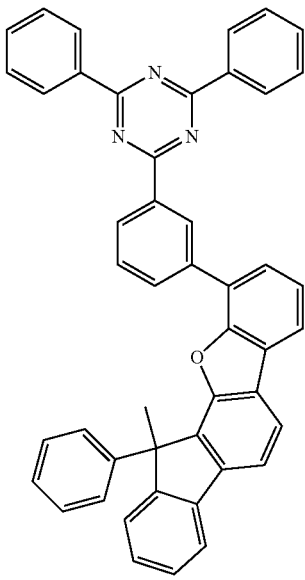
445
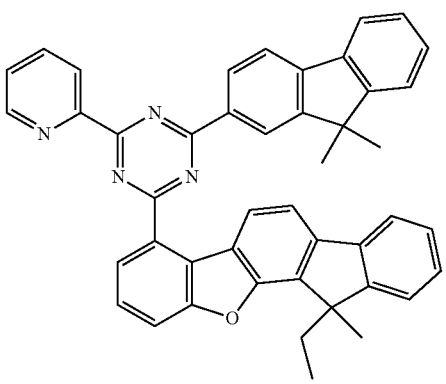
446
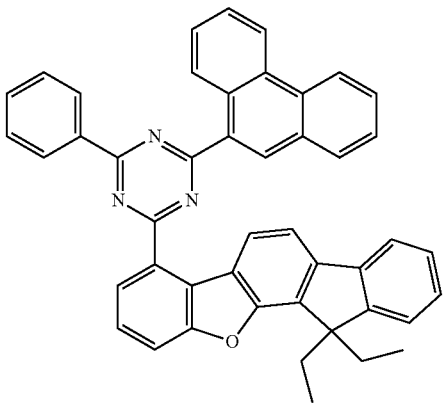

413
-continued
447
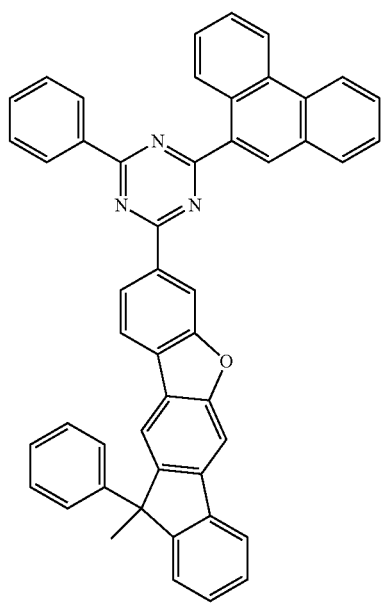
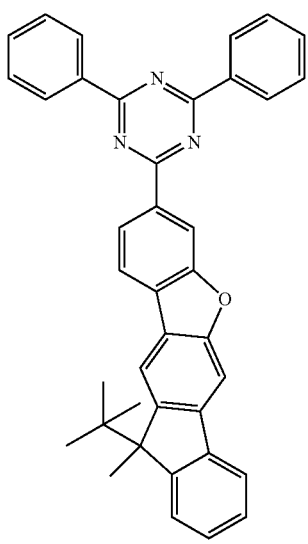
448
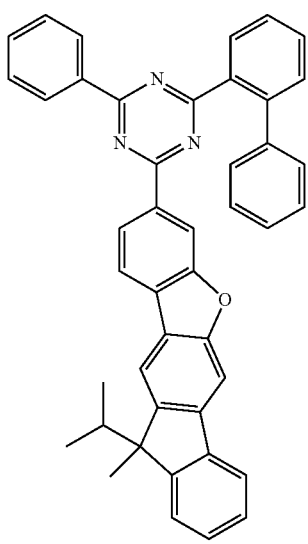
414
-continued
450
449
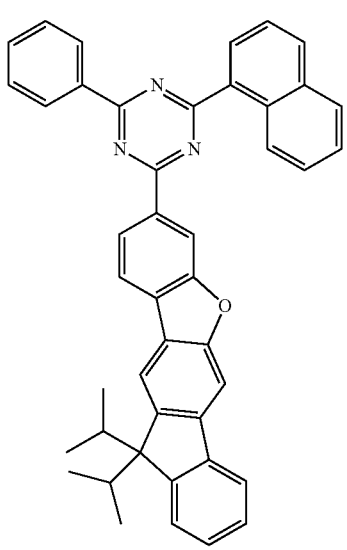
451
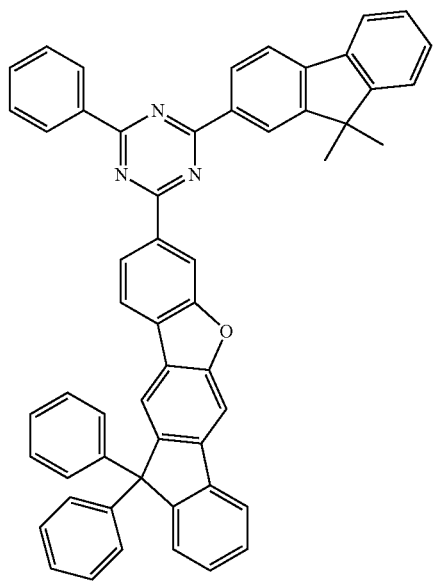

415
-continued
452
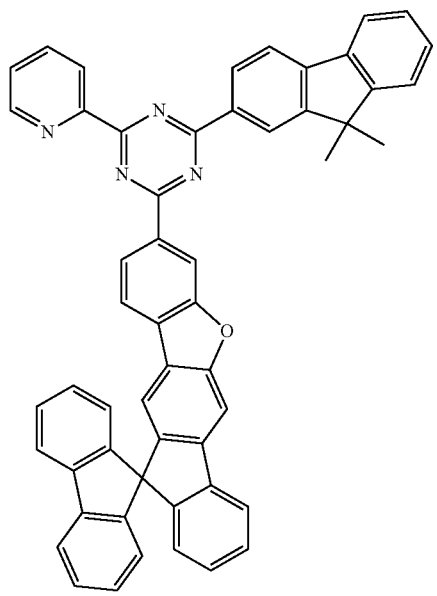
416
-continued
454
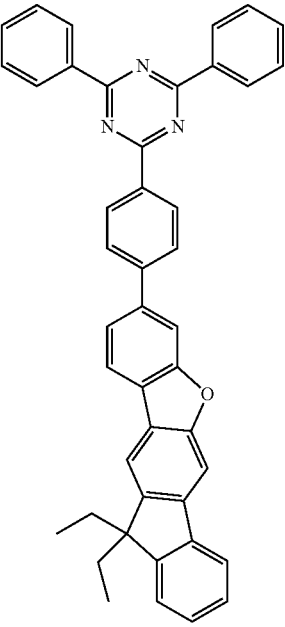
453
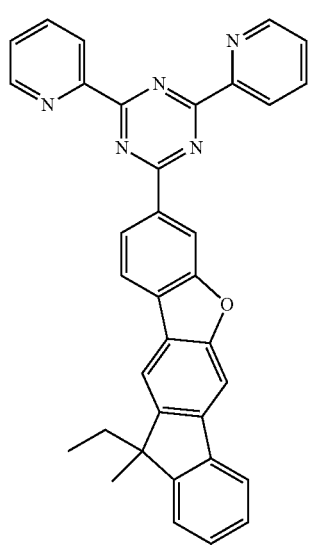
455
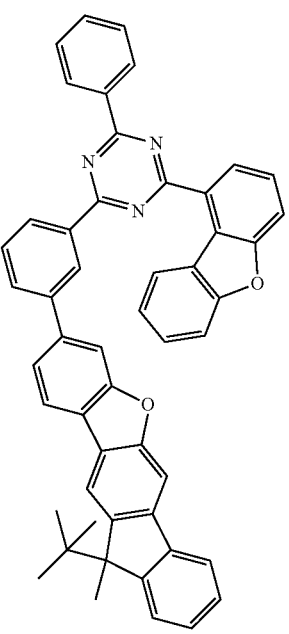

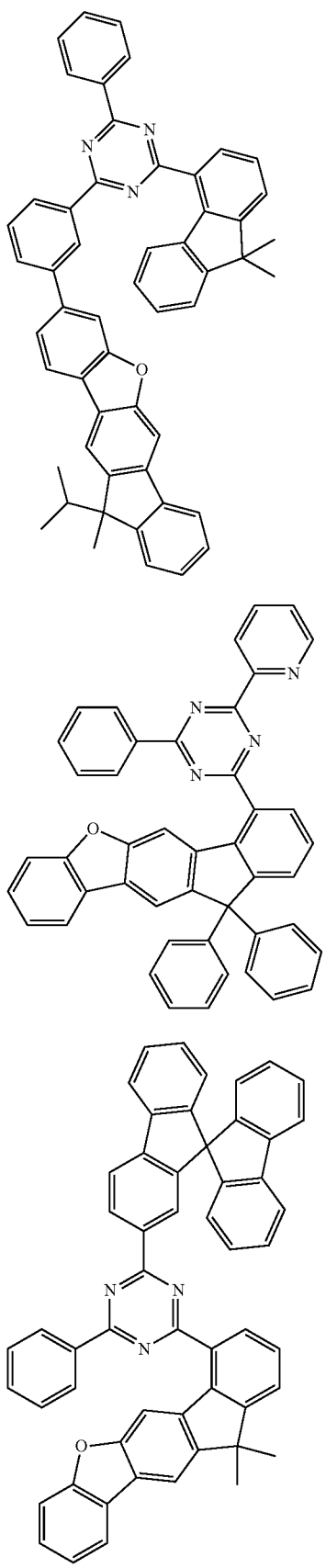
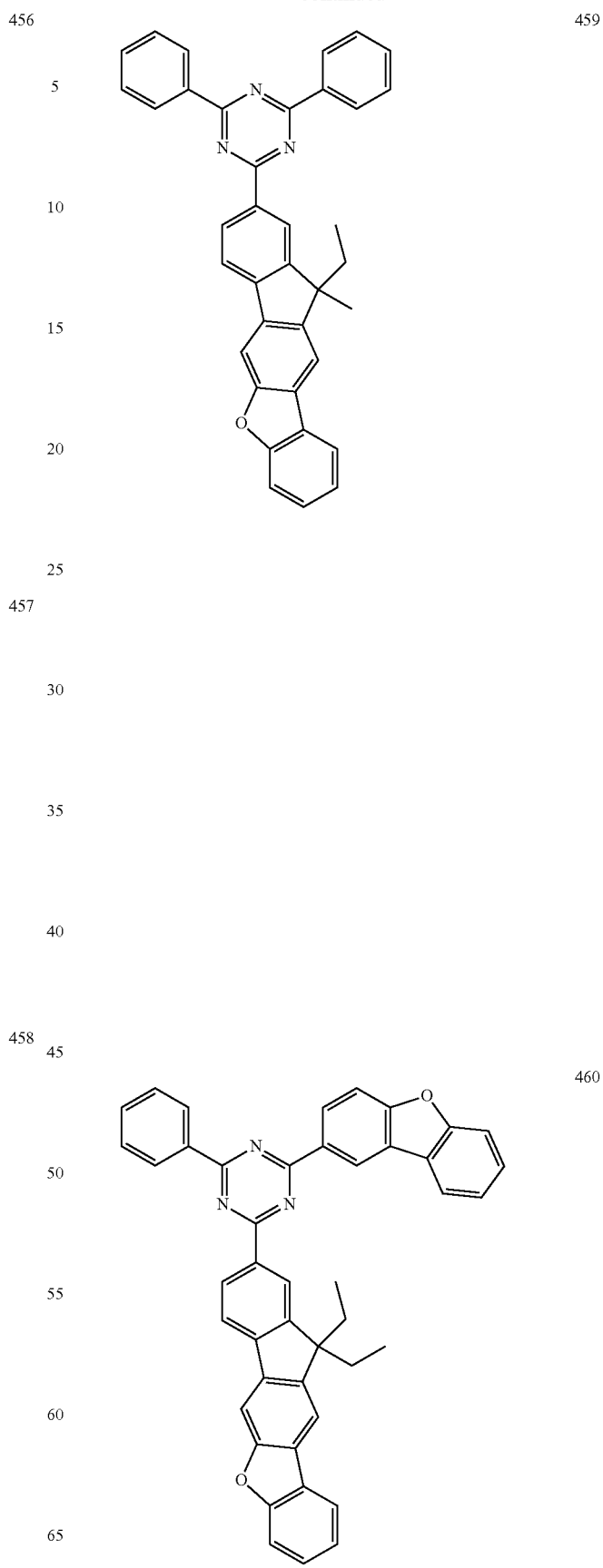

419
-continued
420
-continued
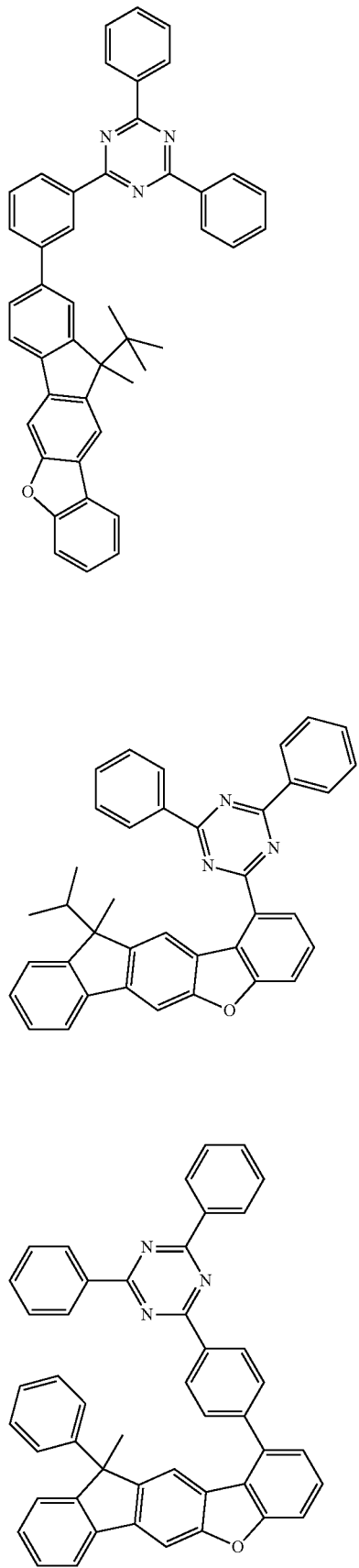
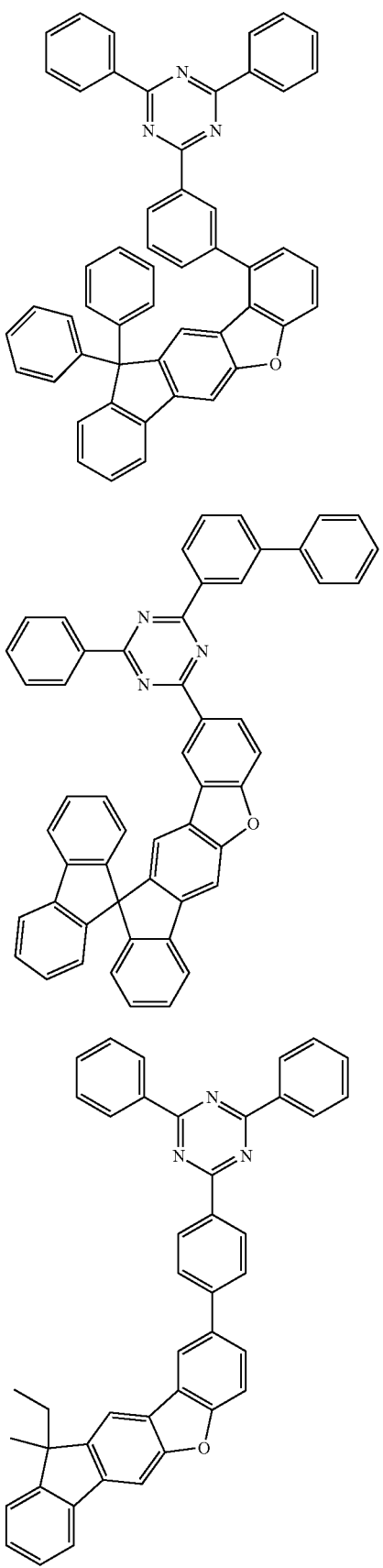

421
-continued
467
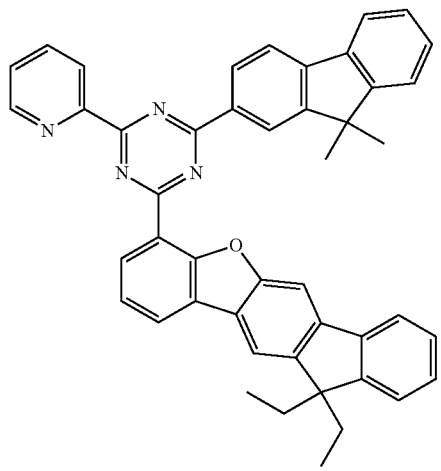
468
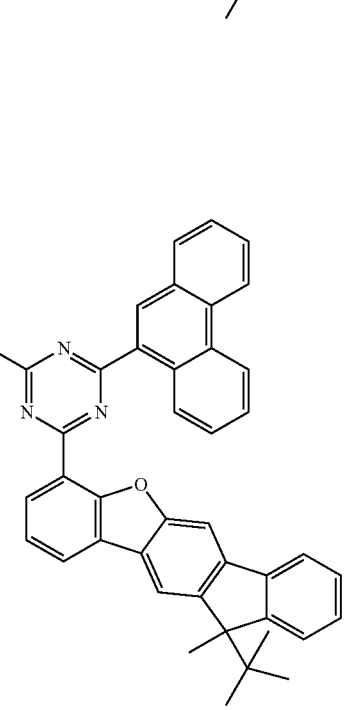
469
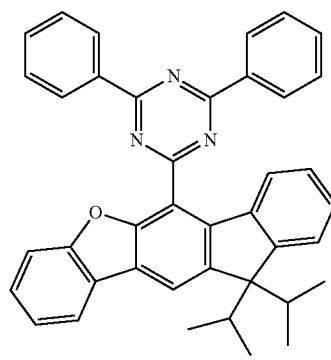
422
-continued
470
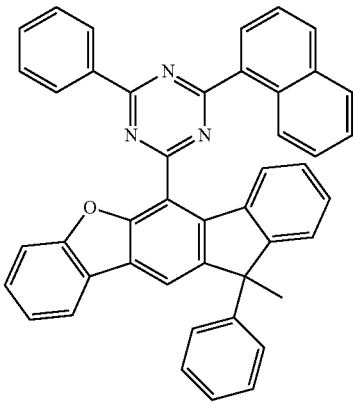
471
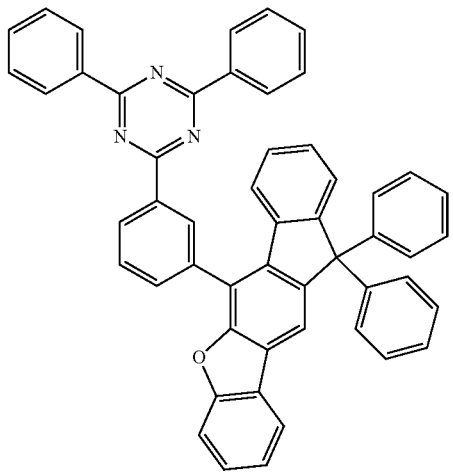
472
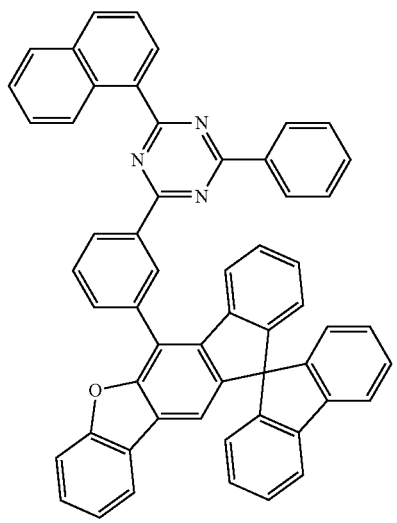

423
-continued
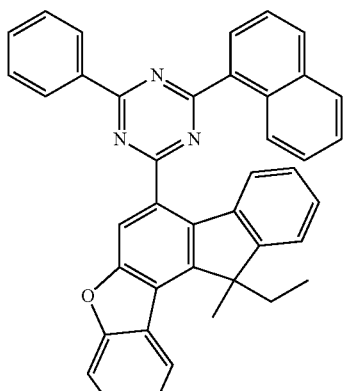
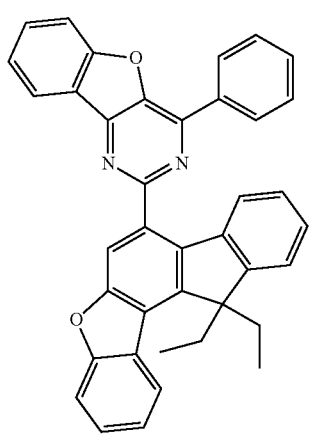
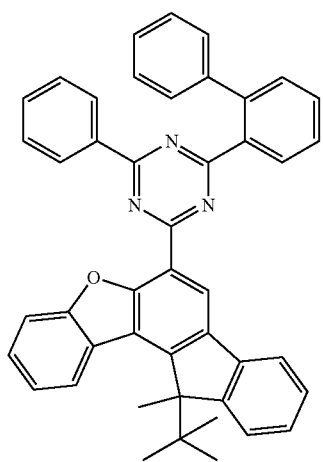
424
-continued
473
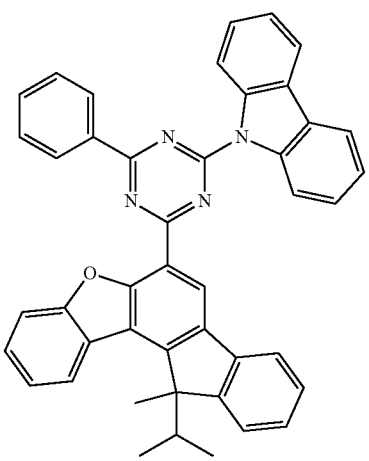
474
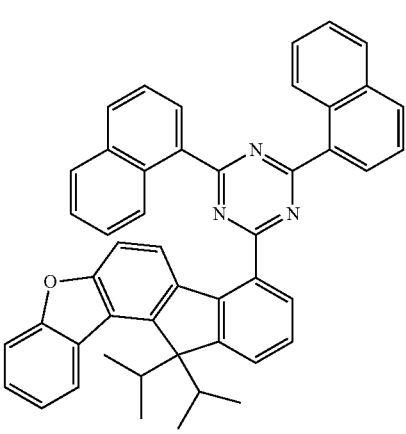
475
476
477
478
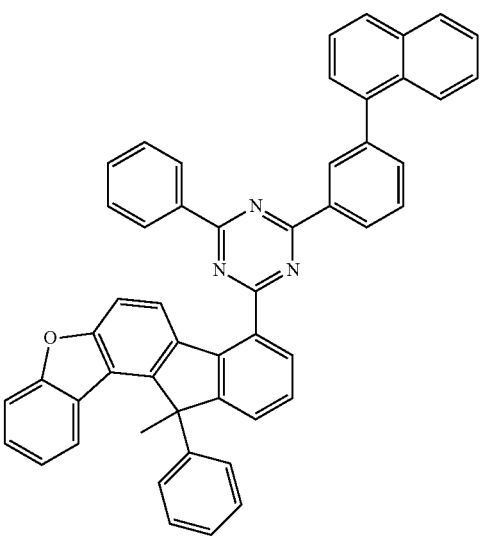

479
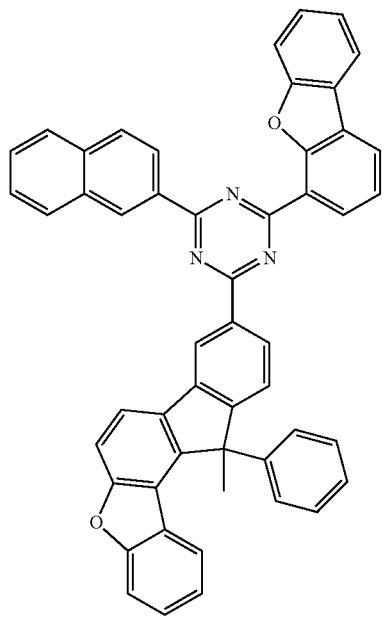
480
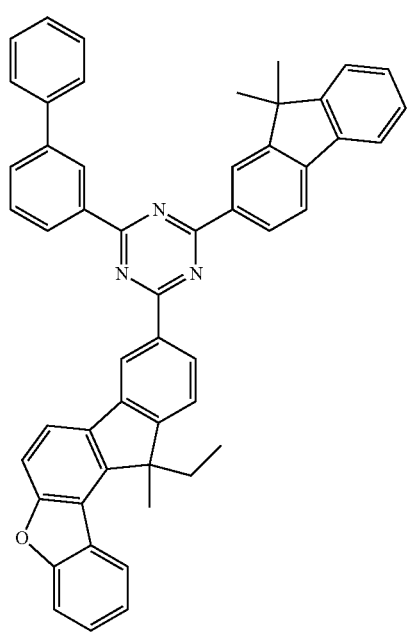
481
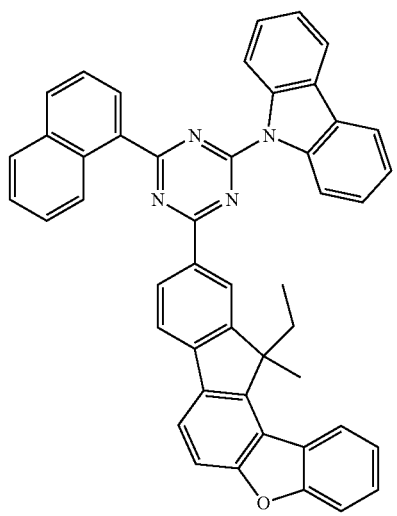
482
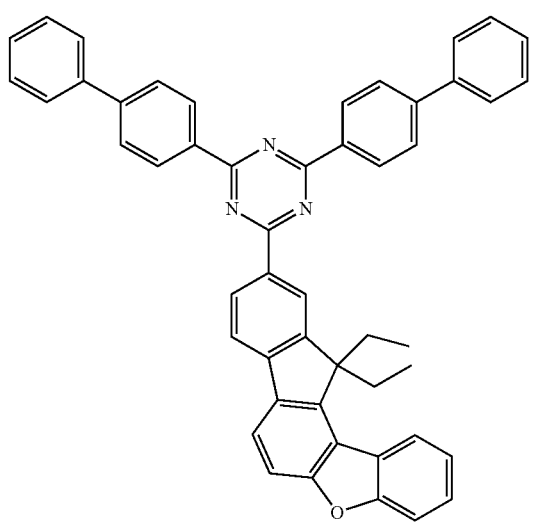
483
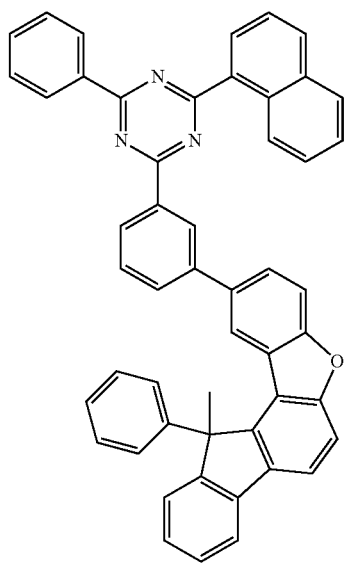

484
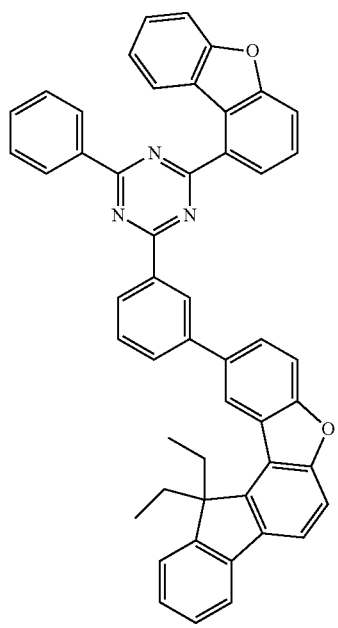
485
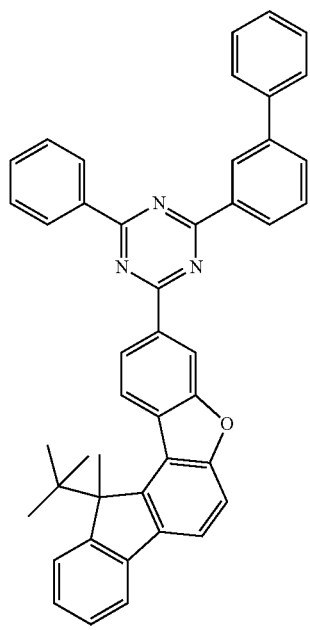
486
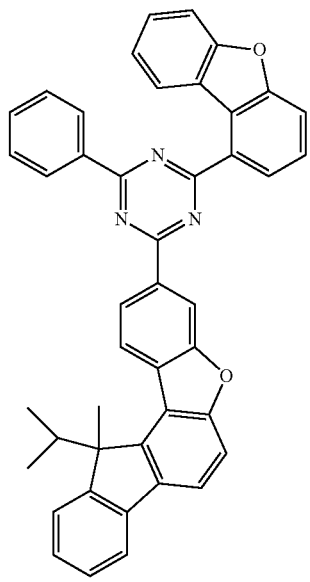
487
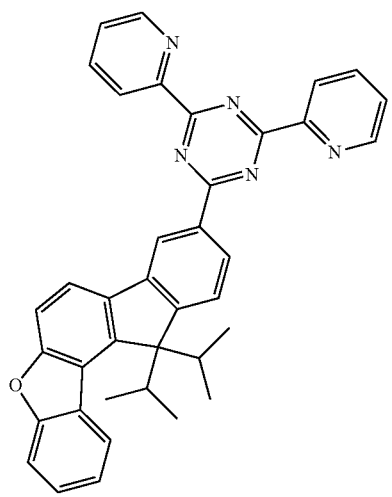
488
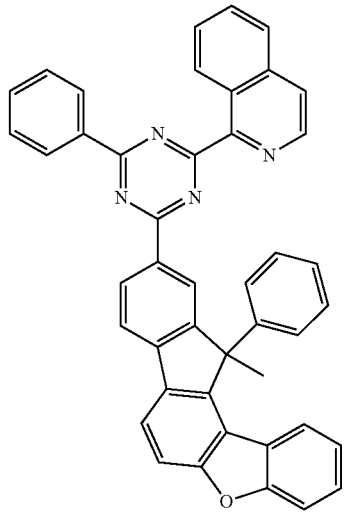

429
-continued
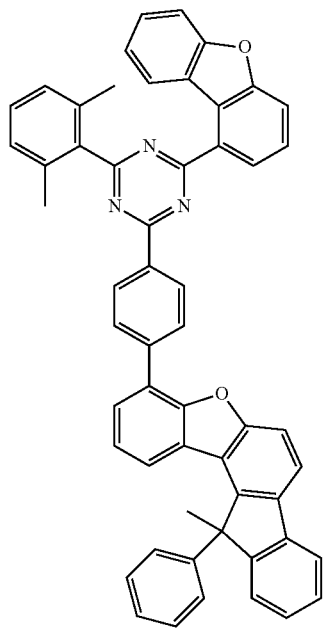
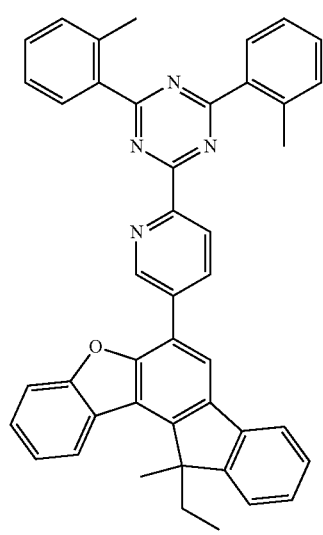
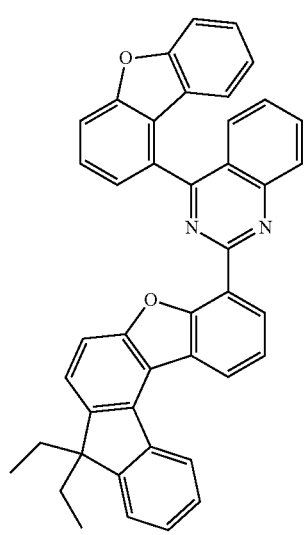
430
-continued
489
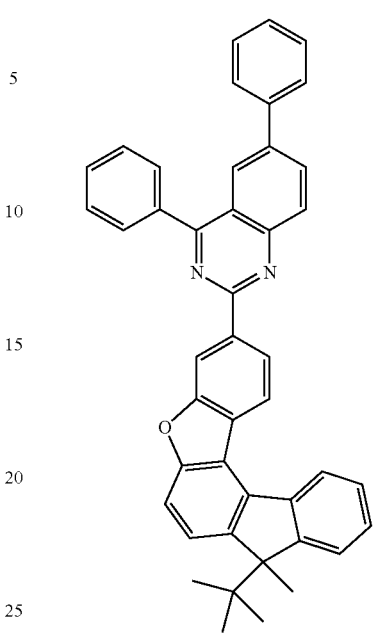
490
493
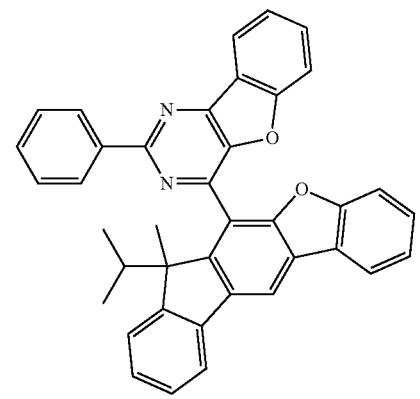
491
494
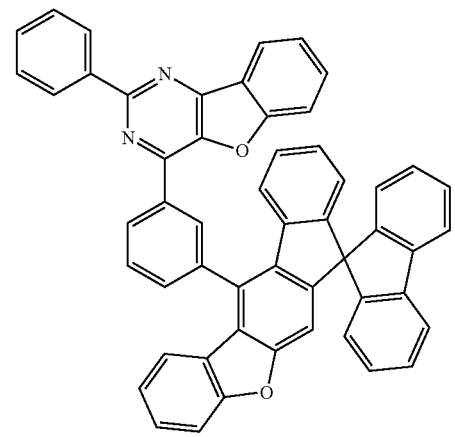

431
-continued
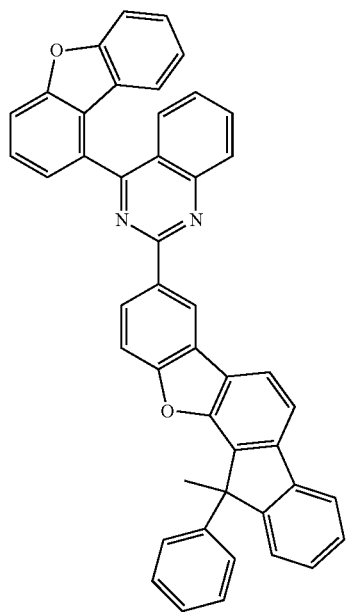
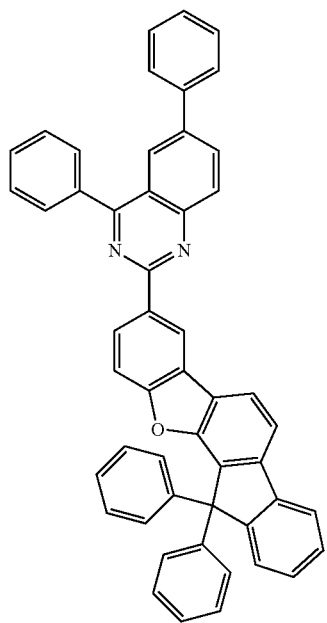
432
-continued
495
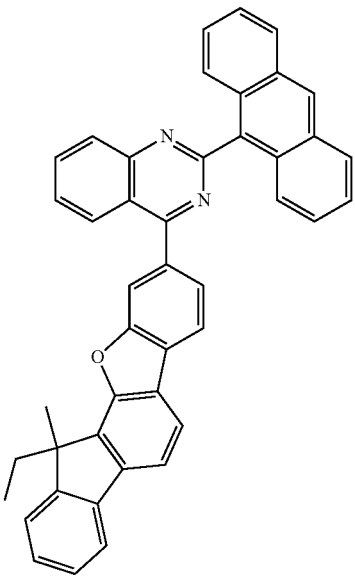
498
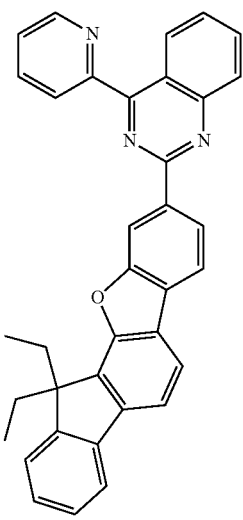
497
499
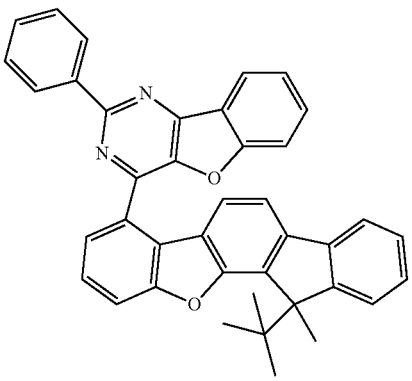

433
-continued
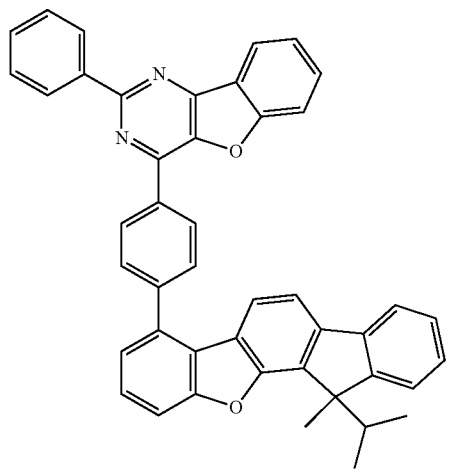
500
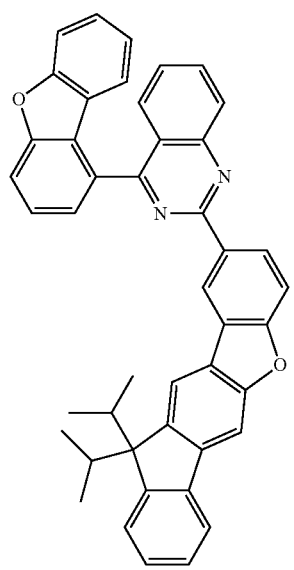
501
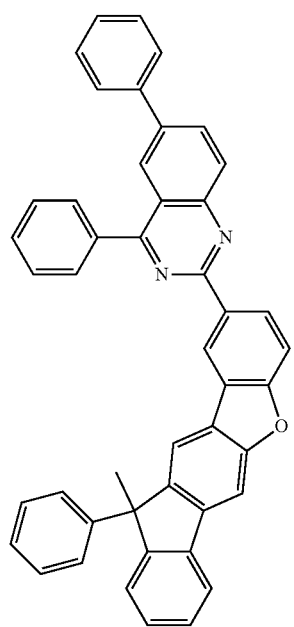
502
434
-continued
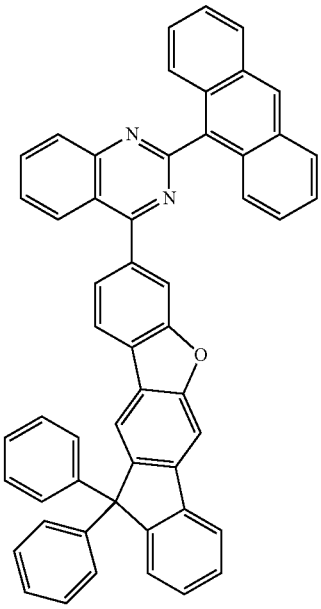
503
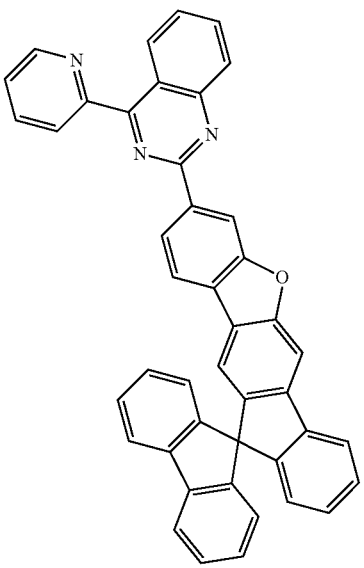
504

435
-continued
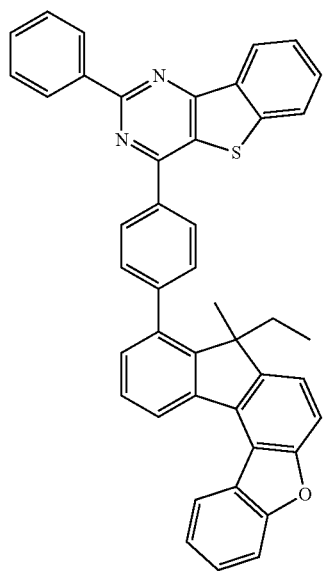
505
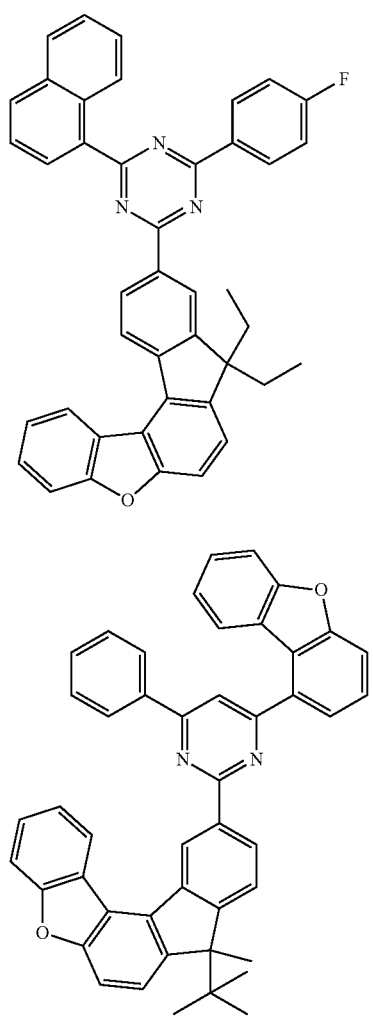
506
507
436
-continued
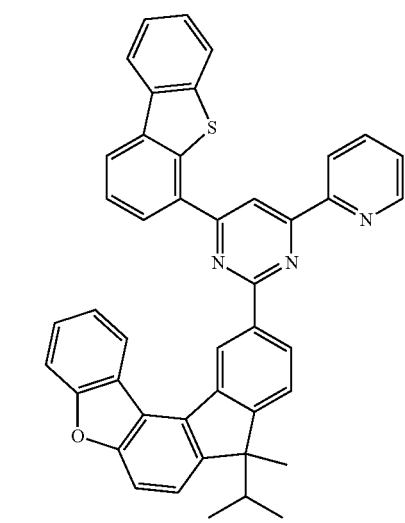
508
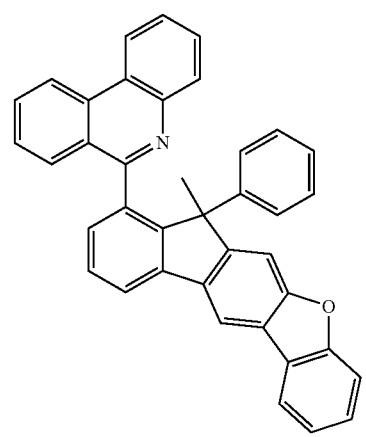
509
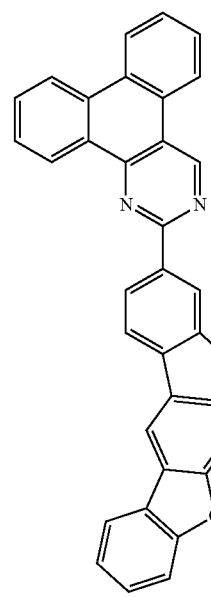
510

511
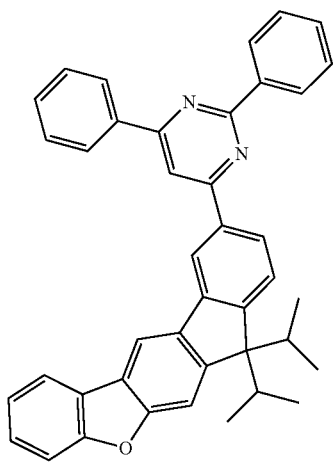
512
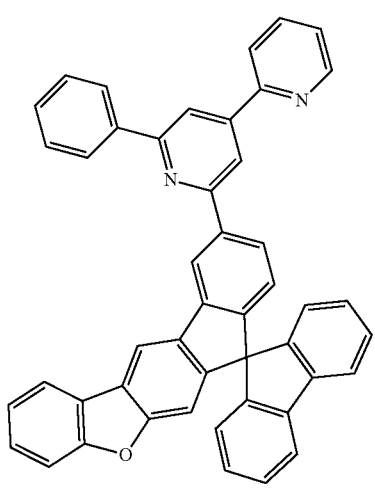
513
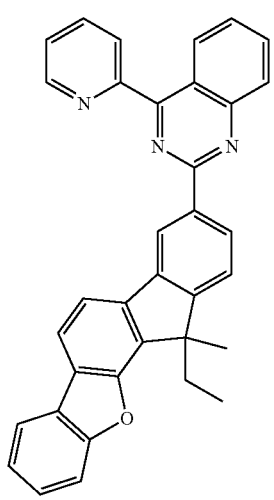
514
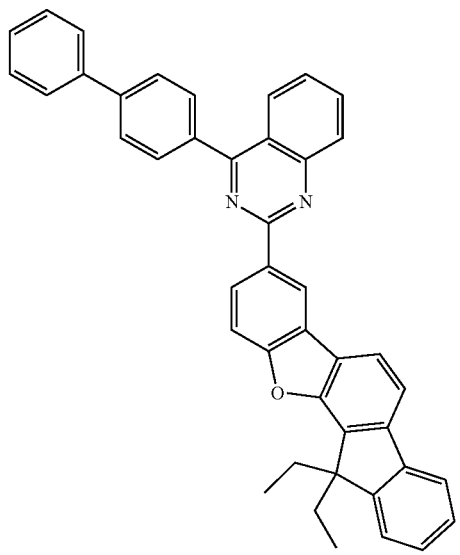
515
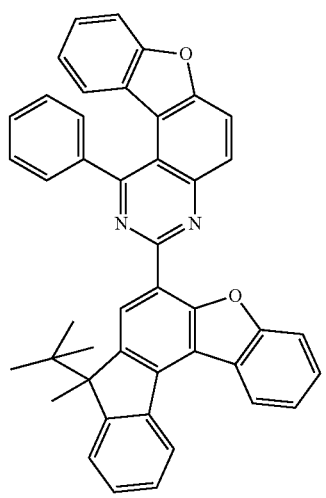
516
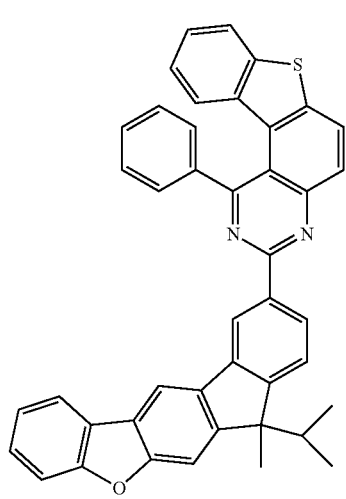

-continued
517
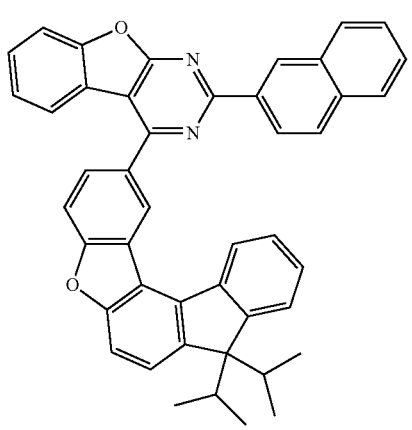
518
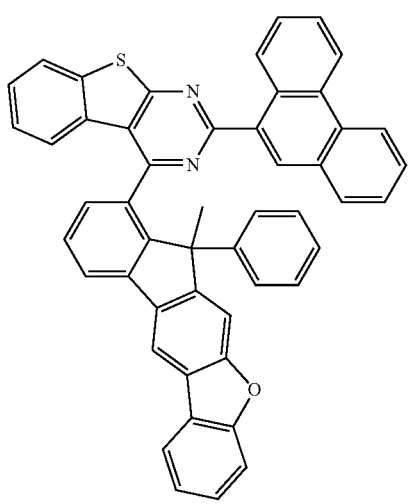
519
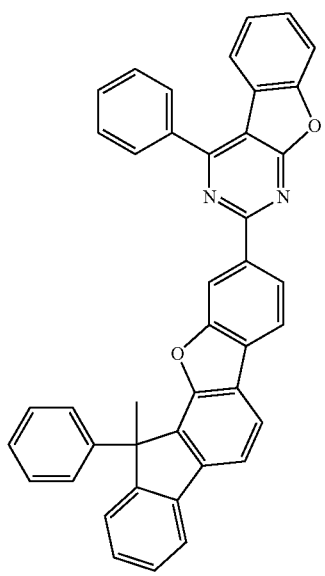
-continued
520
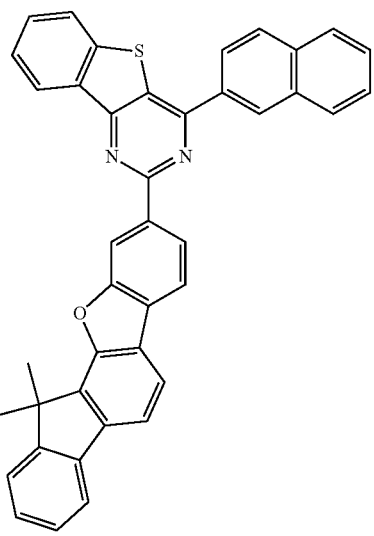
521
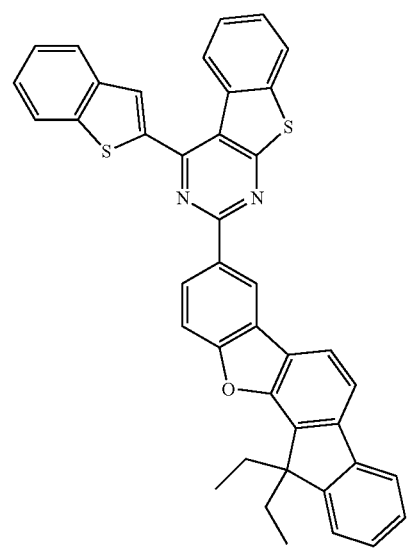
522
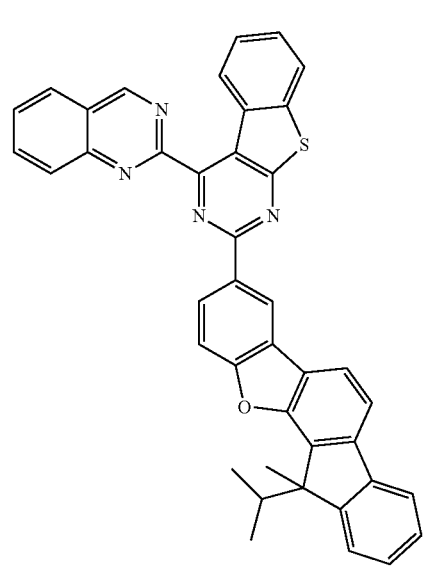

523
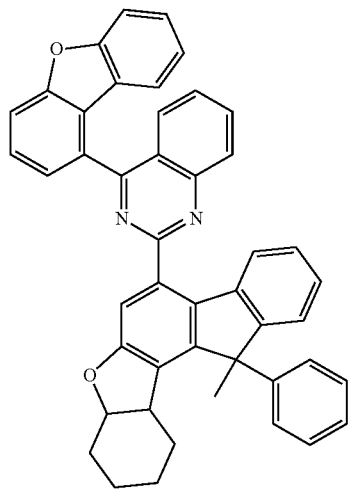
524
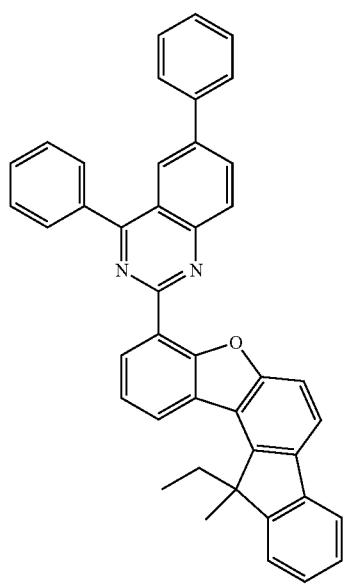
525
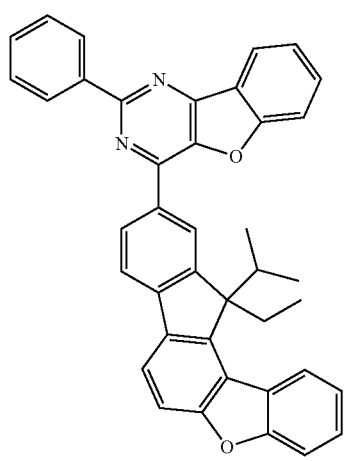
526
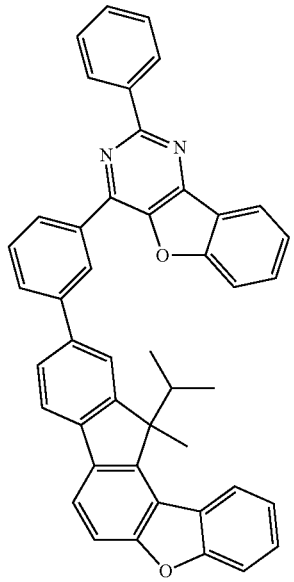
527
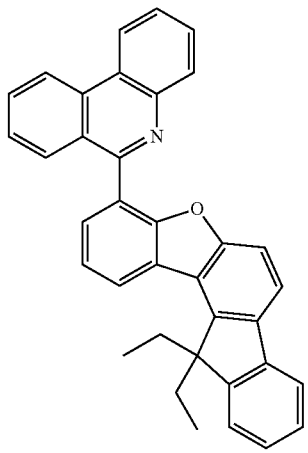
528
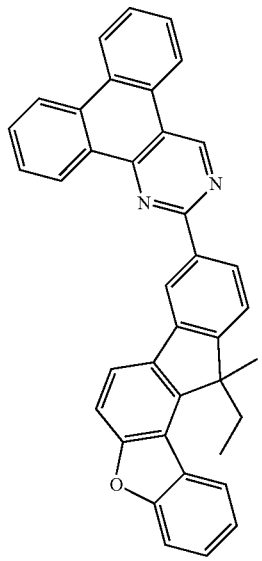

| 529 | 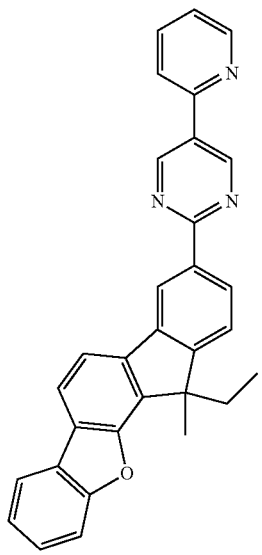 | 532 | 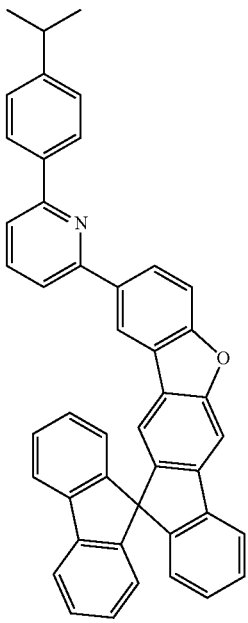 |
| 530 | 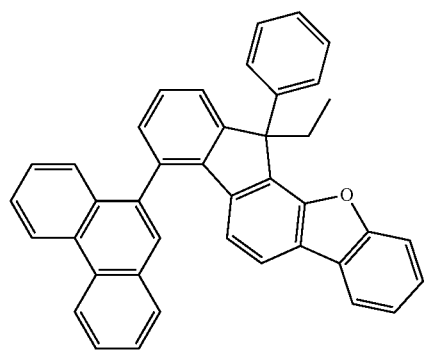 | 533 | 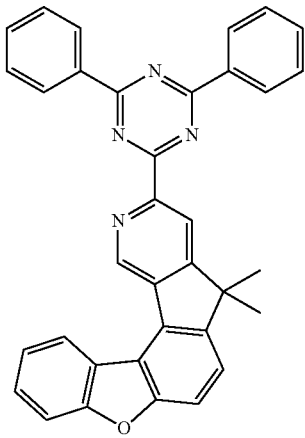 |
| 531 | 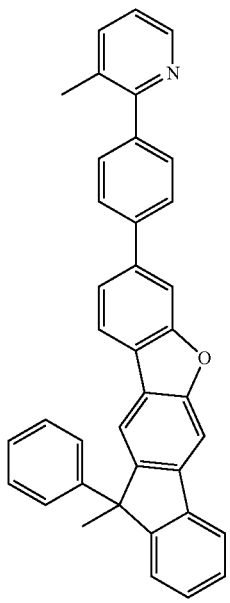 | 534 | 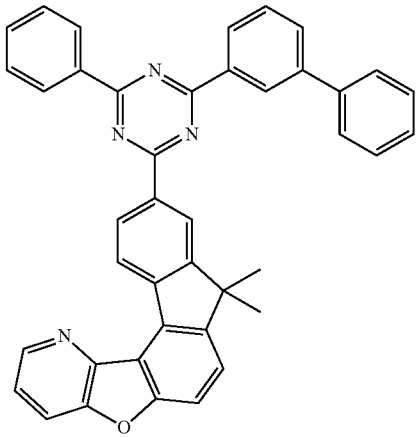 |

445
-continued
535
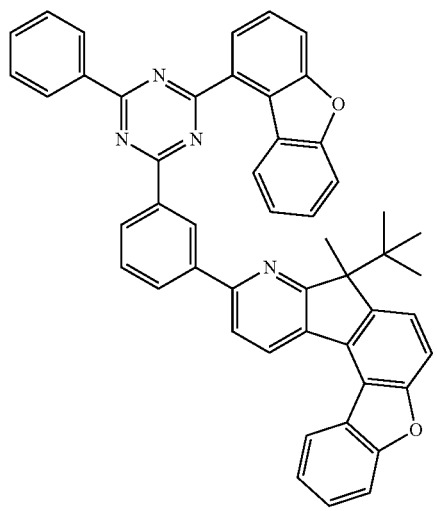
536
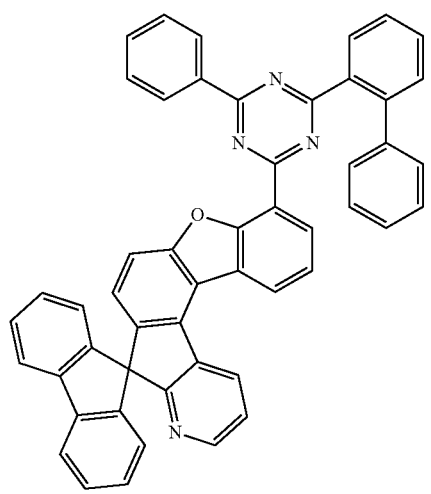
537
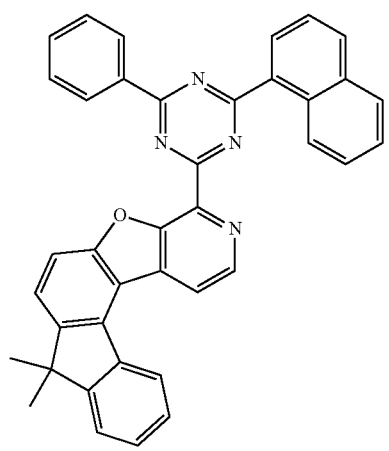
446
-continued
538
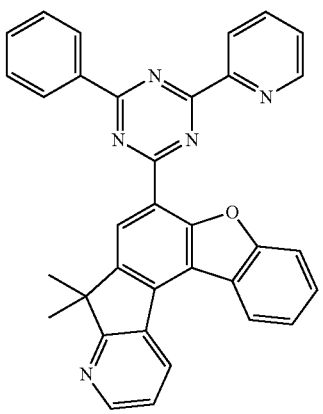
539
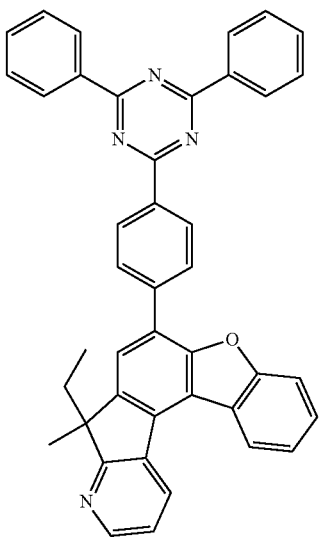
540
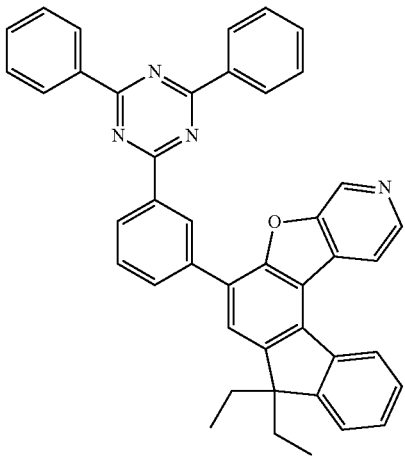

541
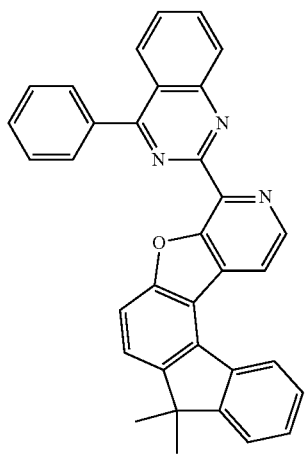
542
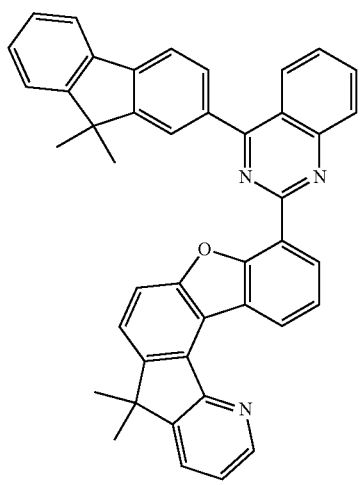
543
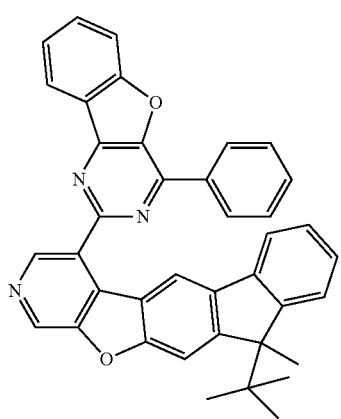
544
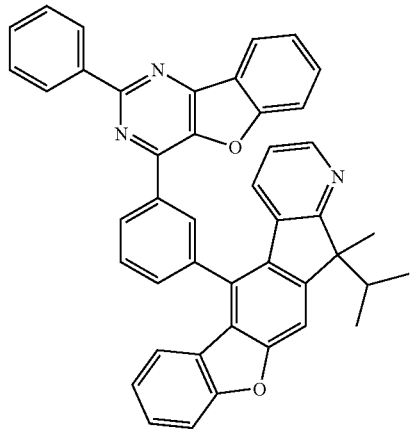
545
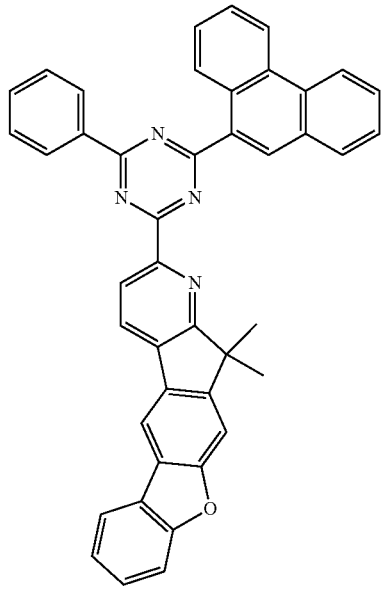
546
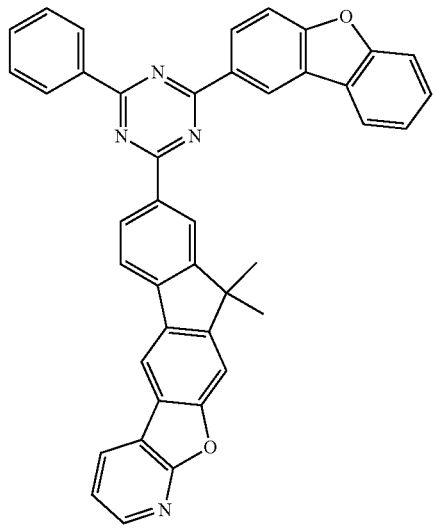

449
-continued
547
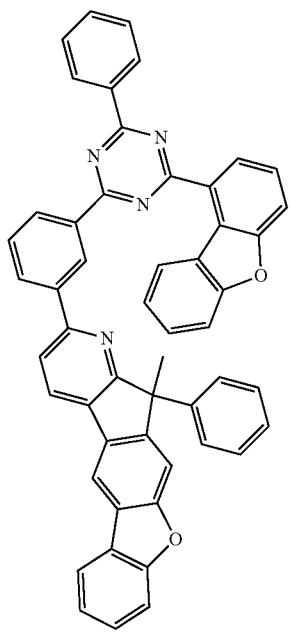
548
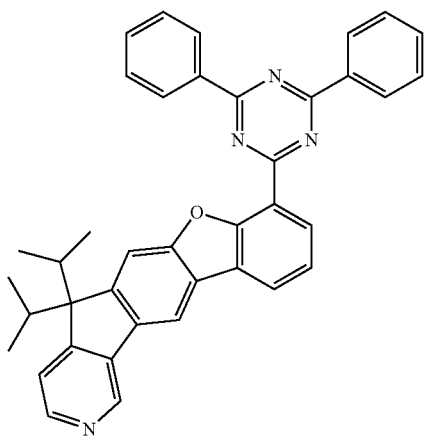
549
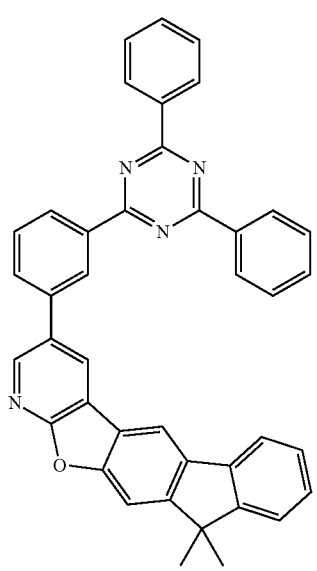
450
-continued
550
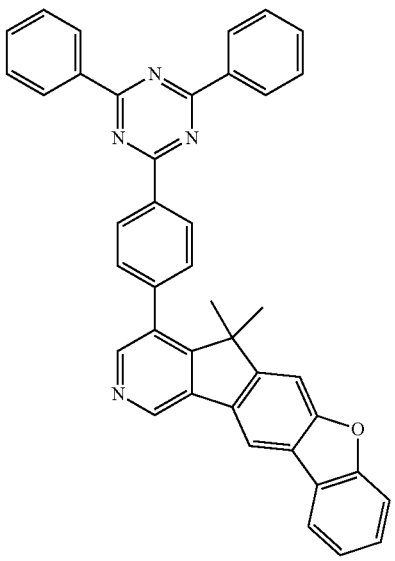
551
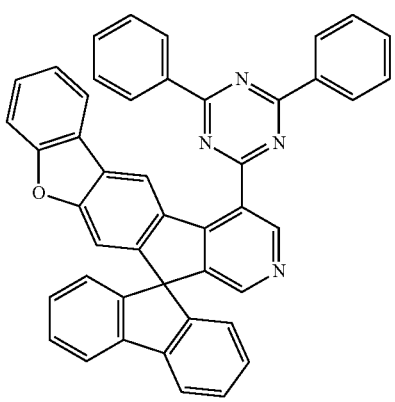
552
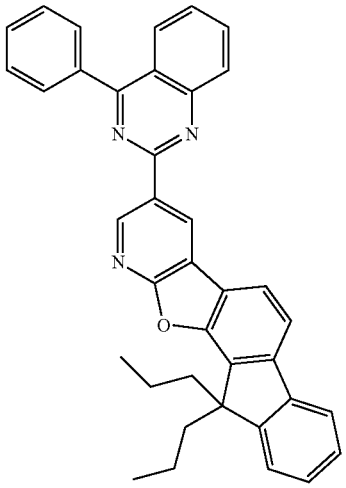

553 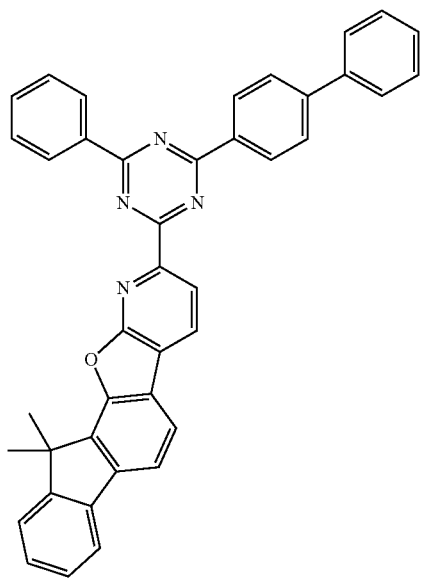
554 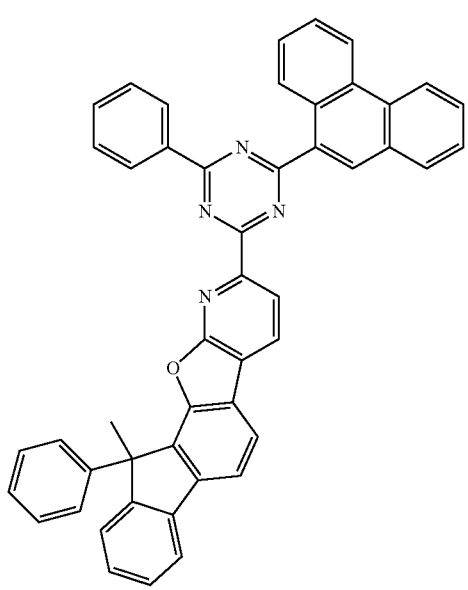
555 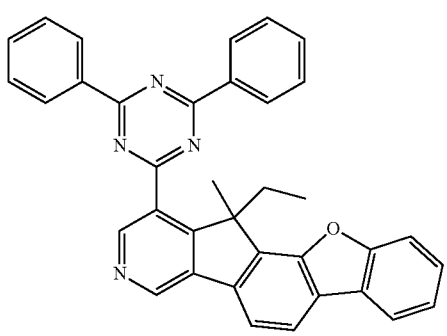
556 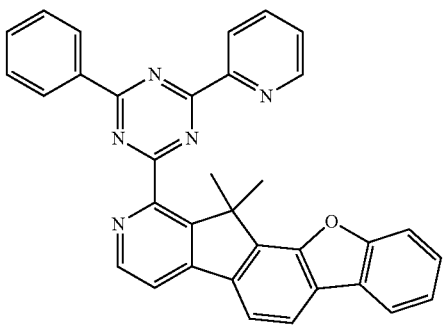
557 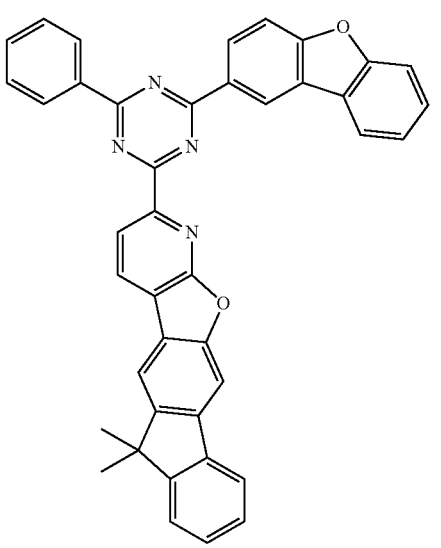
558 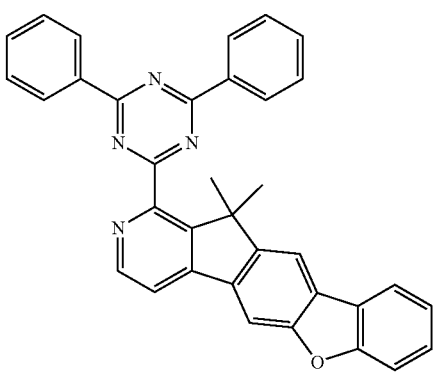
559 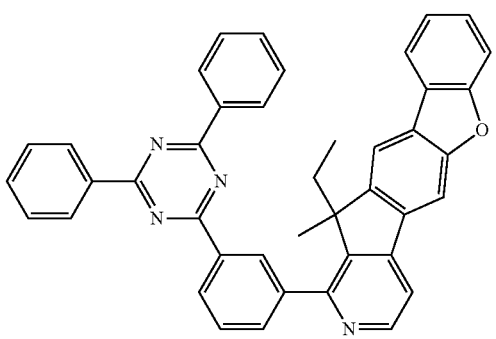

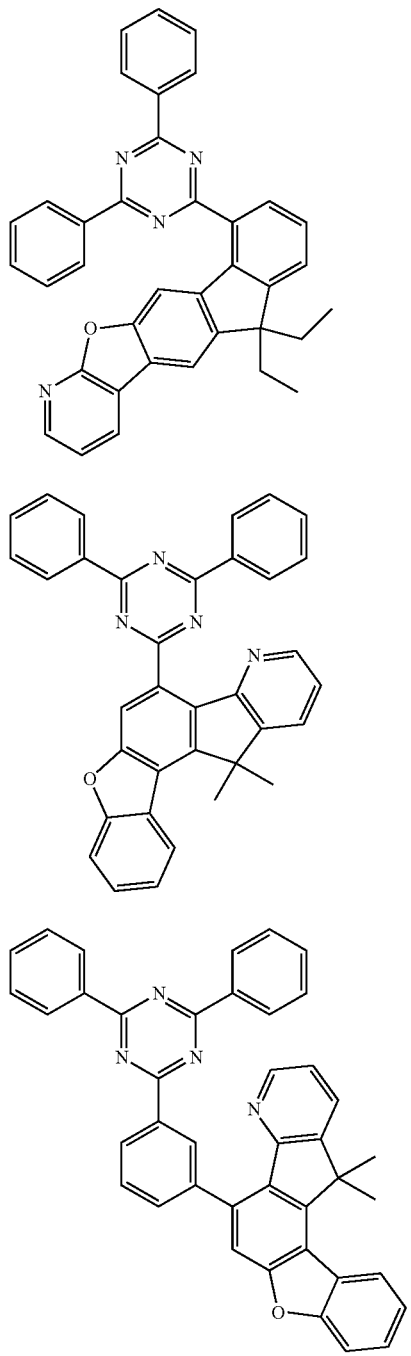
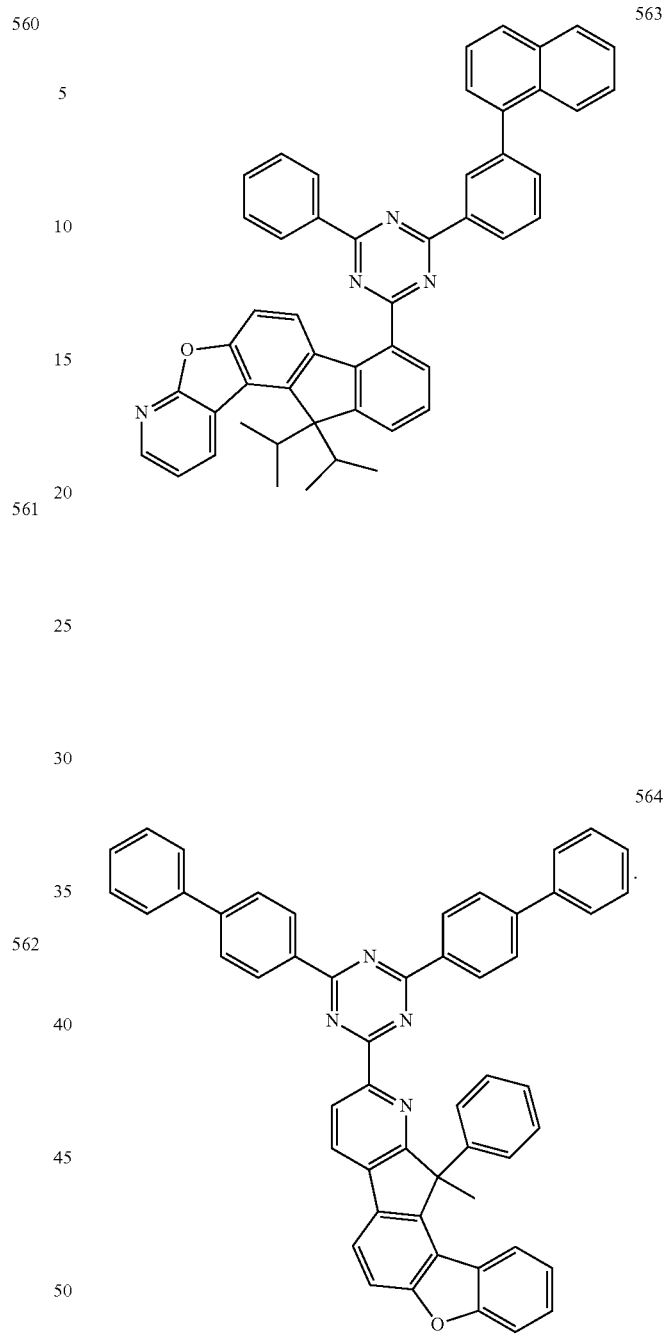
* * * * *